US010858666B2

(12) United States Patent
Verheesen et al.

(10) Patent No.: US 10,858,666 B2
(45) **Date of Patent: *Dec. 8, 2020**

(54) TRANSGENIC PLANTS EXPRESSING A VARIABLE DOMAIN OF A HEAVY CHAIN ANTIBODY (VHH) THAT BINDS TO A SPHINGOLIPID OF A FUNGUS

(71) Applicant: AGROSAVFE N.V., Ghent (BE)

(72) Inventors: Peter Verheesen, Mariakerke (BE); Jan Geerinck, Nieuwkerken-Waas (BE); João Filipe Veloso Vieira, Didcot (GB); Marnix Peferoen, Bellem (BE); Inge Elodie Van Daele, Melle (BE)

(73) Assignee: BIOTALYS, Ghent (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/524,609

(22) PCT Filed: Nov. 5, 2015

(86) PCT No.: PCT/EP2015/075800

§ 371 (c)(1),
(2) Date: May 4, 2017

(87) PCT Pub. No.: WO2016/071438

PCT Pub. Date: May 12, 2016

(65) Prior Publication Data

US 2018/0179551 A1 Jun. 28, 2018

(30) Foreign Application Priority Data

Nov. 5, 2014 (EP) .................................... 14191959

(51) Int. Cl.
*C12N 15/82* (2006.01)
*C07K 16/14* (2006.01)

(52) U.S. Cl.
CPC .......... *C12N 15/8282* (2013.01); *C07K 16/14* (2013.01); *C12N 15/8279* (2013.01); *C07K 2317/22* (2013.01); *C07K 2317/30* (2013.01); *C07K 2317/52* (2013.01); *C07K 2317/565* (2013.01); *C07K 2317/567* (2013.01); *C07K 2317/569* (2013.01)

(58) Field of Classification Search
None
See application file for complete search history.

(56) References Cited

U.S. PATENT DOCUMENTS

| | | | | |
|---|---|---|---|---|
| 6,596,509 | B1 | 7/2003 | Bauer et al. | |
| 8,907,074 | B2 * | 12/2014 | Ryu | C07K 14/415 435/320.1 |
| 9,803,003 | B2 * | 10/2017 | Verheesen | C07K 16/14 |
| 2011/0165649 | A1 | 7/2011 | Tyler et al. | |
| 2011/0244011 | A1 | 10/2011 | Jongedijk et al. | |
| 2012/0042416 | A1 | 2/2012 | Schleker et al. | |
| 2013/0224226 | A1 | 8/2013 | Verheesen et al. | |
| 2013/0225403 | A1 | 8/2013 | Verheesen et al. | |
| 2013/0227747 | A1 | 8/2013 | Verheesen et al. | |
| 2014/0128579 | A1 | 5/2014 | Jongedijk et al. | |
| 2015/0087517 | A1 | 3/2015 | Verheesen et al. | |
| 2016/0075769 | A1 | 3/2016 | Verheesen et al. | |
| 2016/0145325 | A1 | 5/2016 | Verheesen et al. | |
| 2018/0022791 | A1 * | 1/2018 | Verheesen | C07K 16/14 424/172.1 |
| 2018/0179551 | A1 | 6/2018 | Verheesen et al. | |
| 2018/0222966 | A1 * | 8/2018 | Verheesen | A01N 37/46 |

FOREIGN PATENT DOCUMENTS

| | | | |
|---|---|---|---|
| DE | 10234116 | A1 | 2/2004 |
| EP | 368684 | A1 | 3/1994 |
| EP | 1118669 | A2 | 7/2001 |
| EP | 1134231 | A1 | 9/2001 |
| EP | 1198985 | A1 | 4/2002 |
| EP | 1433793 | A1 | 6/2004 |
| EP | 2298922 | A1 | 3/2011 |
| JP | 2005027654 | A | 2/2005 |
| JP | 4213586 | B2 | 1/2009 |
| NZ | 580505 | A | 3/2011 |
| WO | 9404678 | A1 | 3/1994 |
| WO | 9425591 | A1 | 11/1994 |
| WO | 9504079 | A1 | 2/1995 |

(Continued)

OTHER PUBLICATIONS

Da Silva et al. Glucosylceramides in Colletotrichum gleosporioides are involved in the differentiation of conidia into mycelial cells. (2004) FEBS Letters; vol. 561; pp. 137-143 (Year: 2004).*
Kunze et al. The similarity between N-terminal targeting signals for protein import into different organelles and its evolutionary relevance. (2015) Frontiers in Physiology; vol. 6; pp. 1-27 (Year: 2015).*
Liao et al. Plantibodies: A novel strategy to create pathogen-resistant plants. (2006) Biotechnology and Genetic Engineering Reviews; vol. 23; pp. 253-271 (Year: 2006).*
De Marco, A. Biotechnological applications of recombinant single-domain antibody fragments. (2011) Microbial Cell Factories; vol. 10; pp. 1-14 (Year: 2011).*
Singh et al. Sphingolipidomics: an important mechanistic tool for studying fungal pathogens. (2016) Front. Microbiol. ; vol. 7; pp. 1-14 (Year: 2016).*

(Continued)

*Primary Examiner* — Cathy Kingdon Worley
(74) *Attorney, Agent, or Firm* — Patent Law Works, LLP

(57) ABSTRACT

This disclosure relates to a transgenic plant or plant tissue or plant cell comprising at least one polynucleotide encoding a polypeptide comprising a variable domain of a heavy-chain antibody (VHH) specifically binding to a sphingolipid of a fungus. This disclosure further relates to a method for protecting at least part of a plant, plant tissue or plant cell from an infection with a plant pathogen, for inhibiting the growth of a plant pathogen on at least part of a plant, plant tissue or plant cell, or for increasing pathogen resistance of at least part of a plant, plant tissue or plant cell.

19 Claims, 7 Drawing Sheets

Specification includes a Sequence Listing.

(56) References Cited

FOREIGN PATENT DOCUMENTS

| | | | | |
|---|---|---|---|---|
| WO | 9609398 A1 | 3/1996 | | |
| WO | 9634103 A1 | 10/1996 | | |
| WO | 9749805 A2 | 12/1997 | | |
| WO | 9937681 A2 | 7/1999 | | |
| WO | WO0023593 A2 | 4/2000 | | |
| WO | 0040968 A1 | 7/2000 | | |
| WO | 0043507 A1 | 7/2000 | | |
| WO | 0065057 A1 | 11/2000 | | |
| WO | 0121817 A | 3/2001 | | |
| WO | 0140310 A2 | 6/2001 | | |
| WO | 0144301 A1 | 6/2001 | | |
| WO | 0190190 A2 | 11/2001 | | |
| WO | 03025020 A1 | 3/2003 | | |
| WO | 03035694 A2 | 5/2003 | | |
| WO | 03050531 A2 | 6/2003 | | |
| WO | 03054016 A2 | 7/2003 | | |
| WO | 03055527 A2 | 7/2003 | | |
| WO | 03089475 A2 | 10/2003 | | |
| WO | 2004041862 A2 | 5/2004 | | |
| WO | 2004041863 A2 | 5/2004 | | |
| WO | 2004041865 A2 | 5/2004 | | |
| WO | 2004041867 A2 | 5/2004 | | |
| WO | 2004062551 A2 | 7/2004 | | |
| WO | 2006003388 A2 | 1/2006 | | |
| WO | 2006030220 A1 | 3/2006 | | |
| WO | WO2008128289 A1 | 10/2008 | | |
| WO | 2010019442 A1 | 2/2010 | | |
| WO | WO2010066740 A1 | 6/2010 | | |
| WO | 2011023522 A1 | 3/2011 | | |
| WO | 2011085070 A1 | 7/2011 | | |
| WO | WO 2011/085070 A2 * | 7/2011 | ............. | C07K 19/00 |
| WO | 2012011396 A1 | 1/2012 | | |
| WO | 2012025619 A1 | 3/2012 | | |
| WO | WO2012025602 A1 | 3/2012 | | |
| WO | WO2012025621 A1 | 3/2012 | | |
| WO | 2014177595 A1 | 11/2014 | | |
| WO | WO2014191146 A1 | 12/2014 | | |
| WO | 2016071438 A2 | 5/2016 | | |

OTHER PUBLICATIONS

Goodrow, et al. Hapten design for compound-selective antibodies: ELISAS for environmentally deleterious small molecules. (1998) Analytica Chimica; vol. 376; pp. 83-91 (Year: 1998).*

Korouzhdehy et al. Expression of biological active VHH camelid single domain antibody in transgenic tobacco. (2011) African J. of Biotech.; vol. 10; pp. 4234-4241 (Year: 2011).*

Teh et al. High-level expression of Camelid nanobodies in Nicotiana benthamiana. (2010) Transgenic Research; vol. 19; pp. 575-586 (Year: 2010).*

PCT International Search Report and Written Opinion, PCT/EP2015/075800, dated Dec. 5, 2016.

PCT International Search Report, PCT/EP2015/075800, dated Dec. 5, 2016.

Da Silva et al., Glucosylceramides in Colletotrichum gloeosporioides are involved in the differentiation of conidia into mycelial cells, Elsevier, vol. 561, No. 1-3, Mar. 12, 2004, pp. 137-143.

Liao et al., Plantibodies: A Novel Strategy to Create Pathogen-Resistant Plants, Biotechnology and Genetic Engineering Reviews, vol. 23, No. 1, Dec. 1, 2006, pp. 253-272.

Niimrichter et al., Fungal Glucosylceramides: From Structural Components to Biologically Active Targets of New Antimicrobials, Frontiers in Microbiology, vol. 2, Jan. 1, 2011.

PCT International Preliminary Report on Patentability, PCT/EP2015/075800, dated Apr. 13, 2017.

Casset et al., A Peptide Mimetic of an Anti-CD4 Monoclonal Antibody by Rational Design, (2003) BBRC 307, 198-205.

Chen et al., Selection and Analysis of an Optimized Anti-VEGF Antibody: Crystal Structure of an Affinity-matured Fab in Complex with Antigen, J. Mol. Bio. (1999) 293, 865-881.

Houghten et al., New Approaches to Immunization, Vaccines, 1986, Edited by Fred Brown: Cold Spring Harbor Laboratory.

MacCallum et al., Antibody-Antigen Interactions: Contact Analysis and Binding Site Topography, J. Mol. Biol. (1996) 262, 732-745.

Meng et al., A glucosylceramide with antimicrobial activity from the edible mushroom *Pleurotus citrinopileatus*, J. Wood Sci., 2012, pp. 81-86, vol. 58.

Nimrichter et al., Monoclonal Antibody to Glucosylceramide Inhibits the Growth of Fonsecaea Pedrosoi and Enhances the Antifungal Action of Mouse Macrophages, vol. 6, Issue 7, Jun. 2004, pp. 657-665.

Nimrichter et al., Structure, Cellular Distribution, Antigenicity, and Biological Functions of Fonsecaea Pedrosoi ceramide Monohexosides, Infection and Immunity. Dec. 2005, vol. 73, No. 12, pp. 7860-07868.

Pascalis et al., Grafting of "Abbreviated" Complementarity-Determining Regions Containing Specificity-Determing Residues Essential for Ligand Contact to Engineer a Less Immunogenic Humanized Monoclonal Antibody, The Journal of Immunology (2002) 169, 3076-3084.

PCT International Search Report, PCT/EP2014/058771, dated Sep. 17, 2014.

PCT International Search Report, PCT/EP2014/058772, dated Aug. 16, 2011.

Pinto et al., Characterization of Glucosylceramides in Pseudallescheria boydii and their involvement in fungal lifferentiation, Glycobiology, (2002) vol. 12 No. 4, 251-260.

Qureshi et al., Detection of Antibody Against fungal Glucosylcereamide in Immunocompromised Patients: A Potential New Diagnostic Approach for Cryptococcosis, Mycopathologia (2012) 173, pp. 419-425.

Toledo et al., Characterization of Monoclonal Antibody MEST-2 Specific to Glucosylceramide of Fungi and Plants, Glycobiology, (2001) vol. 11 No. 2, pp. 105-112.

Toledo et al., Effect of Anti-Glycosphingolipid Monoclonal Antibodies in Pathogenic Fungal Growth and Differentiation., Microbiology (2010) vol. 10 pp. 12 pgs.

Vajdos et al., Comprehensive Functional Maps of the Antigenbinding Site of an Anti-ErbB2 Antibody Obtained with Shotgun Scanning Mutagenesis, J. Mol. Biol. (2002) 320, 415-428.

Wu et al., Humanization of a Murine Monoclonal Antibody by Simultaneious Optimization of Framework and CDR Residues, J. Mol. Biol. (1999) 294, 151-162.

Korouzhdehy, et al. Expression of Biological Active VHH Camelid Single Domain Antibody in Transgenic Tobacco. African Journal of Biotechnology. 10-20 (2011): 4234-4241.

Teh, et al. High-level Expression of Camelid Nanobodies in Nicotiana Benthamiana. Transgenic Research. 19.4 (2010): 575-586.

EPO Communication, Application No. 19188008.7, Extended European Search Report, dated Oct. 17, 2019, 11 pgs.

Jobling, Stephen A., et al. "Immunomodulation of Enzyme Function in Plants by Single-Domain Antibody Fragments" Nature Biotechnology, vol. 21, No. 1, 2003, pp. 77-80.

* cited by examiner

TRANSGENIC PLANTS EXPRESSING A VARIABLE DOMAIN OF A HEAVY CHAIN ANTIBODY (VHH) THAT BINDS TO A SPHINGOLIPID OF A FUNGUS

CROSS-REFERENCE TO RELATED APPLICATIONS

This application is a national phase entry under 35 U.S.C. § 371 of International Patent Application PCT/EP2015/075800, filed Nov. 5, 2015, designating the United States of America and published in English as International Patent Publication WO 2016/071438 A2 on May 12, 2016, which claims the benefit under Article 8 of the Patent Cooperation Treaty to European Patent Application Serial No. 14191959.7, filed Nov. 5, 2014.

TECHNICAL FIELD

This application relates to the field of transgenic plants. In particular, this disclosure relates to a transgenic plant or plant tissue or plant cell comprising at least one polynucleotide comprising at least one sequence encoding a variable domain of a heavy-chain antibody (VHH) specifically binding to a sphingolipid of a fungus. This disclosure further relates to a method for protecting at least part of a plant or plant tissue or plant cell from an infection with a plant pathogen, for inhibiting the growth of a plant pathogen on at least part of a plant or plant tissue or plant cell, or for increasing pathogen resistance of at least part of a plant or plant tissue or plant cell, comprising expressing in at least part of the plant or plant tissue or plant cell at least one polynucleotide encoding a VHH specifically binding to a pathogen.

STATEMENT ACCORDING TO 37 C.F.R. § 1.821(C) OR (E)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

BACKGROUND

Crop protection, required for effective agriculture, relies heavily on the use of pesticides, which are applied to the crops by spraying them onto the crop, applying during watering of the crops or incorporating them into the soil. Pesticides are often organic chemical molecules and their repeated application to crops poses toxicity threats to both agricultural workers during handling and to the environment, due to spray drift, persistence in the soil or washing off into surface or ground water. It would be advantageous to be able to use alternative compounds that are less toxic to humans and the environment, but that at the same time provide effective control of plant pests. Proteinaceous pesticides with specificity against a certain plant pest target may be very advantageous in this respect, as they are expected to be short-lived in the environment and to have less toxic off-target effects. However, there are only a few proteinaceous or peptidergic pesticides known. Some examples are Bt toxins, lectins, defensins, fabatins, tachyplesin, magainin, harpin (see WO 2010/019442), pea albumin 1-subunit b (PA1b). However, these proteinaceous pesticides are either small peptides with compact structures, stabilized by several disulphide bridges, or are larger proteins (>300 amino acids) that occur in crystalline form (cry toxins). It is indeed known in the field of agriculture that biologicals and, in particular, proteins, are challenging structures for developing pesticides, as they generally have far too little stability to maintain their pesticidal function in an agrochemical formulation, in particular, for applications in the field.

BRIEF SUMMARY

The applicants herein have successfully developed transgenic plants comprising a polynucleotide encoding polypeptides with surprisingly high specificity, affinity and potency against targets of plant or crop pests, in particular, plant pathogens, such as plant pathogenic fungi. Moreover, it is shown that these polypeptides retain their integrity, stability and activity upon in planta expression and that efficacious pest or pathogenic control can surprisingly be achieved.

The applicants herein have realized a transgenic plant comprising a polynucleotide, wherein the expression of the polynucleotide in at least part of the transgenic plant (i.e., in planta expression of the polynucleotide) protects at least part of the transgenic plant from an infection or other biological interaction with a plant pathogenic fungus.

Hence, a first aspect of this disclosure relates to a transgenic plant or plant tissue or plant cell comprising at least one polynucleotide comprising at least one sequence encoding a variable domain of a heavy-chain antibody (VHH) specifically binding to a sphingolipid of a fungus.

In certain embodiments of the transgenic plants or plant tissues or plant cells, methods, or uses, as taught herein, a VHH as taught herein specifically binds to a sphingolipid of a fungus. In certain embodiments, a VHH as taught herein specifically binds to a ceramide of a fungus. In certain embodiments, a VHH as taught herein specifically binds to a glycosphingolipid of a fungus. In certain embodiments, a VHH as taught herein specifically binds to a cerebroside of a fungus. In certain preferred embodiments, a VHH as taught herein specifically binds to a glucocerebroside of a fungus.

The applicants herein have found that a VHH as taught herein specifically binds to a sphingolipid of a fungus and binds to a sphingolipid of a plant pathogenic fungus.

Hence, in certain embodiments, this disclosure relates to a transgenic plant or plant tissue or plant cell comprising at least one polynucleotide comprising at least one sequence encoding a VHH specifically binding to a sphingolipid of a fungus, preferably to a ceramide of a fungus, preferably to a glycosphingolipid of a fungus, more preferably to a cerebroside of a fungus, even more preferably to a glucocerebroside of a fungus, and wherein the VHH binds to a sphingolipid of a plant pathogenic fungus, preferably to a ceramide of a plant pathogenic fungus, preferably to a glycosphingolipid of a plant pathogenic fungus, more preferably to a cerebroside of a plant pathogenic fungus, even more preferably to a glucocerebroside of a plant pathogenic fungus.

In certain embodiments, this disclosure relates to a transgenic plant or plant tissue or plant cell comprising at least one polynucleotide comprising at least one sequence encoding a VHH specifically binding to a sphingolipid of a fungus, and wherein the VHH binds to a sphingolipid of a plant pathogenic fungus, preferably to a ceramide of a plant pathogenic fungus, preferably to a glycosphingolipid of a plant pathogenic fungus, more preferably to a cerebroside of a plant pathogenic fungus, even more preferably to a glucocerebroside of a plant pathogenic fungus.

In certain embodiments, this disclosure relates to a transgenic plant or plant tissue or plant cell comprising at least one polynucleotide comprising at least one sequence encoding a VHH specifically binding to a ceramide of a fungus, and wherein the VHH binds to a sphingolipid of a plant pathogenic fungus, preferably to a ceramide of a plant pathogenic fungus, preferably to a glycosphingolipid of a plant pathogenic fungus, more preferably to a cerebroside of a plant pathogenic fungus, even more preferably to a glucocerebroside of a plant pathogenic fungus.

In certain embodiments, this disclosure relates to a transgenic plant or plant tissue or plant cell comprising at least one polynucleotide comprising at least one sequence encoding a VHH specifically binding to a glycosphingolipid of a fungus, and wherein the VHH binds to a sphingolipid of a plant pathogenic fungus, preferably to a ceramide of a plant pathogenic fungus, preferably to a glycosphingolipid of a plant pathogenic fungus, more preferably to a cerebroside of a plant pathogenic fungus, even more preferably to a glucocerebroside of a plant pathogenic fungus.

In certain embodiments, this disclosure relates to a transgenic plant or plant tissue or plant cell comprising at least one polynucleotide comprising at least one sequence encoding a VHH specifically binding to a cerebroside of a fungus, and wherein the VHH binds to a sphingolipid of a plant pathogenic fungus, preferably to a ceramide of a plant pathogenic fungus, preferably to a glycosphingolipid of a plant pathogenic fungus, more preferably to a cerebroside of a plant pathogenic fungus, even more preferably to a glucocerebroside of a plant pathogenic fungus.

In certain embodiments, this disclosure relates to a transgenic plant or plant tissue or plant cell comprising at least one polynucleotide comprising at least one sequence encoding a VHH specifically binding to a glucocerebroside of a fungus, and wherein the VHH binds to a sphingolipid of a plant pathogenic fungus, preferably to a ceramide of a plant pathogenic fungus, preferably to a glycosphingolipid of a plant pathogenic fungus, more preferably to a cerebroside of a plant pathogenic fungus, even more preferably to a glucocerebroside of a plant pathogenic fungus.

In certain embodiments of the transgenic plants or plant tissues or plant cells, methods, or uses, as taught herein, a VHH as taught herein binds to a sphingolipid of a plant pathogenic fungus. In certain embodiments, a VHH as taught herein binds to a ceramide of a plant pathogenic fungus. In certain embodiments, a VHH as taught herein specifically binds to a glycosphingolipid of a plant pathogenic fungus. In certain embodiments, a VHH as taught herein specifically binds to a cerebroside of a plant pathogenic fungus. In certain preferred embodiments, a VHH as taught herein specifically binds to a glucocerebroside of a plant pathogenic fungus.

In certain embodiments, the transgenic plant or plant tissue or plant cell may have an increased or enhanced level of a VHH as taught herein relative to (i.e., compared with) a non-modified (i.e., non-transformed or untransformed, such as wild-type) plant or plant tissue.

In certain embodiments, the transgenic plant or plant tissue or plant cell may have a level of a VHH as taught herein, which is at least 0.001% of the amount of total soluble protein in the transgenic plant or plant tissue or plant cell, in particular, in an extract of the transgenic plant or plant tissue. For example, the transgenic plant or plant tissue or plant cell may have a level of a VHH as taught herein, which is at least 0.005%, at least 0.01%, at least 0.05%, at least 0.1%, at least 0.2%, at least 0.3%, at least 0.4%, or at least 0.5% of the amount of total soluble protein in the transgenic plant or plant tissue or plant cell, in particular, in an extract of the transgenic plant or plant tissue.

In certain embodiments, the expression of the polynucleotide in at least part of the transgenic plant or plant tissue or plant cell may protect at least part of the transgenic plant or plant tissue or plant cell from an infection with a plant pathogenic fungus. For example, the expression of the polynucleotide in at least part of the transgenic plant or plant tissue or plant cell may protect at least part of the transgenic plant or plant tissue or plant cell from an infection with a plant pathogenic fungus relative to (i.e., compared with) a non-modified (i.e., non-transformed or untransformed, such as wild-type) plant or plant tissue.

In certain embodiments, the expression of the polynucleotide in at least part of the transgenic plant or plant tissue or plant cell may inhibit the growth of a plant pathogenic fungus on at least part of the transgenic plant or plant tissue. For example, the expression of the polynucleotide in at least part of the transgenic plant or plant tissue or plant cell may inhibit the growth of a plant pathogenic fungus on at least part of the transgenic plant or plant tissue or plant cell relative to (i.e., compared with) the growth of the plant pathogenic fungus on a non-modified (i.e., non-transformed or untransformed, such as wild-type) plant or plant tissue.

In certain embodiments, the expression of the polynucleotide in at least part of the transgenic plant or plant tissue or plant cell may increases the resistance of at least part of the transgenic plant or plant tissue or plant cell against a plant pathogenic fungus. For example, the expression of the polynucleotide in at least part of the transgenic plant or plant tissue or plant cell may increases the resistance of at least part of the transgenic plant or plant tissue or plant cell against a plant pathogenic fungus relative to (i.e., compared with) the resistance of a non-modified (i.e., non-transformed or untransformed, such as wild-type) plant or plant tissue or plant cell against the plant pathogenic fungus.

In certain embodiments, the expression of the polynucleotide in at least part of the transgenic plant or plant tissue or plant cell may protect at least part of the transgenic plant or plant tissue or plant cell from an infection with a plant pathogenic fungus, may inhibit the growth of a plant pathogenic fungus on at least part of the transgenic plant or plant tissue or plant cell, and/or may increase the resistance of at least part of the transgenic plant or plant tissue or plant cell against a plant pathogenic fungus.

In certain embodiments of the transgenic plants or plant tissues or plant cells, methods, or uses, as taught herein, the polynucleotide may comprise a promoter suitable for expression in plants, such as the 35S Cauliflower Mosaic Virus (CaMV) promoter, a plant tissue or plant cell specific promoter, or an inducible promoter.

In certain embodiments of the transgenic plants or plant tissues or plant cells, methods, or uses, as taught herein, the polynucleotide may comprise at least one sequence encoding a targeting signal for secretion, for location to the cytoplasm, or for location to cellular compartments or organelles, such as the ER lumen, the apoplast, the vacuole, or intra- and/or exterior membranes.

In certain embodiments of the transgenic plants or plant tissues or plant cells, methods, or uses, as taught herein, the polynucleotide may comprise at least one sequence encoding a tag, preferably a His6, c-myc, FLAG, C-tag, 3×FLAG, His5, His10, HA, T7, strep, HSV, and/or an E-tag.

In certain embodiments of the transgenic plants or plant tissues or plant cells, methods, or uses, as taught herein, the polynucleotide may encode the VHH as such, as a combination with one or more identical or different VHHs, or as a combination with one or more identical or different VHHs with an fragment crystallizable region (Fc region) of an antibody; optionally with a spacer.

In certain embodiments, the polynucleotide may encode the VHH as such, optionally with a spacer. In certain other embodiments, the polynucleotide may encode the VHH as a combination with one or more, such as two or more, identical or different VHHs, optionally with a spacer. In certain other embodiments, the polynucleotide may encode the VHH as a combination with one or more, such as two or more, identical or different VHHs with a fragment crystallizable region (Fc region) of an antibody, optionally with a spacer. Such a spacer advantageously spatially extends two VHHs from each other, thereby enhancing the flexibility of the VHHs relative to each other and/or assuring optimal interaction between each VHH and its antigen.

In certain embodiments of the transgenic plants or plant tissues or plant cells, methods, or uses, as taught herein, the plant may be a plant selected from the group consisting of corn, rice, wheat, barley, sorghum, millet oats, rye, triticale or other cereals, soybean, alfalfa or other leguminous crops, sugar beet, fodder beet, papaya, banana and plantains or other fruits, grapevines, nuts, oilseed rape, sunflower or other oil crops, squash cucumber, melons or other cucurbits, cotton or other fiber plants, sugarcane, palm, jatropha or other fuel crops, cabbages, tomato, pepper or other vegetables, ornamentals, shrubs, poplar, eucalyptus or other trees, evergreens, grasses, coffee plants, tea plants, tobacco plants, hop plants, rubber plants, and latex plants.

In certain embodiments of the transgenic plants or plant tissues or plant cells, methods, or uses, as taught herein, the polynucleotide may comprise a sequence encoding a VHH comprising:

(i) anyone or more of SEQ ID NOS:1 to 84, preferably SEQ ID NOS:1, 2, and/or 70, more preferably SEQ ID NOS:1 and/or 2, and/or
(ii) a CDR1, CDR2, and CDR3 region, wherein (i) the CDR1 region is selected from the group of SEQ ID NOS:85-168, and/or (ii) the CDR2 region is selected from the group of SEQ ID NOS:169-252, and/or (iii) the CDR3 region is selected from the group of SEQ ID NOS:253-335, or the CDR3 region has the amino acid sequence NRY.

In certain embodiments of the transgenic plants or plant tissues or plant cells, methods, or uses, as taught herein, the polynucleotide may comprise a sequence encoding a VHH comprising any one or more of SEQ ID NOS:1 to 84, preferably SEQ ID NOS:1 and/or 2. In certain embodiments, the polynucleotide may comprise a sequence encoding a VHH comprising SEQ ID NO:1, SEQ ID NO:2, and/or SEQ ID NO:70. In certain embodiments, the polynucleotide may comprise a sequence encoding a VHH comprising SEQ ID NO:1 and/or SEQ ID NO:2. In certain embodiments, the polynucleotide may comprise a sequence encoding a VHH comprising SEQ ID NO:1. In certain embodiments, the polynucleotide may comprise a sequence encoding a VHH comprising SEQ ID NO:2. In certain embodiments, the polynucleotide may comprise a sequence encoding a VHH comprising SEQ ID NO:70.

In certain embodiments of the transgenic plants or plant tissues or plant cells, methods, or uses, as taught herein, the polynucleotide may comprise a sequence encoding a VHH comprising a CDR1, CDR2, and CDR3 region, wherein (i) the CDR1 region is selected from the group of SEQ ID NOS:85-168, and/or (ii) the CDR2 region is selected from the group of SEQ ID NOS:169-252, and/or (iii) the CDR3 region is selected from the group of SEQ ID NOS:253-335, or the CDR3 region has the amino acid sequence NRY.

In certain embodiments, the polynucleotide may comprise a sequence encoding a VHH comprising a CDR1, CDR2, and CDR3 region, wherein (i) the CDR1 region is selected from SEQ ID NOS:85 and/or 86, and/or (ii) the CDR2 region is selected from SEQ ID NOS:169 and/or 170, and/or (iii) the CDR3 region is selected from SEQ ID NOS:253 and/or 254. In certain embodiments, the polynucleotide may comprise a sequence encoding a VHH comprising a CDR1, CDR2, and CDR3 region, wherein (i) the CDR1 region is SEQ ID NO:85, and/or (ii) the CDR2 region is SEQ ID NO:169, and/or (iii) the CDR3 region is SEQ ID NO:253. In certain embodiments, the polynucleotide may comprise a sequence encoding a VHH comprising a CDR1, CDR2, and CDR3 region, wherein (i) the CDR1 region is SEQ ID NO:86, and/or (ii) the CDR2 region is SEQ ID NO:170, and/or (iii) the CDR3 region is SEQ ID NO:254.

In certain embodiments of the transgenic plants or plant tissues or plant cells, methods, or uses, as taught herein, the polynucleotide may comprise a sequence encoding a VHH comprising, consisting of, or consisting essentially of four framework regions (FRs) and three complementarity-determining regions (CDRs), a CDR1, CDR2, and CDR3 region, wherein (i) the CDR1 region is selected from the group of SEQ ID NOS:85-168, and/or (ii) the CDR2 region is selected from the group of SEQ ID NOS:169-252, and/or (iii) the CDR3 region is selected from the group of SEQ ID NOS:253-335, or the CDR3 region has the amino acid sequence NRY.

In certain embodiments, the polynucleotide may comprise a sequence encoding a VHH comprising four framework regions and three CDRs, a CDR1, CDR2, and CDR3 region, wherein (i) the CDR1 region is selected from SEQ ID NOS:85 and/or 86, and/or (ii) the CDR2 region is selected from SEQ ID NOS:169 and/or 170, and/or (iii) the CDR3 region is selected from SEQ ID NOS:253 and/or 254. In certain embodiments, the polynucleotide may comprise a sequence encoding a VHH comprising four framework regions and three CDRs, a CDR1, CDR2, and CDR3 region, wherein (i) the CDR1 region is SEQ ID NO:85, and/or (ii) the CDR2 region is SEQ ID NO:169, and/or (iii) the CDR3 region is SEQ ID NO:253. In certain embodiments, the polynucleotide may comprise a sequence encoding a VHH comprising four framework regions and three CDRs, a CDR1, CDR2, and CDR3 region, wherein (i) the CDR1 region is SEQ ID NO:86, and/or (ii) the CDR2 region is SEQ ID NO:170, and/or (iii) the CDR3 region is SEQ ID NO:254.

In certain embodiments of the transgenic plants or plant tissues or plant cells, methods, or uses, as taught herein, the polynucleotide may comprise a sequence encoding a VHH comprising a CDR1, CDR2 and CDR3 region chosen from the list of comprising:

a CDR1 region having SEQ ID NO:85, a CDR2 region having has SEQ ID NO:169, and a CDR3 region having SEQ ID NO:253, and/or
a CDR1 region having SEQ ID NO:86, a CDR2 region having has SEQ ID NO:170, and a CDR3 region having SEQ ID NO:254, and/or
a CDR1 region having SEQ ID NO:87, a CDR2 region having has SEQ ID NO:171, and a CDR3 region having SEQ ID NO:255, and/or
a CDR1 region having SEQ ID NO:88, a CDR2 region having has SEQ ID NO:172, and a CDR3 region having SEQ ID NO:256, and/or a CDR1 region having SEQ ID NO:89, a CDR2 region having has SEQ ID NO:173, and a CDR3 region having SEQ ID NO:257, and/or a CDR1 region having SEQ ID NO:90, a CDR2 region having has SEQ ID NO:174, and a CDR3 region having SEQ ID NO:258, and/or a CDR1 region having SEQ ID NO:91, a CDR2 region having has SEQ ID NO:175, and a CDR3 region having SEQ ID NO:259, and/or a CDR1 region having SEQ ID NO:92, a CDR2 region having has SEQ ID NO:176, and a CDR3 region having SEQ ID NO:260, and/or a CDR1 region having SEQ ID NO:93, a CDR2 region having has SEQ ID NO:177, and a CDR3 region having SEQ ID NO:261, and/or a CDR1 region having SEQ ID NO:94, a CDR2 region having has SEQ ID NO:178, and a CDR3 region having SEQ ID NO:262, and/or a CDR1 region having SEQ ID NO:95, a CDR2 region having has SEQ ID NO:179, and a CDR3 region having SEQ ID NO:263, and/or a CDR1 region having SEQ ID NO:96, a CDR2 region having has SEQ ID NO:180, and a CDR3 region having SEQ ID NO:264, and/or a CDR1 region having SEQ ID NO:97, a CDR2 region having has SEQ ID NO:181, and a CDR3 region having SEQ ID NO:265, and/or a CDR1 region having SEQ ID NO:98, a CDR2 region having has SEQ ID NO:182, and a CDR3 region having SEQ ID NO:266, and/or a CDR1 region having SEQ ID NO:99, a CDR2 region having has SEQ ID NO:183, and a CDR3 region having SEQ ID NO:267, and/or a CDR1 region having SEQ ID NO:100, a CDR2 region having has SEQ ID NO:184, and a CDR3 region having SEQ ID NO:268, and/or a CDR1 region having SEQ ID NO:101, a CDR2 region having has SEQ ID NO:185, and a CDR3 region having SEQ ID NO:269, and/or a CDR1 region having SEQ ID NO:102, a CDR2 region having has SEQ ID NO:186, and a CDR3 region having SEQ ID NO:270, and/or a CDR1 region having SEQ ID NO:103, a CDR2 region having has SEQ ID NO:187, and a CDR3 region having SEQ ID NO:271, and/or a CDR1 region having SEQ ID NO:104, a CDR2 region having has SEQ ID NO:188, and a CDR3 region having SEQ ID NO:272, and/or a CDR1 region having SEQ ID NO:105, a CDR2 region having has SEQ ID NO:189, and a CDR3 region having SEQ ID NO:273, and/or a CDR1 region having SEQ ID NO:106, a CDR2 region having has SEQ ID NO:190, and a CDR3 region having SEQ ID NO:274, and/or a CDR1 region having SEQ ID NO:107, a CDR2 region having has SEQ ID NO:191, and a CDR3 region having SEQ ID NO:275, and/or a CDR1 region having SEQ ID NO:108, a CDR2 region having has SEQ ID NO:192, and a CDR3 region having SEQ ID NO:276, and/or a CDR1 region having SEQ ID NO:109, a CDR2 region having has SEQ ID NO:193, and a CDR3 region having SEQ ID NO:277, and/or a CDR1 region having SEQ ID NO:110, a CDR2 region having has SEQ ID NO:194, and a CDR3 region having SEQ ID NO:278, and/or a CDR1 region having SEQ ID NO:111, a CDR2 region having has SEQ ID NO:195, and a CDR3 region having SEQ ID NO:279, and/or a CDR1 region having SEQ ID NO:112, a CDR2 region having has SEQ ID NO:196, and a CDR3 region having SEQ ID NO:280, and/or a CDR1 region having SEQ ID NO:113, a CDR2 region having has SEQ ID NO:197, and a CDR3 region having SEQ ID NO:281, and/or a CDR1 region having SEQ ID NO:114, a CDR2 region having has SEQ ID NO:198, and a CDR3 region having SEQ ID NO:282, and/or a CDR1 region having SEQ ID NO:115, a CDR2 region having has SEQ ID NO:199, and a CDR3 region having SEQ ID NO:283, and/or a CDR1 region having SEQ ID NO:116, a CDR2 region having has SEQ ID NO:200, and a CDR3 region having SEQ ID NO:284, and/or a CDR1 region having SEQ ID NO:117, a CDR2 region having has SEQ ID NO:201, and a CDR3 region having SEQ ID NO:285, and/or a CDR1 region having SEQ ID NO:118, a CDR2 region having has SEQ ID NO:202, and a CDR3 region having SEQ ID NO:286, and/or a CDR1 region having SEQ ID NO:119, a CDR2 region having has SEQ ID NO:203, and a CDR3 region having SEQ ID NO:287, and/or a CDR1 region having SEQ ID NO:120, a CDR2 region having has SEQ ID NO:204, and a CDR3 region having SEQ ID NO:288, and/or a CDR1 region having SEQ ID NO:121, a CDR2 region having has SEQ ID NO:205, and a CDR3 region having SEQ ID NO:289, and/or a CDR1 region having SEQ ID NO:122, a CDR2 region having has SEQ ID NO:206, and a CDR3 region having SEQ ID NO:290, and/or a CDR1 region having SEQ ID NO:123, a CDR2 region having has SEQ ID NO:207, and a CDR3 region having SEQ ID NO:291, and/or a CDR1 region having SEQ ID NO:124, a CDR2 region having has SEQ ID NO:208, and a CDR3 region having SEQ ID NO:292, and/or a CDR1 region having SEQ ID NO:125, a CDR2 region having has SEQ ID NO:209, and a CDR3 region having SEQ ID NO:293, and/or a CDR1 region having SEQ ID NO:126, a CDR2 region having has SEQ ID NO:210, and a CDR3 region having SEQ ID NO:294, and/or a CDR1 region having SEQ ID NO:127, a CDR2 region having has SEQ ID NO:211, and a CDR3 region having SEQ ID NO:295, and/or a CDR1 region having SEQ ID NO:128, a CDR2 region having has SEQ ID NO:212, and a CDR3 region having SEQ ID NO:296, and/or a CDR1 region having SEQ ID NO:129, a CDR2 region having has SEQ ID NO:213, and a CDR3 region having SEQ ID NO:297, and/or a CDR1 region having SEQ ID NO:130, a CDR2 region having has SEQ ID NO:214, and a CDR3 region having SEQ ID NO:298, and/or a CDR1 region having SEQ ID NO:131, a CDR2 region having has SEQ ID NO:215, and a CDR3 region having SEQ ID NO:299, and/or a CDR1 region having SEQ ID NO:132, a CDR2 region having has SEQ ID NO:216, and a CDR3 region having SEQ ID NO:300, and/or a CDR1 region having SEQ ID NO:133, a CDR2 region having has SEQ ID NO:217, and a CDR3 region having SEQ ID NO:301, and/or a CDR1 region having SEQ ID NO:134, a CDR2 region having has SEQ ID NO:218, and a CDR3 region having SEQ ID NO:302, and/or a CDR1 region having SEQ ID NO:135, a CDR2 region having has SEQ ID NO:219, and a CDR3 region having SEQ ID NO:303, and/or a CDR1 region having SEQ ID NO:136, a CDR2 region having has SEQ ID NO:220, and a CDR3 region having SEQ ID NO:304, and/or a CDR1 region having SEQ ID NO:137, a CDR2 region having has SEQ ID NO:221, and a CDR3 region having SEQ ID NO:305, and/or a CDR1 region having SEQ ID NO:138, a CDR2 region having has SEQ ID NO:222, and a CDR3 region having SEQ ID NO:306, and/or a CDR1 region having SEQ ID NO:139, a CDR2 region having has SEQ ID NO:223, and a CDR3 region having the amino acid sequence NRY, and/or a CDR1 region having SEQ ID NO:140, a CDR2 region having has SEQ ID NO:224, and a CDR3 region having SEQ ID NO:307, and/or a CDR1 region having SEQ ID NO:141, a CDR2 region having has SEQ ID NO:225, and a CDR3 region having SEQ ID NO:308, and/or a CDR1 region having SEQ ID NO:142, a CDR2 region having has SEQ ID NO:226, and a CDR3 region having SEQ ID NO:309, and/or a CDR1 region having SEQ ID NO:143, a CDR2 region having has SEQ ID NO:227, and a CDR3 region having SEQ ID NO:310, and/or a CDR1 region having SEQ ID NO:144, a CDR2 region having has SEQ ID NO:228, and a CDR3 region having SEQ ID NO:311, and/or a CDR1 region having SEQ ID NO:145, a CDR2 region having has SEQ ID NO:229, and a CDR3 region having SEQ ID NO:312, and/or a CDR1 region having SEQ ID NO:146, a CDR2 region having has SEQ ID NO:230, and a CDR3 region having SEQ ID NO:313, and/or a CDR1 region having SEQ ID NO:147, a CDR2 region having has SEQ ID NO:231, and a CDR3 region having SEQ ID NO:314, and/or a CDR1 region having SEQ ID NO:148, a CDR2 region having has SEQ ID NO:232, and a CDR3 region having SEQ ID NO:315, and/or a CDR1 region having SEQ ID NO:149, a CDR2 region having has SEQ ID NO:233, and a CDR3 region having SEQ ID NO:316, and/or a CDR1 region having SEQ ID NO:150, a CDR2 region having has SEQ ID NO:234, and a CDR3 region having SEQ ID NO:317, and/or a CDR1 region having SEQ ID NO:151, a CDR2 region having has SEQ ID NO:235, and a CDR3 region having SEQ ID NO:318, and/or a CDR1 region having SEQ ID NO:152, a CDR2 region having has SEQ ID NO:236, and a CDR3 region having SEQ ID NO:319, and/or a CDR1 region having SEQ ID NO:153, a CDR2 region having has SEQ ID NO:237, and a CDR3 region having SEQ ID NO:320, and/or a CDR1 region having SEQ ID NO:154, a CDR2 region having has SEQ ID NO:238, and a CDR3 region having SEQ ID NO:321, and/or a CDR1 region having SEQ ID NO:155, a CDR2 region having has SEQ ID NO:239, and a CDR3 region having SEQ ID NO:322, and/or a CDR1 region having SEQ ID NO:156, a CDR2 region having has SEQ ID NO:240, and a CDR3 region having SEQ ID NO:323, and/or a CDR1 region having SEQ ID NO:157, a CDR2 region having has SEQ ID NO:241, and a CDR3 region having SEQ ID NO:324, and/or a CDR1 region having SEQ ID NO:158, a CDR2 region having has SEQ ID NO:242, and a CDR3 region having SEQ ID NO:325, and/or a CDR1 region having SEQ ID NO:159, a CDR2 region having has SEQ ID NO:243, and a CDR3 region having SEQ ID NO:326, and/or a CDR1 region having SEQ ID NO:160, a CDR2 region having has SEQ ID NO:244, and a CDR3 region having SEQ ID NO:327, and/or a CDR1 region having SEQ ID NO:161, a CDR2 region having has SEQ ID NO:245, and a CDR3 region having SEQ ID NO:328, and/or a CDR1 region having SEQ ID NO:162, a CDR2 region having has SEQ ID NO:246, and a CDR3 region having SEQ ID NO:329, and/or a CDR1 region having SEQ ID NO:163, a CDR2 region having has SEQ ID NO:247, and a CDR3 region having SEQ ID NO:330, and/or a CDR1 region having SEQ ID NO:164, a CDR2 region having has SEQ ID NO:248, and a CDR3 region having SEQ ID NO:331, and/or a CDR1 region having SEQ ID NO:165, a CDR2 region having has SEQ ID NO:249, and a CDR3 region having SEQ ID NO:332, and/or a CDR1 region having SEQ ID NO:166, a CDR2 region having has SEQ ID NO:250, and a CDR3 region having SEQ ID NO:333, and/or a CDR1 region having SEQ ID NO:167, a CDR2 region having has SEQ ID NO:251, and a CDR3 region having SEQ ID NO:334, and/or a CDR1 region having SEQ ID NO:168, a CDR2 region having has SEQ ID NO:252, and a CDR3 region having SEQ ID NO:335.

In certain embodiments of the transgenic plants or plant tissues or plant cells, methods, or uses, as taught herein, the polynucleotide may comprise a sequence encoding a VHH comprising a CDR1, CDR2 and CDR3 region chosen from the list of comprising:

a CDR1 region having SEQ ID NO:85, a CDR2 region having has SEQ ID NO:169, and a CDR3 region having SEQ ID NO:253, and/or a CDR1 region having SEQ ID NO:86, a CDR2 region having has SEQ ID NO:170, and a CDR3 region having SEQ ID NO:254.

In certain embodiments of the transgenic plants or plant tissues or plant cells, methods, or uses, as taught herein, the polynucleotide may comprise a sequence encoding a VHH comprising a CDR1 region having SEQ ID NO:85, a CDR2 region having has SEQ ID NO:169, and a CDR3 region having SEQ ID NO:253.

In certain embodiments of the transgenic plants or plant tissues or plant cells, methods, or uses, as taught herein, the polynucleotide may comprise a sequence encoding a VHH comprising a CDR1 region having SEQ ID NO:86, a CDR2 region having has SEQ ID NO:170, and a CDR3 region having SEQ ID NO:254.

A further aspect relates to harvestable parts and propagation materials of a transgenic plant or plant tissue or plant cell as defined herein, comprising at least one polynucleotide as defined herein. Accordingly, a further aspect provides harvestable parts and propagation materials of a transgenic plant or plant tissue or plant cell as defined herein, comprising at least one polynucleotide comprising at least one sequence encoding a VHH specifically binding to a sphingolipid of a fungus, preferably to a ceramide of a fungus, preferably to a glycosphingolipid of a fungus, more preferably to a cerebroside of a fungus, even more preferably to a glucocerebroside of a fungus. In certain embodiments, the VHH binds to a sphingolipid of a plant pathogenic fungus, preferably to a ceramide of a plant pathogenic fungus, preferably to a glycosphingolipid of a plant pathogenic fungus, more preferably to a cerebroside of a plant pathogenic fungus, even more preferably to a glucocerebroside of a plant pathogenic fungus.

In certain embodiments, the harvestable parts and propagation materials of a transgenic plant or plant tissue or plant cell are selected from the group consisting of seeds, fruits, grains, bulbs, bolls, tubers, progeny, and hybrids.

A further aspect relates to an extract of a transgenic plant or plant tissue or plant cell as defined herein, comprising at least one polynucleotide as defined herein, the extract comprising VHH. Accordingly, a further aspect provides an extract of a transgenic plant or plant tissue or plant cell as defined herein, comprising at least one VHH specifically binding to a sphingolipid of a fungus, preferably to a ceramide of a fungus, preferably to a glycosphingolipid of a fungus, more preferably to a cerebroside of a fungus, even more preferably to a glucocerebroside of a fungus. In certain embodiments, the VHH binds to a sphingolipid of a plant pathogenic fungus, preferably to a ceramide of a plant pathogenic fungus, preferably to a glycosphingolipid of a plant pathogenic fungus, more preferably to a cerebroside of a plant pathogenic fungus, even more preferably to a glucocerebroside of a plant pathogenic fungus.

A further aspect relates to compositions comprising an extract of a transgenic plant or plant tissue or plant cell as defined herein. Accordingly, a further aspect provides a composition comprising an extract of a transgenic plant or plant tissue or plant cell as defined herein, comprising at least one VHH specifically binding to a sphingolipid of a fungus, preferably to a ceramide of a fungus, preferably to a glycosphingolipid of a fungus, more preferably to a cerebroside of a fungus, even more preferably to a glucocerebroside of a fungus. In certain embodiments, the VHH binds to a sphingolipid of a plant pathogenic fungus, preferably to a ceramide of a plant pathogenic fungus, preferably to a glycosphingolipid of a plant pathogenic fungus, more preferably to a cerebroside of a plant pathogenic fungus, even more preferably to a glucocerebroside of a plant pathogenic fungus.

A further aspect relates to a method for the production of a transgenic plant or plant tissue or plant cell comprising the introduction of at least one polynucleotide as defined herein into the genome of a plant or plant tissue. Hence, a further aspect provides a method for the production of a transgenic plant or plant tissue or plant cell comprising the introduction of at least one polynucleotide comprising at least one sequence encoding a VHH specifically binding to a sphingolipid of a fungus into the genome of a plant or plant tissue. In certain embodiments, this disclosure relates to a method for the production of a transgenic plant or plant tissue or plant cell comprising the introduction of at least one polynucleotide comprising at least one sequence encoding a VHH specifically binding to a ceramide of a fungus into the genome of a plant or plant tissue. In certain embodiments, this disclosure relates to a method for the production of a transgenic plant or plant tissue or plant cell comprising the introduction of at least one polynucleotide comprising at least one sequence encoding a VHH specifically binding to a glycosphingolipid of a fungus into the genome of a plant or plant tissue. In certain embodiments, this disclosure relates to a method for the production of a transgenic plant or plant tissue or plant cell comprising the introduction of at least one polynucleotide comprising at least one sequence encoding a VHH specifically binding to a cerebroside of a fungus into the genome of a plant or plant tissue. In certain embodiments, this disclosure relates to a method for the production of a transgenic plant or plant tissue or plant cell comprising the introduction of at least one polynucleotide comprising at least one sequence encoding a VHH specifically binding to a glucocerebroside of a fungus into the genome of a plant or plant tissue. In certain embodiments, the VHH binds to a sphingolipid of a plant pathogenic fungus, preferably to a ceramide of a plant pathogenic fungus, preferably to a glycosphingolipid of a plant pathogenic fungus, more preferably to a cerebroside of a plant pathogenic fungus, even more preferably to a glucocerebroside of a plant pathogenic fungus.

A further aspect relates to the use of at least one polynucleotide as defined herein, for the production of a transgenic plant or plant tissue. A further aspect thus provides the use of at least one polynucleotide comprising at least one sequence encoding a VHH specifically binding to a sphingolipid of a fungus, for the production of a transgenic plant or plant tissue. In certain embodiments, the disclosure relates to the use of at least one polynucleotide comprising at least one sequence encoding a VHH specifically binding to a ceramide of a fungus, for the production of a transgenic plant or plant tissue. In certain embodiments, the disclosure relates to the use of at least one polynucleotide comprising at least one sequence encoding a VHH specifically binding to a glycosphingolipid of a fungus, for the production of a transgenic plant or plant tissue. In certain embodiments, the disclosure relates to the use of at least one polynucleotide comprising at least one sequence encoding a VHH specifically binding to a cerebroside of a fungus, for the production of a transgenic plant or plant tissue. In certain embodiments, the disclosure relates to the use of at least one polynucleotide comprising at least one sequence encoding a VHH specifically binding to a glucocerebroside of a fungus, for the production of a transgenic plant or plant tissue. In certain embodiments, the VHH binds to a sphingolipid of a plant pathogenic fungus, preferably to a ceramide of a plant pathogenic fungus, preferably to a glycosphingolipid of a plant pathogenic fungus, more preferably to a cerebroside of a plant pathogenic fungus, even more preferably to a glucocerebroside of a plant pathogenic fungus.

The applicants herein have found that a VHH specifically binding to a pathogen (and binding to a plant pathogen), which is produced in at least part of the transgenic plant (e.g., in planta expression of a polynucleotide encoding the VHH specifically binding to a pathogen), has antimicrobial effects per se, in particular, microbiostatic effects, on the plant pathogen. The applicants found that a VHH as taught herein does not act as a "targeting agent" of an antimicrobial substance or composition to the plant pathogen but as an antimicrobial agent per se, in particular, as a microbiostatic agent per se, on the plant pathogen.

Accordingly, a further aspect of this disclosure relates to a method for protecting at least part of a plant or plant tissue or plant cell from an infection with a plant pathogen, for inhibiting the growth of a plant pathogen on at least part of a plant or plant tissue or plant cell, and/or for increasing pathogen resistance of at least part of a plant or plant tissue or plant cell, comprising expressing in at least part of the plant or plant tissue or plant cell at least one polynucleotide encoding a variable domain of a heavy-chain antibody (VHH) specifically binding to a pathogen. In certain embodiments, the VHH may specifically bind to a sphingolipid of a pathogen, preferably to a ceramide of a pathogen, preferably to a glycosphingolipid of a pathogen, more preferably to a cerebroside of a pathogen, even more preferably to a glucocerebroside of a pathogen.

In certain embodiments, this disclosure relates to a method for protecting at least part of a plant or plant tissue or plant cell from an infection with a plant pathogen, for inhibiting the growth of a plant pathogen on at least part of a plant or plant tissue or plant cell, and/or for increasing pathogen resistance of at least part of a plant or plant tissue or plant cell, comprising expressing in at least part of the plant or plant tissue or plant cell at least one polynucleotide encoding a VHH specifically binding to a pathogen, and wherein the VHH binds to a plant pathogen, preferably to a sphingolipid of a plant pathogen, preferably to a ceramide of a plant pathogen, preferably to a glycosphingolipid of a plant pathogen, more preferably to a cerebroside of a plant pathogen, even more preferably to a glucocerebroside of a plant pathogen.

A further aspect of this disclosure relates to a method for protecting at least part of a plant or plant tissue or plant cell from an infection with a plant pathogen, for inhibiting the growth of a plant pathogen on at least part of a plant or plant tissue or plant cell, and/or for increasing pathogen resistance of at least part of a plant or plant tissue or plant cell, comprising treating at least part of a plant or plant tissue or plant cell with an extract of a transgenic plant or plant tissue or plant cell as defined herein, comprising at least one polynucleotide as defined herein, the extract comprising VHH.

A further aspect of this disclosure relates to a method for protecting at least part of a plant or plant tissue or plant cell from an infection with a plant pathogen, for inhibiting the growth of a plant pathogen on at least part of a plant or plant tissue or plant cell, and/or for increasing pathogen resistance of at least part of a plant or plant tissue or plant cell, comprising treating at least part of a plant or plant tissue or plant cell with a composition comprising an extract of a transgenic plant or plant tissue or plant cell as defined herein, comprising at least one polynucleotide as defined herein, the extract comprising VHH.

A further aspect relates to the use of an extract of a transgenic plant or plant tissue or plant cell as defined herein, comprising at least one polynucleotide as defined herein, the extract comprising VHH, for protecting at least part of a plant or plant tissue or plant cell from an infection with a plant pathogen, for inhibiting the growth of a plant pathogen on at least part of a plant or plant tissue or plant cell, and/or for increasing pathogen resistance of at least part of a plant or plant tissue or plant cell.

A further aspect relates to the use of a composition comprising an extract of a transgenic plant or plant tissue or plant cell as defined herein, comprising at least one polynucleotide as defined herein, the extract comprising VHH, for protecting at least part of a plant or plant tissue or plant cell from an infection with a plant pathogen, for inhibiting the growth of a plant pathogen on at least part of a plant or plant tissue or plant cell, and/or for increasing pathogen resistance of at least part of a plant or plant tissue or plant cell.

In certain embodiments of the methods or uses, as taught herein, the VHH may specifically bind to a pathogen, and the VHH may bind to a plant pathogen, preferably to a sphingolipid of a plant pathogen, preferably to a ceramide of a plant pathogen, preferably to a glycosphingolipid of a plant pathogen, more preferably to a cerebroside of a plant pathogen, even more preferably to a glucocerebroside of a plant pathogen.

In certain embodiments of the methods or uses, as taught herein, the VHH may specifically bind to a sphingolipid of a pathogen, and the VHH may bind to a plant pathogen, preferably to a sphingolipid of a plant pathogen, preferably to a ceramide of a plant pathogen, preferably to a glycosphingolipid of a plant pathogen, more preferably to a cerebroside of a plant pathogen, even more preferably to a glucocerebroside of a plant pathogen.

In certain embodiments of the methods or uses, as taught herein, the VHH may specifically bind to a ceramide of a pathogen, and the VHH may bind to a plant pathogen, preferably to a sphingolipid of a plant pathogen, preferably to a ceramide of a plant pathogen, preferably to a glycosphingolipid of a plant pathogen, more preferably to a cerebroside of a plant pathogen, even more preferably to a glucocerebroside of a plant pathogen.

In certain embodiments of the methods or uses, as taught herein, the VHH may specifically bind to a glycosphingolipid of a pathogen, and the VHH may bind to a plant pathogen, preferably to a sphingolipid of a plant pathogen, preferably to a ceramide of a plant pathogen, preferably to a glycosphingolipid of a plant pathogen, more preferably to a cerebroside of a plant pathogen, even more preferably to a glucocerebroside of a plant pathogen.

In certain embodiments of the methods or uses, as taught herein, the VHH may specifically bind to a cerebroside of a pathogen, and the VHH may bind to a plant pathogen, preferably to a sphingolipid of a plant pathogen, preferably to a ceramide of a plant pathogen, preferably to a glycosphingolipid of a plant pathogen, more preferably to a cerebroside of a plant pathogen, even more preferably to a glucocerebroside of a plant pathogen.

In certain embodiments of the methods or uses, as taught herein, the VHH may specifically bind to a glucocerebroside of a pathogen, and the VHH may bind to a plant pathogen, preferably to a sphingolipid of a plant pathogen, preferably to a ceramide of a plant pathogen, preferably to a glycosphingolipid of a plant pathogen, more preferably to a cerebroside of a plant pathogen, even more preferably to a glucocerebroside of a plant pathogen.

In certain embodiments, this disclosure relates to a method for protecting at least part of a plant or plant tissue or plant cell from an infection or other biological interaction with a plant pathogen, comprising expressing in at least part of the plant or plant tissue or plant cell at least one polynucleotide encoding a VHH specifically binding to a pathogen.

In certain embodiments, this disclosure relates to a method for inhibiting the growth of a plant pathogen on at least part of a plant or plant tissue or plant cell, comprising expressing in at least part of the plant or plant tissue or plant cell at least one polynucleotide encoding a VHH specifically binding to a pathogen.

In certain embodiments, this disclosure relates to a method for increasing pathogen resistance of at least part of a plant or plant tissue or plant cell, comprising expressing in at least part of the plant or plant tissue or plant cell at least one polynucleotide encoding a VHH specifically binding to a pathogen. In certain embodiments, this disclosure relates to a method for increasing resistance of at least part of a plant or plant tissue or plant cell against a plant pathogen, comprising expressing in at least part of the plant or plant tissue or plant cell at least one polynucleotide encoding a VHH specifically binding to a pathogen.

In certain embodiments, this disclosure relates to a method as taught herein, for protecting at least part of a plant or plant tissue or plant cell from an infection with a plant pathogenic fungus, for inhibiting the growth of a plant pathogenic fungus on at least part of a plant or plant tissue or plant cell, and/or for increasing resistance of at least part of a plant or plant tissue or plant cell against the plant pathogenic fungus, comprising expressing in at least part of the plant or plant tissue or plant cell at least one polynucleotide as defined herein. Hence, in certain embodiments, this disclosure relates to a method as taught herein, for protecting at least part of a plant or plant tissue or plant cell from an infection with a plant pathogenic fungus, for inhibiting the growth of a plant pathogenic fungus on at least part of a plant or plant tissue or plant cell, and/or for increasing resistance of at least part of a plant or plant tissue or plant cell against the plant pathogenic fungus, comprising expressing in at least part of the plant or plant tissue or plant cell at least one polynucleotide comprising at least one sequence encoding a VHH specifically binding to a sphingolipid of a fungus. In certain embodiments, this disclosure relates to a method as taught herein, for protecting at least part of a plant or plant tissue or plant cell from an infection with a plant pathogenic fungus, for inhibiting the growth of a plant pathogenic fungus on at least part of a plant or plant tissue or plant cell, and/or for increasing resistance of at least part of a plant or plant tissue or plant cell against the plant pathogenic fungus, comprising expressing in at least part of the plant or plant tissue or plant cell at least one polynucleotide comprising at least one sequence encoding a VHH specifically binding to a ceramide of a fungus. In certain embodiments, this disclosure relates to a method as taught herein, for protecting at least part of a plant or plant tissue or plant cell from an infection with a plant pathogenic fungus, for inhibiting the growth of a plant pathogenic fungus on at least part of a plant or plant tissue or plant cell, and/or for increasing resistance of at least part of a plant or plant tissue or plant cell against the plant pathogenic fungus, comprising expressing in at least part of the plant or plant tissue or plant cell at least one polynucleotide comprising at least one sequence encoding a VHH specifically binding to a glycosphingolipid of a fungus. In certain embodiments, this disclosure relates to a method as taught herein, for protecting at least part of a plant or plant tissue or plant cell from an infection with a plant pathogenic fungus, for inhibiting the growth of a plant pathogenic fungus on at least part of a plant or plant tissue or plant cell, and/or for increasing resistance of at least part of a plant or plant tissue or plant cell against the plant pathogenic fungus, comprising expressing in at least part of the plant or plant tissue or plant cell at least one polynucleotide comprising at least one sequence encoding a VHH specifically binding to a cerebroside of a fungus. in certain embodiments, this disclosure relates to a method as taught herein, for protecting at least part of a plant or plant tissue or plant cell from an infection with a plant pathogenic fungus, for inhibiting the growth of a plant pathogenic fungus on at least part of a plant or plant tissue or plant cell, and/or for increasing resistance of at least part of a plant or plant tissue or plant cell against the plant pathogenic fungus, comprising expressing in at least part of the plant or plant tissue or plant cell at least one polynucleotide comprising at least one sequence encoding a VHH specifically binding to a glucocerebroside of a fungus. In certain embodiments, the VHH binds to a sphingolipid of a plant pathogenic fungus, preferably to a ceramide of a plant pathogenic fungus, preferably to a glycosphingolipid of a plant pathogenic fungus, more preferably to a cerebroside of a plant pathogenic fungus, even more preferably to a glucocerebroside of a plant pathogenic fungus.

A further aspect relates to the use of at least one polynucleotide encoding a variable domain of a heavy-chain antibody (VHH) specifically binding to a pathogen, for protecting at least part of a plant or plant tissue or plant cell from an infection with a plant pathogen, for inhibiting the growth of a plant pathogen on at least part of a plant or plant tissue or plant cell, and/or for increasing pathogen resistance of at least part of a plant or plant tissue or plant cell, wherein the polynucleotide is expressed in at least part of the plant or plant tissue. In certain embodiments, the VHH may specifically bind to a sphingolipid of a pathogen, preferably to a ceramide of a pathogen, preferably to a glycosphingolipid of a pathogen, more preferably to a cerebroside of a pathogen, even more preferably to a glucocerebroside of a pathogen.

In certain embodiments, this disclosure relates to the use of at least one polynucleotide encoding a VHH specifically binding to a pathogen, for protecting at least part of a plant or plant tissue or plant cell from an infection with a plant pathogen, for inhibiting the growth of a plant pathogen on at least part of a plant or plant tissue or plant cell, and/or for increasing pathogen resistance of at least part of a plant or plant tissue or plant cell, wherein the polynucleotide is expressed in at least part of the plant or plant tissue or plant cell, and wherein the VHH binds to a plant pathogen, preferably to a sphingolipid of a plant pathogen, preferably to a ceramide of a plant pathogen, preferably to a glycosphingolipid of a plant pathogen, more preferably to a cerebroside of a plant pathogen, even more preferably to a glucocerebroside of a plant pathogen.

In certain embodiments, this disclosure relates to the use of at least one polynucleotide encoding a VHH specifically binding to a pathogen, for protecting at least part of a plant or plant tissue or plant cell from an infection or other biological interaction with a plant pathogen, wherein the polynucleotide is expressed in at least part of the plant or plant tissue.

In certain embodiments, this disclosure relates to the use of at least one polynucleotide encoding a VHH specifically binding to a pathogen, for inhibiting the growth of a plant pathogen on at least part of a plant or plant tissue or plant cell, wherein the polynucleotide is expressed in at least part of the plant or plant tissue.

In certain embodiments, this disclosure relates to the use of at least one polynucleotide encoding a VHH specifically binding to a pathogen, for increasing pathogen resistance of at least part of a plant or plant tissue or plant cell, wherein the polynucleotide is expressed in at least part of the plant or plant tissue. In certain embodiments, this disclosure relates to the use of at least one polynucleotide encoding a VHH specifically binding to a pathogen, for increasing resistance of at least part of a plant or plant tissue or plant cell against a plant pathogen, wherein the polynucleotide is expressed in at least part of the plant or plant tissue.

In certain embodiments, this disclosure relates to the uses as taught herein, for protecting at least part of a plant or plant tissue or plant cell from an infection with a plant pathogenic fungus, for inhibiting the growth of a plant pathogenic fungus on at least part of a plant or plant tissue or plant cell, and/or for increasing pathogen resistance of at least part of a plant or plant tissue or plant cell, wherein the polynucleotide is as defined herein. In certain embodiments, this disclosure relates to the uses as taught herein, for protecting at least part of a plant or plant tissue or plant cell from an infection with a plant pathogenic fungus, for inhibiting the growth of a plant pathogenic fungus on at least part of a plant or plant tissue or plant cell, and/or for increasing pathogen resistance of at least part of a plant or plant tissue or plant cell, wherein the polynucleotide comprises at least one sequence encoding a VHH specifically binding to a sphingolipid of a fungus. In certain embodiments, the polynucleotide may comprise at least one sequence encoding a VHH specifically binding to a ceramide of a fungus. In certain embodiments, the polynucleotide may comprise at least one sequence encoding a VHH specifically binding to a glycosphingolipid of a fungus. In certain embodiments, the polynucleotide may comprise at least one sequence encoding a VHH specifically binding to a cerebroside of a fungus. In certain embodiments, the polynucleotide may comprise at least one sequence encoding a VHH specifically binding to a glucocerebroside of a fungus. In certain embodiments, the VHH binds to a sphingolipid of a plant pathogenic fungus, preferably to a ceramide of a plant pathogenic fungus, preferably to a glycosphingolipid of a plant pathogenic fungus, more preferably to a cerebroside of a plant pathogenic fungus, even more preferably to a glucocerebroside of a plant pathogenic fungus.

The methods and uses embodying the principles of this disclosure advantageously allow protecting a plant or plant tissue or plant cell from an infection or other interaction with a plant pathogen, inhibiting the growth of the plant pathogen on at least part of a plant or plant tissue or plant cell, or increasing pathogen resistance of at least part of a plant or plant tissue or plant cell by the in planta expression of a polynucleotide encoding a VHH specifically binding to a pathogen.

In certain embodiments of the methods or uses as taught herein, a VHH as taught herein may act as an antimicrobial agent. In certain embodiments of the methods or uses as taught herein, a VHH as taught herein may act as a microbiostatic agent.

The applicants herein have found polynucleotides encoding a VHH specifically binding to a sphingolipid of a fungus, preferably to a ceramide of a fungus, more preferably to a glycosphingolipid of a fungus, even more preferably to a cerebroside of a fungus, yet more preferably to a glucocerebroside of a fungus. Accordingly, a further aspect of the disclosure relates to a transgenic plant or plant tissue or plant cell comprising at least one polynucleotide comprising at least one nucleic acid sequence selected from SEQ ID NO:336 and/or SEQ ID NO:337. In certain embodiments of the transgenic plants or plant tissues or plant cells, methods, or uses as taught herein, the polynucleotide may comprise the nucleic acid sequence of SEQ ID NO:336. In certain embodiments of the transgenic plants or plant tissues or plant cells, methods, or uses as taught herein, the polynucleotide may comprise the nucleic acid sequence of SEQ ID NO:337.

The above and further aspects and preferred embodiments of the disclosure are described in the following sections and in the appended claims. The subject-matter of appended claims is hereby specifically incorporated in this specification.

BRIEF DESCRIPTION OF THE DRAWINGS

FIG. 3A demonstrates the binding of the VHHs 54C08, 54C111, 54E05, 54F02, and 56A05. FIG. 3B demonstrates the binding of the VHHs 56A09, 56C09, 56E05, 56F11, 56H07, and 57A06. FIG. 3C demonstrates the binding of the HVVs 57B01, 57B11, 57C07, 57C09, and 57E11.

variable domain of a heavy-chain antibody; His: His6 tag, consists of 6 His repeats (SEQ ID NO:348); KDEL: ER retention signal (SEQ ID NO:349); 2S2: seed storage protein gene signal peptide (SEQ ID NO:350); Fc: Fc from mouse IgG3 (SEQ ID NO:351); linker: 9GS spacer (SEQ ID NO:352); CW: cell wall; PM: plasma membrane; ER: endoplasmatic reticulum; TGN: trans-Golgi network; CCV: Clathrin-coated vesicle.

Figure 8:
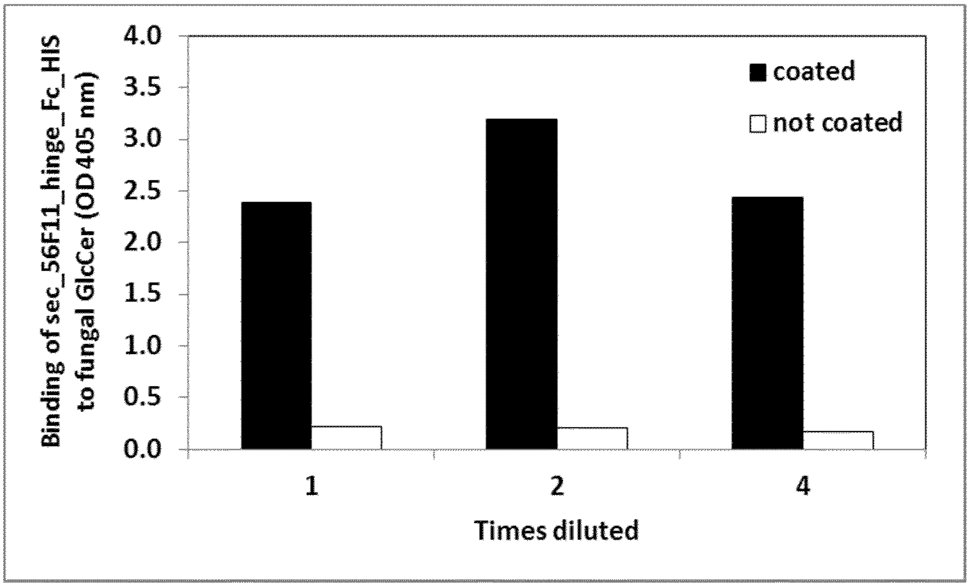

FIG. 8: Binding of sec_56F11_hinge_Fc_HIS to coated fungal GlcCer. Specific binding to coated wells, but not to uncoated wells, was observed for sec_56F11_hinge_Fc_HIS in leaf extract of overexpressing plants.

Figure 9A:
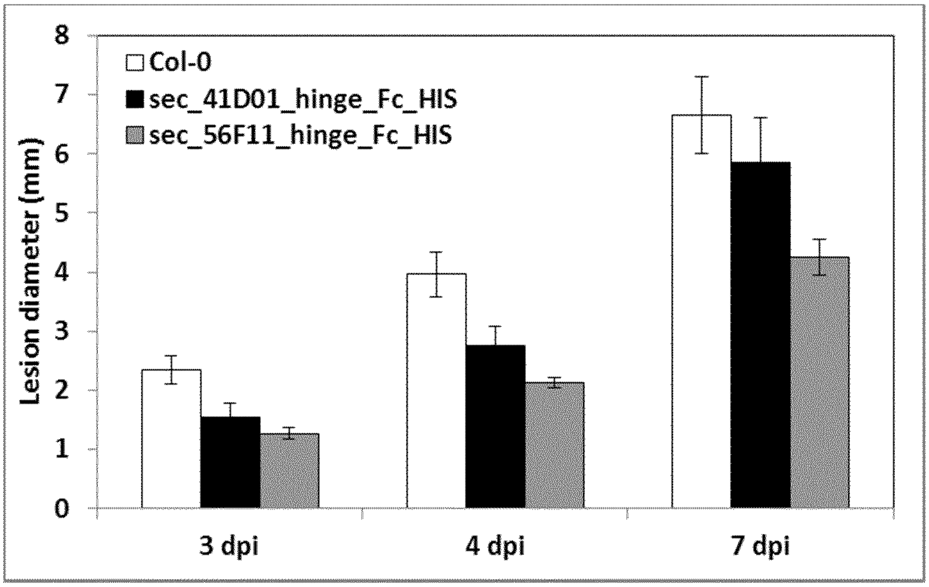
Figure 9B:
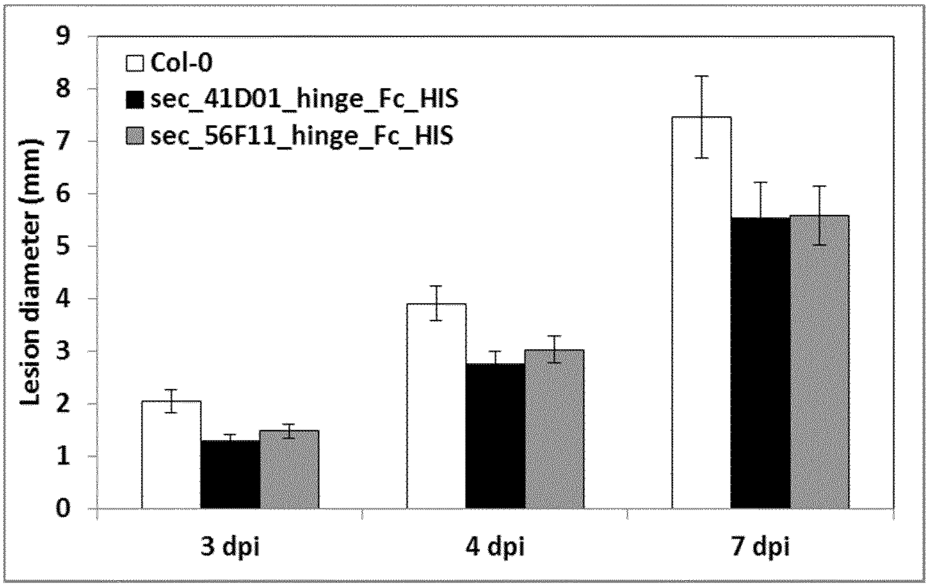

FIGS. 9A and 9B: FIG. 9A demonstrates increased resistance against *Botrytis cinerea* of plants expressing VHH specifically binding fungal GlcCer. Twenty plants per line and doncition, divided over 5 boxes, were analyzed. Smaller lesions were observed on the leaves of VHH-overexpressing plants inoculated with *B. cinerea* spores. FIG. 9B is a repeat of the experiment shown in FIG. 9A with 24 plants per line and doncition, divided over 6 boxes.

DETAILED DESCRIPTION

This disclosure will be described with respect to particular embodiments but the disclosure is not limited thereto.

Statements (features) and embodiments of the transgenic plants or plant tissues or plant cells, methods, or uses, as disclosed herein are set forth herein below. Each of the statements and embodiments of the disclosure so defined may be combined with any other statement and/or embodiment unless clearly indicated to the contrary. In particular, any feature or features or statements indicated as being preferred or advantageous may be combined with any other feature or features or statement indicated as being preferred or advantageous. Hereto, this disclosure is, in particular, captured by any one or any combination of one or more of the below numbered aspects and embodiments 1 to 91, with any other statement and/or embodiments.

Numbered statements as disclosed in the present application are:

1. A transgenic plant or plant tissue or plant cell comprising at least one polynucleotide comprising at least one sequence encoding a variable domain of a heavy-chain antibody (VHH) specifically binding to a sphingolipid of a fungus.
2. The transgenic plant or plant tissue or plant cell according to statement 1, wherein the sphingolipid is a ceramide.
3. The transgenic plant or plant tissue or plant cell according to statement 1 or 2, wherein the sphingolipid is a glycosphingolipid.
4. The transgenic plant or plant tissue or plant cell according to any one of statements 1 to 3, wherein the sphingolipid is a cerebroside.
5. The transgenic plant or plant tissue or plant cell according to any one of statements 1 to 4, wherein the sphingolipid comprises a C19 sphingoid base with a C-9 methyl group, and two double bonds (Δ4, Δ8).
6. The transgenic plant or plant tissue or plant cell according to any one of statements 1 to 5, wherein the sphingolipid has, comprises, consists of, or is represented by the following structure:

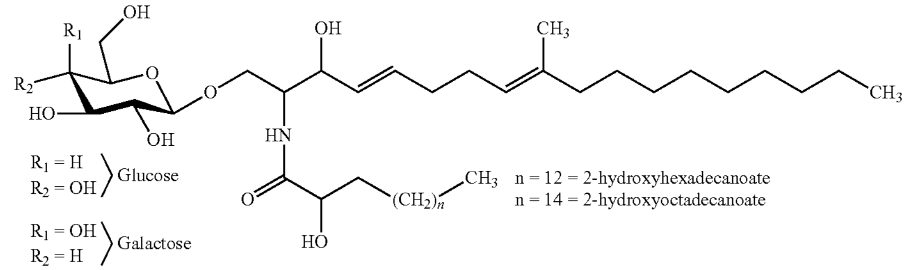

7. The transgenic plant or plant tissue or plant cell according to any one of statements 1 to 6, wherein the sphingolipid has, comprises, consists of, or is represented by any of the following structures:

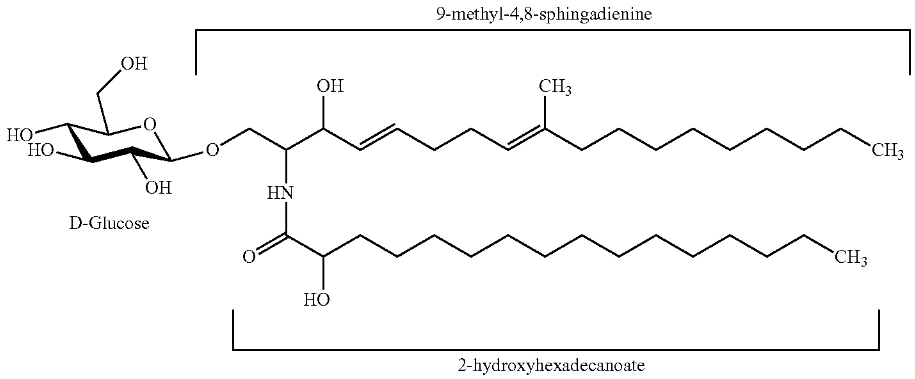

-continued
9-methyl-4,8-sphingadienine
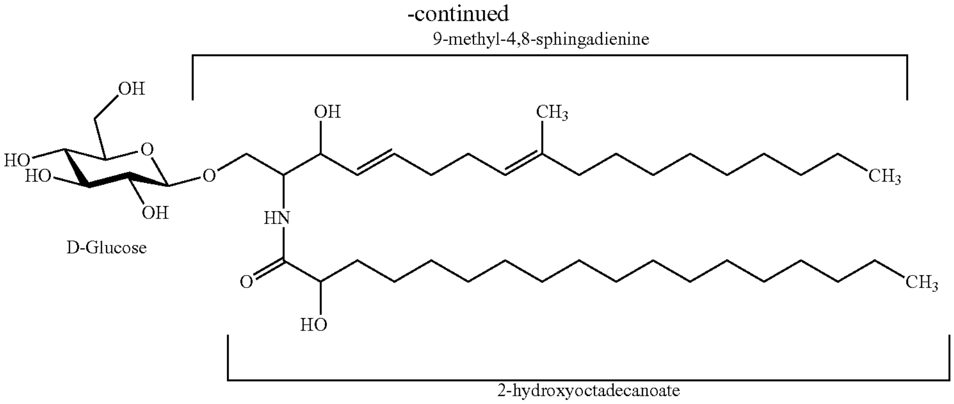
D-Glucose
2-hydroxyoctadecanoate
9-methyl-4,8-sphingadienine
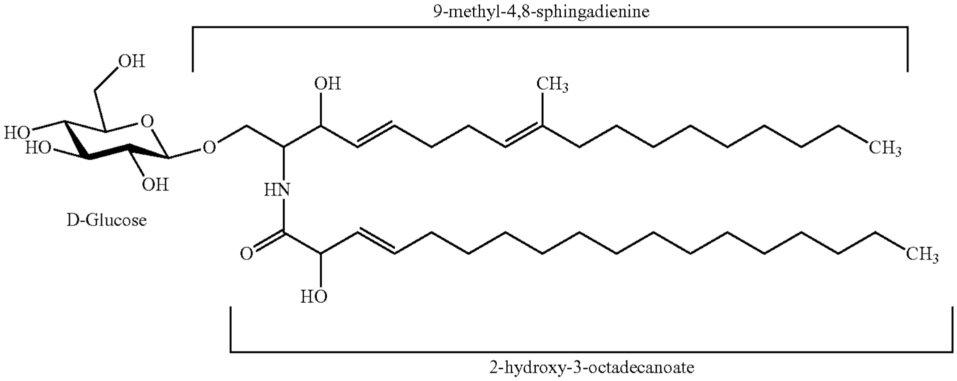
D-Glucose
2-hydroxy-3-octadecanoate
9-methyl-4,8-sphingadienine
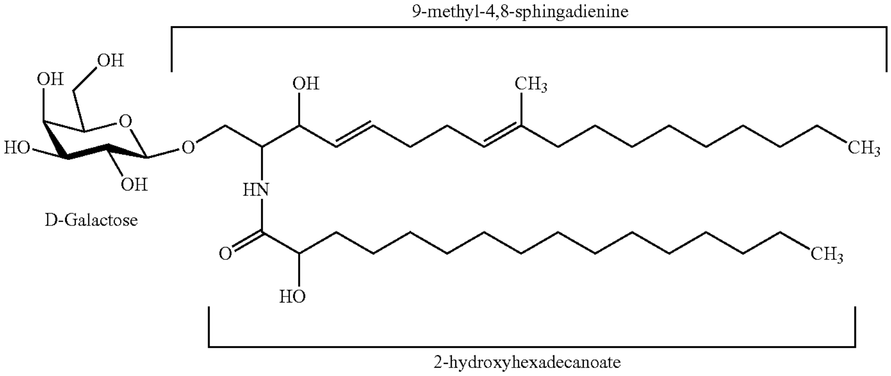
D-Galactose
2-hydroxyhexadecanoate
9-methyl-4,8-sphingadienine
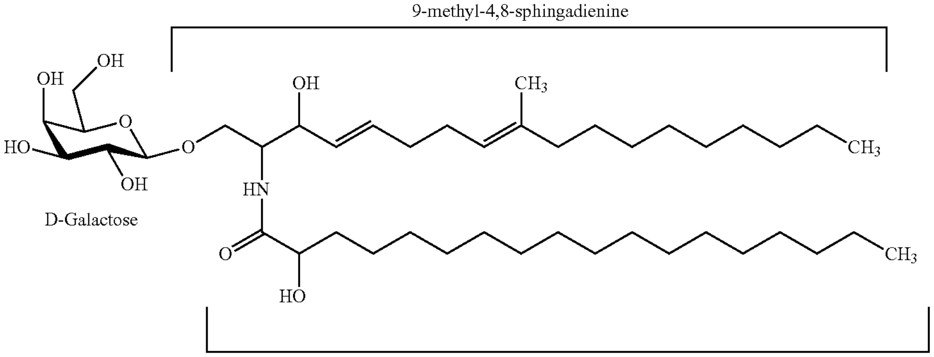
D-Galactose
2-hydroxyoctadecanoate -continued 9-methyl-4,8-sphingadienine

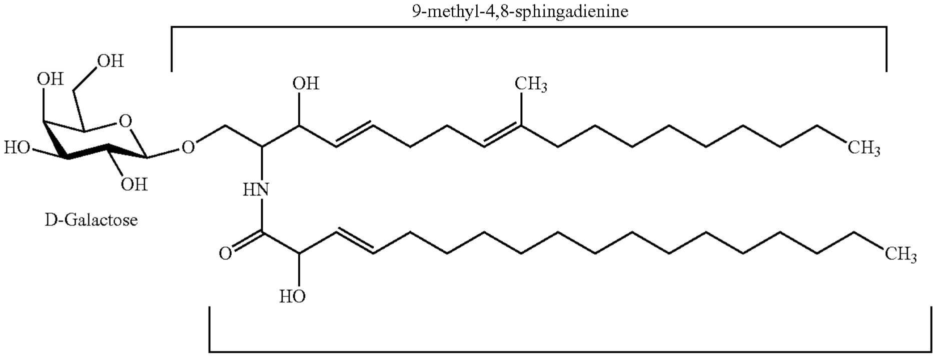

D-Galactose 2-hydroxy-3-octadecanoate

8. The transgenic plant or plant tissue or plant cell according to any one of statements 1 to 7, wherein the sphingolipid is a glucocerebroside.
9. The transgenic plant or plant tissue or plant cell according to any one of statements 1 to 8, wherein the sphingolipid has, comprises, consists of, or is represented by the following structure:

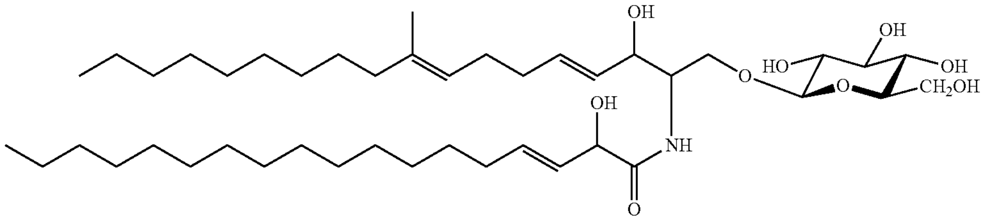

or N-2'-hydroxyhexadecanoyl-1-ß-D-glucopyranosyl-9-methyl-4,8-sphingadienine.

10. The transgenic plant or plant tissue or plant cell according to any one of statements 1 to 9, wherein the expression of the polynucleotide in at least part of the transgenic plant or plant tissue or plant cell (i) protects at least part of the transgenic plant or plant tissue or plant cell from an infection with a plant pathogenic fungus, (ii) inhibits the growth of a plant pathogenic fungus on at least part of the transgenic plant or plant tissue or plant cell, and/or (iii) increases the resistance of at least part of the transgenic plant or plant tissue or plant cell against a plant pathogenic fungus.
11. The transgenic plant or plant tissue or plant cell according to any one of statements 1 to 10, wherein the expression of the polynucleotide in at least part of the transgenic plant or plant tissue or plant cell protects at least part of the transgenic plant or plant tissue or plant cell from an infection with a plant pathogenic fungus.
12. The transgenic plant or plant tissue or plant cell according to any one of statements 1 to 11, wherein the expression of the polynucleotide in at least part of the transgenic plant or plant tissue or plant cell protects at least part of the transgenic plant or plant tissue or plant cell from an infection or other biological interaction with a plant pathogenic fungus.
13. The transgenic plant or plant tissue or plant cell according to any one of statements 1 to 12, wherein the expression of the polynucleotide in at least part of the transgenic plant or plant tissue or plant cell inhibits the growth of a plant pathogenic fungus on at least part of the transgenic plant or plant tissue.
14. The transgenic plant or plant tissue or plant cell according to any one of statements 1 to 13, wherein the expression of the polynucleotide in at least part of the transgenic plant or plant tissue or plant cell increases the resistance of at least part of the transgenic plant or plant tissue or plant cell against a plant pathogenic fungus.
15. The transgenic plant or plant tissue or plant cell according to any one of statements 1 to 14, wherein the expression of the polynucleotide in at least part of the transgenic plant or plant tissue or plant cell (i) protects at least part of the transgenic plant or plant tissue or plant cell from an infection with a plant pathogenic fungus, (ii) inhibits the growth of a plant pathogenic fungus on at least part of the transgenic plant or plant tissue or plant cell, and (iii) increases the resistance of at least part of the transgenic plant or plant tissue or plant cell against a plant pathogenic fungus.
16. The transgenic plant or plant tissue or plant cell according to any one of statements 1 to 15, wherein the polynucleotide comprises a promoter suitable for expression in plants, a plant tissue or plant cell specific promoter, or an inducible promoter.
17. The transgenic plant or plant tissue or plant cell according to any one of statements 1 to 16, wherein the polynucleotide comprises a promoter suitable for expression in plants such as a the 35S Cauliflower Mosaic Virus (CaMV) promoter.
18. The transgenic plant or plant tissue or plant cell according to any one of statements 1 to 17, wherein the polynucleotide comprises at least one sequence encoding a targeting signal for secretion, for location to the cytoplasm, or for location to cellular compartments or organelles, such as the endoplasmatic reticulum (ER) lumen, the apoplast, the vacuole, or intra- and/or exterior membranes.

19. The transgenic plant or plant tissue or plant cell according to any one of statements 1 to 18, wherein the polynucleotide comprises at least one sequence encoding a tag, preferably a His6, c-myc, FLAG, C-tag, 3×FLAG, His5, HA, T7, strep, HSV, and/or an E-tag.
20. The transgenic plant or plant tissue or plant cell according to any one of statements 1 to 19, wherein the polynucleotide encodes the VHH as such, as a combination with one or more identical or different VHHs, or as a combination with one or more identical or different VHHs with a fragment crystallizable region (Fc region); optionally with a spacer.
21. The transgenic plant or plant tissue or plant cell according to any one of statements 1 to 20, wherein the polynucleotide encodes the VHH as such, optionally with a spacer.
22. The transgenic plant or plant tissue or plant cell according to any one of statements 1 to 21, wherein the polynucleotide encodes the VHH as a combination with one or more identical or different VHHs, optionally with a spacer.
23. The transgenic plant or plant tissue or plant cell according to any one of statements 1 to 22, wherein the polynucleotide encodes the VHH as a combination with one or more identical or different VHHs with a fragment crystallizable region (Fc region), optionally with a spacer.
24. The transgenic plant or plant tissue or plant cell according to any one of statements 1 to 23, wherein the plant is a plant selected from the group consisting of corn, rice, wheat, barley, sorghum, millet oats, rye, triticale or other cereals, soybean, alfalfa or other leguminous crops, sugar beet, fodder beet, papaya, banana and plantains or other fruits, grapevines, nuts, oilseed rape, sunflower or other oil crops, squash cucumber, melons or other cucurbits, cotton or other fiber plants, sugarcane, palm, jatropha or other fuel crops, cabbages, tomato, pepper or other vegetables, ornamentals, shrubs, poplar, eucalyptus or other trees, evergreens, grasses, coffee plants, tea plants, tobacco plants, hop plants, rubber plants, and latex plants.
25. The transgenic plant or plant tissue or plant cell according to any one of statements 1 to 24, wherein the plant is selected from the group consisting of banana, barley oat rye, canola, corn, cotton, potato, rice, soybean, tobacco, and wheat, preferably wheat triticale.
26. The transgenic plant or plant tissue or plant cell according to any one of statements 1 to 25, wherein the plant is selected from the group consisting of canola, corn, rice, soybean, and wheat.
27. The transgenic plant or plant tissue or plant cell according to any one of statements 1 to 26, wherein the plant is selected from the group consisting of rice, soybean, and wheat.
28. The transgenic plant or plant tissue or plant cell according to any one of statements 1 to 27, wherein the polynucleotide comprises a sequence encoding a VHH comprising any one or more of SEQ ID NOS:1 to 84.
29. The transgenic plant or plant tissue or plant cell according to any one of statements 1 to 28, wherein the polynucleotide comprises a sequence encoding a VHH comprising SEQ ID NO:1, SEQ ID NO:2, and/or SEQ ID NO:70.
30. The transgenic plant or plant tissue or plant cell according to any one of statements 1 to 29, wherein the polynucleotide comprises a sequence encoding a VHH comprising SEQ ID NOS:1 and/or 2.
31. The transgenic plant or plant tissue or plant cell according to any one of statements 1 to 30, wherein the polynucleotide comprises a sequence encoding a VHH comprising SEQ ID NO:1.
32. The transgenic plant or plant tissue or plant cell according to any one of statements 1 to 31, wherein the polynucleotide comprises a sequence encoding a VHH comprising SEQ ID NO:2.
33. The transgenic plant or plant tissue or plant cell according to any one of statements 1 to 32, wherein the polynucleotide comprises a sequence encoding a VHH comprising SEQ ID NO:70.
34. The transgenic plant or plant tissue or plant cell according to any one of statements 1 to 33, wherein the polynucleotide comprises a sequence encoding a VHH comprising: a CDR1, CDR2, and CDR3 region, wherein (i) the CDR1 region is selected from the group of SEQ ID NOS:85-168, and/or (ii) the CDR2 region is selected from the group of SEQ ID NOS:169-252, and/or (iii) the CDR3 region is selected from the group of SEQ ID NOS:253-335, or the CDR3 region has the amino acid sequence NRY.
35. The transgenic plant or plant tissue or plant cell according to any one of statements 1 to 34, wherein the polynucleotide comprises a sequence encoding a VHH comprising a CDR1, CDR2 and CDR3 region chosen from the list of comprising:
   - a CDR1 region having SEQ ID NO:85, a CDR2 region having has SEQ ID NO:169, and a CDR3 region having SEQ ID NO:253, and/or
   - a CDR1 region having SEQ ID NO:86, a CDR2 region having has SEQ ID NO:170, and a CDR3 region having SEQ ID NO:254, and/or
   - a CDR1 region having SEQ ID NO:87, a CDR2 region having has SEQ ID NO:171, and a CDR3 region having SEQ ID NO:255, and/or
   - a CDR1 region having SEQ ID NO:88, a CDR2 region having has SEQ ID NO:172, and a CDR3 region having SEQ ID NO:256, and/or
   - a CDR1 region having SEQ ID NO:89, a CDR2 region having has SEQ ID NO:173, and a CDR3 region having SEQ ID NO:257, and/or
   - a CDR1 region having SEQ ID NO:90, a CDR2 region having has SEQ ID NO:174, and a CDR3 region having SEQ ID NO:258, and/or
   - a CDR1 region having SEQ ID NO:91, a CDR2 region having has SEQ ID NO:175, and a CDR3 region having SEQ ID NO:259, and/or
   - a CDR1 region having SEQ ID NO:92, a CDR2 region having has SEQ ID NO:176, and a CDR3 region having SEQ ID NO:260, and/or
   - a CDR1 region having SEQ ID NO:93, a CDR2 region having has SEQ ID NO:177, and a CDR3 region having SEQ ID NO:261, and/or
   - a CDR1 region having SEQ ID NO:94, a CDR2 region having has SEQ ID NO:178, and a CDR3 region having SEQ ID NO:262, and/or
   - a CDR1 region having SEQ ID NO:95, a CDR2 region having has SEQ ID NO:179, and a CDR3 region having SEQ ID NO:263, and/or
   - a CDR1 region having SEQ ID NO:96, a CDR2 region having has SEQ ID NO:180, and a CDR3 region having SEQ ID NO:264, and/or a CDR1 region having SEQ ID NO:97, a CDR2 region having has SEQ ID NO:181, and a CDR3 region having SEQ ID NO:265, and/or a CDR1 region having SEQ ID NO:98, a CDR2 region having has SEQ ID NO:182, and a CDR3 region having SEQ ID NO:266, and/or a CDR1 region having SEQ ID NO:99, a CDR2 region having has SEQ ID NO:183, and a CDR3 region having SEQ ID NO:267, and/or a CDR1 region having SEQ ID NO:100, a CDR2 region having has SEQ ID NO:184, and a CDR3 region having SEQ ID NO:268, and/or a CDR1 region having SEQ ID NO:101, a CDR2 region having has SEQ ID NO:185, and a CDR3 region having SEQ ID NO:269, and/or a CDR1 region having SEQ ID NO:102, a CDR2 region having has SEQ ID NO:186, and a CDR3 region having SEQ ID NO:270, and/or a CDR1 region having SEQ ID NO:103, a CDR2 region having has SEQ ID NO:187, and a CDR3 region having SEQ ID NO:271, and/or a CDR1 region having SEQ ID NO:104, a CDR2 region having has SEQ ID NO:188, and a CDR3 region having SEQ ID NO:272, and/or a CDR1 region having SEQ ID NO:105, a CDR2 region having has SEQ ID NO:189, and a CDR3 region having SEQ ID NO:273, and/or a CDR1 region having SEQ ID NO:106, a CDR2 region having has SEQ ID NO:190, and a CDR3 region having SEQ ID NO:274, and/or a CDR1 region having SEQ ID NO:107, a CDR2 region having has SEQ ID NO:191, and a CDR3 region having SEQ ID NO:275, and/or a CDR1 region having SEQ ID NO:108, a CDR2 region having has SEQ ID NO:192, and a CDR3 region having SEQ ID NO:276, and/or a CDR1 region having SEQ ID NO:109, a CDR2 region having has SEQ ID NO:193, and a CDR3 region having SEQ ID NO:277, and/or a CDR1 region having SEQ ID NO:110, a CDR2 region having has SEQ ID NO:194, and a CDR3 region having SEQ ID NO:278, and/or a CDR1 region having SEQ ID NO:111, a CDR2 region having has SEQ ID NO:195, and a CDR3 region having SEQ ID NO:279, and/or a CDR1 region having SEQ ID NO:112, a CDR2 region having has SEQ ID NO:196, and a CDR3 region having SEQ ID NO:280, and/or a CDR1 region having SEQ ID NO:113, a CDR2 region having has SEQ ID NO:197, and a CDR3 region having SEQ ID NO:281, and/or a CDR1 region having SEQ ID NO:114, a CDR2 region having has SEQ ID NO:198, and a CDR3 region having SEQ ID NO:282, and/or a CDR1 region having SEQ ID NO:115, a CDR2 region having has SEQ ID NO:199, and a CDR3 region having SEQ ID NO:283, and/or a CDR1 region having SEQ ID NO:116, a CDR2 region having has SEQ ID NO:200, and a CDR3 region having SEQ ID NO:284, and/or a CDR1 region having SEQ ID NO:117, a CDR2 region having has SEQ ID NO:201, and a CDR3 region having SEQ ID NO:285, and/or a CDR1 region having SEQ ID NO:118, a CDR2 region having has SEQ ID NO:202, and a CDR3 region having SEQ ID NO:286, and/or a CDR1 region having SEQ ID NO:119, a CDR2 region having has SEQ ID NO:203, and a CDR3 region having SEQ ID NO:287, and/or a CDR1 region having SEQ ID NO:120, a CDR2 region having has SEQ ID NO:204, and a CDR3 region having SEQ ID NO:288, and/or a CDR1 region having SEQ ID NO:121, a CDR2 region having has SEQ ID NO:205, and a CDR3 region having SEQ ID NO:289, and/or a CDR1 region having SEQ ID NO:122, a CDR2 region having has SEQ ID NO:206, and a CDR3 region having SEQ ID NO:290, and/or a CDR1 region having SEQ ID NO:123, a CDR2 region having has SEQ ID NO:207, and a CDR3 region having SEQ ID NO:291, and/or a CDR1 region having SEQ ID NO:124, a CDR2 region having has SEQ ID NO:208, and a CDR3 region having SEQ ID NO:292, and/or a CDR1 region having SEQ ID NO:125, a CDR2 region having has SEQ ID NO:209, and a CDR3 region having SEQ ID NO:293, and/or a CDR1 region having SEQ ID NO:126, a CDR2 region having has SEQ ID NO:210, and a CDR3 region having SEQ ID NO:294, and/or a CDR1 region having SEQ ID NO:127, a CDR2 region having has SEQ ID NO:211, and a CDR3 region having SEQ ID NO:295, and/or a CDR1 region having SEQ ID NO:128, a CDR2 region having has SEQ ID NO:212, and a CDR3 region having SEQ ID NO:296, and/or a CDR1 region having SEQ ID NO:129, a CDR2 region having has SEQ ID NO:213, and a CDR3 region having SEQ ID NO:297, and/or a CDR1 region having SEQ ID NO:130, a CDR2 region having has SEQ ID NO:214, and a CDR3 region having SEQ ID NO:298, and/or a CDR1 region having SEQ ID NO:131, a CDR2 region having has SEQ ID NO:215, and a CDR3 region having SEQ ID NO:299, and/or a CDR1 region having SEQ ID NO:132, a CDR2 region having has SEQ ID NO:216, and a CDR3 region having SEQ ID NO:300, and/or a CDR1 region having SEQ ID NO:133, a CDR2 region having has SEQ ID NO:217, and a CDR3 region having SEQ ID NO:301, and/or a CDR1 region having SEQ ID NO:134, a CDR2 region having has SEQ ID NO:218, and a CDR3 region having SEQ ID NO:302, and/or a CDR1 region having SEQ ID NO:135, a CDR2 region having has SEQ ID NO:219, and a CDR3 region having SEQ ID NO:303, and/or a CDR1 region having SEQ ID NO:136, a CDR2 region having has SEQ ID NO:220, and a CDR3 region having SEQ ID NO:304, and/or a CDR1 region having SEQ ID NO:137, a CDR2 region having has SEQ ID NO:221, and a CDR3 region having SEQ ID NO:305, and/or a CDR1 region having SEQ ID NO:138, a CDR2 region having has SEQ ID NO:222, and a CDR3 region having SEQ ID NO:306, and/or a CDR1 region having SEQ ID NO:139, a CDR2 region having has SEQ ID NO:223, and a CDR3 region having the amino acid sequence NRY, and/or a CDR1 region having SEQ ID NO:140, a CDR2 region having has SEQ ID NO:224, and a CDR3 region having SEQ ID NO:307, and/or a CDR1 region having SEQ ID NO:141, a CDR2 region having has SEQ ID NO:225, and a CDR3 region having SEQ ID NO:308, and/or
a CDR1 region having SEQ ID NO:142, a CDR2 region having has SEQ ID NO:226, and a CDR3 region having SEQ ID NO:309, and/or
a CDR1 region having SEQ ID NO:143, a CDR2 region having has SEQ ID NO:227, and a CDR3 region having SEQ ID NO:310, and/or
a CDR1 region having SEQ ID NO:144, a CDR2 region having has SEQ ID NO:228, and a CDR3 region having SEQ ID NO:311, and/or
a CDR1 region having SEQ ID NO:145, a CDR2 region having has SEQ ID NO:229, and a CDR3 region having SEQ ID NO:312, and/or
a CDR1 region having SEQ ID NO:146, a CDR2 region having has SEQ ID NO:230, and a CDR3 region having SEQ ID NO:313, and/or
a CDR1 region having SEQ ID NO:147, a CDR2 region having has SEQ ID NO:231, and a CDR3 region having SEQ ID NO:314, and/or
a CDR1 region having SEQ ID NO:148, a CDR2 region having has SEQ ID NO:232, and a CDR3 region having SEQ ID NO:315, and/or
a CDR1 region having SEQ ID NO:149, a CDR2 region having has SEQ ID NO:233, and a CDR3 region having SEQ ID NO:316, and/or
a CDR1 region having SEQ ID NO:150, a CDR2 region having has SEQ ID NO:234, and a CDR3 region having SEQ ID NO:317, and/or
a CDR1 region having SEQ ID NO:151, a CDR2 region having has SEQ ID NO:235, and a CDR3 region having SEQ ID NO:318, and/or
a CDR1 region having SEQ ID NO:152, a CDR2 region having has SEQ ID NO:236, and a CDR3 region having SEQ ID NO:319, and/or
a CDR1 region having SEQ ID NO:153, a CDR2 region having has SEQ ID NO:237, and a CDR3 region having SEQ ID NO:320, and/or
a CDR1 region having SEQ ID NO:154, a CDR2 region having has SEQ ID NO:238, and a CDR3 region having SEQ ID NO:321, and/or
a CDR1 region having SEQ ID NO:155, a CDR2 region having has SEQ ID NO:239, and a CDR3 region having SEQ ID NO:322, and/or
a CDR1 region having SEQ ID NO:156, a CDR2 region having has SEQ ID NO:240, and a CDR3 region having SEQ ID NO:323, and/or
a CDR1 region having SEQ ID NO:157, a CDR2 region having has SEQ ID NO:241, and a CDR3 region having SEQ ID NO:324, and/or
a CDR1 region having SEQ ID NO:158, a CDR2 region having has SEQ ID NO:242, and a CDR3 region having SEQ ID NO:325, and/or
a CDR1 region having SEQ ID NO:159, a CDR2 region having has SEQ ID NO:243, and a CDR3 region having SEQ ID NO:326, and/or
a CDR1 region having SEQ ID NO:160, a CDR2 region having has SEQ ID NO:244, and a CDR3 region having SEQ ID NO:327, and/or
a CDR1 region having SEQ ID NO:161, a CDR2 region having has SEQ ID NO:245, and a CDR3 region having SEQ ID NO:328, and/or
a CDR1 region having SEQ ID NO:162, a CDR2 region having has SEQ ID NO:246, and a CDR3 region having SEQ ID NO:329, and/or
a CDR1 region having SEQ ID NO:163, a CDR2 region having has SEQ ID NO:247, and a CDR3 region having SEQ ID NO:330, and/or
a CDR1 region having SEQ ID NO:164, a CDR2 region having has SEQ ID NO:248, and a CDR3 region having SEQ ID NO:331, and/or
a CDR1 region having SEQ ID NO:165, a CDR2 region having has SEQ ID NO:249, and a CDR3 region having SEQ ID NO:332, and/or
a CDR1 region having SEQ ID NO:166, a CDR2 region having has SEQ ID NO:250, and a CDR3 region having SEQ ID NO:333, and/or
a CDR1 region having SEQ ID NO:167, a CDR2 region having has SEQ ID NO:251, and a CDR3 region having SEQ ID NO:334, and/or
a CDR1 region having SEQ ID NO:168, a CDR2 region having has SEQ ID NO:252, and a CDR3 region having SEQ ID NO:335.

36. The transgenic plant or plant tissue or plant cell according to any one of statements 1 to 35, wherein the polynucleotide comprises a sequence encoding a VHH comprising a CDR1 region having SEQ ID NO:85, a CDR2 region having has SEQ ID NO:169, and a CDR3 region having SEQ ID NO:253.
37. The transgenic plant or plant tissue or plant cell according to any one of statements 1 to 35, wherein the polynucleotide comprises a sequence encoding a VHH comprising a CDR1 region having SEQ ID NO:86, a CDR2 region having has SEQ ID NO:170, and a CDR3 region having SEQ ID NO:254.
38. Harvestable parts and propagation materials of a transgenic plant or plant tissue or plant cell according to any one of statements 1 to 37, comprising at least one polynucleotide as defined in any one of statements 1 to 37.
39. The harvestable parts and propagation materials according to statement 38, wherein the harvestable parts and propagation materials of a transgenic plant or plant tissue or plant cell are selected from the group consisting of seeds, fruits, grains, bulbs, bolls, tubers, progeny, and hybrids.
40. A method for the production of a transgenic plant or plant tissue or plant cell comprising the introduction of at least one polynucleotide as defined in any one of statements 1 to 37 into the genome of a plant or plant tissue.
41. The use of at least one polynucleotide as defined in any one of statements 1 to 37, for the production of a transgenic plant or plant tissue.
42. A method for protecting at least part of a plant or plant tissue or plant cell from an infection with a plant pathogen, for inhibiting the growth of a plant pathogen on at least part of a plant or plant tissue or plant cell, and/or for increasing pathogen resistance of at least part of a plant or plant tissue or plant cell, comprising expressing in at least part of the plant or plant tissue or plant cell at least one polynucleotide encoding a variable domain of a heavy-chain antibody (VHH) specifically binding to a pathogen.
43. The method according to statement 42, for protecting at least part of a plant or plant tissue or plant cell from an infection with a plant pathogenic fungus, for inhibiting the growth of a plant pathogenic fungus on at least part of a plant or plant tissue or plant cell, and/or for increasing resistance of at least part of a plant or plant tissue or plant cell against the plant pathogenic fungus, comprising expressing in at least part of the plant or plant tissue or plant cell at least one polynucleotide as defined any one of statements 1 to 37.

44. The method according to statement 42 or 43, wherein the VHH specifically binds to a sphingolipid of a pathogen.
45. The method according to any one of statements 42 to 44, wherein the VHH specifically binds to a ceramide of a pathogen.
46. The method according to any one of statements 44 to 45, wherein the VHH specifically binds to a glycosphingolipid of a pathogen.
47. The method according to any one of statements 44 to 46, wherein the VHH specifically binds to a cerebroside of a pathogen.
48. The method according to any one of statements 44 to 47, wherein the VHH specifically binds to a glucocerebroside of a pathogen.
49. The method according to any one of statements 44 to 48, wherein the VHH binds to a plant pathogen.
50. The method according to any one of statements 44 to 49, wherein the VHH binds to a sphingolipid of a plant pathogen.
51. The method according to any one of statements 44 to 50, wherein the VHH binds to a ceramide of a plant pathogen.
52. The method according to any one of statements 44 to 51, wherein the VHH binds to a glycosphingolipid of a plant pathogen.
53. The method according to any one of statements 44 to 52, wherein the VHH binds to a cerebroside of a plant pathogen.
54. The method according to any one of statements 44 to 53, wherein the VHH binds to a glucocerebroside of a plant pathogenic fungus.
55. The method according to statements 44 to 54, wherein the VHH specifically binds to a fungus.
56. The method according to statements 44 to 55, wherein the VHH specifically binds to a sphingolipid of a fungus.
57. The method according to any one of statements 44 to 56, wherein the VHH specifically binds to a ceramide of a fungus.
58. The method according to any one of statements 44 to 57, wherein the VHH specifically binds to a glycosphingolipid of a fungus.
59. The method according to any one of statements 44 to 58, wherein the VHH specifically binds to a cerebroside of a fungus.
60. The method according to any one of statements 44 to 59, wherein the VHH specifically binds to a glucocerebroside of a fungus.
61. The method according to any one of statements 44 to 60, wherein the VHH binds to a plant pathogenic fungus.
62. The method according to any one of statements 44 to 61, wherein the VHH binds to a sphingolipid of a plant pathogenic fungus.
63. The method according to any one of statements 44 to 62, wherein the VHH binds to a ceramide of a plant pathogenic fungus.
64. The method according to any one of statements 44 to 63, wherein the VHH binds to a glycosphingolipid of a plant pathogenic fungus.
65. The method according to any one of statements 44 to 64, wherein the VHH binds to a cerebroside of a plant pathogenic fungus.
66. The method according to any one of statements 44 to 65, wherein the VHH binds to a glucocerebroside of a plant pathogenic fungus.
67. Use of at least one polynucleotide encoding a variable domain of a heavy-chain antibody (VHH) specifically binding to a pathogen, for protecting at least part of a plant or plant tissue or plant cell from an infection with a plant pathogen, for inhibiting the growth of a plant pathogen on at least part of a plant or plant tissue or plant cell, and/or for increasing pathogen resistance of at least part of a plant or plant tissue or plant cell, wherein the polynucleotide is expressed in at least part of the plant or plant tissue.
68. The use according to statement 67, for protecting at least part of a plant or plant tissue or plant cell from an infection with a plant pathogenic fungus, for inhibiting the growth of a plant pathogenic fungus on at least part of a plant or plant tissue or plant cell, and/or for increasing pathogen resistance of at least part of a plant or plant tissue or plant cell, wherein the polynucleotide is defined as in any one of statements 1 to 37.
69. The use according to statement 67 or 64, wherein the VHH specifically binds to a sphingolipid of a pathogen.
70. The use according to any one of statements 67 to 69, wherein the VHH specifically binds to a ceramide of a pathogen.
71. The use according to any one of statements 67 to 70, wherein the VHH specifically binds to a glycosphingolipid of a pathogen.
72. The use according to any one of statements 67 to 71, wherein the VHH specifically binds to a cerebroside of a pathogen.
73. The use according to any one of statements 67 to 72, wherein the VHH specifically binds to a glucocerebroside of a pathogen.
74. The use according to any one of statements 67 to 73, wherein the VHH binds to a plant pathogen.
75. The use according to any one of statements 67 to 74, wherein the VHH binds to a sphingolipid of a plant pathogen.
76. The use according to any one of statements 67 to 75, wherein the VHH binds to a ceramide of a plant pathogen.
77. The use according to any one of statements 67 to 76, wherein the VHH binds to a glycosphingolipid of a plant pathogen.
78. The use according to any one of statements 67 to 77, wherein the VHH binds to a cerebroside of a plant pathogen.
79. The use according to any one of statements 67 to 78, wherein the VHH binds to a glucocerebroside of a plant pathogenic fungus.
80. The use according to statements 67 to 79, wherein the VHH specifically binds to a fungus.
81. The use according to statements 67 to 80, wherein the VHH specifically binds to a sphingolipid of a fungus.
82. The use according to any one of statements 67 to 81, wherein the VHH specifically binds to a ceramide of a fungus.
83. The use according to any one of statements 67 to 82, wherein the VHH specifically binds to a glycosphingolipid of a fungus.
84. The use according to any one of statements 67 to 83, wherein the VHH specifically binds to a cerebroside of a fungus.

85. The use according to any one of statements 67 to 84, wherein the VHH specifically binds to a glucocerebroside of a fungus.
86. The use according to any one of statements 67 to 85, wherein the VHH binds to a plant pathogenic fungus.
87. The use according to any one of statements 67 to 86, wherein the VHH binds to a sphingolipid of a plant pathogenic fungus.
88. The use according to any one of statements 67 to 87, wherein the VHH binds to a ceramide of a plant pathogenic fungus.
89. The use according to any one of statements 67 to 88, wherein the VHH binds to a glycosphingolipid of a plant pathogenic fungus.
90. The use according to any one of statements 67 to 89, wherein the VHH binds to a cerebroside of a plant pathogenic fungus.
91. The use according to any one of statements 67 to 90, wherein the VHH binds to a glucocerebroside of a plant pathogenic fungus.
92. An extract of a transgenic plant or plant tissue or plant cell according to any one of statements 1 to 37, the extract comprising VHH.
93. A composition comprising the extract of statement 92.
94. A method for protecting at least part of a plant or plant tissue or plant cell from an infection with a plant pathogen, for inhibiting the growth of a plant pathogen on at least part of a plant or plant tissue or plant cell, and/or for increasing pathogen resistance of at least part of a plant or plant tissue or plant cell, comprising treating at least part of a plant or plant tissue or plant cell with the extract of statement 92 or the composition of statement 93.
95. Use of the extract of statement 92 or the composition of claim 93 for protecting at least part of a plant or plant tissue or plant cell from an infection with a plant pathogen, for inhibiting the growth of a plant pathogen on at least part of a plant or plant tissue or plant cell, and/or for increasing pathogen resistance of at least part of a plant or plant tissue or plant cell.

Definitions

This disclosure will be described with respect to particular embodiments but the disclosure is not limited thereto but only by the claims. Any reference signs in the claims shall not be construed as limiting the scope.

Where the term "comprising" is used in the present description and claims, it does not exclude other elements or steps.

Where an indefinite or definite article is used when referring to a singular noun, e.g., "a," "an," or "the," this includes a plural of that noun unless something else is specifically stated.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The following terms or definitions are provided solely to aid in the understanding of the disclosure. Unless specifically defined herein, all terms used herein have the same meaning as they would to one skilled in the art of this disclosure. Practitioners are particularly directed to Sambrook et al., *Molecular Cloning: A Laboratory Manual, 2$^{nd}$* ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art. The definitions provided herein should not be construed to have a scope less than understood by a person of ordinary skill in the art.

Unless indicated otherwise, all methods, steps, techniques and manipulations that are not specifically described in detail can be performed and have been performed in a manner known per se, as will be clear to the skilled person. Reference is, for example, again made to the standard handbooks, to the general background art referred to above and to the further references cited therein.

As used herein, the terms "polypeptide," "protein," "peptide," and "amino acid sequence" are used interchangeably, and refer to a polymeric form of amino acids of any length, which can include coded and non-coded amino acids, chemically or biochemically modified or derivatized amino acids, and polypeptides having modified peptide backbones.

As used herein, amino acid residues will be indicated either by their full name or according to the standard three-letter or one-letter amino acid code.

As used herein, the terms "nucleic acid molecule," "polynucleotide," "polynucleic acid," and "nucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

As used herein, the term "homology" denotes at least secondary structural similarity between two macromolecules, particularly between two polypeptides or polynucleotides, from same or different taxons, wherein the similarity is due to shared ancestry. Hence, the term "homologues" denotes so-related macromolecules having secondary and optionally tertiary structural similarity.

For comparing two or more polynucleotide sequences, the "(percentage of) sequence identity" between a first polynucleotide sequence and a second polynucleotide sequence may be calculated using methods known by the person skilled in the art, e.g., by optimally aligning the polynucleotide sequences and introducing gaps, if necessary, followed by dividing the number of nucleotides in the first polynucleotide sequence that are identical to the nucleotides at the corresponding positions in the second polynucleotide sequence in a comparison window by the number of positions in the comparison window (the window size), and multiplying by 100%. Optimal sequence alignment of two or more polynucleotide sequences over a comparison window can be obtained by using a known computer algorithm for sequence alignment such as NCBI Blast (Altschul et al., *Mol. Biol.* 1990 Oct. 5; 215 (3):403-410). Another example of an algorithm that is suitable for polynucleotide sequence alignments is the CLUSTALW program (J. D. Thompson, et al., *Nucl. Acids Res.* 1994 Nov. 11; 22 (22):4673-4680). CLUSTALW performs multiple pairwise comparisons between groups of sequences and assembles them into a multiple alignment based on homology. For comparing two or more polypeptide sequences, the "(percentage of) sequence identity" between a first polypeptide sequence and a second polypeptide sequence may be calculated using methods known by the person skilled in the art, e.g., by optimally aligning the polypeptide sequences and introducing gaps, if necessary, followed by dividing the number of amino acids in the first polypeptide sequence that are identical to the amino acids at the corresponding positions in the second polypeptide sequence in a comparison window by the number of positions in the comparison window (the window size), and multiplying by 100%. Optimal sequence alignment of two or more polypeptide sequences over a comparison window can be obtained by using a known computer algorithm for sequence alignment such as NCBI Blast (Altschul et all, *J. Mol. Boil.* 1990 Oct. 5; 215 (3):403-410). Another example of an algorithm that is suitable for polypeptide sequence alignments is the CLUSTALW program (J. D. Thompson et al., *Nucl. Acids Res.* 1994 Nov. 11; 22 (22):4673-4680). CLUSTALW performs multiple pairwise comparisons between groups of sequences and assembles them into a multiple alignment based on homology. For amino acid alignments, the BLOSUM algorithm can be used as a protein weight matrix (Henikoff and Henikoff, *PNAS USA* 1992 Nov. 15; 89 (22):10915-10919). In determining the degree of sequence homology between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Conservative amino acid substitutions are counted as identities in order to calculate the percentage homology between two polypeptide sequences. Possible conservative amino acid substitutions will be clear to the person skilled in the art.

As used herein, "comparison window" makes reference to a contiguous and specified segment of an optimal alignment of polynucleotide or polypeptide sequences, wherein the sequences in the comparison window may comprise gaps for optimal alignment of the two sequences. The comparison window for determining sequence identity or homology may be as long as the longest of the aligned sequences, or as long as the shortest of the aligned sequences, or as long as the alignment including gaps in any of the sequences introduced to optimize the alignment. Comparison windows may be about 5000 positions long, or about 2000 positions, or about 1000 positions, or about 800 positions, or about 600 positions long, or about 500 positions long, or about 400 positions long, or about 300 positions long, or about 200 positions long, or about 100 positions long, or about 50 positions long, or about 40 positions long, or about 30 positions long, or about 20 positions long, or about 10 positions long. Amino acid sequences and nucleic acid sequences are said to be "exactly the same" if they have 100% sequence identity over their entire length.

As used herein, the terms "complementarity-determining region" or "CDR" within the context of antibodies refer to variable regions of either the H (heavy) or the L (light) chains (also abbreviated as VH and VL, respectively) and contain the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have three CDR regions, each non-contiguous with the others (termed L1, L2, L3, H1, H2, H3) for the respective light (L) and heavy (H) chains.

The term "affinity," as used herein, refers to the degree to which a polypeptide, in particular, an immunoglobulin, such as an antibody, or an immunoglobulin fragment, such as a VHH, binds to an antigen so as to shift the equilibrium of antigen and polypeptide toward the presence of a complex formed by their binding. Thus, for example, where an antigen and antibody (fragment) are combined in relatively equal concentration, an antibody (fragment) of high affinity will bind to the available antigen so as to shift the equilibrium toward high concentration of the resulting complex. The dissociation constant is commonly used to describe the affinity between the protein binding domain and the antigenic target. Typically, the dissociation constant is lower than $10^{-5}$ M. Preferably, the dissociation constant is lower than $10^{-6}$ M, and more preferably, lower than $10^{-7}$ M. Most preferably, the dissociation constant is lower than $10^{-8}$ M.

The terms "specifically bind" and "specific binding," as used herein, generally refers to the ability of a polypeptide, in particular, an immunoglobulin, such as an antibody, or an immunoglobulin fragment, such as a VHH, to preferentially bind to a particular antigen that is present in a homogeneous mixture of different antigens. In certain embodiments, a specific binding interaction will discriminate between desirable and undesirable antigens in a sample, in some embodiments more than about 10- to 100-fold or more (e.g., more than about 1000- or 10,000-fold).

Accordingly, an amino acid sequence as disclosed herein is said to "specifically bind to" a particular target when that amino acid sequence has affinity for, specificity for and/or is specifically directed against that target (or for at least one part or fragment thereof).

The "specificity" of an amino acid sequence as disclosed herein can be determined based on affinity and/or avidity.

An amino acid sequence as disclosed herein is said to be "specific for a first target antigen of interest as opposed to a second target antigen of interest" when it binds to the first target antigen of interest with an affinity that is at least 5 times, such as at least 10 times, such as at least 100 times, and preferably at least 1000 times higher than the affinity with which that amino acid sequence as disclosed herein binds to the second target antigen of interest. Accordingly, in certain embodiments, when an amino acid sequence as disclosed herein is said to be "specific for" a first target antigen of interest as opposed to a second target antigen of interest, it may specifically bind to (as defined herein) the first target antigen of interest, but not to the second target antigen of interest.

As used herein, the terms "inhibiting," "reducing" and/or "preventing" may refer to (the use of) an amino acid sequence as disclosed herein that specifically binds to a target antigen of interest and inhibits, reduces and/or prevents the interaction between that target antigen of interest, and its natural binding partner. The terms "inhibiting," "reducing" and/or "preventing" may also refer to (the use of) an amino acid sequence as disclosed herein that specifically binds to a target antigen of interest and inhibits, reduces and/or prevents a biological activity of that target antigen of interest, as measured using a suitable in vitro, cellular or in vivo assay. Accordingly, "inhibiting," "reducing" and/or "preventing" may also refer to (the use of) an amino acid sequence as disclosed herein that specifically binds to a target antigen of interest and inhibits, reduces and/or prevents one or more biological or physiological mechanisms, effects, responses, functions pathways or activities in which the target antigen of interest is involved. Such an action of the amino acid sequence as disclosed herein as an antagonist may be determined in any suitable manner and/or using any suitable (in vitro and usually cellular or in vivo) assay known in the art, depending on the target antigen of interest.

Thus, more particularly, "inhibiting," "reducing" and/or "preventing" using amino acid sequence as disclosed herein may mean either inhibiting, reducing and/or preventing the interaction between a target antigen of interest and its natural binding partner, or inhibiting, reducing and/or preventing the activity of a target antigen of interest, or inhibiting, reducing and/or preventing one or more biological or physiological mechanisms, effects, responses, functions pathways or activities in which the target antigen of interest is involved, such as by at least 10%, but preferably at least 20%, for example, by at least 50%, at least 60%, at least 70%, at least 80%, at least 90%, at least 95% or more, as measured using a suitable in vitro, cellular, or in vivo assay, compared to the activity of the target antigen of interest in the same assay under the same conditions but without using the amino acid sequence as disclosed herein. In addition, "inhibiting," "reducing" and/or "preventing" may also mean inducing a decrease in affinity, avidity, specificity and/or selectivity of a target antigen of interest for one or more of its natural binding partners and/or inducing a decrease in the sensitivity of the target antigen of interest for one or more conditions in the medium or surroundings in which the target antigen of interest is present (such as pH, ion strength, the presence of co-factors, etc.), compared to the same conditions but without the presence of the amino acid sequence as disclosed herein. In the context of this disclosure, "inhibiting," "reducing" and/or "preventing" may also involve allosteric inhibition, reduction and/or prevention of the activity of a target antigen of interest.

The inhibiting or antagonizing activity or the enhancing or agonizing activity of an amino acid sequence as disclosed herein may be reversible or irreversible.

In respect of the amino acid sequences as disclosed herein, the terms "binding region," "binding site" or "interaction site" present on the amino acid sequences as disclosed herein shall herein have the meaning of a particular site, region, locus, part, or domain present on the target molecule, which particular site, region, locus, part, or domain is responsible for binding to that target molecule. Such binding region thus essentially consists of that particular site, region, locus, part, or domain of the target molecule, which is in contact with the amino acid sequence when bound to that target molecule.

"Plant" as used herein, means live plants and live plant parts, including fresh fruit, vegetables and seeds. Also, the term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest.

The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

The choice of suitable control plants is a routine part of an experimental setup and may include corresponding wild-type plants or corresponding plants without the gene of interest. The control plant is typically of the same plant species or even of the same variety as the plant to be assessed. The control plant may also be a nullizygote of the plant to be assessed. Nullizygotes are individuals missing the transgene by segregation. A "control plant" as used herein refers not only to whole plants, but also to plant parts, including seeds and seed parts.

The term "plant tissue" as used herein refers to a group of similar plant cells from the same origin that together carry out a specific function. Examples of plant tissues include meristematic tissue, protective tissue, parenchyma, sclerenchyma, collenchyma, xylem, and phloem.

"Crop" as used herein means a plant species or variety that is grown to be harvested as food, livestock fodder, fuel raw material, or for any other economic purpose. As a non-limiting example, the crops can be maize, cereals, such as wheat, rye, barley and oats, sorghum, rice, sugar beet and fodder beet, fruit, such as pome fruit (e.g., apples and pears), citrus fruit (e.g., oranges, lemons, limes, grapefruit, or mandarins), stone fruit (e.g., peaches, nectarines or plums), nuts (e.g., almonds or walnuts), soft fruit (e.g., cherries, strawberries, blackberries or raspberries), the plantain family or grapevines, leguminous crops, such as beans, lentils, peas and soya, oil crops, such as sunflower, safflower, rapeseed, canola, castor or olives, cucurbits, such as cucumbers, melons or pumpkins, fiber plants, such as cotton, flax or hemp, fuel crops, such as sugarcane, miscanthus or switchgrass, vegetables, such as potatoes, tomatoes, peppers, lettuce, spinach, onions, carrots, egg-plants, asparagus or cabbage, ornamentals, such as flowers (e.g., petunias, pelargoniums, roses, tulips, lilies, or chrysanthemums), shrubs, broad-leaved trees (e.g., poplars or willows) and evergreens (e.g., conifers), grasses, such as lawn, turf or forage grass or other useful plants, such as coffee, tea, tobacco, hops, pepper, rubber or latex plants.

A "plant pest," "plant pathogen" or "crop pest," as used herein interchangeably, refers to organisms that specifically cause damage to plants, plant parts or plant products, particularly plants, plant parts or plant products, used in agriculture. Note that the term "plant pest" or "crop pest" is used in the meaning that the pest targets and harms plants. Relevant crop pest examples include, but are not limited to pathogenic fungi (including Ascomycetes (such as *Fusarium* spp., *Thielaviopsis* spp., *Verticillium* spp., and *Magnaporthe* spp.), Basidiomycetes (such as *Rhizoctonia* spp., *Phakospora* spp., and *Puccinia* spp.), and fungal-like Oomycetes (such as *Pythium* spp. and *Phytophthora* spp.), aphids, caterpillars, flies, wasps, and the like, nematodes (living freely in soil or particularly species that parasitize plant roots, such as root-knot nematode and cyst nematodes such as soybean cyst nematode and potato cyst nematode), mites (such as spider mites, thread-footed mites and gall mites) and gastropods (including slugs such as *Deroceras* spp., *Milax* spp., *Tandonia* sp., *Limax* spp., *Arion* spp. and *Veronicella* spp. and snails such as *Helix* spp., *Cernuella* spp., *Theba* spp., *Cochlicella* spp., *Achatina* spp., *Succinea* spp., *Ovachlamys* spp., *Amphibulima* spp., *Zachrysia* spp., *Bradybaena* spp., and *Pomacea* spp.), bacteria (such as *Burkholderia* spp. and Proteobacteria such as *Xanthomonas* spp. and *Pseudomonas* spp.), Phytoplasma, Spiroplasma, viruses (such as tobacco mosaic virus and cauliflower mosaic virus), and protozoa.

"Microbe," as used herein, means fungus, yeast, bacterium, virus, and the like and "microbial" means derived from a microbe.

"Fungus," as used herein, means a eukaryotic organism, belonging to the group of Eumycota. The term "fungus" in this disclosure also includes fungal-like organisms such as the Oomycota. Oomycota (or oomycetes) form a distinct phylogenetic lineage of fungus-like eukaryotic microorganisms. This group was originally classified among the fungi but modern insights support a relatively close relationship with the photosynthetic organisms such as brown algae and diatoms, within the group of heterokonts.

The terms "plant pathogenic fungus" or "fungal plant pathogen," as used herein interchangeably, refer to any fungus as defined herein capable of causing an infection or other biological reaction on a plant.

The term "infection" as used herein refers to any inflammatory condition, disease or disorder in a plant that is caused by a plant pathogen.

"Fungal infection" or "fungal disease" as used herein refers to any inflammatory condition, disease or disorder in a living organism, such as a plant, animal or human, which is caused by a fungus.

The term "antimicrobial agent," as used herein, refers to an agent that kills microorganisms or inhibits the growth of microorganisms. Antimicrobial agents encompass antibacterial, antifungal, antiviral, or antiparasitic agents.

The term "microbicidal agent," as used herein, refers to an agent that kills microorganisms.

The term "microbiostatic agent," as used herein, refers to an agent that inhibits the growth of microorganisms.

The term "fungicidal agent," as used herein, refers to an agent that kills a fungus.

The term "fungistatic agent," as used herein, refers to an agent that inhibits the growth of a fungus.

"Antimicrobial (effect)" or "antimicrobial use," as used herein, includes any effect or use of an agent, in particular, of a VHH, for controlling, modulating or interfering with the harmful activity of a plant pathogen, including killing the plant pathogen, inhibiting the growth or activity of the plant pathogen, altering the behavior of the plant pathogen, and repelling or attracting the plant pathogen in plants, plant parts or in other agro-related settings, such as, for example, in soil.

"Microbicidal (effect)" or "microbicidal use," as used herein, includes any effect or use of an agent, in particular, of a VHH, for controlling, modulating or interfering with the harmful activity of a plant pathogen, including killing the plant pathogen, "Microbiostatic (effect)" or "microbiostatic use," as used herein, includes any effect or use of an agent, in particular, of a VHH, for controlling, modulating or interfering with the harmful activity of a plant pathogen, including inhibiting the growth or activity of the plant pathogen, altering the behavior of the plant pathogen, and repelling or attracting the plant pathogen in plants, plant parts or in other agro-related settings, such as, for example, in soil.

"Antifungal (effect)" or "antifungal use," as used herein, includes any effect or use of an agent, in particular, of a VHH, for controlling, modulating or interfering with the harmful activity of a fungus, including inhibiting the growth or activity of the fungus, altering the behavior of the fungus, and repelling or attracting the fungus in plants, plant parts or in other agro-related settings, such as in soil.

"Fungicidal (effect)" or "Fungicidal use," as used herein, includes any effect or use of an agent, in particular, of a VHH, for controlling, modulating or interfering with the harmful activity of a fungus, including killing the fungus.

"Fungistatic (effect)" or "Fungistatic use," as used herein, includes any effect or use of an agent, in particular, of a VHH, for controlling, modulating or interfering with the harmful activity of a fungus, including inhibiting the growth or activity of the fungus, altering the behavior of the fungus, and repelling or attracting the fungus in plants, plant parts or in other agro-related settings, such as, for example, in soil.

"Pesticidal activity" or "biocidal activity," as used interchangeably herein, means to interfere with the harmful activity of a plant pathogen, including but not limited to killing the plant pathogen, inhibiting the growth or activity of the plant pathogen, altering the behavior of the plant pathogen, repelling or attracting the plant pathogen.

"Biostatic activity," as used herein, means to interfere with the harmful activity of a plant pathogen, including but not limited to inhibiting the growth or activity of the plant pathogen, altering the behavior of the plant pathogen, repelling or attracting the plant pathogen.

Pesticidal, biocidal, or biostatic activity of an active ingredient, substance or principle or a composition or agent comprising a pesticidal, biocidal, or biostatic active ingredient, substance or principle, can be expressed as the minimum inhibitory activity (MIC) of an agent (expressed in units of concentration such as, e.g., mg/mL), without, however, being restricted thereto.

"Fungicidal activity," as used herein, means to interfere with the harmful activity of a fungus, including but not limited to killing the fungus, inhibiting the growth or activity of the fungus, altering the behavior of the fungus, and repelling or attracting the fungus.

"Fungistatic activity," as used herein, means to interfere with the harmful activity of a fungus, including but not limited to inhibiting the growth or activity of the fungus, altering the behavior of the fungus, and repelling or attracting the fungus.

Fungicidal or fungistatic activity of an active ingredient, substance or principle or a composition or agent comprising a pesticidal, biocidal, or biostatic active ingredient, substance or principle, can be expressed as the minimum inhibitory activity (MIC) of an agent (expressed in units of concentration such as, e.g., mg/mL), without, however, being restricted thereto.

As used herein, the term "antibody" refers to polyclonal antibodies, monoclonal antibodies, humanized antibodies, single-chain antibodies, and fragments thereof such as Fab, F(ab)2, Fv, and other fragments that retain the antigen binding function of the parent antibody. As such, an antibody may refer to an immunoglobulin or glycoprotein, or fragment or portion thereof, or to a construct comprising an antigen-binding portion comprised within a modified immunoglobulin-like framework, or to an antigen-binding portion comprised within a construct comprising a non-immunoglobulin-like framework or scaffold.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab)2, Fv, and others that retain the antigen binding function of the antibody. Monoclonal antibodies of any mammalian species can be used in this disclosure. In practice, however, the antibodies will typically be of rat or murine origin because of the availability of rat or murine cell lines for use in making the required hybrid cell lines or hybridomas to produce monoclonal antibodies.

As used herein, the term "polyclonal antibody" refers to an antibody composition having a heterogeneous antibody population. Polyclonal antibodies are often derived from the pooled serum from immunized animals or from selected humans.

The terms "variable domain of a heavy-chain antibody" or "VHH" or "heavy chain variable domain of an antibody," as used herein interchangeably, refer to the variable domain of the heavy chain of a heavy-chain antibody, which is naturally devoid of light chains, including but not limited to the variable domain of the heavy chain of heavy-chain antibodies of camelids or sharks.

The skilled person may understand that functional variants of VHH include any immunoglobulin single variable domain. Examples of immunoglobulin single variable domains include an immunoglobulin single variable domain selected form the group consisting of an immunoglobulin single variable domain derived from a heavy-chain antibody, an immunoglobulin single variable domain derived from a light chain variable domain sequence, an immunoglobulin single variable domain derived from a heavy chain variable domain sequence, an immunoglobulin single variable domain derived from a conventional four-chain antibody, a domain antibody, a single domain antibody, a "dAb" (Domantis/GSK), a VHH, or Nanobody (Ablynx).

As further described herein, the amino acid sequence and structure of a variable domain of a heavy-chain antibody can be considered, without however being limited thereto, to be comprised of four framework regions or "FRs," which are referred to in the art and herein as "framework region 1" or "FR1"; as "framework region 2" or "FR2"; as "framework region 3" or "FR3"; and as "framework region 4" or "FR4," respectively, which framework regions are interrupted by three complementarity-determining regions or "CDRs," which are referred to in the art as "complementarity-determining region 1" or "CDR1"; as "complementarity-determining region 2" or "CDR2"; and as "complementarity-determining region 3" or "CDR3," respectively.

As also further described herein, the total number of amino acid residues in a variable domain of a heavy-chain antibody or VHH can be in the region of 110-130, preferably is 112-115, and most preferably is 113. It should however be noted that parts, fragments or analogs of a variable domain of a heavy-chain antibody are not particularly limited as to their length and/or size, as long as such parts, fragments or analogs retain (at least part of) the functional activity, such as the pesticidal, biocidal, biostatic activity, fungicidal or fungistatic activity (as defined herein) and/or retain (at least part of) the binding specificity of the original a variable domain of a heavy-chain antibody from which these parts, fragments or analogs are derived from. Parts, fragments or analogs retaining (at least part of) the functional activity, such as the pesticidal, biocidal, biostatic activity, fungicidal or fungistatic activity (as defined herein) and/or retaining (at least part of) the binding specificity of the original variable domain of a heavy-chain antibody from which these parts, fragments or analogs are derived from are also further referred to herein as "functional fragments" of a variable domain of a heavy-chain antibody.

Figure 2:
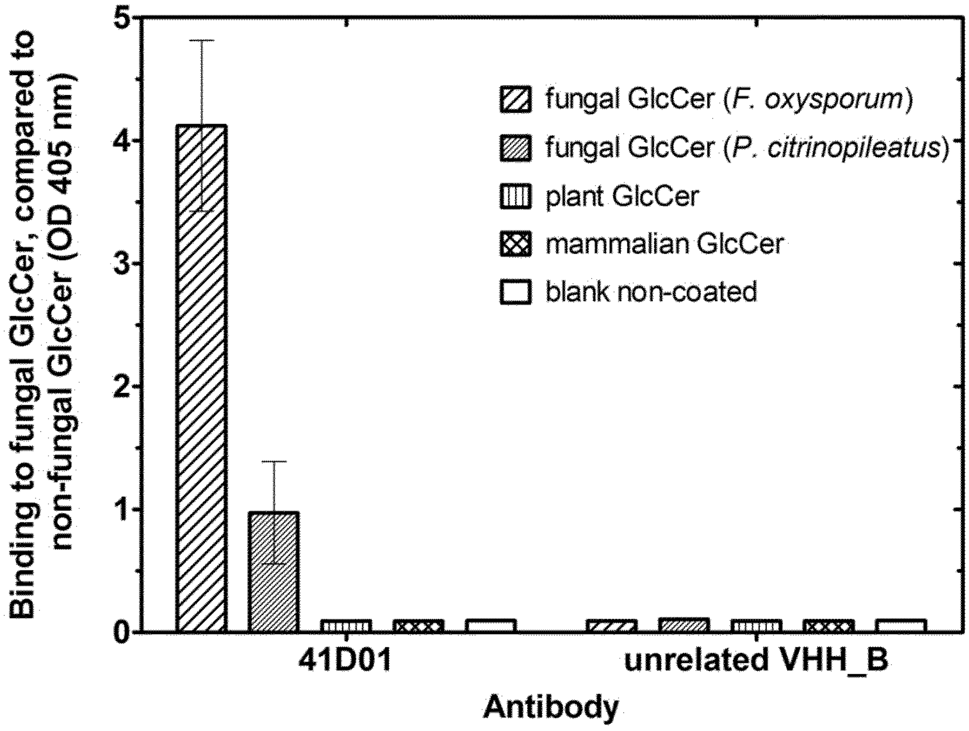
FIG. 2: Binding specificity of VHH 41D01. Binding of purified VHH 41D01 at 0.1 μg/ml to coated fungal GlcCer from *Fusarium oxysporum* or *Pleurotus citrinopileatus*, and non-fungal GlcCer from plant (soy), or mammal (pork). Bars represent average OD 405 nm values, error bars represent standard errors of the mean of n=6. Anti-GlcCer VHH 41D01 specifically binds fungal GlcCer and not plant or mammalian GlcCer.
Figure 3A:
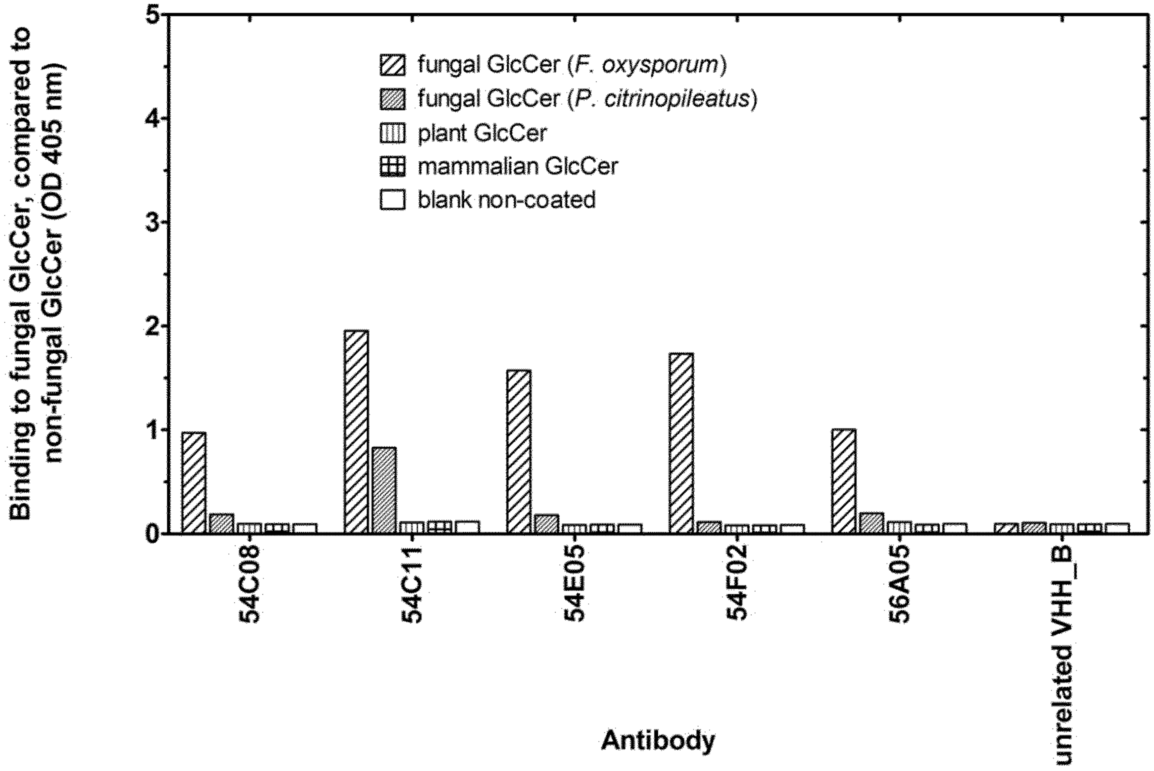
FIGS. 3A-3C: Binding specificity of VHH. Binding of purified VHH at 1 μg/ml to coated fungal GlcCer from *Fusarium oxysporum* or *Pleurotus citrinopileatus*, non-fungal GlcCer from plant (soy), and non-fungal mammalian GlcCer (pig). Different anti-GlcCer VHH specifically bind to different fungal GlcCer, but do not bind to plant GlcCer or mammalian GlcCer.
Figure 3B:
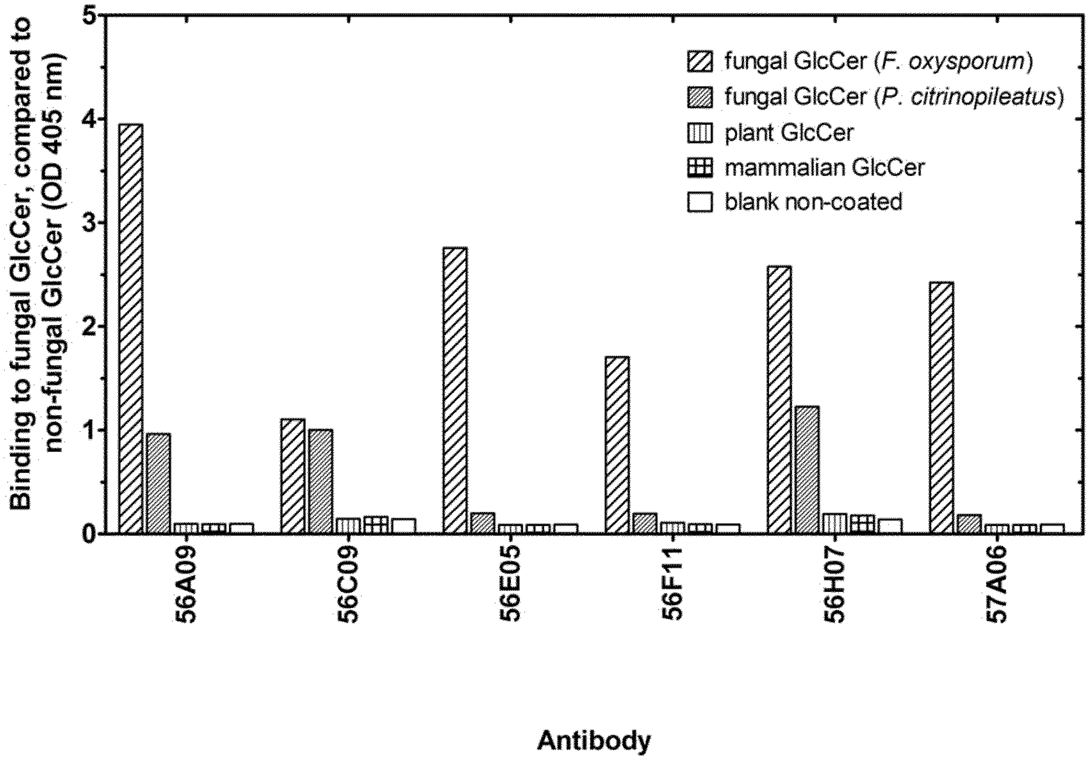
Figure 3C:
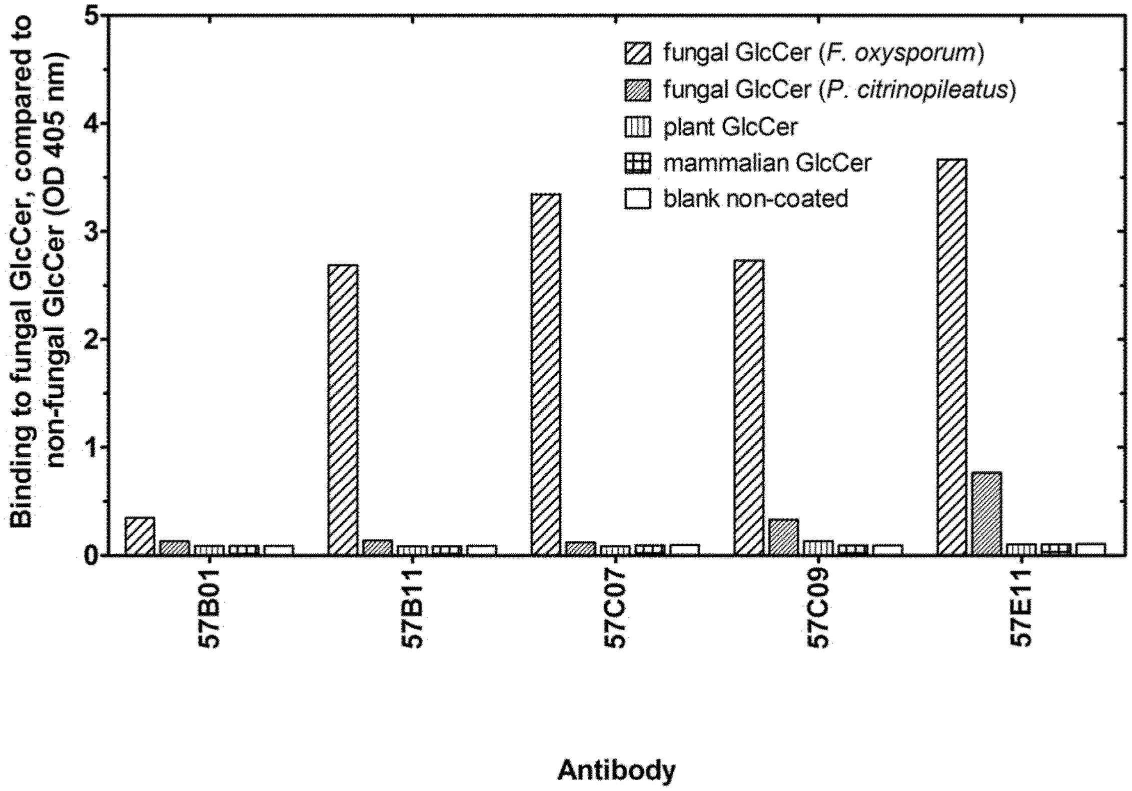

The amino acid residues of a variable domain of a heavy-chain antibody are numbered according to the general numbering for variable domains given by Kabat et al. ("*Sequence of proteins of immunological interest*," U.S. Public Health Services, NIH Bethesda, Md., Publication No. 91), as applied to $V_{HH}$ domains from Camelids in the article of Riechmann and Muyldermans, referred to above (see, for example, FIG. 2 of that reference). According to this numbering, FR1 of a variable domain of a heavy-chain antibody comprises the amino acid residues at positions 1-30, CDR1 of a variable domain of a heavy-chain antibody comprises the amino acid residues at positions 31-36, FR2 of a variable domain of a heavy-chain antibody comprises the amino acids at positions 36-49, CDR2 of a variable domain of a heavy-chain antibody comprises the amino acid residues at positions 50-65, FR3 of a variable domain of a heavy-chain antibody comprises the amino acid residues at positions 66-94, CDR3 of a variable domain of a heavy-chain antibody comprises the amino acid residues at positions 95-102, and FR4 of a variable domain of a heavy-chain antibody comprises the amino acid residues at positions 103-113. In this respect, it should be noted that—as is well known in the art for $V_{HH}$ domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDRs, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.

Alternative methods for numbering the amino acid residues of a variable domain of a heavy-chain antibody are the method described by Chothia et al. (Nature 342, 877-883 (1989)), the so-called "AbM definition" and the so-called "contact definition." However, in the present description, claims and figures, the numbering according to Kabat as applied to $V_{HH}$ domains by Riechmann and Muyldermans will be followed, unless indicated otherwise.

For a general description of heavy-chain antibodies and the variable domains thereof, reference is made, inter alia, to the following references, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx NV; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551 by Ablynx NV and the further published patent applications by Ablynx NV; Hamers-Casterman et al., *Nature* 1993 Jun. 3; 363 (6428):446-8; Davies and Riechmann, *FEBS Lett.* 1994 Feb. 21; 339 (3):285-90; Muyldermans et al., *Protein Eng.* 1994 September; 7 (9):1129-3; Davies and Riechmann, *Biotechnology* (NY) 1995 May; 13 (5):475-9; Gharoudi et al., *9th Forum of Applied Biotechnology*, Med. Fac. Landbouw Univ. Gent. 1995; 60/4a part I: 2097-2100; Davies and Riechmann, *Protein Eng.* 1996 June; 9 (6):531-7; Desmyter et al., *Nat. Struct. Biol.* 1996 September; 3 (9):803-11; Sheriff et al., *Nat. Struct. Biol.* 1996 September; 3 (9):733-6; Spinelli et al., *Nat. Struct. Biol.* 1996 September; 3 (9):752-7; Arbabi Ghahroudi et al., *FEBS Lett.* 1997 Sep. 15; 414 (3):521-6; Vu et al., *Mol. Immunol.* 1997 November-December; 34 (16-17):1121-31; Atarhouch et al., *Journal of Carnel. Practice and Research* 1997; 4:177-182; Nguyen et al., *J. Mol. Biol.* 1998 Jan. 23; 275 (3):413-8; Lauwereys et al., *EMBO J.* 1998 Jul. 1; 17 (13):3512-20; Frenken et al., *Res. Immunol.* 1998 July-August; 149 (6):589-99; Transue et al., *Proteins* 1998 Sep. 1; 32 (4):515-22; Muyldermans and Lauwereys, *J. Mol. Recognit.* 1999 March-April; 12 (2): 131-40; van der Linden et al., *Biochim. Biophys. Acta* 1999 Apr. 12; 1431 (1):37-46; Decanniere et al., *Structure Fold. Des.* 1999 Apr. 15; 7 (4):361-70; Ngyuen et al., *Mol. Immunol.* 1999 June; 36 (8):515-24; Woolven et al., *Immunogenetics* 1999 October; 50 (1-2):98-101; Riechmann and Muyldermans, *J Immunol. Methods* 1999 Dec. 10; 231 (1-2):25-38; Spinelli et al., *Biochemistry* 2000 Feb. 15; 39 (6):1217-22; Frenken et al., *J. Biotechnol.* 2000 Feb. 28; 78 (1):11-21; Nguyen et al., *EMBO J.* 2000 Mar. 1; 19 (5):921-30; van der Linden et al., *J Immunol. Methods* 2000 Jun. 23; 240 (1-2):185-95; Decanniere et al., *J. Mol. Biol.* 2000 Jun. 30; 300 (1):83-91; van der Linden et al., *J. Biotechnol.* 2000 Jul. 14; 80 (3):261-70; Harmsen et al., *Mol. Immunol.* 2000 August; 37 (10):579-90; Perez et al., *Biochemistry* 2001 Jan. 9; 40 (1):74-83; Conrath et al., *J. Biol. Chem.* 2001 Mar. 9; 276 (10):7346-50; Muyldermans et al., *Trends Biochem. Sci.* 2001 April; 26 (4):230-5; S. Muyldermans, *J. Biotechnol.* 2001 June; 74 (4):277-302; Desmyter et al., *J. Biol. Chem.* 2001 Jul. 13; 276 (28):26285-90; Spinelli et al., *J. Mol. Biol.* 2001 Aug. 3; 311 (1):123-9; Conrath et al., *Antimicrob. Agents Chemother.* 2001 October; 45 (10):2807-12; Decanniere et al., *J. Mol. Biol.* 2001 Oct. 26; 313 (3):473-8; Nguyen et al., *Adv. Immunol.* 2001; 79:261-96; Muruganandam et al., *FASEB J.* 2002 February; 16 (2):240-2; Ewert et al., *Biochemistry* 2002 Mar. 19; 41 (11):3628-36; Dumoulin et al., *Protein Sci.* 2002 March; 11 (3):500-15; Cortez-Retamozo et al., *Int. J. Cancer* 2002 Mar. 20; 98 (3):456-62; Su et al., *Mol. Biol. Evol.* 2002 March; 19 (3):205-15; J. M. van der Vaart, *Methods Mol. Biol.* 2002; 178:359-66; Vranken et al., *Biochemistry* 2002 Jul. 9; 41 (27):8570-9; Nguyen et al., *Immunogenetics* 2002 April; 54 (1):39-47; Renisio et al., *Proteins* 2002 Jun. 1; 47 (4):546-55; Desmyter et al., *J. Biol. Chem.* 2002 Jun. 28; 277 (26):23645-50; Ledeboer et al., *J. Dairy Sci.* 2002 June; 85 (6):1376-82; De Genst et al., *J Biol. Chem.* 2002 Aug. 16; 277 (33):29897-907; Ferrat et al., *Biochem. J* 2002 Sep. 1; 366 (Pt. 2):415-22; Thomassen et al., *Enzyme and Microbiol. Technol.* 2002; 30:273-8; Harmsen et al., *Appl. Microbiol. Biotechnol.* 2002 December; 60 (4):449-54; Jobling et al., *Nat. Biotechnol.* 2003 January; 21 (1):77-80; Conrath et al., *Dev. Comp. Immunol.* 2003 February; 27 (2):87-103; Pleschberger et al., *Bioconjug. Chem.* 2003 March-April; 14 (2):440-8; Lah et al., *J. Biol. Chem.* 2003 Apr. 18; 278 (16):14101-11; Nguyen et al., *Immunology* 2003 May; 109 (1):93-101; Joosten et al., *Microb. Cell Fact.* 2003 Jan. 30; 2 (1):1; Li et al., *Proteins* 2003 Jul. 1; 52 (1):47-50; Loris et al., *Biol. Chem.* 2003 Jul. 25; 278 (30):28252-7; van Koningsbruggen et al., *J. Immunol. Methods* 2003 August; 279 (1-2):149-61; Dumoulin et al., *Nature* 2003 Aug. 14; 424 (6950):783-8; Bond et al., *J. Mol. Biol.* 2003 Sep. 19; 332 (3):643-55; Yau et al., *J. Immunol. Methods* 2003 Oct. 1; 281 (1-2):161-75; Dekker et al., *J. Virol.* 2003 November; 77 (22):12132-9; Meddeb-Mouelhi et al., *Toxicon.* 2003 December; 42 (7):785-91; Verheesen et al., *Biochim. Biophys. Acta* 2003 Dec. 5; 1624 (1-3):21-8; Zhang et al., *J. Mol. Biol.* 2004 Jan. 2; 335 (1):49-56; Stijlemans et al., *J. Biol. Chem.* 2004 Jan. 9; 279 (2):1256-61; Cortez-Retamozo et al., *Cancer Res.* 2004 Apr. 15; 64 (8):2853-7; Spinelli et al., *FEBS Lett.* 2004 Apr. 23; 564 (1-2):35-40; Pleschberger et al., *Bioconjug. Chem.* 2004 May-June; 15 (3):664-71; Nicaise et al., *Protein Sci.* 2004 July; 13 (7):1882-91; Omidfar et al., *Tumour Biol.* 2004 July-August; 25 (4):179-87; Omidfar et al., *Tumour Biol.* 2004 September-December; 25 (5-6):296-305; Szynol et al., *Antimicrob. Agents Chemother.* 2004 September; 48 (9): 3390-5; Saerens et al., *J. Biol. Chem.* 2004 Dec. 10; 279 (50):51965-72; De Genst et al., *J. Biol. Chem.* 2004 Dec. 17; 279 (51):53593-601; Dolk et al., *Appl. Environ. Microbiol.* 2005 January; 71 (1):442-50; Joosten et al., *Appl. Microbiol. Biotechnol.* 2005 January; 66 (4):384-92; Dumoulin et al., *J. Mol. Biol.* 2005 Feb. 25; 346 (3):773-88; Yau et al., *J. Immunol. Methods* 2005 February; 297 (1-2):213-24; De Genst et al., *J. Biol. Chem.* 2005 Apr. 8; 280 (14):14114-21; Huang et al., *Eur. J. Hum. Genet.* 2005 Apr. 13; Dolk et al., *Proteins* 2005 May 15; 59 (3):555-64; Bond et al., *J. Mol. Biol.* 2005 May 6; 348 (3):699-709; Zarebski et al., *J Mol. Biol.* 2005 Apr. 21; [E-publication ahead of print].

Generally, it should be noted that the term "variable domain of a heavy-chain antibody," "variable domain" or "heavy chain variable domain" as used herein in its broadest sense is not limited to a specific biological source or to a specific method of preparation. For example, as will be discussed in more detail below, the VHHs as taught herein can be obtained by expression of a nucleotide sequence encoding a naturally occurring $V_{HH}$ domain, or by preparing a nucleic acid encoding a $V_{HH}$ using techniques for nucleic acid synthesis, followed by expression of the nucleic acid thus obtained, or by any combination of the foregoing. Suitable methods and techniques for performing the foregoing will be clear to the skilled person based on the disclosure herein and, for example, include the methods and techniques described in more detail herein.

However, according to a specific embodiment, the variable domain of a heavy-chain antibody as disclosed herein do not have an amino acid sequence that is exactly the same as (i.e., as a degree of sequence identity of 100% with) the amino acid sequence of a naturally occurring VHH domain, such as the amino acid sequence of a naturally occurring VHH domain from a camelid or shark.

As used herein, the terms "determining," "measuring," "assessing," "monitoring" and "assaying" are used interchangeably and include both quantitative and qualitative determinations.

All documents cited in the present specification are hereby incorporated by reference in their entirety. Unless otherwise defined, all terms herein used in describing the disclosure, including technical and scientific terms, have the meaning as commonly understood by one of ordinary skill in the art to which this disclosure belongs. By means of further guidance, term definitions are included to better appreciate the teaching of this disclosure.

Transgenic Plants

This disclosure relates to a transgenic plant or plant tissue or plant cell comprising at least one polynucleotide encoding a VHH specifically binding to a sphingolipid of a fungus.

As used herein, the wording "at least one polynucleotide comprising at least one sequence encoding a VHH" and "at least one polynucleotide encoding a VHH" may be used interchangeably.

The term "transgenic plant or plant tissue" generally refers to plants or plant tissues or plant cells that have been genetically engineered to create plants with new characteristics. A transgenic plant or plant tissue or plant cell can also be identified as a genetically modified organism (GMO).

The term "transgenic plant" also encompasses commodity products derived from the transgenic plant or plant tissue or plant cell, wherein the commodity product comprises a detectable amount of the transgenic or recombinant polynucleotide and wherein the commodity product is selected from the group consisting of plant biomass, oil, meal, food, animal feed, flour, flakes, bran, lint, fiber, paper, protein, starch, silage, hulls, and processed seed, and wherein optionally the commodity product is non-regenerable.

In certain embodiments, the plant may be selected from the group consisting of maize, soya bean, alfalfa, cotton, sunflower, *Brassica* oil seeds such as *Brassica napus* (e.g., canola, rape-seed), *Brassica rapa, B. juncea* (e.g., (field) mustard) and *Brassica carinata, Arecaceae* sp. (e.g., oil-palm, coconut), rice, wheat, sugar beet, sugar cane, oats, rye, barley, millet and sorghum, triticale, flax, nuts, grapes and vine and various fruit and vegetables from various botanic taxa, e.g., *Rosaceae* sp. (e.g., pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g., olive tree), *Actinidaceae* sp., *Lauraceae* sp. (e.g., avocado, cinnamon, camphor), *Musaceae* sp. (e.g., banana trees and plantations), *Rubiaceae* sp. (e.g., coffee), *Theaceae* sp. (e.g., tea), *Sterculiceae* sp., *Rutaceae* sp. (e.g., lemons, oranges, mandarins and grapefruit); *Solanaceae* sp. (e.g., tomatoes, potatoes, peppers, capsicum, aubergines, tobacco), *Liliaceae* sp., *Compositae* sp. (e.g., lettuce, artichokes and chicory, including root chicory, endive or common chicory), *Umbelliferae* sp. (e.g., carrots, parsley, celery and celeriac), *Cu-curbitaceae* sp. (e.g., cucumbers, including gherkins, pumpkins, watermelons, calabashes and melons), *Alliaceae* sp. (e.g., leeks and onions), *Cruciferae* sp. (e.g., white cabbage, red cabbage, broccoli, cauliflower, Brussels sprouts, pak choi, kohlrabi, radishes, horseradish, cress and Chinese cabbage), *Leguminosae* sp. (e.g., peanuts, peas, lentils and beans, e.g., common beans and broad beans), *Chenopodiaceae* sp. (e.g., Swiss chard, fodder beet, spinach, beetroot), *Linaceae* sp. (e.g., hemp), *Cannabeacea* sp. (e.g., cannabis), *Malvaceae* sp. (e.g., okra, cocoa), *Papaveraceae* sp. (e.g., poppy), *Asparagaceae* sp. (e.g., asparagus); useful plants and ornamental plants in the garden and woods including turf, lawn, grass and *Stevia rebaudiana*, and genetically modified types of these plants.

In certain embodiments, the plant may be a crop selected from the group consisting of field crops, grasses, fruits, vegetables, lawns, trees, and ornamental plants.

In certain embodiments, the plant may be a harvestable part of the plant selected from the group consisting of a fruit, a flower, a nut, a vegetable, a fruit or vegetable with inedible peel, preferably selected from avocados, bananas, plantains, lemons, grapefruits, melons, oranges, pineapples, kiwi fruits, guavas, mandarins, mangoes and pumpkin, is preferred, more preferably bananas, oranges, lemons and peaches, in particular, bananas. In certain embodiments, the plant may be a cut flower of ornamental plants, preferably selected from Alstroemeria, Carnation, Chrysanthemum, Freesia, Gerbera, Gladiolus, baby's breath (*Gypsophila* spec), *Helianthus, Hydrangea, Lilium, Lisianthus*, roses and summer flowers. In certain embodiments, the plant may be cut grass or wood.

In certain embodiments, the plant may be a plant used for research purposes such as *Arabidopsis*, corn, tobacco, or poplar.

In certain embodiments, the plant may be a plant selected from the group consisting of corn, rice, wheat, barley, sorghum, millet oats, rye, triticale or other cereals, soybean, alfalfa or other leguminous crops, sugar beet, fodder beet, papaya, banana and plantains or other fruits, grapevines, nuts, oilseed rape, sunflower or other oil crops, squash cucumber, melons or other cucurbits, cotton or other fiber plants, sugarcane, palm, jatropha or other fuel crops, cabbages, tomato, pepper or other vegetables, ornamentals, shrubs, poplar, eucalyptus or other trees, evergreens, grasses, coffee plants, tea plants, tobacco plants, hop plants, rubber plants, and latex plants.

In certain preferred embodiments, the plant may be selected from the group consisting of banana, barley oat rye, canola, corn, cotton, potato, rice, soybean, tobacco, and wheat.

In certain more preferred embodiments, the plant may be selected from the group consisting of canola, corn, rice, soybean, and wheat.

In certain even more preferred embodiments, the plant may be selected from the group consisting of rice, soybean, and wheat.

Methods for the generation of transgenic plant including recombinant DNA techniques are well-known in the art.

Specifically recombinant methodologies generally involve inserting a DNA molecule expressing an amino acid sequence, protein or polypeptide of interest into an expression system to which the DNA molecule is heterologous (i.e., not normally present in the host). The heterologous DNA molecule is inserted into the expression system or vector in proper sense orientation and correct reading frame. The vector contains the necessary elements for the transcription and translation of the inserted protein-coding sequences. Transcription of DNA is dependent upon the presence of a promoter. Similarly, translation of mRNA in prokaryotes depends upon the presence of the proper prokaryotic signals, which differ from those of eukaryotes. For a review on maximizing gene expression, see Roberts and Lauer, *Methods in Enzymology* 68:473 (1979. Regardless of the specific regulatory sequences employed, the DNA molecule is cloned into the vector using standard cloning procedures in the art, as described by Sambrook et al, *Molecular Cloning: A Laboratory Manual*, Cold Springs Laboratory, Cold Springs Harbor, N.Y. (1989). Once the isolated DNA molecule encoding the protein has been cloned into an expression system, it is ready to be incorporated into a host cell. Such incorporation can be carried out by the various forms of transformation, depending upon the vector/host cell system.

In certain embodiments, this disclosure provides nucleic acid sequences capable of encoding a VHH in a transgenic plant or plant tissue or plant cell as defined herein. These nucleic acid sequences can also be in the form of a vector or a genetic construct or polynucleotide. As used herein, the terms "genetic construct" and "nucleic acid construct" are used interchangeably. The nucleic acid sequences as disclosed herein may be synthetic or semi-synthetic sequences, nucleotide sequences that have been isolated from a library (and, in particular, an expression library), nucleotide sequences that have been prepared by PCR using overlapping primers, or nucleotide sequences that have been prepared using techniques for DNA synthesis known per se. In certain embodiments, the polynucleotide may comprise nucleic acid sequence of SEQ ID NO:336 and/or SEQ ID NO:337.

The genetic constructs as disclosed herein may be DNA or RNA, and are preferably double-stranded DNA. The genetic constructs of the disclosure may also be in a form suitable for transformation of the intended host cell or host organism in a form suitable for integration into the genomic DNA of the intended host cell or in a form suitable for independent replication, maintenance and/or inheritance in the intended host organism. For instance, the genetic constructs of the disclosure may be in the form of a vector, such as, for example, a plasmid, cosmid, YAC, a viral vector or transposon. In particular, the vector may be an expression vector, i.e., a vector that can provide for expression in vitro and/or in vivo (e.g., in a suitable host cell, host organism and/or expression system).

Accordingly, in another further aspect, this disclosure also provides vectors comprising one or more nucleic acid sequences of the disclosure.

Also disclosed are chimeric genes comprising the following operably linked DNA elements: a) a plant expressible promoter, b) a DNA region, which, when transcribed, yields a mRNA molecule capable of being translated into a polypeptide and c) a 3' end region comprising transcription termination and polyadenylation signals functioning in cells of the plant.

A "chimeric gene" or "chimeric construct" is a recombinant nucleic acid sequence in which a promoter (e.g., a plant expressible promoter) or regulatory nucleic acid sequence is operatively linked to, or associated with, a nucleic acid sequence that codes for an mRNA, such that the regulatory nucleic acid sequence is able to regulate transcription or expression of the associated nucleic acid coding sequence when introduced into a cell such as a plant cell. The regulatory nucleic acid sequence of the chimeric gene is not normally operatively linked to the associated nucleic acid sequence as found in nature.

In certain embodiments, the polynucleotide may comprise a promoter suitable for expression in plants, a plant tissue or plant cell specific promoter, or an inducible promoter.

The terms "plant promoter" or "promoter suitable for expression in plants" as used herein refers to a nucleic acid sequence comprising regulatory elements, which mediate the expression of a coding sequence in plant cells. For expression in plants, the nucleic acid molecule must be linked operably to or comprise a suitable promoter that expresses the gene at the right point in time and with the required spatial expression pattern.

The term "operably linked" as used herein refers to a functional linkage between the promoter sequence and the gene of interest, such that the promoter sequence is able to initiate transcription of the gene of interest.

Plant expressible promoters comprise nucleic acid sequences that are able to direct the expression of a transgene in a plant. Examples of plant expressible promoters are constitutive promoters that are transcriptionally active during most, but not necessarily all, phases of growth and development and under most environmental conditions, in at least one cell, tissue or organ, other promoters are inducible promoters, other examples are tissue specific promoters, still other examples are abiotic stress inducible promoters.

The term "plant tissue or plant cell specific promoter" refers to promoters that are transcriptionally active in a specific type of plant cells or plant tissues.

The term "inducible promoter" refers to promoters that allow regulating gene expression levels at particular stages of plant development and in particular tissues of interest. Examples of inducible systems include AlcR/AlcA (ethanol inducible); GR fusions, GVG, and pOp/LhGR (dexamethasone inducible); XVE/OlexA (beta-estradiol inducible); and heat shock induction.

The chimeric gene (or the expression cassette) when transformed in a plant expresses a nucleic acid, which results in expression of a protein.

Also disclosed is a recombinant vector that comprises an expression cassette (or a chimeric gene) as herein described before.

The term "terminator" encompasses a control sequence that is a DNA sequence at the end of a transcriptional unit that signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

In certain embodiments of the transgenic plants or plant tissues or plant cells, methods, or uses, as taught herein, the polynucleotide may comprise at least one sequence encoding an antibody fragment consisting of a variable domain of a heavy-chain antibody (VHH). In certain embodiments, the polynucleotide may encode an antibody fragment consisting of a variable domain of a heavy-chain antibody (VHH).

In certain embodiments, the polynucleotide may not comprise a sequence encoding a light chain of an antibody, such as an immunoglobulin light chain. In certain embodiments, the polynucleotide may not encode an immunoglobulin.

In certain embodiments, the transgenic plant or plant tissue or plant cell may not comprise any polynucleotide (comprising at least one sequence) encoding a light chain of an antibody, such as an immunoglobulin light chain. In certain embodiments, the transgenic plant or plant tissue or plant cell may not comprise any polynucleotide (comprising at least one sequence) encoding an immunoglobulin.

In certain embodiments, the polynucleotide may comprise at least one sequence encoding a targeting signal for secretion, for location to the cytoplasm, or for location to cellular compartments or organelles, such as the ER lumen, the apoplast, the vacuole, or intra- and/or exterior membranes.

Examples of a targeting signal for secretion include the 2S2 signal peptide. Examples of a targeting signal for location to cellular compartments or organelles, such as the ER lumen include the ER retention signal (KDEL (SEQ ID NO:349)).

In certain embodiments, the polynucleotide may comprise an ATG start codon for location to the cytoplasm.

In certain embodiments, the polynucleotide may encode the VHH as such, as a combination with one or more identical or different VHHs, or as a combination with one or more identical or different VHHs with a fragment crystallizable region (Fc region); optionally with a spacer.

The term "fragment crystallizable region" or "Fc region" refers to the tail region of an antibody. The Fc region may interact with cell surface receptors called Fc receptors and some proteins of the complement system. The Fc region of IgG, IgA and IgD antibody isotypes is composed of two identical protein fragments, derived from the second and third constant domains of the antibody's two heavy chains. The Fc region of IgM and IgE contains three heavy chain constant domains (CH domains 2 to 4) in each polypeptide chain.

Such an Fc region may advantageously enhance the stability of the VHH and/or may increase the expression of the VHH.

In certain embodiments, the Fc region may be an Fc region of an IgG antibody, an IgA antibody, an IgD antibody, an IgM antibody, or an IgE antibody. In certain preferred embodiments, the Fc region may be an Fc region of an IgG antibody, an IgA antibody, or an IgD antibody. In certain more preferred embodiments, the Fc region may be an Fc region of an IgG antibody.

In certain embodiments, the Fc region may be an Fc region of a mouse antibody (i.e., mouse Fc region). In certain preferred embodiments, the Fc region may be an Fc region of a human antibody (i.e., human Fc region).

In certain preferred embodiments, the Fc region may be the Fc region of mouse IgG3 antibody. In certain preferred embodiments, the Fc region may be the Fc region of the human IgG1 antibody (hGFc; Van Droogenbroeck et al., 2007, *Proc. Natl. Acad. Sci. U.S.A.* 104 (4):1430-5).

The term "monovalent" as used herein refers to an antibody or antibody fragment comprising one binding site.

The term "bivalent" as used herein refers to an antibody or antibody fragment comprising two or more binding sites.

The terms "spacer" or "linker," as used herein interchangeably, refer to at least one amino acid spatially separating at least two VHHs. An exemplary spacer includes the 9GS spacer consisting of GGGGSGGGS (SEQ ID NO:352).

In certain embodiments of the transgenic plants or plant tissues or plant cells, methods, or uses, as taught herein, the VHHs as disclosed herein may be optionally linked to one or more further groups, moieties, or residues via one or more linkers. These one or more further groups, moieties or residues can serve for binding to other targets of interest. It should be clear that such further groups, residues, moieties and/or binding sites may or may not provide further functionality to the VHH as disclosed herein and may or may not modify the properties of the VHH as disclosed herein. Such groups, residues, moieties or binding units may also, for example, be chemical groups that can be biologically active.

These groups, moieties or residues are, in particular embodiments, linked N- or C-terminally to the VHH as disclosed herein.

For example, the introduction or linkage of such functional groups to a variable domain heavy-chain antibody can result in an increase in the solubility and/or the stability of the variable domain heavy-chain antibody, in a reduction of the toxicity of the variable domain heavy-chain antibody, or in the elimination or attenuation of any undesirable side effects of the variable domain heavy-chain antibody, and/or in other advantageous properties.

In particular embodiments, the one or more groups, residues, moieties are linked to the variable domain heavy-chain antibody via one or more suitable linkers or spacers.

In further particular embodiments, two or more target-specific variable domain heavy-chain antibodies disclosed herein may be linked to each other or may be interconnected. In particular embodiments, the two or more variable domain heavy-chain antibodies may be linked to each other via one or more suitable linkers or spacers. Suitable spacers or linkers for use in the coupling of different variable domain heavy-chain antibodies as disclosed herein will be clear to the skilled person and may generally be any linker or spacer used in the art to link peptides and/or proteins.

Some particularly suitable linkers or spacers include, for example, but are not limited to, polypeptide linkers such as glycine linkers, serine linkers, mixed glycine/serine linkers, glycine- and serine-rich linkers or linkers composed of largely polar polypeptide fragments, or homo- or heterobifunctional chemical crosslinking compounds such as glutaraldehyde or, optionally PEG-spaced, maleimides or NHS esters.

For example, a polypeptide linker or spacer may be a suitable amino acid sequence having a length between 1 and 50 amino acids, such as between 1 and 30, and, in particular, between 1 and 10 amino acid residues. It should be clear that the length, the degree of flexibility and/or other properties of the linker(s) may have some influence on the properties of the VHHs, including but not limited to the affinity, specificity or avidity for the fungal target. It should be clear that when two or more linkers are used, these linkers may be the same or different. In the context and disclosure of this application, the person skilled in the art will be able to determine the optimal linkers for the purpose of coupling VHHs as disclosed herein without any undue experimental burden.

"Selectable marker," "selectable marker gene" or "reporter gene" includes any gene that confers a phenotype on a cell in which it is expressed to facilitate the identification and/or selection of cells that are transfected or transformed with a nucleic acid construct of the disclosure. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptll that phosphorylates neomycin and kanamycin, or hpt, phosphorylating hygromycin, or genes conferring resistance to, for example, bleomycin, streptomycin, tetracycline, chloramphenicol, ampicillin, gentamycin, geneticin (G418), spectinomycin or blasticidin), to herbicides (for example, bar that provides resistance to BASTA®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilization of xylose, or antinutritive markers such as the resistance to 2-deoxyglucose). Expression of visual marker genes results in the formation of color (for example, β-glucuronidase, GUS or β-galactosidase with its colored substrates, for example, X-Gal), luminescence (such as the luciferin/luciferase system) or fluorescence (Green Fluorescent Protein, GFP, and derivatives thereof). This list represents only a small number of possible markers. The skilled worker is familiar with such markers.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can, for example, be used in mutants, in which these genes are not functional by, for example, deletion by conventional methods. Furthermore, nucleic acid molecules encoding a selectable marker can be introduced into a host cell on the same vector that comprises the sequence encoding the polypeptides of the disclosure or used in the methods of the disclosure, or else in a separate vector. Cells that have been stably transfected with the introduced nucleic acid can be identified, for example, by selection (for example, cells that have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the disclosure for introducing the nucleic acids advantageously employs techniques that enable the removal or excision of these marker genes. One such a method is what is known as co-transformation. The co-transformation method employs two vectors simultaneously for the transformation, one vector bearing the nucleic acid according to the disclosure and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e., the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed that make possible, or facilitate, the detection of such events. A further advantageous method relies on what is known as recombination systems; whose advantage is that elimination by crossing can be dispensed with. The best-known system of this type is what is known as the Cre/lox system. Crel is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., *J. Biol. Chem.* 275, 2000:22255-22267; Velmurugan et al., *J. Cell. Biol.* 149, 2000:553-566). A site-specific integration into the plant genome of the nucleic acid sequences according to the disclosure is possible.

A transgenic plant for the purposes of the disclosure is thus understood as meaning, as above, that the nucleic acids used in the method of the disclosure are not present in, or originating from, the genome of the plant, or are present in the genome of the plant but not at their natural locus in the genome of the plant, it being possible for the nucleic acids to be expressed homologously or heterologously. However, as mentioned, transgenic also means that, while the nucleic acids according to the disclosure or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the disclosure at an unnatural locus in the genome, i.e., homologous or, heterologous expression of the nucleic acids takes place. Preferred transgenic plants are mentioned herein.

The term "expression" or "gene expression" means the transcription of a specific gene or specific genes or specific genetic construct. The term "expression" or "gene expression," as used herein, refers to transcription of a polynucleotide or gene or genetic construct into structural RNA (rRNA, tRNA) or mRNA with or without subsequent translation of the latter into a protein. The process includes transcription of DNA and processing of the resulting mRNA product.

The term "increased expression" or "overexpression" as used herein means any form of expression that is additional to the original wild-type expression level. For the purposes of this disclosure, the original wild-type expression level might also be zero, i.e., absence of expression or immeasurable expression.

Methods for increasing expression of genes or gene products are well documented in the art and include, for example, overexpression driven by appropriate promoters (as described herein before), the use of transcription enhancers or translation enhancers. Isolated nucleic acids that serve as promoter or enhancer elements may be introduced in an appropriate position (typically upstream) of a non-heterologous form of a polynucleotide so as to upregulate expression of a nucleic acid encoding the polypeptide of interest. If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) *Mol. Cell Biol.* 8:4395-4405; Callis et al. (1987) *Genes Dev.* 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: *The Maize Handbook*, Chapter 116, Freeling and Walbot, Eds., Springer, N.Y. (1994).

The term "encoding," as used herein, refers to the transcription of a polynucleotide or gene or genetic construct into structural RNA (rRNA, tRNA) or mRNA with the subsequent translation of the latter into a protein.

The term "introduction" or "transformation" as referred to herein encompass the transfer of an exogenous polynucleotide or chimeric gene (or expression cassette) into a host cell, irrespective of the method used for transfer. Plant tissue or plant cells capable of subsequent clonal propagation, whether by organogenesis or embryogenesis, may be transformed with a genetic construct of this disclosure and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen, and microprojection. Methods may be selected from the calcium/polyethylene glycol method for protoplasts (F. A. Krens et al., (1982) *Nature* 296:72-74; I. Negrutiu et al. (1987) *Plant Mol. Biol.* 8:363-373); electroporation of protoplasts (R. D. Shillito et al. (1985) *Bio/Technol.* 3:1099-1102); microinjection into plant material (A. Crossway et al. (1986) *Mol. Gen. Genet.* 202:179-185); DNA or RNA-coated particle bombardment (T. M. Klein et al. (1987) *Nature* 327:70) infection with (non-integrative) viruses and the like.

Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the disclosure to allow a suspension of transformed agrobacteria to act on the intact plant or at least on the flower primordia. The plant is subsequently grown on until the seeds of the treated plant are obtained (Clough and Bent, *Plant J.* (1998) 16, 735-743). Methods for *Agrobacterium*-mediated transformation of rice include well-known methods for rice transformation, such as those described in any of the following: European patent application EP1198985, Aldemita and Hodges (*Planta* 199:612-617, 1996); Chan et al. (*Plant Mol. Biol.* 22 (3):491-506, 1993), Hiei et al. (*Plant J.* 6 (2):271-282, 1994), which disclosures are incorporated by reference herein as if fully set forth. In the case of corn transformation, the preferred method is as described in either Ishida et al. (*Nat. Biotechnol.* 14 (6):745-50, 1996) or Frame et al. (*Plant Physiol.* 129 (1):13-22, 2002), which disclosures are incorporated by reference herein as if fully set forth. The methods are further described by way of example in B. Jenes et al., "Techniques for Gene Transfer" in: *Transgenic Plants*, Vol. 1, Engineering and Utilization, eds. S. D. Kung and R. Wu, Academic Press (1993) 128-143 and in *Potrykus Annu. Rev. Plant Physiol. Plant Molec. Biol.* 42:205-225 (1991)). The nucleic acids or the construct to be expressed is preferably cloned into a vector, which is suitable for transforming *Agrobacterium tumefaciens*, for example, pBin19 (Bevan et al. (1984) *Nucl. Acids Res.* 12-8711) or pMP90 (Koncz and Schell (1986) *Mol. Gen. Genet.* 204:383-396). Agrobacteria transformed by such a vector can then be used in known manner for the transformation of plants, such as plants used as a model, like *Arabidopsis* (*Arabidopsis thaliana* is within the scope of this disclosure, but not considered as a crop plant), or crop plants such as, by way of example, tobacco plants, for example, by immersing bruised leaves or chopped leaves in an agrobacterial solution and then culturing them in suitable media. The transformation of plants by means of *Agrobacterium tumefaciens* is described, for example, by Hofgen and Willmitzer in *Nucl. Acid Res.* (1988) 16:9877, or is known inter alia from F. F. White, "Vectors for Gene Transfer in Higher Plants," in *Transgenic Plants*, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and, in particular, those cells that develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic (K. A. Feldman and M. D. Marks (1987) *Mol. Gen. Genet.* 208:1-9; K. Feldmann (1992) in C. Koncz, N.-H. Chua and J. Shell, eds, *Methods in Arabidopsis Research*, Word Scientific, Singapore, pp. 274-289). Alternative methods are based on the repeated removal of the inflorescences and incubation of the excision site in the center of the rosette with transformed agrobacteria, whereby transformed seeds can likewise be obtained at a later point in time (Chang (1994) *Plant J.* 5:551-558; Katavic (1994) *Mol. Gen. Genet.* 245:363-370). However, an especially effective method is the vacuum infiltration method with its modifications such as the "floral dip" method. In the case of vacuum infiltration of *Arabidopsis*, intact plants under reduced pressure are treated with an agrobacterial suspension (N. Bechthold (1993) *C.R. Acad. Sci. Paris Life Sci.* 316:1194-1199), while in the case of the "floral dip" method the developing floral tissue is incubated briefly with a surfactant-treated agrobacterial suspension (S. J. Clough and A. F. Bent (1998) *The Plant J.* 16:735-743). A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process that has been schematically displayed in Klaus et al., 2004 (*Nature Biotechnology* 22 (2):225-229). Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001), "Transgenic plastids in basic research and plant biotechnology," *J. Mol. Biol.* 2001 Sep. 21; 312 (3):425-38, or P. Maliga (2003), "Progress towards commercialization of plastid transformation technology," *Trends Biotechnol.* 21:20-28. Further, biotechnological progress has recently been reported in the form of marker-free plastid transformants, which can be produced by a transient co-integrated maker gene (Klaus et al., 2004, *Nature Biotechnology* 22 (2):225-229).

The genetically modified plant cells can be regenerated via all methods with which the skilled worker is familiar. Suitable methods can be found in the abovementioned publications by S. D. Kung and R. Wu, Potrykus or Hofgen and Willmitzer.

Generally after transformation, plant cells or cell groupings are selected for the presence of one or more markers that are encoded by plant-expressible genes co-transferred with the gene of interest, following which, the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organization. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

In certain embodiments, the transgenic plant or plant tissue or plant cell may have an increased or enhanced level of a VHH as taught herein relative to (i.e., compared with) a non-modified (i.e., non-transformed or untransformed, such as wild-type) plant or plant tissue.

The level of a VHH as taught herein can be determined by any method known in the art for measuring the concentration of a protein. For instance, the level of a VHH as taught herein can be determined by an enzyme-linked immunosorbent assay (ELISA). The level of a VHH can be expressed as a percentage of the amount of VHH relative to the total protein amount.

The terms "quantity," "amount" and "level" are synonymous and generally well-understood in the art. With respect to proteins, the terms may particularly refer to an absolute quantification of the protein in a sample, or to a relative quantification of the protein in the sample, i.e., relative to another value such as relative to a reference value (e.g., the total protein content).

In certain embodiments, the transgenic plant or plant tissue or plant cell may have a level of a VHH as taught herein, which is at least 0.001% of the amount of total soluble protein in the transgenic plant or plant tissue or plant cell, in particular, in an extract of the transgenic plant or plant tissue. For example, the transgenic plant or plant tissue or plant cell may have a level of a VHH as taught herein, which is at least 0.005%, at least 0.01%, at least 0.05%, at least 0.1%, at least 0.2%, at least 0.3%, at least 0.4%, or at least 0.5% of the amount of total soluble protein in the transgenic plant or plant tissue or plant cell, in particular, in an extract of the transgenic plant or plant tissue.

Total soluble proteins of plants or plant tissues or plant cells can be extracted. Routine procedures can be used to determine the amount of total soluble protein in extracts of plants or plant tissues. Preferably, the protein concentration is determined by a colorimetric method, such as Bradford analysis known in the art. A Western blot using anti-VHH antibody fragment antibodies can be used to verify that VHH antibody fragments are expressed in transgenic plants. Preferably, anti-histidine antibodies are used to detect VHH that carry a hexahistidine tag. Preferably, anti-Fc antibodies are used to detect VHH fused to antibody Fc fragments. The concentration of VHH in a sample can be calculated comparing samples with a standard series of VHH in known amounts. The level of VHH expression can be calculated from the VHH and total soluble protein concentration.

In one aspect, the applicants herein have identified transgenic plants or plant tissues or plant cells comprising at least one VHH, which can specifically bind to a sphingolipid of a fungus and bind to a sphingolipid of a plant pathogenic fungus. Importantly, through this interaction with a specific molecular structure of the plant pathogenic fungus, the transgenic plant or plant tissue or plant cell disclosed herein is capable of controlling, modulating, inhibiting, preventing or reducing one or more biological activities of the plant pathogen, such that the growth of the plant pathogen is controlled, modulated, inhibited, prevented or reduced. In certain embodiments, the transgenic plants or plant tissues or plant cells as taught herein are capable of killing a plant pathogenic fungus through the specific interaction of at least one VHH, which can specifically bind to a sphingolipid of a fungus and which is expressed in the plant or plant tissue.

Accordingly, the transgenic plants or plant tissues or plant cells as disclosed herein can be used to modulate, such as to change, decrease or inhibit, the biological function of a plant pathogenic fungus by binding to a binding site present on a sphingolipid target of that plant pathogenic fungus thereby affecting the natural biological activities (such as, but not limited to, growth) of the plant pathogenic fungus and/or one or more biological pathways in which the structural target of that plant pathogenic fungus is involved.

In certain embodiments of the transgenic plants or plant tissues or plant cells, methods, or uses, as taught herein, the VHHs as taught herein may be capable of specific binding (as defined herein) to a plant pathogen target or a plant pathogen antigen; and more preferably capable of binding to a plant pathogen target or a plant pest antigen or plant pathogen antigen with an affinity as defined herein (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein).

In particular embodiments, the disclosure provides a transgenic plant or plant tissue or plant cell, for combating plant pests, more particularly a plant fungus, which comprises at least one polypeptide or amino acid sequence of between 80 and 200 amino acids as the active substance.

In certain embodiments, the disclosure provides a transgenic plant or plant tissue or plant cell, for combating plant pests, which comprises at least two polypeptides or at least two amino acid sequences of between 80 and 200 amino acids as the active substance.

In certain embodiments, the disclosure provides a transgenic plant or plant tissue or plant cell, for combating plant pests, which comprises at least three polypeptides or at least three amino acid sequences of between 80 and 200 amino acids as the active substance.

The transgenic plant or plant tissue or plant cell according to the disclosure for combating plant pests, as defined before, means that the transgenic plant or plant tissue or plant cell, more in particular, the VHH as defined before, encoded in the transgenic plant or plant tissue or plant cell, is able to interfere with, preferably to reduce or to arrest, the harmful effects of one or more plant pests on one or more plants, preferably crops.

Thus, in one embodiment, the transgenic plant or plant tissue or plant cell comprises a polypeptide of between 80 and 200 amino acids as the active substance.

In more specific embodiments the transgenic plant or plant tissue or plant cell comprises a polypeptide of between 80-100 amino acids, 800-120 amino acids, 80-140 amino acids, 80-160 amino acids or 80-180 amino acids.

In yet another embodiment the transgenic plant or plant tissue or plant cell comprises a polypeptide of between 100-200 amino acids, 100-180 amino acids, 100-160 amino acids, 100-150 amino acids, 100-140 amino acids or 100-120 amino acids.

In yet another embodiment the transgenic plant or plant tissue or plant cell comprises a polypeptide of between 110-200 amino acids, 110-180 amino acids, 110-160 amino acids, 110-140 amino acids or 110-130 amino acids.

In yet another embodiment, the transgenic plant or plant tissue or plant cell comprises a polypeptide of between 120-200 amino acids, 120-180 amino acids, 120-160 amino acids, or 120-140 amino acids.

In yet another embodiment, the transgenic plant or plant tissue or plant cell comprises a polypeptide of between 140-200 amino acids, 140-180 amino acids, or 140-160 amino acids.

In yet another embodiment, the transgenic plant or plant tissue or plant cell comprises a polypeptide of between 160-200 amino acids or 160-180 amino acids.

The at least one variable domain of a heavy-chain antibody (VHH) comprised in the transgenic plant or plant tissue or plant cell disclosed herein can be a naturally occurring polypeptide, or alternatively can be entirely artificially designed. Non-limiting examples of such naturally occurring polypeptides include heavy chain antibodies (hcAb).

According to particular embodiments, the disclosure provides a number of stretches of amino acid residues (i.e., small peptides) that are particularly suited for binding to a sphingolipid antigen or a sphingolipid target, such as but not limited to a fungal sphingolipid antigen or a fungal sphingolipid target.

These stretches of amino acid residues may be present in, and/or may be incorporated into, the VHH as disclosed herein, in particular, in such a way that they form (part of) the antigen binding site of that VHH. As these stretches of amino acid residues were first generated as CDR sequences of antibodies, such as heavy chain antibodies, or of $V_H$ or $V_{HH}$ sequences that were raised against a sphingolipid target (or may be based on and/or derived from such CDR sequences, as further described herein), they will also generally be referred to herein as "CDR sequences" (i.e., as CDR1 sequences, CDR2 sequences and CDR3 sequences, respectively). It should however be noted that the disclosure in its broadest sense is not limited to a specific structural role or function that these stretches of amino acid residues may have in the VHH as disclosed herein, as long as these stretches of amino acid residues allow the VHHs as disclosed herein to specifically bind to a sphingolipid target. Thus, generally, the disclosure in its broadest sense relates to transgenic plant or plant tissues or plant cells comprising at least one polynucleotide encoding a variable domain of a heavy-chain antibody (VHH) that is capable of binding to a sphingolipid target and that comprises a combination of CDR sequences as described herein.

Thus, in certain embodiments, the VHHs as disclosed herein may be variable domains that comprise at least one amino acid sequence that is chosen from the group consisting of the CDR1 sequences, CDR2 sequences and CDR3 sequences that are described herein. In particular, a heavy chain variable domain as disclosed herein may comprise at least one antigen binding site, wherein the antigen binding site comprises at least one combination of a CDR1 sequence, a CDR2 sequence and a CDR3 sequence that are described herein.

Any variable domain of a heavy-chain antibody as taught herein and having one these CDR sequence combinations is preferably such that it can specifically bind (as defined herein) to a sphingolipid target or a sphingolipid antigen, and more in particular, such that it specifically binds to a sphingolipid of a plant pathogen, in particular, with dissociation constant (Kd) of $10^{-8}$ moles/liter or less of the variable domain in solution.

Specific binding of a variable domain of a heavy-chain antibody to a sphingolipid target can be determined in any suitable manner known per se, including, for example, biopanning, Scatchard analysis and/or competitive binding assays, such as radioimmunoassays (RIA), enzyme immunoassays (EIA) and sandwich competition assays, and the different variants thereof known in the art.

In a preferred embodiment, the polypeptide of between 80 and 200 amino acids, is obtained by affinity selection against a particular pest target molecule and the polypeptide has a high affinity for the pest target molecule: typically, the dissociation constant of the binding between the polypeptide and its pest target molecule is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M.

In particular embodiments, the at least one variable domain of a heavy-chain antibody as taught herein has a minimum inhibitory concentration (MIC) value for the plant pathogenic fungus of 1.0 μg/mL or less of the variable domain in solution.

Also disclosed herein are polypeptides of between 80 and 200 amino acids or a sub-range as disclosed herein before, obtained by affinity selection to a specific plant pest target, which is able to inhibit the growth and/or the activity of a crop pest at a minimum inhibitory concentration of about 0.00001 to 1 μM. In specific embodiments the minimum inhibitory concentrations are between 0.0001 to 1 μM, are between 0.001 to 1 μM, between 0.01 to 1 μM, between 0.1 to 1 μM, between 0.0001 to 0.1 μM, between 0.001 to 0.1 μM, between 0.01 to 0.1 μM, between 0.00001 to 0.01 μM, between 0.0001 to 0.01 μM, between 0.001 to 0.01 μM.

The Minimal Inhibitory Concentration or the MIC value is the lowest concentration of an agent such as a polypeptide that inhibits the visible growth of the crop or plant pest after incubation. For example, the minimum fungicidal concentration (MFC) is considered as the lowest concentration of polypeptide that prevents growth and reduces the fungal inoculum by a 99.90% within 24 hours. MFCs (Minimal Fungal Concentrations) can be determined on agar plates but can also be conveniently determined in fluids (e.g., in microwell plates) depending on the type of the fungus and the assay conditions.

In certain embodiments of the transgenic plants or plant tissues or plant cells, methods, or uses, as taught herein, the polynucleotide may comprise a sequence encoding a VHH comprising, consisting of, or consisting essentially of a CDR1, CDR2 and CDR3 region chosen from the list of comprising:

a CDR1 region having SEQ ID NO:85, a CDR2 region having has SEQ ID NO:169, and a CDR3 region having SEQ ID NO:253, and/or a CDR1 region having SEQ ID NO:86, a CDR2 region having has SEQ ID NO:170, and a CDR3 region having SEQ ID NO:254, and/or a CDR1 region having SEQ ID NO:87, a CDR2 region having has SEQ ID NO:171, and a CDR3 region having SEQ ID NO:255, and/or a CDR1 region having SEQ ID NO:88, a CDR2 region having has SEQ ID NO:172, and a CDR3 region having SEQ ID NO:256, and/or a CDR1 region having SEQ ID NO:89, a CDR2 region having has SEQ ID NO:173, and a CDR3 region having SEQ ID NO:257, and/or a CDR1 region having SEQ ID NO:90, a CDR2 region having has SEQ ID NO:174, and a CDR3 region having SEQ ID NO:258, and/or a CDR1 region having SEQ ID NO:91, a CDR2 region having has SEQ ID NO:175, and a CDR3 region having SEQ ID NO:259, and/or a CDR1 region having SEQ ID NO:92, a CDR2 region having has SEQ ID NO:176, and a CDR3 region having SEQ ID NO:260, and/or a CDR1 region having SEQ ID NO:93, a CDR2 region having has SEQ ID NO:177, and a CDR3 region having SEQ ID NO:261, and/or a CDR1 region having SEQ ID NO:94, a CDR2 region having has SEQ ID NO:178, and a CDR3 region having SEQ ID NO:262, and/or a CDR1 region having SEQ ID NO:95, a CDR2 region having has SEQ ID NO:179, and a CDR3 region having SEQ ID NO:263, and/or a CDR1 region having SEQ ID NO:96, a CDR2 region having has SEQ ID NO:180, and a CDR3 region having SEQ ID NO:264, and/or a CDR1 region having SEQ ID NO:97, a CDR2 region having has SEQ ID NO:181, and a CDR3 region having SEQ ID NO:265, and/or a CDR1 region having SEQ ID NO:98, a CDR2 region having has SEQ ID NO:182, and a CDR3 region having SEQ ID NO:266, and/or a CDR1 region having SEQ ID NO:99, a CDR2 region having has SEQ ID NO:183, and a CDR3 region having SEQ ID NO:267, and/or a CDR1 region having SEQ ID NO:100, a CDR2 region having has SEQ ID NO:184, and a CDR3 region having SEQ ID NO:268, and/or a CDR1 region having SEQ ID NO:101, a CDR2 region having has SEQ ID NO:185, and a CDR3 region having SEQ ID NO:269, and/or a CDR1 region having SEQ ID NO:102, a CDR2 region having has SEQ ID NO:186, and a CDR3 region having SEQ ID NO:270, and/or a CDR1 region having SEQ ID NO:103, a CDR2 region having has SEQ ID NO:187, and a CDR3 region having SEQ ID NO:271, and/or a CDR1 region having SEQ ID NO:104, a CDR2 region having has SEQ ID NO:188, and a CDR3 region having SEQ ID NO:272, and/or a CDR1 region having SEQ ID NO:105, a CDR2 region having has SEQ ID NO:189, and a CDR3 region having SEQ ID NO:273, and/or a CDR1 region having SEQ ID NO:106, a CDR2 region having has SEQ ID NO:190, and a CDR3 region having SEQ ID NO:274, and/or a CDR1 region having SEQ ID NO:107, a CDR2 region having has SEQ ID NO:191, and a CDR3 region having SEQ ID NO:275, and/or a CDR1 region having SEQ ID NO:108, a CDR2 region having has SEQ ID NO:192, and a CDR3 region having SEQ ID NO:276, and/or a CDR1 region having SEQ ID NO:109, a CDR2 region having has SEQ ID NO:193, and a CDR3 region having SEQ ID NO:277, and/or a CDR1 region having SEQ ID NO:110, a CDR2 region having has SEQ ID NO:194, and a CDR3 region having SEQ ID NO:278, and/or a CDR1 region having SEQ ID NO:111, a CDR2 region having has SEQ ID NO:195, and a CDR3 region having SEQ ID NO:279, and/or a CDR1 region having SEQ ID NO:112, a CDR2 region having has SEQ ID NO:196, and a CDR3 region having SEQ ID NO:280, and/or a CDR1 region having SEQ ID NO:113, a CDR2 region having has SEQ ID NO:197, and a CDR3 region having SEQ ID NO:281, and/or a CDR1 region having SEQ ID NO:114, a CDR2 region having has SEQ ID NO:198, and a CDR3 region having SEQ ID NO:282, and/or a CDR1 region having SEQ ID NO:115, a CDR2 region having has SEQ ID NO:199, and a CDR3 region having SEQ ID NO:283, and/or a CDR1 region having SEQ ID NO:116, a CDR2 region having has SEQ ID NO:200, and a CDR3 region having SEQ ID NO:284, and/or a CDR1 region having SEQ ID NO:117, a CDR2 region having has SEQ ID NO:201, and a CDR3 region having SEQ ID NO:285, and/or a CDR1 region having SEQ ID NO:118, a CDR2 region having has SEQ ID NO:202, and a CDR3 region having SEQ ID NO:286, and/or a CDR1 region having SEQ ID NO:119, a CDR2 region having has SEQ ID NO:203, and a CDR3 region having SEQ ID NO:287, and/or a CDR1 region having SEQ ID NO:120, a CDR2 region having has SEQ ID NO:204, and a CDR3 region having SEQ ID NO:288, and/or a CDR1 region having SEQ ID NO:121, a CDR2 region having has SEQ ID NO:205, and a CDR3 region having SEQ ID NO:289, and/or a CDR1 region having SEQ ID NO:122, a CDR2 region having has SEQ ID NO:206, and a CDR3 region having SEQ ID NO:290, and/or a CDR1 region having SEQ ID NO:123, a CDR2 region having has SEQ ID NO:207, and a CDR3 region having SEQ ID NO:291, and/or a CDR1 region having SEQ ID NO:124, a CDR2 region having has SEQ ID NO:208, and a CDR3 region having SEQ ID NO:292, and/or a CDR1 region having SEQ ID NO:125, a CDR2 region having has SEQ ID NO:209, and a CDR3 region having SEQ ID NO:293, and/or a CDR1 region having SEQ ID NO:126, a CDR2 region having has SEQ ID NO:210, and a CDR3 region having SEQ ID NO:294, and/or a CDR1 region having SEQ ID NO:127, a CDR2 region having has SEQ ID NO:211, and a CDR3 region having SEQ ID NO:295, and/or a CDR1 region having SEQ ID NO:128, a CDR2 region having has SEQ ID NO:212, and a CDR3 region having SEQ ID NO:296, and/or a CDR1 region having SEQ ID NO:129, a CDR2 region having has SEQ ID NO:213, and a CDR3 region having SEQ ID NO:297, and/or a CDR1 region having SEQ ID NO:130, a CDR2 region having has SEQ ID NO:214, and a CDR3 region having SEQ ID NO:298, and/or a CDR1 region having SEQ ID NO:131, a CDR2 region having has SEQ ID NO:215, and a CDR3 region having SEQ ID NO:299, and/or
a CDR1 region having SEQ ID NO:132, a CDR2 region having has SEQ ID NO:216, and a CDR3 region having SEQ ID NO:300, and/or
a CDR1 region having SEQ ID NO:133, a CDR2 region having has SEQ ID NO:217, and a CDR3 region having SEQ ID NO:301, and/or
a CDR1 region having SEQ ID NO:134, a CDR2 region having has SEQ ID NO:218, and a CDR3 region having SEQ ID NO:302, and/or
a CDR1 region having SEQ ID NO:135, a CDR2 region having has SEQ ID NO:219, and a CDR3 region having SEQ ID NO:303, and/or
a CDR1 region having SEQ ID NO:136, a CDR2 region having has SEQ ID NO:220, and a CDR3 region having SEQ ID NO:304, and/or
a CDR1 region having SEQ ID NO:137, a CDR2 region having has SEQ ID NO:221, and a CDR3 region having SEQ ID NO:305, and/or
a CDR1 region having SEQ ID NO:138, a CDR2 region having has SEQ ID NO:222, and a CDR3 region having SEQ ID NO:306, and/or
a CDR1 region having SEQ ID NO:139, a CDR2 region having has SEQ ID NO:223, and a CDR3 region having the amino acid sequence NRY, and/or
a CDR1 region having SEQ ID NO:140, a CDR2 region having has SEQ ID NO:224, and a CDR3 region having SEQ ID NO:307, and/or
a CDR1 region having SEQ ID NO:141, a CDR2 region having has SEQ ID NO:225, and a CDR3 region having SEQ ID NO:308, and/or
a CDR1 region having SEQ ID NO:142, a CDR2 region having has SEQ ID NO:226, and a CDR3 region having SEQ ID NO:309, and/or
a CDR1 region having SEQ ID NO:143, a CDR2 region having has SEQ ID NO:227, and a CDR3 region having SEQ ID NO:310, and/or
a CDR1 region having SEQ ID NO:144, a CDR2 region having has SEQ ID NO:228, and a CDR3 region having SEQ ID NO:311, and/or
a CDR1 region having SEQ ID NO:145, a CDR2 region having has SEQ ID NO:229, and a CDR3 region having SEQ ID NO:312, and/or
a CDR1 region having SEQ ID NO:146, a CDR2 region having has SEQ ID NO:230, and a CDR3 region having SEQ ID NO:313, and/or
a CDR1 region having SEQ ID NO:147, a CDR2 region having has SEQ ID NO:231, and a CDR3 region having SEQ ID NO:314, and/or
a CDR1 region having SEQ ID NO:148, a CDR2 region having has SEQ ID NO:232, and a CDR3 region having SEQ ID NO:315, and/or
a CDR1 region having SEQ ID NO:149, a CDR2 region having has SEQ ID NO:233, and a CDR3 region having SEQ ID NO:316, and/or
a CDR1 region having SEQ ID NO:150, a CDR2 region having has SEQ ID NO:234, and a CDR3 region having SEQ ID NO:317, and/or
a CDR1 region having SEQ ID NO:151, a CDR2 region having has SEQ ID NO:235, and a CDR3 region having SEQ ID NO:318, and/or
a CDR1 region having SEQ ID NO:152, a CDR2 region having has SEQ ID NO:236, and a CDR3 region having SEQ ID NO:319, and/or
a CDR1 region having SEQ ID NO:153, a CDR2 region having has SEQ ID NO:237, and a CDR3 region having SEQ ID NO:320, and/or
a CDR1 region having SEQ ID NO:154, a CDR2 region having has SEQ ID NO:238, and a CDR3 region having SEQ ID NO:321, and/or
a CDR1 region having SEQ ID NO:155, a CDR2 region having has SEQ ID NO:239, and a CDR3 region having SEQ ID NO:322, and/or
a CDR1 region having SEQ ID NO:156, a CDR2 region having has SEQ ID NO:240, and a CDR3 region having SEQ ID NO:323, and/or
a CDR1 region having SEQ ID NO:157, a CDR2 region having has SEQ ID NO:241, and a CDR3 region having SEQ ID NO:324, and/or
a CDR1 region having SEQ ID NO:158, a CDR2 region having has SEQ ID NO:242, and a CDR3 region having SEQ ID NO:325, and/or
a CDR1 region having SEQ ID NO:159, a CDR2 region having has SEQ ID NO:243, and a CDR3 region having SEQ ID NO:326, and/or
a CDR1 region having SEQ ID NO:160, a CDR2 region having has SEQ ID NO:244, and a CDR3 region having SEQ ID NO:327, and/or
a CDR1 region having SEQ ID NO:161, a CDR2 region having has SEQ ID NO:245, and a CDR3 region having SEQ ID NO:328, and/or
a CDR1 region having SEQ ID NO:162, a CDR2 region having has SEQ ID NO:246, and a CDR3 region having SEQ ID NO:329, and/or
a CDR1 region having SEQ ID NO:163, a CDR2 region having has SEQ ID NO:247, and a CDR3 region having SEQ ID NO:330, and/or
a CDR1 region having SEQ ID NO:164, a CDR2 region having has SEQ ID NO:248, and a CDR3 region having SEQ ID NO:331, and/or
a CDR1 region having SEQ ID NO:165, a CDR2 region having has SEQ ID NO:249, and a CDR3 region having SEQ ID NO:332, and/or
a CDR1 region having SEQ ID NO:166, a CDR2 region having has SEQ ID NO:250, and a CDR3 region having SEQ ID NO:333, and/or
a CDR1 region having SEQ ID NO:167, a CDR2 region having has SEQ ID NO:251, and a CDR3 region having SEQ ID NO:334, and/or
a CDR1 region having SEQ ID NO:168, a CDR2 region having has SEQ ID NO:252, and a CDR3 region having SEQ ID NO:335.

In certain embodiments of the transgenic plants or plant tissues or plant cells, methods, or uses, as taught herein, the polynucleotide may comprise a sequence encoding a VHH comprising a CDR1, CDR2 and CDR3 region chosen from the list of comprising:

a CDR1 region having SEQ ID NO:85, a CDR2 region having has SEQ ID NO:169, and a CDR3 region having SEQ ID NO:253, and/or
a CDR1 region having SEQ ID NO:86, a CDR2 region having has SEQ ID NO:170, and a CDR3 region having SEQ ID NO:254.

In certain embodiments of the transgenic plants or plant tissues or plant cells, methods, or uses, as taught herein, the polynucleotide may comprise a sequence encoding a VHH comprising a CDR1 region having SEQ ID NO:85, a CDR2 region having has SEQ ID NO:169, and a CDR3 region having SEQ ID NO:253.

In certain embodiments of the transgenic plants or plant tissues or plant cells, methods, or uses, as taught herein, the polynucleotide may comprise a sequence encoding a VHH comprising a CDR1 region having SEQ ID NO:86, a CDR2 region having has SEQ ID NO:170, and a CDR3 region having SEQ ID NO:254.

In particular embodiments, the VHH as taught herein are heavy chain variable domains that essentially consist of four framework regions (FR1 to FR4, respectively) and three complementarity-determining regions (CDR1 to CDR3, respectively); or any suitable fragment of such an heavy chain variable domain (which will then usually contain at least some of the amino acid residues that form at least one of the CDRs, as further described herein).

Functional variants of the VHH as taught herein may, in particular, be a domain antibody (or an heavy chain variable domain that is suitable for use as a domain antibody), a single domain antibody (or an heavy chain variable domain that is suitable for use as a single domain antibody), or a "dAb" (or an heavy chain variable domain that is suitable for use as a dAb); other single variable domains, or any suitable fragment of any one thereof. For a general description of (single) domain antibodies, reference is also made to the prior art cited above, as well as to EP 0 368 684. For the term "dAbs," reference is made, for example, to Ward et al. (*Nature* 1989 Oct. 12; 341 (6242):544-6), to Holt et al., *Trends Biotechnol.* 2003, 21 (11):484-490; as well as to, for example, WO 06/030220, WO 06/003388 and other published patent applications of Domantis Ltd.

Thus, in particular embodiments, this disclosure provides a variable domain of a heavy-chain antibody with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity-determining regions 1 to 3, respectively, and are as further defined herein.

SEQ ID NOS:1 to 84 (see Table 1) give the amino acid sequences of a number of variable domains of a heavy-chain antibody that have been raised against a sphingolipid target, in particular, against glucosylceramide.

TABLE 1

VHH sequences

| Name | SEQ ID | VHH Amino acid sequence |
|---|---|---|
| 41D01 | 1 | QVQLQESGGGLVQAGGSLRLSCAASGRTFSRYGMGWFRQLPGKQRELVTSIT RGGTTTYADSVKGRFTISRDNAKNTVYLQMNSLKPEDTAVYYCNARSIWRDY WGQGTQVTVSS |
| 56F11 | 2 | QVQLQESGGGLVQSGGSLRLSCVHSKTTFTRNAMGWYRQALGKERELVATIT SGGTTNYADSVKGRFTISMDSAKNTVYLQMNSLKPEDTAVYYCNVNTRRIFG GTVREYWGQGTQVTVSS |
| 40F07 | 3 | QVQLQESGGGLVQAGGSLRLSCVASGTTFSSYTMGWYRQAPGKQRELLASIE GGGNTDYADSVKGRFTISRDNARNTVYLQMNSLKTEDTAVYYCNAARTWSIF RNYWGQGTQVTVSS |
| 41D06 | 4 | QVQLQESGGGLVQAGGSLRLSCAASGGIFGINAMRWYRQAPGKQRELVASISS GGNTNYSESVKGRFTISRDDANYTVYLQMNSLKPEDTAVYYCNFVRLWFPDY WGQGTQVTVSS |
| 41G10 | 5 | QVQLQESGGGLVQPGGSLTLSCAATKTGFSINAMGWYRQAPGKQREMVATIT SGGTTNYADSVKGRFAISRDNAKNTVSLQMNTLKPEDTALYYCNTEARRYFT RASQVYWGQGTQVTVSS |
| 41H05 | 6 | QVQLQESGGGLVQPGGSLRLSCAASGGIFSINAMGWYRQDPGKQREMVATITS GANTNYTDSVKGRFTISRDNAKNTVYLQMNSLKPEDTAVYYCNAVGRRWYG GYVELWGQGTQVTVSS |
| 42C11 | 7 | QVQLQESGGGLVQPGGSLRLSCAASGSIFSTYVMGWYRQAIGKQRELVATITS SGKTNYAASVKGRFTVSRDITKNTMYLQMNSLKPEDTAVYYCGADRWVLTR WSNYWGQGTQVTVSS |
| 42C12 | 8 | QVQLQESGGGLVQPGGSLRLSCAASGSISSLGWYRQAPGKQREFVASATSGGD TTYADSVKGRFTISRDNSKNTVYLQMNSLKPEDTAVYYCKGQRGVAWTRKE YWGQGTQVTVSS |
| 50D03 | 9 | QVQLQESGGGLVQPGGSLRLSCAASGSIFSTYAMGWYRQAIGKQRELVATITS SGKTNYAASVKGRFTISRDITKNTMYLQMNSLKPEDTAVYYCGADRWVLTR WSNYWGQGTQVTVSS |
| 50D07 | 10 | QVQLQESGGGLVQPGGSLRLSCTASGNIVNIRDMGWYRQVPGKQRELVATITS DQSTNYADSVKGRFTTTRDNAKKTVYLQMDSLKPEDTAGYYCNARVRTVLR GWRDYWGQGTQVTVSS |
| 50E02 | 11 | QVQLQESGGGLVQPGGSLRLSCAASGSIFSINAMGWYRQAPGKQRELVAAITS DGSTNYADSVKGRFTISRDNAKNTAYLQMNSLKPEDTAVYYCNLRRRTFLKSS DYWGQGTQVTVSS |
| 51B08 | 12 | QVQLQESGGGLVQAGDSLRLSCAASGRRFGSYAMGWFRQVPGKERELVAGIS SGGSTKYADSVRGRFTISRDNAKNTVSLQMKSLKPEDTAVYYCNAKYGRWTY TGRPEYDSWGQGTQVTVSS |

TABLE 1-continued

| VHH sequences | | |
|---|---|---|
| Name | SEQ ID | VHH Amino acid sequence |
| 51C06 | 13 | QVQLQESGGGLVQPGGSLRLSCAASGSIFSSDTMGWYRRAPGKQRELVAAITTGGNTNYADSVKGRFTISRDNAKNTVYLQMNSLQPEDTAVYYCNCRRRWSRDFWGQGTQVTVSS |
| 51C08 | 14 | QVQLQESGGGLVQPGGSLRLSCAASGTIFSIKTMGWYRQAPGKQRELVATISNGGSTNYADSVKGRFTISRDNAKNTVYLQMNSLKPEDTAVYYCNARQQFIGAPYEYWGQGTQVTVSS |
| 52A01 | 15 | QVQLQESGGGLVQAGGSLRLSCTASGAITFSLGTMGWYRQAPGKQRELVASISTGSTNYADSVKGRFTISRDIIKNILYLQMNSLKPEDTAVYSCNARLLWSNYWGQGTQVTVSS |
| 52B01 | 16 | QVQLQESGGGLVQAGESLRLSCAASGSTFSINVMGWYRQAPGEQRELVATISRGGSTNYADSVKGRFTISRDNAKVTVYLQMDSLKPEDTAVYYCNAAGWVGVTNYWGQGTQVTVSS |
| 52G05 | 17 | QVQLQESGGGLVQAGGSLRLSCAASGSTGSISAMGWYRQAPGKQRELVASITRRGSTNYADSVKDRFTISRDNAWNTVYLQMNSLKPEDTAVYYCNARRYYTRNDYWGQGTQVTVSS |
| 53A01 | 18 | QVQLQESGGGLGQAGGSLRLSCEVSGTTFSINTMGWHRQAPGKQRELVASISSGGWTNYADSVKGRFTISRDNAKKTVYLQMNNLKPEDTAVYYCRWGAIGNWYGQGTQVTVSS |
| 53F05 | 19 | QVQLQESGGGLVQPGGSLRLSCAASVRIFGLNAMGWYRQGPGKQRELVASITTGGSTNYAEPVKGRFTISRDNANNTVYLQMNNLKPEDTAVYYCNAERRWGLPNYWGQGTQVTVSS |
| 54A02 | 20 | QVQLQESGGGLVEAGGSLRLSCAASGRTFSRYGMGWFRQAPGKEREFVAANRWSGGSTYYADSVRGRFTISRDNAKNTVYLQMNSLKPEDTAVYYCAAYAHITAWGMRNDYEYDYWGQGTQVTVSS |
| 54B01 | 21 | QVQLQESGGGLVQAGGSLRLSCAATGRTFSRYTMGWFRQAPGKERDFVAGITWTGGSTDYADSVKGRFTISRDNAKNTVYLQMNSLKPEDTAVYYCAAGNLLRLAGQLRRGYDSWGQGTQVTVSS |
| 54C01 | 22 | QVQLQESGGGLVQAGGSLRLSCAASGRTGSRYAMGWFRQAPGKEREFVAAISWSGGSTYYADSVKDRFTISRDNAKNTVYLQMHSLKPEDTAVYYCATRNRAGPHYSRGYTAGQEYDYWGQGTQVTVSS |
| 54C04 | 23 | QVQLQESGGGLVQPGGSLRLSCAASGRIFSINAMGWYRQGPGKERELVVDMTSGGSINYADSVSGRFTISRDNAKNTVYLQMNSLKPEDTAVYYCHANLRTAFWRNGNDYWGQGTQVTVSS |
| 54C08 | 24 | QVQLQESGGGLVQPGGSLRLSCAASGSISSINAMGWYRQAPGKQRELVASITSGGSTNYADSVKGRFTISRDNAKNTVNLQMNSLKPEDTAVYYCSAGPWYRRSWGRGTQVTVSS |
| 54C10 | 25 | QVQLQESGGGLVQPGESLRLSCAASASIFWVNDMGWYRQAPGKQRELVAQITRRGSTNYADSVKGRFTISRDNAKDEVYLQMNSLKPEDTAVYYCNADLAVRGRYWGQGTQVTVSS |
| 54C11 | 26 | QVQLQESGGGLVQPGGSLRLSCAASGSFFPVNDMAWYRQALGNERELVANITRGGSTNYADSVKGRFTISRDNAKNTVYLQMNTLKPEDTAVYYCNVRIGFGWTAKAYWGQGTQVTVSS |
| 54D03 | 27 | QVQLQESGGGLVQPGGSLRLSCAASGGIFGINAMRWYRQAPGKQRELVASISSGGNTNYSESVKGRFTISRDDANYTVYLQMNSLKPEDTAVYYCNFVRLWFPDYWGQGTQVTVSS |
| 54D06 | 28 | QVQLQESGGGLVQPGGSLRLSCAASGSTIRINAMGWYRQAPGKQRELVATITRGGITNYADSVKGRFTISRDNAKFTVYLQMNSLKPEDTAVYYCNARSWVGPEYWGQGTQVTVSS |
| 54D10 | 29 | QVQLQESGGGLVQPGGSLRLSCAASGMTYSIHAMGWYRQAPGKERELVAITSTSGTTDYTDSVKGRFTISRDGANNTVYLQMNSLKSEDTAVYYCHVKTRTWYNGKYDYWGQGTQVTVSS |
| 54E01 | 30 | QVQLQESGGGLVQPGGSLRLSCTASGSIFSINPMGWYRQAPGKQRELVAAITSGGSTNYADYVKGRFTISRDNAKNVVYLQMNSLKPEDTAVYYCNGRSTLWRRDYWGQGTQVTVSS |
| 54E05 | 31 | QVQLQESGGGLVQPGGSLRLSCAASGSIFSINTMGWYRQAPGKQRELVAAITNRGSTNYADFVKGRFTISRDNAKNTVYLQMNSLKPDDTAVYYCNAHRSWPRYDSWGQGTQVTVSS |

TABLE 1-continued

| VHH sequences | | |
|---|---|---|
| Name | SEQ ID | VHH Amino acid sequence |
| 54E10 | 32 | QVQLQESGGGLVQPGGSLRLSCAASGSIFSFNAMGWYRQAPGKQRELVAAITR GGSTNYADSVKGRFTISRDNANNTVYLQMNSLKPEDTAVYYCNAESRIFRRYD YWGPGTQVTVSS |
| 54F01 | 33 | QVQLQESGGGLVQPGGSLRLSCVTSGSIFGLNLMGWYRQAPGKQRELVATITR GGSTNYADSVKGRFTISRDNAKKTVYLQMNSLKPEDTAVYYCNVDRGWSSY WGQGTQVTVSS |
| 54F02 | 34 | QVQLQESGGGLVQPGGSLRLSCVTSGSIRSINTMGWYRQAPGNERELVATITSG GTTNYADSVKNRFTISRDNAKNTVYLQMNSLKPEDTAVYYCNLHQRAWARS YVYWGQGTQVTVSS |
| 54G01 | 35 | QVQLQESGGGSVQPGGSLRLSCAASGSIFAVNAMGWYRQAPGHQRELVAIISS NSTSNYADSVKGRFTISRDNAKNTVYLQMNSLKPEDTAVYFCYAKRSWFSQE YWGQGTQVTVSS |
| 54G08 | 36 | QVQLQESGGGLVQPGGSLRLSCAASGSIFSFNLMGWYRQAPGKQRELVAAITS SSNTNYADSVKGRFTISRDNAKNTVYLQMNSLKPEDTAVYYCNAQYTITPWGI KKDYWGQGTQVTVSS |
| 54G09 | 37 | QVQLQESGGGLMQPGGSLRLSCTASGNIVNIRDMGWYRQVPGKQRELVATITS DQSTNYADSVKGRFTTTRDNAKKTVYLQMDSLKPEDTAGYYCNARVRTVLR GWRDYWGQGTQVTVSS |
| 55B02 | 38 | QVQLQESGGGLVQPGESLRLSCVGSGSIFNINSMNWYRQASGKQRELVADMR SDGSTNYADSVKGRFTISRDNARKTVYLQMNSLKPEDTAVYYCHANSIFRSRD YWGQGTQVTVSS |
| 55B05 | 39 | QVQLQESGGGVVQAGDSLRLSCAASGRTFGGYTVAWFRQAPGKEREFVARIS WSGIMAYYAESVKGRFTISRDNAKNTVYLQMNSLKPEDTAVYYCASRSQIRSP WSSLDDYDRWGQGTQVTVSS |
| 55C05 | 40 | QVQLQESGGGLVQPGGSLRLSCVVSGSISSMKAMGWHRQAPGKERELVAQIT RGDSTNYADSVKGRFTISRDNAKNTVYLQMNSLKPDDTGVYYCNADRFFGRD YWGKGTQVTVSS |
| 55D08 | 41 | QVQLQESGGGLVQPGGSLRLSCAASRSILSISAMGWYRQGPGKQREPVATITSA GSSNYSDSVKGRFTISRDNAKNTAYLQMNSLKPEDTAVYYCKTVYSRPLLGPL EVWGQGTQVTVSS |
| 55E02 | 42 | QVQLQESGGGLVQTGGSLRLSCVASGSMFSSNAMAWYRQAPGKQRELVARIL SGGSTNYADSVKGRFTISRGNAKNTVYLQMNSLKPEDTAVYYCNAVRYLVNY WGQGTQVTVSS |
| 55E07 | 43 | QVQLQESGGGSVQVGDSLTLSCVASGRSLDIYGMGWFRQAPGKEREFVARITS GGSTYYADSVKGRFTLSRDNAKNTVYLQMNSLKPEDTAVYYCAAGVVVATS PKFYAYWGQGTQVTVSS |
| 55E09 | 44 | QVQLQESGGGLVQAGGSLRLSCAASKRIFSTYTMGWFRQAPGKEREFVAAIIW SGGRTRYADSVKGRFTISRDNARNTVHLQMNSLEPEDTAVYYCYTRRLGTGY WGQGTQVTVSS |
| 55E10 | 45 | QVQLQESGGGLVQAGGSLRLSCAASGSTFSIQTIGWYRQAPGKQRDRVATISS GGSTNYADSVKGRFTISRDNAKKTVYLQMNNLKPEDTAVYYCNLRYWFRDY WGQGTQVTVSS |
| 55F04 | 46 | QVQLQESGGGLVQPGGSLRLSCAASGSTFSINVRGWYRQAPGKQRELVATITS DGSTNYADSVKGRFTISRDNAKNTAYLQMNSLKPEDTAVYYCNAVRLFRQY WGQGTQVTVSS |
| 55F09 | 47 | QVQLQESGGGLVQPGGSLRLSCAASGSIFRLNAMGWYRQAPGKQRELVAAITP GGGNTTYADSVKGRFTISRDNALNTIYLQMNSLKPEDTAVYYCNAGGSSRWY SSRYYPGGYWGQGTQVTVSS |
| 55F10 | 48 | QVQLQESGGGLVQAGGSLRLSCATSGGTFSRYAMGWFRQAPGKERELVATIR RSGSSTYYLDSTKGRFTISRDNAKNTVYLQMNSLKLEDTAVYYCAADSSARAL VGGPGNRWDYWGQGTQVTVSS |
| 55G02 | 49 | QVQLQESGGGLVQPGGSLRLSCAASGSIGSINVMGWYRQYPGKQRELVAFITS GGITNYTDSVKGRFAISRDNAQNTVYLQMNSLTPEDTAVYYCHLKNAKNVRP GYWGQGTQVTVSS |
| 55G08 | 50 | QVQLQESGGGLVQPGGSLRLSCRASGGIFGINAMRWYRQAPGKQRELVASISS GGTTDYVESVKGRFTISRDNATNTVDLQMSALKPEDTAVYYCNFVRFWFPDY WGQGTQVTVSS |

TABLE 1-continued

| VHH sequences | | |
|---|---|---|
| Name | SEQ ID | VHH Amino acid sequence |
| 56A05 | 51 | QVQLQESGGGLVQAGGSLRLSCAASGITFMSNTMGWYRQAPGKQRELVASIS SGGSTNYADSVKGRFTISRDNAKKTVYLQMNSLKPEDTAVYYCNARRNVFISS WGQGTQVTVSS |
| 56A06 | 52 | QVQLQESGGGLVQPGGSLRLSCVASGSISVYGMGWYRQAPGKQRELVARITNI GTTNYADSVKGRFTISRDNAKNTVYLQMNSLQPEDTAVYYCNLRRLGRDYW GQGTQVTVSS |
| 56A09 | 53 | QVQLQESGGGLVQPGGSLRLSCAASRTALRLNSMGWYRQAPGSQRELVATIT RGGTTNYADSVKGRFTISREIGNNTVYLQMNSLEPEDTAVYYCNANFGILVGR EYWGKGTQVTVSS |
| 56C09 | 54 | QVQLQESGGGLVQAGGSLRLSCAVSGSIFSILSMAWYRQTPGKQRELVANITS VGSTNYADSVKGRFTISRDIAKKTLYLQMNNLKPEDTAIYYCNTRMPFLGDSW GQGTQVTVSS |
| 56C12 | 55 | QVQLQESGGGLVQAGGSLRLSCAVSAFSFSNRAVSWYRQAPGKSREWVASIS GIRITTYTNSVKGRFIISRDNAKKTVYLQMNDLRPEDTGVYRCYMNRYSGQGT QVTVSS |
| 56D06 | 56 | QVQLQESGGGSVQPGGSLRLSCAASGTVFFSISAMGWYRQAPGKQRELVAGIS RGGSTKYGDFVKGRFTISRDNGKKTIWLQMNNLQPEDTAIYYCRLTSITGTYL WGQGTQVTVSS |
| 56D07 | 57 | QVQLQESGGGLVQPGGSLRLSCAASGSIFSMKVMGWYRQGPGKLRELVAVIT SGGRTNYAESVKGRFTISRDNAKNTVSLQMNSLQPEDTAVYYCYYKTIRPYW GQGTQVTVSS |
| 56D10 | 58 | QVQLQESGGGLVQAGGSLRLSCAASGITFRITTMGWYRQAPGKQRELVASSSS GGTTNYASSVKGRFTISRDNAKNTVYLQMNSLRPEDTAVYYCNARKFITTPWS TDYWGQGTQVTVSS |
| 56E04 | 59 | QVQLQESGGGLVQPGDSLRLSCTPSGSIFNHKATGWYRQAPGSQRELVAKITT GGTTNYADSVKGRFTISRDNAKNTVYLQMSSLKPEDTAVYYCNAERYFATTL WGQGTQVTVSS |
| 56E05 | 60 | QVQLQESGGGLVQAGGSLRLSCAASGITFSNNAGGWYRQAPGQQRELVARISS GGNTNYTDSVKGRFTISRDITKNTLSLQMNNLKPEDSAVYYCNAQRRVILGPR NYWGQGTQVTVSS |
| 56E08 | 61 | QVQLQESGGGLVQAGGSLRLSCAASGNIFRINDMGWYRQAPGNQRELVATITS ANITNYADSVKGRFTISRDNAKNTVYLQMNSLNPEDTAVYYCTAQAKKWRIG PWSDYWGQGTQVTVSS |
| 56F07 | 62 | QVQLQESGGGLVQPGGSLRLSCAASGRIFSINDMAWYRQAPGKQRELVAIITN DDSTTYADSVKGRFTISRDNAKNTVYLQMNSLKPEDTAVYYCNADINTAIWR RKYWGQGTQVTVSS |
| 56G07 | 63 | QVQLQESGGGLVQPGGSLRLSCAVSGSRIFIHDMGWHRQAPGEPRELVATITPF GRRNYSEYVKGRFTVSRDIARNTMSLQMSNLKAEDTGMYYCNVRVNGVDY WGQGTQVTVSS |
| 56G08 | 64 | QVQLQESGGGLVQAGGSLRLSCAISGITFRRPFGISRMGWYRQAPGKERELVA TLSRAGTSRYVDSVKGRFTISRDDAKNTLYLQMVSLNPEDTAVYYCYIAQLGT DYWGQGTQVTVSS |
| 56G10 | 65 | QVQLQESGGGLVQAGGSLRLSCVASGITLRMYQVGWYRQAPGKQRELVAEIS SRGTTMYADSVKGRFTISRDGAKNIVYLQMNSLEPEDTAVYYCNARAFAFGR NSWGQGTQVTVSS |
| 56H04 | 66 | QVQLQESGGGSVQAGGSLRLSCAVSGGTFSNKAMGWYRQSSGKQRALVARIS TVGTAHYADSVKGRFTVSKDNAGNTLYLQMNSLKPEDTAVYYCNAQAGRLY LRNYWGQGTQVTVSS |
| 56H05 | 67 | QVQLQESGGGLVQPGESLRLSCVAAASTSITTFNTMAWYRQAPGKQRELVAQI NNRDNTEYADSVKGRFIISRGNAKNTSNLQMNDLKSEDTGIYYCNAKRWSWS TGFWGQGTQVTVSS |
| 56H07 | 68 | QVQLQESGGGLVQAGGSLRLSCTASGLTFALGTMGWYRQAPGKQRELVASIS TGSTNYADSVKGRFTISRDIIKNILYLQMNSLKPEDTAVYSCNARLWWSNYWG QGTQVTVSS |
| 56H08 | 69 | QVQLQESGGGLVQAGGSLRLSCTASGRTSSVNPMGWYRQAPGKQRELVAVIS SDGSTNYADSVKGRFTVSRDNAKNTLYLQMNSLKPEDTAVYYCNANRRWSW GSEYWGQGTQVTVSS |

TABLE 1-continued

VHH sequences

| Name | SEQ ID | VHH Amino acid sequence |
|---|---|---|
| 57A06 | 70 | QVQLQESGGGLVQAGGSLRLSCAASGITFTNNAGGWYRQAPGQQRELVARISS GGNTNYTDSVKGRFTISRDITKNTLSLQMNNLKPEDSAVYYCNAQRRVILGPR NYWGQGTQVTVSS |
| 57B01 | 71 | QVQLQESGGGLVQAGGSLRLSCEAPVSTFNINAMAWYRQAPGKSRELVARISS GGSTNYADSVKGRFTISRDNAKNTVYLQMNSLKPEDTAVYICYVNRHWGWD YWGQGTQVTVSS |
| 57B07 | 72 | QVQLQESGGGLVQPGGTLRLSCVASGSFRSINAMGWYRQAPGKQRELVATVD SGGYTNYADSVKGRFTISRDNAKNTVYLQMSSLTPEDTAVYYCYAGIYKWPW SVDARDYWGQGTQVTVSS |
| 57B11 | 73 | QVQLQESGGGLVQAGGSLRLSCAASGSSISMNSMGWYRQAPGKERERVALIR SSGGTYYADSVKGRFTISRDNAKNTVYLQMNNLKPEDTAVYYCQARRTWLSS ESWGQGTQVTVSS |
| 57C07 | 74 | QVQLQESGGGLVQAGGSLRLSCAVSGSTFGINTMGWYRQAPEKQRELVASISR GGMTNYADSVKGRFIISRDNAKNTVYLQMNSLKPEDTAVYVCNAGIRSRWYG GPITTYWGQGTQVTVSS |
| 57C09 | 75 | QVQLQESGGGLVQAGGSLRLSCAASGSTGSINAMGWYRQGPGKQRDLVASIS SGGATNYADSVKGRFTISRDNSKNTVYLQMSSLKPEDTAVYYCNAKKSRWSW SIVHDYWGQGTQVTVSS |
| 57D02 | 76 | QVQLQESGGGSVQTGGSLTLSCTTSGSIFGRSDMGWYRQAPGKQRELVATITR RSRTNYAEFVKGRFTISRDSAKNLVTLQMNSLKPEDTNVYYCNARWGAGGIFS TWGQGTQVTVSS |
| 57D09 | 77 | QVQLQESGGGLVQPGESLRLSCAASGSMSIDAMGWYRQAPGDQRELVASITT GGSTNYADSVKGRFTISRDNAKNTVWLQMNSLKPEDTAVYYCNAKVRLRWF RPPSDYWGQGTQVTVSS |
| 57D10 | 78 | QVQLQESGGGLVQPGGSLRLSCAASGRLLSISTMGWYRRTPEDQREMVASITK DGTTNYADSVKGRLTISRDNAKNTVYLQMNSLKPDDTAVYVCNARATTWVP YRRDAEFWGQGTQVTVSS |
| 57E07 | 79 | QVQLQESGGGLVQAGGSLRLSCAASGSIFGINDMGWYRQAPGKQRDLVADIT RSGSTHYVDSVKGRFTISRDNAKNTVYLQMNSLKPEDTAVYYCNADSGSHW WNRRDYWGQGTQVTVSS |
| 57E11 | 80 | QVQLQESGGGLVQPGGSLKLSCAASGFTFSINTMGWYRQAPGKQRELVARISR LRVTNYADSVKGRFTISRDNAKNTVYLQMNSLKPEDTAVYYCNAANWGLAG NEYWGQGTQVTVSS |
| 57G01 | 81 | QVQLQESGGGLVQAGGSLRPSCTASGSTLLINSMGWYRQAPGKQRELVATISN SGTTNYVDAVKGRFAISRDNANHTVYLQMNSLEPEDTAVYYCNAQTFWRRN YWGQGTQVTVSS |
| 57G07 | 82 | QVQLQESGGGLVQAGGSLRLSCAVSGSTSRINAMGWYRQAPGKKRESVATIR RGGNTKYADSVKGRFTISRDNANNTVYLQLNSLKPEDTAVYYCNAHSWLDY DYWGRGTQVTVSS |
| 57G08 | 83 | QVQLQESGGGLVQAGGSLRLSCASRRRINGITMGWYRQAPGKQRELVATIDIH NSTKYADSVKGRFIISRDNGKSMLYLQMNSLKPEDTAVYYCNRIPTFGRYWGQ GTQVTVSS |
| 57H08 | 84 | QVQLQESGGGLVQAGGSLRLSCVASGSTFYTFSTKNVGWYRQAPGKQRELVA QQRYDGSTNYADSLQGRFTISRDNAKRTVYLQMNSLKPEDTAVYICNVNRGFI SYWGQGTQVTVSS |

In particular, the disclosure in some specific embodiments provides transgenic plants or plant tissues or plant cells comprising a polynucleotide encoding at least one VHH that is directed against a sphingolipid target and that has at least 80%, preferably at least 85%, such as 90% or 95% or more sequence identity with at least one of the heavy chain variable domains of SEQ ID NOS:1 to 84 (see Table 1), and nucleic acid sequences that encode such heavy chain variable domains.

Some particularly preferred VHH as disclosed herein are those that can bind to and/or are directed against a sphingolipid of a plant pathogen and that have at least 90% amino acid identity with at least one of the VHH of SEQ ID NOS:1 to 84 (see Table 1), in which, for the purposes of determining the degree of amino acid identity, the amino acid residues that form the CDR sequences are disregarded.

In these heavy chain variable domains, the CDR sequences (see Table 2) are generally as further defined herein.

TABLE 2

| CDR sequences | | | | | | |
|---|---|---|---|---|---|---|
| Name | CDR1 sequence | SEQ ID | CDR2 sequence | SEQ ID | CDR3 sequence | SEQ ID |
| 41D01 | RYGMG | 85 | SITRGGTTTYADSVKG | 169 | RSIWRDY | 253 |
| 56F11 | RNAMG | 86 | TITSGGTTNYADSVKG | 170 | NTRRIFGGTVREY | 254 |
| 40F07 | SYTMG | 87 | SIEGGGNTDYADSVKG | 171 | ARTWSIFRNY | 255 |
| 41D06 | INAMR | 88 | SISSGGNTNYSESVKG | 172 | VRLWFPDY | 256 |
| 41G10 | INAMG | 89 | TITSGGTTNYADSVKG | 173 | EARRYFTRASQVY | 257 |
| 41H05 | INAMG | 90 | TITSGANTNYTDSVKG | 174 | VGRRWYGGYVEL | 258 |
| 42C11 | TYVMG | 91 | TITSSGKTNYAASVKG | 175 | DRWVLTRWSNY | 259 |
| 42C12 | ISSLG | 92 | SATSGGDTTYADSVKG | 176 | QRGVAWTRKEY | 260 |
| 50D03 | TYAMG | 93 | TITSSGKTNYAASVKG | 177 | DRWVLTRWSNY | 261 |
| 50D07 | IRDMG | 94 | TITSDQSTNYADSVKG | 178 | RVRTVLRGWRDY | 262 |
| 50E02 | INAMG | 95 | AITSDGSTNYADSVKG | 179 | RRRTFLKSSDY | 263 |
| 51B08 | SYAMG | 96 | GISSGGSTKYADSVRG | 180 | KYGRWTYTGRPEY DS | 264 |
| 51C06 | SDTMG | 97 | AITTGGNTNYADSVKG | 181 | RRRWSRDF | 265 |
| 51C08 | IKTMG | 98 | TISNGGSTNYADSVKG | 182 | RQQFIGAPYEY | 266 |
| 52A01 | LGTMG | 99 | SISTGSTNYADSVKG | 183 | RLLWSNY | 267 |
| 52B01 | INVMG | 100 | TISRGGSTNYADSVKG | 184 | AGWVGVTNY | 268 |
| 52G05 | ISAMG | 101 | SITRRGSTNYADSVKD | 185 | RRYYTRNDY | 269 |
| 53A01 | INTMG | 102 | SISSGGWTNYADSVKG | 186 | GAIGNW | 270 |
| 53F05 | LNAMG | 103 | SITTGGSTNYAEPVKG | 187 | ERRWGLPNY | 271 |
| 54A02 | RYGMG | 104 | ANRWSGGSTYYADSVR G | 188 | YAHITAWGMRND YEYDY | 272 |
| 54B01 | RYTMG | 105 | GITWTGGSTDYADSVK G | 189 | GNLLRLAGQLRRG YDS | 273 |
| 54C01 | RYAMG | 106 | AISWSGGSTYYADSVK D | 190 | RNRAGPHYSRGYT AGQEYDY | 274 |
| 54C04 | INAMG | 107 | DMTSGGSINYADSVSG | 191 | NLRTAFWRNGNDY | 275 |
| 54C08 | INAMG | 108 | SITSGGSTNYADSVKG | 192 | GPWYRRS | 276 |
| 54C10 | VNDMG | 109 | QITRRGSTNYADSVKG | 193 | DLAVRGRY | 277 |
| 54C11 | VNDMA | 110 | NITRGGSTNYADSVKG | 194 | RIGFGWTAKAY | 278 |
| 54D03 | INAMR | 111 | SISSGGNTNYSESVKG | 195 | VRLWFPDY | 279 |
| 54D06 | INAMG | 112 | TITRGGITNYADSVKG | 196 | RSWVGPEY | 280 |
| 54D10 | IHAMG | 113 | ITSTSGTTDYTDSVKG | 197 | KTRTWYNGKYDY | 281 |
| 54E01 | INPMG | 114 | AITSGGSTNYADYVKG | 198 | RSTLWRRDY | 282 |
| 54E05 | INTMG | 115 | AITNRGSTNYADFVKG | 199 | HRSWPRYDS | 283 |
| 54E10 | FNAMG | 116 | AITRGGSTNYADSVKG | 200 | ESRIFRRYDY | 284 |
| 54F01 | LNLMG | 117 | TITRGGSTNYADSVKG | 201 | DRGWSSY | 285 |
| 54F02 | INTMG | 118 | TITSGGTTNYADSVKN | 202 | HQRAWARSYVY | 286 |
| 54G01 | VNAMG | 119 | IISSNSTSNYADSVKG | 203 | KRSWFSQEY | 287 |
| 54G08 | FNLMG | 120 | AITSSSNTNYADSVKG | 204 | QYTITPWGIKKDY | 288 |

TABLE 2-continued

CDR sequences

| Name | CDR1 sequence | SEQ ID | CDR2 sequence | SEQ ID | CDR3 sequence | SEQ ID |
|---|---|---|---|---|---|---|
| 54G09 | IRDMG | 121 | TITSDQSTNYADSVKG | 205 | RVRTVLRGWRDY | 289 |
| 55B02 | INSMN | 122 | DMRSDGSTNYADSVKG | 206 | NSIFRSRDY | 290 |
| 55B05 | GYTVA | 123 | RISWSGIMAYYAESVKG | 207 | RSQIRSPWSSLDDY DR | 291 |
| 55C05 | MKAMG | 124 | QITRGDSTNYADSVKG | 208 | DRFFGRDY | 292 |
| 55D08 | ISAMG | 126 | TITSAGSSNYSDSVKG | 210 | VYSRPLLGPLEV | 294 |
| 55E07 | IYGMG | 127 | RITSGGSTYYADSVKG | 211 | GVVVATSPKFYAY | 295 |
| 55E09 | TYTMG | 128 | AIIWSGGRTRYADSVKG | 212 | RRLGTGY | 296 |
| 55E10 | IQTIG | 129 | TISSGGSTNYADSVKG | 213 | RYWFRDY | 297 |
| 55F04 | INVRG | 130 | TITSDGSTNYADSVKG | 214 | VRLFRQY | 298 |
| 55F09 | LNAMG | 131 | AITPGGGNTTYADSVKG | 215 | GGSSRWYSSRYYP GGY | 299 |
| 55F10 | RYAMG | 132 | TIRRSGSSTYYLDSTKG | 216 | DSSARALVGGPGN RWDY | 300 |
| 55G02 | INVMG | 133 | FITSGGITNYTDSVKG | 217 | KNAKNVRPGY | 301 |
| 55G08 | INAMR | 134 | SISSGGTTDYVESVKG | 218 | VRFWFPDY | 302 |
| 56A05 | SNTMG | 135 | SISSGGSTNYADSVKG | 219 | RRNVFISS | 303 |
| 56A06 | VYGMG | 136 | RITNIGTTNYADSVKG | 220 | RRLGRDY | 304 |
| 56A09 | LNSMG | 137 | TITRGGTTNYADSVKG | 221 | NFGILVGREY | 305 |
| 56C09 | ILSMA | 138 | NITSVGSTNYADSVKG | 222 | RMPFLGDS | 306 |
| 56C12 | NRAVS | 139 | SISGIRITTYTNSVKG | 223 | NRY | |
| 56D06 | ISAMG | 140 | GISRGGSTKYGDFVKG | 224 | TSITGTYL | 307 |
| 56D07 | MKVMG | 141 | VITSGGRTNYAESVKG | 225 | KTIRPY | 308 |
| 56D10 | ITTMG | 142 | SSSSGGTTNYASSVKG | 226 | RKFITTPWSTDY | 309 |
| 56E04 | HKATG | 143 | KITTGGTTNYADSVKG | 227 | ERYFATTL | 310 |
| 56E05 | NNAGG | 144 | RISSGGNTNYTDSVKG | 228 | QRRVILGPRNY | 311 |
| 56E08 | INDMG | 145 | TITSANITNYADSVKG | 229 | QAKKWRIGPWSDY | 312 |
| 56F07 | INDMA | 146 | IITNDDSTTYADSVKG | 230 | DINTAIWRRKY | 313 |
| 56G07 | IHDMG | 147 | TITPFGRRNYSEYVKG | 231 | RVNGVDY | 314 |
| 56G08 | ISRMG | 148 | TLSRAGTSRYVDSVKG | 232 | AQLGTDY | 315 |
| 56G10 | MYQVG | 149 | EISSRGTTMYADSVKG | 233 | RAFAFGRNS | 316 |
| 56H04 | NKAMG | 150 | RISTVGTAHYADSVKG | 234 | QAGRLYLRNY | 317 |
| 56H05 | FNTMA | 151 | QINNRDNTEYADSVKG | 235 | KRWSWSTGF | 318 |
| 56H07 | LGTMG | 152 | SISTGSTNYADSVKG | 236 | RLWWSNY | 319 |
| 56H08 | VNPMG | 153 | VISSDGSTNYADSVKG | 237 | NRRWSWGSEY | 320 |
| 57A06 | NNAGG | 154 | RISSGGNTNYTDSVKG | 238 | QRRVILGPRNY | 321 |
| 57B01 | INAMA | 155 | RISSGGSTNYADSVKG | 239 | NRHWGWDY | 322 |
| 57B07 | INAMG | 156 | TVDSGGYTNYADSVKG | 240 | GIYKWPWSVDARD Y | 323 |

TABLE 2-continued

| CDR sequences | | | | | | |
|---|---|---|---|---|---|---|
| Name | CDR1 sequence | SEQ ID | CDR2 sequence | SEQ ID | CDR3 sequence | SEQ ID |
| 57B11 | MNSMG | 157 | LIRSSGGTYYADSVKG | 241 | RRTWLSSES | 324 |
| 57C07 | INTMG | 158 | SISRGGMTNYADSVKG | 242 | GIRSRWYGGPITTY | 325 |
| 57C09 | INAMG | 159 | SISSGGATNYADSVKG | 243 | KKSRWSWSIVHDY | 326 |
| 57D02 | RSDMG | 160 | TITRRSRTNYAEFVKG | 244 | RWGAGGIFST | 327 |
| 57D09 | IDAMG | 161 | SITTGGSTNYADSVKG | 245 | KVRLRWFRPPSDY | 328 |
| 57D10 | ISTMG | 162 | SITKDGTTNYADSVKG | 246 | RA1TWVPYRRDAE F | 329 |
| 57E07 | INDMG | 163 | DITRSGSTHYVDSVKG | 247 | DSGSHWWNRRDY | 330 |
| 57E11 | INTMG | 164 | RISRLRVTNYADSVKG | 248 | ANWGLAGNEY | 331 |
| 57G01 | INSMG | 165 | TISNSGTTNYVDAVKG | 249 | QTFWRRNY | 332 |
| 57G07 | INAMG | 166 | TIRRGGNTKYADSVKG | 250 | HSWLDYDY | 333 |
| 57G08 | GITMG | 167 | TIDIHNSTKYADSVKG | 251 | IPTFGRY | 334 |
| 57H08 | TKNVG | 168 | QQRYDGSTNYADSLQG | 252 | NRGFISY | 335 |

Again, such VHHs may be derived in any suitable manner and from any suitable source, and may, for example, be naturally occurring $V_{HH}$ sequences (i.e., from a suitable species of Camelid) or synthetic or semi-synthetic heavy-chain variable domains, including but not limited to "camelized" immunoglobulin sequences (and, in particular, camelized heavy chain variable domain sequences), as well as those that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein.

This disclosure also encompasses parts, fragments, analogs, mutants, variants, and/or derivatives of the VHHs as disclosed herein and/or polypeptides comprising or essentially consisting of one or more of such parts, fragments, analogs, mutants, variants, and/or derivatives, as long as these parts, fragments, analogs, mutants, variants, and/or derivatives are suitable for the purposes envisaged herein. Such parts, fragments, analogs, mutants, variants, and/or derivatives according to the disclosure are still capable of specifically binding to the sphingolipid target.

Targets

In certain embodiments, the VHH as taught herein are obtained by affinity selection against a particular pest target. Obtaining suitable polypeptides by affinity selection against a particular pest target may, for example, be performed by screening a set, collection or library of cells that express polypeptides on their surface (e.g., bacteriophages) for binding against a pest target molecule, which molecule is known in the art to be a target for a pesticide; all of which may be performed in a manner known per se, essentially comprising the following non-limiting steps: a) obtaining an isolated solution or suspension of a pest target molecule, which molecule is known to be a target for a pesticide; b) biopanning phages or other cells from a polypeptide library against the target molecule; c) isolating the phages or other cells binding to the target molecule; d) determining the nucleotide sequence encoding the polypeptide insert from individual binding phages or other cells; e) producing an amount of polypeptide according to this sequence using recombinant protein expression and f) determining the affinity of the polypeptide for the pest target and optionally g) testing the pesticidal activity of the polypeptide in a bioassay for the pest. Various methods may be used to determine the affinity between the polypeptide and the pest target molecule, including, for example, enzyme linked immunosorbent assays (ELISA) or Surface Plasmon Resonance (SPR) assays, which are common practice in the art, for example, as described in Sambrook et al. (2001), *Molecular Cloning, A Laboratory Manual*, Third Edition, Cold Spring Harbor Laboratory Press, Cold Spring Harbor, N.Y. The dissociation constant is commonly used to describe the affinity between a polypeptide and its pest target molecule. Typically, the dissociation constant of the binding between the polypeptide and its pest target molecule is lower than $10^{-5}$ M, more preferably, the dissociation constant is lower than $10^{-6}$ M, even more preferably, the dissociation constant is lower than $10^{-7}$ M, most preferably, the dissociation constant is lower than $10^{-8}$ M.

Pest target molecules as disclosed herein are molecules occurring in or on pest organisms and that, when bound and/or inhibited, kill or arrest, inhibit or reduce the growth or pesticidal activity of the pest organism. Such suitable target molecules are readily available from existing literature or patent databases for the skilled person and include, without limitation secreted parasitism proteins such as 16D10 as suitable pest target molecules for root knot nematodes (Huang et al (2006) *PNAS* 103:14302-14306), the V-ATPase proton pump as suitable pest target molecule for coleopteran, hemipteran, dipteran insect species and nematodes (A. J. Knight and C. A. Behm (2011) Ex. Parasitol. September 19), the tetraspanin PLS1 as suitable fungal pest target molecule for *B. cinerea* and *M. grisea* (Gourgues et al (2002) *Biochem. Biophys. Res. Commun.* 297:1197) or the proton-pumping-ATPase as antifungal target (E. K. Manavathu et al. (1999) *Antimicrob. Agents and Chemotherapy*, December p. 2950). It is understood that preferred pest target molecules are accessible in the extra-cellular space (as opposed to intracellular pest targets).

More particularly, the sphingolipid targets to which the VHHs as disclosed herein bind, constitute a distinctive group of membrane lipids characterized by a long-chain (monounsaturated), di-hydroxy amine structure (sphingosine). Sphingolipids are essential components of the plasma membrane of cells where they are typically found in the outer leaflet. They are membrane constituents of some bacterial groups, particularly anaerobes. These groups include *Bacteroides, Prevotella, Porphyromonas, Fusobacterium, Sphingomonas, Sphingobacterium, Bdellovibrio, Cystobacter, Mycoplasma, Flectobacillus*, and possibly *Acetobacter*. Fungi in which sphingolipids have been found comprise *Saccharomyces, Candida, Histoplasma, Phytophthora, Cryptococcus, Aspergillus, Neurospora, Schizosaccharomyces, Fusicoccum, Shizophyllum, Amanita, Hansenula, Lactarius, Lentinus, Penicillium, Clitocybe, Paracoccidioides, Agaricus, Sporothrix*, and oomycete plant pathogens.

The basic building block of fungal sphingolipids is sphinganine, which can be converted either to ceramide and finally to ceramide monohexosides (CMH; cerebrosides), or to phytoceramide and finally to ceramide dihexosides (CDH) or to glycoinositol phosphorylceramides (GIPCs). Non-limiting examples of sphinglolipids against which the VHH as disclosed herein are directed include for instance 9-methyl 4,8-sphingadienine, glycosylceramides, glucosylceramide, monoglucosylceramides, oligoglucosylceramides, gangliosides, sulfatides, ceramides, sphingosine-1-phosphate, ceramide-1-phosphate, galactosylceramide, inositol-phosphorylceramide (IPC), mannosyl-inositol-phosphorylceramide (MIPC), galactosyl-inositol-phosphorylceramide, mannosyl-(inositol-phosphoryl)$_2$-ceramide (M(IP)$_2$C), dimannosyl-inositol-phosphorylceramide (M2IPC), galactosyl-dimannosyl-inositol-phosphorylceramide (GalM2IPC), mannosyl-di-inositol-diphosphorylceramide, di-inositol-diphosphorylceramide, trigalactosyl-glycosylceramide.

Non-limiting examples of sphingolipids against which the VHH as disclosed herein are directed include for instance glycosylceramides, glucosylceramide, sphingomyelin, monoglycosylceramides, oligoglycosylceramides, gangliosides, sulfatides, ceramides, sphingosine-1-phosphate and ceramide-1-phosphate.

In certain preferred embodiments of the transgenic plant or plant tissue or plant cell, methods, or uses, as taught herein, the sphingolipid is a ceramide. In a further preferred embodiment, the sphingolipid is a glycosphingolipid. In a further preferred embodiment, the sphingolipid is a cerebroside (i.e., monoglycosylceramide). In a further preferred embodiment, the sphingolipid is a glucocerebroside (i.e., glucosylceramide).

In certain preferred embodiments of the transgenic plant or plant tissue or plant cell, methods, or uses, as taught herein, the fungal sphingolipid is a fungal ceramide. In a further preferred embodiment, the fungal sphingolipid is a fungal glycosphingolipid. In a further preferred embodiment, the fungal sphingolipid is a fungal cerebroside (i.e., monoglycosylceramide). In a further preferred embodiment, the fungal sphingolipid is a fungal glucocerebroside (i.e., glucosylceramide).

In certain embodiments, the sphingolipid as described herein is glucosylceramide (glucocerebroside) from *Pleurotus citrinopileatus*.

In certain embodiments of the transgenic plants or plant tissues or plant cells, methods, or uses, as taught herein, the sphingolipid may comprise a C19 sphingoid base with a C-9 methyl group, and two double bonds (Δ4, Δ8).

In certain embodiments of the transgenic plants or plant tissues or plant cells, methods, or uses, as taught herein, the sphingolipid may have, may comprise, consist of, or be represented by any of the following structures:

9-methyl-4,8-sphingadienine

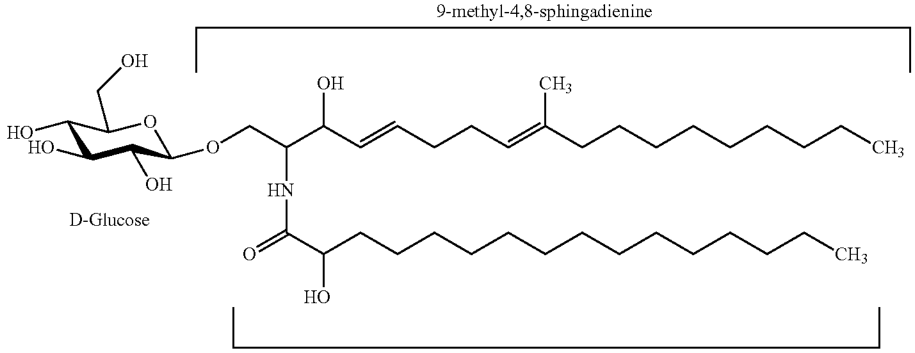

D-Glucose 2-hydroxyhexadecanoate 9-methyl-4,8-sphingadienine

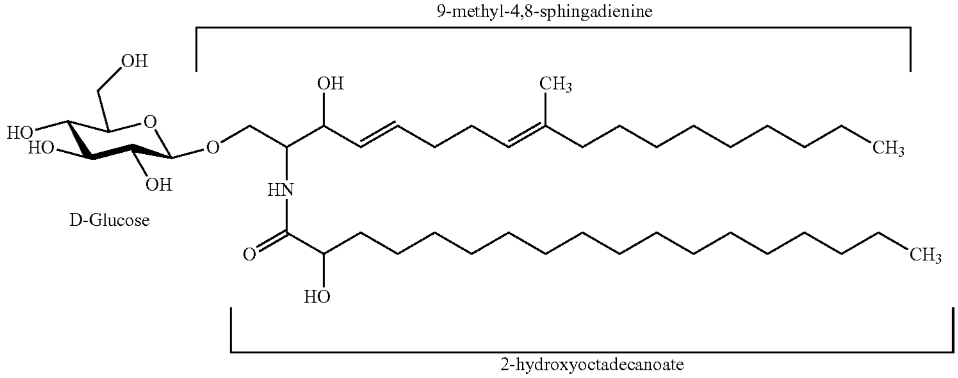

D-Glucose 2-hydroxyoctadecanoate

-continued 9-methyl-4,8-sphingadienine

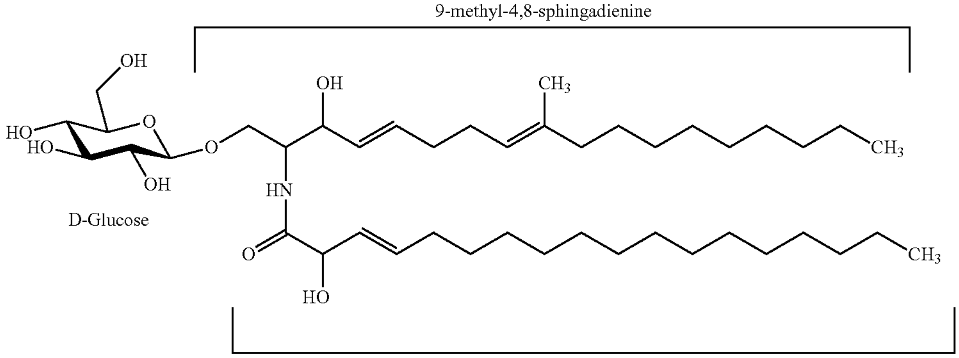

D-Glucose 2-hydroxy-3-octadecanoate 9-methyl-4,8-sphingadienine

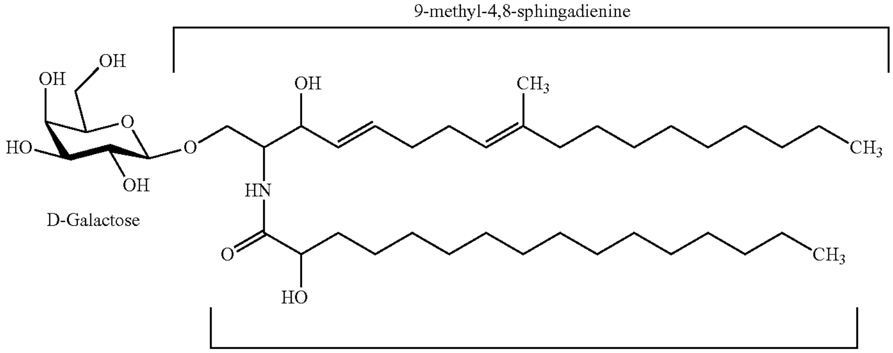

D-Galactose 2-hydroxyhexadecanoate 9-methyl-4,8-sphingadienine

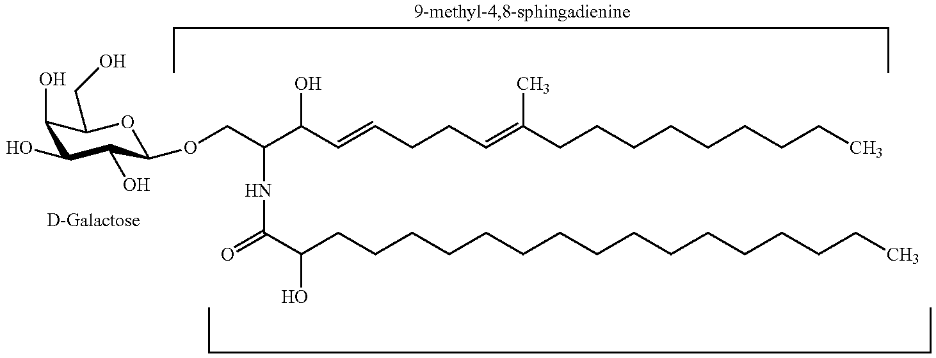

D-Galactose 2-hydroxyoctadecanoate 9-methyl-4,8-sphingadienine

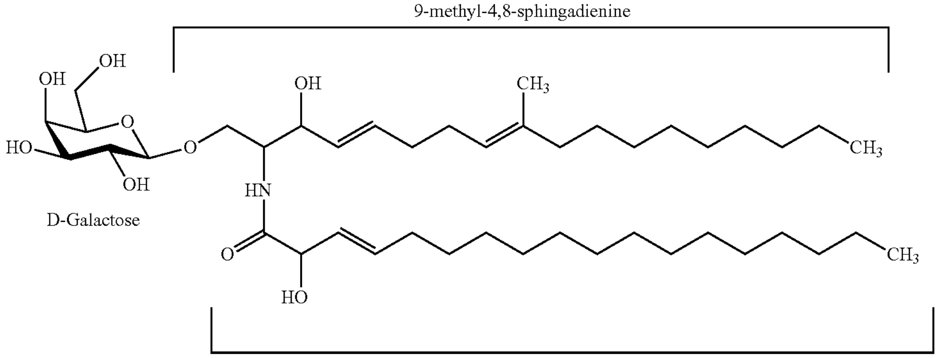

D-Galactose 2-hydroxy-3-octadecanoate

In certain embodiments of the transgenic plants or plant tissues or plant cells, methods, or uses, as taught herein, the sphingolipid as described herein may have, or comprise any of the following structures.

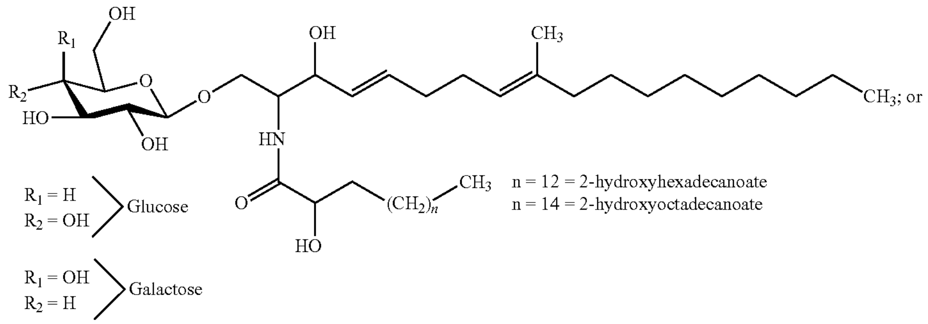

n = 12 = 2-hydroxyhexadecanoate
n = 14 = 2-hydroxyoctadecanoate or

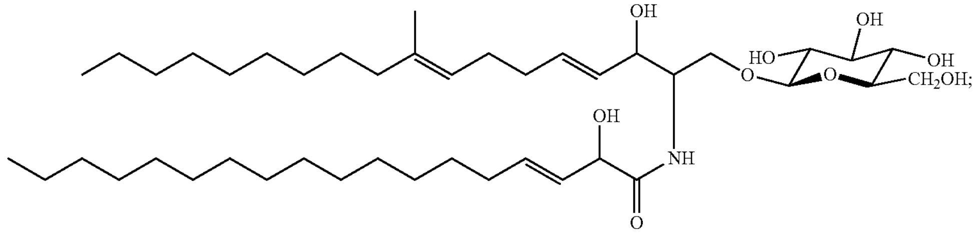

or N-2'-hydroxyhexadecanoyl-1-ß-D-glucopyranosyl-9-methyl-4,8-sphingadienine.

In certain embodiments, the plant pathogen is a fungus, such as a plant pathogenic fungus, as defined before. Fungi can be highly detrimental for plants and can cause substantial harvest losses in crops. Plant pathogenic fungi include necrotrophic fungi and biotrophic fungi, and include ascomycetes, basidiomycetes and oomycetes.

Examples of plant pathogenic fungi are known in the art and include, but are not limited to, those selected from the group consisting of the Genera: *Alternaria, Ascochyta, Botrytis, Cercospora, Colletotrichum, Diplodia, Erysiphe, Fusarium, Leptosphaeria, Gaeumanomyces, Helminthosporium, Macrophomina, Nectria, Peronospora, Phoma, Phymatotrichum, Phytophthora, Plasmopara, Podosphaera, Puccinia, Puthium, Pyrenophora, Pyricularia, Pythium, Rhizoctonia, Scerotium, Sclerotinia, Septoria, Thielaviopsis, Uncinula, Venturia*; and *Verticillium*. Specific examples of plant pathogenic fungi that may be combated by the transgenic plants or plant tissues or plant cells, methods, or uses, as taught herein include *Erysiphe graminis* in cereals, *Erysiphe cichoracearum* and *Sphaerotheca fuliginea* in cucurbits, *Podosphaera leucotricha* in apples, *Uncinula necator* in vines, *Puccinia* sp. in cereals, *Rhizoctonia* sp. in cotton, potatoes, rice and lawns, *Ustilago* sp. in cereals and sugarcane, *Venturia inaequalis* (scab) in apples, *Helminthosporium* sp. in cereals, *Septoria nodorum* in wheat, *Septoria tritici* in wheat, *Rhynchosporium secalis* on barley, *Botrytis cinerea* (gray mold) in strawberries, tomatoes and grapes, *Cercospora arachidicola* in groundnuts, *Peronospora tabacina* in tobacco, or other *Peronospora* in various crops, *Pseudocercosporella herpotrichoides* in wheat and barley, *Pyrenophera teres* in barley, *Pyricularia oryzae* in rice, *Phytophthora infestans* in potatoes and tomatoes, *Fusarium* sp. (such as *Fusarium oxysporum*) and *Verticillium* sp. in various plants, *Plasmopara viticola* in grapes, *Alternaria* sp. in fruit and vegetables, *Pseudoperonospora cubensis* in cucumbers, *Mycosphaerella fijiensis* in banana, *Ascochyta* sp. in chickpeas, *Leptosphaeria* sp. on canola, and *Colletotrichum* sp. in various crops.

In certain embodiments of the transgenic plants or plant tissues or plant cells, methods, or uses, as taught herein, the plant pathogenic fungus that may be combated by the transgenic plants or plant tissues or plant cells include the plant pathogenic fungi as defined in Table 3.

In certain embodiments of the transgenic plants or plant tissues or plant cells, methods, or uses, as taught herein, the plant pathogenic fungus that may be combated by the transgenic plants or plant tissues or plant cells include the plant pathogenic fungi as defined in Table 3 in combination with the transgenic plants or plant tissues or plant cells as defined in Table 3.

TABLE 3

List of plant pathogenic fungi and their combination with transgenic plants or plant tissues or plant cells, in particular, crops

| Crop | Plant pathogenic fungus | Common name of fungal disease |
|---|---|---|
| Banana | *Mycosphaerella fi jiensis* | Black Sigatoka |
| Banana | *Mycosphaerella musicola* | Yellow Sigatoka |
| Barley oat rye | *Alternaria* spp. | Kernel blight |
| Barley oat rye | *Puccinia hordei* | Leaf rust |
| Barley oat rye | *Drechslera graminea = Pyrenophora graminea* | Barley stripe |
| Barley oat rye | *Pyrenophora teres* | Net blotch |
| Barley oat rye | *Erysiphe graminis* f. sp. *hordei* | Powdery mildew |
| Barley oat rye | *Stagonospora nodorum* | *Stagonospora* blotch |
| Canola | *Alternaria* spp. | *Alternaria* blackspot |
| Canola | *Leptosphaeria maculans* | Blackleg |

TABLE 3-continued

List of plant pathogenic fungi and their combination with transgenic plants or plant tissues or plant cells, in particular, crops

| Crop | Plant pathogenic fungus | Common name of fungal disease |
|---|---|---|
| Canola | *Sclerotinia sclerotiorum* | *Sclerotinia* stem rot |
| Corn | *Puccinia sorghi* | Rust |
| Corn | *Colletotrichum graminicola* | Anthracnose leaf blight |
| Corn | *Aureobasidium zeae* | Eye spot |
| Corn | *Cercospora sorghi* | Gray leaf spot |
| Corn | *Setosphaeria turcica* | Northern corn leaf blight |
| Corn | *Cochliobolus carbonum* | Northern corn leaf spot |
| Corn | *Cochliobolus heterostrophus* | Southern corn leaf blight |
| Corn | *Rhizoctonia solani* | *Rhizoctonia* root and stalk rot |
| Corn | *Helmithosporium* spp. (*maydis*, *turcicum*, *carbonum*) | Leaf lights |
| Corn | *Puccinia* spp. | Rust |
| Corn | *Phytium* spp. | |
| Corn | *Cercospora zeae-maydis* | Gray Leaf Spot |
| Corn | *Physoderma maydis* | *Physoderma* Brown Spot |
| Corn | *Diplodia maydis* | *Diplodia* Ear Rot |
| Cotton | *Glomerella gossypii* | Anthracnose |
| Cotton | *Ascochyta gossypii* | *Ascochyta* blight, Boll rot |
| Cotton | *Fusarium verticillioides* | Hardlock |
| Cotton | *Puccinia schedonnardi* | Cotton rust |
| Cotton | *Puccinia cacabata* | Southwestern cotton rust |
| Cotton | *Glomerella gossypii* | Anthracnose |
| Cotton | *Puccinia cacabata* | Southwestern cotton rust |
| Cotton | *Pythium aphanidermatum* | *Pythium* seedling blight |
| Cotton | *Rhizoctonia solani* | *Rhizoctonia* seedling blight |
| Potato | *Colletotrichum coccodes* | Black dot |
| Potato | *Alternaria solani* | Early blight |
| Potato | *Phytophthora infestans* | Late blight |
| Potato | *Erysiphe cichoracearum* | Powdery mildew |
| Potato | *Rhizoctonia solani* | Black scurf |
| Potato | *Helminthosporium solani* | Silver scurf |
| Potato | *Sclerotinia sclerotiorum* | White Mold |
| Rice | *Rhizoctonia solani* | Sheath blight |
| Rice | *Ceratobasidium oryzae-sativae* = *Rhizoctonia oryzae-sativae* | Aggregate sheath spot |
| Rice | *Gaeumannomyces graminis* var. *graminis* | Black sheath rot |
| Rice | *Magnaporthe salvinii* = *Sclerotium oryzae* = *Nakateae sigmoidea* | Stem rot |
| Rice | *Cochliobolus miyabeanus* | Brown leaf spot |
| Rice | *Entyloma oryzae* | Leaf smut |
| Rice | *Cercospora janseana* = *Cercospora oryzae* | Narrow brown leaf spot |
| Rice | *Tilletia barclayana* = *Neovossia barclayana* | Kernel smut |
| Rice | *Pyricularia grisea* | Leaf/Panicle blast |
| Rice | *Ustilaginoidea virens* | False Smut |
| Soybean | *Rhizoctonia solani* | Aerial blight |
| Soybean | *Alternaria* spp. | *Alternaria* leaf spot |
| Soybean | *Colletotrichum truncatum* | Anthracnose |
| Soybean | *Septoria glycines* | Brown spot |
| Soybean | *Cercospora kikuchii* | *Cercospora* blight and leaf spot |
| Soybean | *Cercospora sojina* | Frogeye leaf spot |
| Soybean | *Diaporthe phaseolorum* | Pod and stem blight |
| Soybean | *Phakopsora* spp. | Rust |
| Soybean | *Rhizoctonia solani* | *Rhizoctonia* solani |
| Soybean | *Sclerotium rolfsii* | Southern blight |
| Soybean | *Sclerotinia sclerotiorum* | White Mold |
| Tobacco | *Peronospora tabacina* | Blue mold |
| Tobacco | *Cercospora nicotianae* | Frogeye leaf spot |
| Tobacco | *Rhizoctonia solani* | Target spot |
| Wheat | *Puccinia triticina* = *Puccinia recondita* f. sp. *tritic* | Leaf rust |
| Wheat | *Septoria tritici*, *Septoria nodorum* | *Septoria* leaf and glume blotch |
| Wheat | *Puccinia graminis* | Stem rust |
| Wheat | *Puccinia striiformis* | Stripe rust |
| Wheat | *Pyrenophora triticirepentis* | Tan spot |
| Wheat | *Erysiphe graminis* | Powdery mildew |
| Wheat | *Blumeria* spp., *Erysiphe* spp. | Powdery mildew |
| Wheat | *Stagonospora nordorum* | Glume Blotch |
| Wheat | *Blumeria* spp., *Erysiphe* spp. | Powdery mildew |
| Wheat | *Stagonospora nordorum* | Glume Blotch |
| Wheat | *Drechslera tritici-repentis* | *Helminthosporium* leaf blight |

TABLE 3-continued

List of plant pathogenic fungi and their combination with transgenic plants or plant tissues or plant cells, in particular, crops

| Crop | Plant pathogenic fungus | Common name of fungal disease |
|---|---|---|
| Wheat | *Bipolaris sorokiniana* | Spot Blotch |
| Wheat | *Tapesia* spp. | Foot Rot/Eyespot |

In certain embodiments of the transgenic plants or plant tissues or plant cells, methods, or uses, as taught herein, the plant pathogenic fungus may be a plant pathogenic fungus from the genus chosen from the group consisting of *Alternaria, Ascochyta, Botrytis, Cercospora, Colletotrichum, Diplodia, Erysiphe, Fusarium, Leptosphaeria, Gaeumanomyces, Helminthosporium, Macrophomina, Nectria, Penicillium, Peronospora, Phoma, Phymatotrichum, Phytophthora, Plasmopara, Podosphaera, Puccinia, Pyrenophora, Pyricularia, Pythium, Rhizoctonia, Scerotium, Sclerotinia, Septoria, Thielaviopsis, Uncinula, Venturia, Verticillium, Magnaporthe, Blumeria, Mycosphaerella, Ustilago, Melampsora, Phakospora, Monilinia, Mucor, Rhizopus*, and *Aspergillus*.

In certain embodiments, the transgenic plants or plant tissues or plant cells as taught herein may comprise at least one polynucleotide comprising at least one sequence encoding a VHH, which specifically binds to a sphingolipid of a fungus from the fungal species *Botrytis, Fusarium* or *Penicillium*. In further particular embodiments, the fungal sphingolipid is a ceramide, such as, in particular, glucosylceramide.

In particular embodiments, this disclosure provides transgenic plants or plant tissues or plant cells as taught herein may comprise at least one polynucleotide comprising at least one sequence encoding VHHs that are specifically directed against a structural molecular component of the fungus, i.e., a fungal sphingolipid. The applicants have surprisingly succeeded in identifying such VHHs while it is generally described in the art that it is (technically) difficult to generate proteins or amino acid sequences having a unique and specific interaction with non-protein molecular structures.

Based on the present teaching, further non-limiting examples of suitable fungal pest target molecules can be envisaged by the person skilled in the art and comprise, for example, chitin synthase, β-1,3-glucan synthase, succinate dehydrogenase, fungal glycosylceramides, or the tetraspanin PLS1.

Also disclosed herein are plant pathogenic bacteria including, but not limited to, *Acidovorax avenae* subsp. *avenae* (causing bacterial brown stripe of rice), *Acidovorax avenae* subsp. *cattleyae* (causing bacterial brown spot of cattleya), *Acidovorax konjaci* Konnyaku (causing bacterial leaf blight), *Agrobacterium rhizogenes* (causing hairy root of melon), *Agrobacterium tumefaciens* (causing crown gall), *Burkholderia andropogonis* (causing bacterial spot of carnation), *Burkholderia caryophylli* (causing bacterial wilt of carnation), *Burkholderia cepacia* (causing bacterial brown spot of cymbidium), *Burkholderia gladioli* pv. *gladioli* (causing neck rot of gladiolus), *Burkholderia glumae* (causing bacterial grain rot of rice), *Burkholderia plantarii* (causing bacterial seedling blight of rice), *Clavibacter michiganensis* subsp. *michiganensis* (causing bacterial canker of tomato), *Clavibacter michiganensis* subsp. *sepedonicus* (causing ring rot of potato), *Clostridium* spp. (causing slimy rot of potato), *Curtobacterium flaccumfaciens* (causing bacterial canker of onion), *Erwinia amylovora* (causing fire blight of pear), *Erwinia ananas* (causing bacterial palea browning of rice), *Erwinia carotovora* subsp. *atroseptica* (causing black leg of potato), *Erwinia carotovora* subsp. *carotovora* (causing bacterial soft rot of vegetables), *Erwinia chrysanthemi* (causing bacterial seedling blight of taro), *Erwinia chrysanthemi* pv. *zeae* (causing bacterial foot rot of rice), *Erwinia herbicola* pv. *millettiae* (causing bacterial gall of *wisteria*), *Pseudomonas cichorii* (causing bacterial spot of chrysanthemum), *Pseudomonas corrugate* Pith (causing necrosis of tomato), *Pseudomonas fuscovaginae* (causing sheath brown rot of rice), *Pseudomonas marginalis* pv. *marginalis* (causing soft rot of cabbage) *Pseudomonas rubrisubalbicans* (causing mottled stripe of sugar cane), *Pseudomonas syringae* pv. *aptata* (causing bacterial blight of sugar beet), *Pseudomonas syringae* pv. *atropurpurea* (causing halo blight of ryegrass), *Pseudomonas syringae* pv. *castaneae* (causing bacterial canker of chestnut), *Pseudomonas syringae* pv. *glycinea* (causing bacterial blight of soybean), *Pseudomonas syringae* pv. *lachrymans* (causing bacterial spot of cucumber), *Pseudomonas syringae* pv. *maculicola* (causing bacterial black spot of cabbage), *Pseudomonas syringae* pv. *mori* (causing bacterial blight of mulberry), *Pseudomonas syringae* pv. *morsprunorum* (causing bacterial canker of plums), *Pseudomonas syringae* pv. *oryzae* (causing halo blight of rice), *Pseudomonas syringae* pv. *phaseolicola* (causing halo blight of kidney bean), *Pseudomonas syringae* pv. *pisi* (causing bacterial blight of garden pea), *Pseudomonas syringae* pv. *sesame* (causing bacterial spot of sesame), *Pseudomonas syringae* pv. *striafaciens* (causing bacterial stripe blight of oats), *Pseudomonas syringae* pv. *syringae* (causing bacterial brown spot of small red bead), *Pseudomonas syringae* pv. *tabaci* (causing wild fire of tobacco), *Pseudomonas syringae* pv. *theae* (causing bacterial shoot blight of tea), *Pseudomonas syringae* pv. *tomato* (causing bacterial leaf spot of tomato), *Pseudomonas viridiflava* (causing bacterial brown spot of kidney bean), *Ralstonia solanacearum* (causing bacterial wilt), *Rathayibacter rathayi* (causing bacterial head blight of orchardgrass), *Streptomyces* scabies (causing common scab of potato), *Streptomyces ipomoea* (causing soil rot of sweet potato), *Xanthomonas albilineans* (causing white streak of sugar cane), *Xanthomonas campestris* pv. *cerealis* (causing bacterial streak of rye), *Xanthomonas campestris* pv. *campestris* (causing black rot), *Xanthomonas campestris* pv. *citri* (causing canker of citrus), *Xanthomonas campestris* pv. *cucurbitae* (causing bacterial brown spot of cucumber), *Xanthomonas campestris* pv. *glycines* (causing bacterial pastule of soybean), *Xanthomonas campestris* pv. *incanae* (causing black rot of stock), *Xanthomonas campestris* pv. (causing angular leaf spot of cotton *malvacearum*), *Xanthomonas campestris* pv. (causing bacterial canker of mango), *Mangiferaeindicae Xanthomonas campestris* pv. *mellea* (causing wisconsin bacterial leaf spot of tobacco), *Xanthomonas campestris* pv. (causing bacterial spot of great nigromaculans burdock), *Xanthomonas campestris* pv.

*phaseoli* (causing bacterial pastule of kidney bean), *Xanthomonas campestris* pv. *pisi* (causing bacterial stem-rot of kidney bean), *Xanthomonas campestris* pv. *pruni* (causing bacterial shot hole of peach), *Xanthomonas campestris* pv. *raphani* (causing bacterial spot of Japanese radish), *Xanthomonas campestris* pv. *ricini* (causing bacterial spot of castor-oil plant), *Xanthomonas campestris* pv. *theicola* (causing canker of tea), *Xanthomonas campestris* pv. *translucens* (causing bacterial blight of orchardgrass), *Xanthomonas campestris* pv. *vesicatoria* (causing bacterial spot of tomato), *Xanthomonas oryzae* pv. *oryzae* (causing bacterial leaf blight of rice).

Also disclosed herein are plant pests such as insects, arachnids, helminths, viruses, nematodes and molluscs encountered in agriculture, in horticulture, in forests, in gardens and in leisure facilities. The transgenic plants or plant tissues or plant cells as taught herein are active against normally sensitive and resistant species and against all or some stages of development. These plant pests include: pests from the phylum: Arthropoda, in particular, from the class of the arachnids, for example, *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Centruroides* spp., *Chorioptes* spp., *Dermanyssus gallinae, Dermatophagoides pteronyssius, Dermatophagoides farinae, Dermacentor* spp., *Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vaejovis* spp., and *Vasates lycopersici.*

Still other examples are from the order of the Anoplura (Phthiraptera), for example, *Damalinia* spp., *Haematopinus* spp., *Linognathus* spp., *Pediculus* spp., *Ptirus pubis*, and *Trichodectes* spp.

Still other examples are from the order of the Chilopoda, for example, *Geophilus* spp., and *Scutigera* spp.

Still other examples are from the order of the Coleoptera, for example, *Acalymma vittatum, Acanthoscelides obtectus, Adoretus* spp., *Agelastica alni, Agriotes* spp., *Alphitobius diaperinus, Amphimallon solstitialis, Anobium punctatum, Anoplophora* spp., *Anthonomus* spp., *Anthrenus* spp., *Apion* spp., *Apogonia* spp., *Atomaria* spp., *Atagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popilia japonica, Premnotrypes* spp., *Prostephanus truncatus, Psylliodes* spp., *Ptinus* spp., *Rhizobius ventralis, Rhizopertha dominica, Sitophilus* spp., *Sphenophorus* spp., *Stegobium paniceum, Sternechus* spp., *Symphyletes* spp., *Tanymecus* spp., *Tenebrio molitor, Tribolium* spp., *Trogoderma* spp., *Tychius* spp., *Xylotrechus* spp., and *Zabrus* spp.

Still other examples are from the order of the Collembola, for example, *Onychiurus armatus.*

Still other examples are from the order of the Diplopoda, for example, *Blaniulus guttulatus.*

Still other examples are from the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Chrysops* spp., *Cochliomyia* spp., *Contarinia* spp., *Cordylobia anthropophaga, Culex* spp., *Culicoides* spp., *Culiseta* spp., *Cuterebra* spp., *Dacus oleae, Dasyneura* spp., *Delia* spp., *Dermatobia hominis, Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Liriomyza* spp., *Lucilia* spp., *Lutzomia* spp., *Mansonia* spp., *Musca* spp., *Nezara* spp., *Oestrus* spp., *Oscinellafrit, Pegomyia* spp., *Phlebotomus* spp., *Phorbia* spp., *Phormia* spp., *Prodiplosis* spp., *Psila rosae, Rhagoletis* spp., *Sarcophaga* spp., *Simulium* spp., *Stomoxys* spp., *Tabanus* spp., *Tannia* spp., *Tetanops* spp., *Tipula* spp.

Still other examples are from the order of the Heteroptera, for example, *Anasa tristis, Antestiopsis* spp., *Boisea* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., and *Triatoma* spp.

Still other examples are from the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma pin, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp.,

*Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephalafestina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifoli*, and *Zygina* spp.

Still other examples are from the order of the Hymenoptera, for example, *Acromyrmex* spp., *Athalia* spp., *Atta* spp., *Diprion* spp., *Hoplocampa* spp., *Lasius* spp., *Monomorium pharaonis, Solenopsis invicta, Tapinoma* spp., and *Vespa* spp.

Still other examples are from the order of the Isopoda, for example, *Armadillidium vulgare, Oniscus asellus*, and *Porcello scaber.*

Still other examples are from the order of the Isoptera, for example, *Coptotermes* spp., *Cornitermes cumulans, Cryptotermes* spp., *Incisitermes* spp., *Microtermes obesi, Odontotermes* spp., and *Reticulitermes* spp.

Still other examples are from the order of the Lepidoptera, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp., *Lithocolletis* spp., *Lithophane antennata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichophaga tapetzella, Trichoplusia* spp., *Tuta absoluta, Virachola* spp.

Still other examples are from the order of the Orthoptera, for example, *Acheta domesticus, Blatta orientalis, Blattella germanica, Dichroplus* spp., *Gryllotalpa* spp., *Leucophaea maderae, Locusta* spp., *Melanoplus* spp., *Periplaneta* spp., *Pulex irritans, Schistocerca gregaria*, and *Supella longipalpa.*

Still other examples are from the order of the Siphonaptera, for example, *Ceratophyllus* spp., *Ctenocephalides* spp., *Tunga penetrans*, and *Xenopsylla cheopis.*

Still other examples are from the order of the Symphyla, for example, *Scutigerella* spp.

Still other examples are from the order of the Thysanoptera, for example, *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni*, and *Thrips* spp.

Still other examples are from the order of the Zygentoma (=Thysanura), for example, *Lepisma saccharina, Thermobia domestica*, for example, *Lepisma saccharina*, and *Thermobia domestica.*

In another embodiment, pests of the phylum Mollusca, in particular, from the class of the Bivalvia, for example, *Dreissena* spp., are also important plant pests.

In another embodiment, pests of the class of the Gastropoda are important plant pests, for example, *Anion* spp., *Biomphalaria* spp., *Bulinus* spp., *Deroceras* spp., *Galba* spp., *Lymnaea* spp., *Oncomelania* spp., *Pomacea* spp., and *Succinea* spp.

In yet another embodiment, plant pests are from the phylum Nematoda are important plant pests, i.e., phytoparasitic nematodes, thus meaning plant parasitic nematodes that cause damage to plants. Plant nematodes encompass plant parasitic nematodes and nematodes living in the soil. Plant parasitic nematodes include, but are not limited to, ectoparasites such as *Xiphinema* spp., *Longidorus* spp., and *Trichodorus* spp.; semiparasites such as *Tylenchulus* spp.; migratory endoparasites such as *Pratylenchus* spp., *Radopholus* spp., and *Scutellonerna* spp.; sedentary parasites such as *Heterodera* spp., *Globodera* spp., and *Meloidogyne* spp., and stem and leaf endoparasites such as *Ditylenchus* spp., *Aphelenchoides* spp., and *Hirshmaniella* spp. In addition, harmful root parasitic soil nematodes are cyst-forming nematodes of the genera *Heterodera* or *Globodera*, and/or root knot nematodes of the genus *Meloidogyne*. Harmful species of these genera are, for example, *Meloidogyne incognata, Heterodera glycines* (soybean cyst nematode), *Globodera pallida* and *Globodera rostochiensis* (potato cyst nematode). Still other important genera of importance as plant pests comprise *Rotylenchulus* spp., *Paratriclodorus* spp., *Pratylenchus penetrans, Radolophus simui, Ditylenchus dispaci, Tylenchulus semipenetrans, Xiphinema* spp., and *Bursaphelenchus* spp., and the like, in particular, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans*, and *Xiphinema* spp.

Also disclosed herein as being plant pests are plant viruses selected from analfamovirus, an allexivirus, an alphacryptovirus, an anulavirus, an apscaviroid, an aureusvirus, an avenavirus, an aysunviroid, a badnavirus, a begomovirus, a benyvirus, a betacryptovirus, a betaflexiviridae, a bromovirus, a bymovirus, a capillovirus, a carlavirus, a carmovirus, a caulimovirus, a cavemovirus, a cheravirus, a closterovirus, a cocadviroid, a coleviroid, a comovirus, a crinivirus, a cucumovirus, a curtovirus, a cytorhabdovirus, a dianthovirus, an enamovirus, an umbravirus and B-type satellite virus, a fabavirus, a fijivirus, a furovirus, a hordeivirus, a hostuviroid, an idaeovirus, an ilarvirus, an ipomovirus, a luteovirus, a machlomovirus, a macluravirus, a marafivirus, a mastrevirus, a nanovirus, a necrovirus, a nepovirus, a nucleorhabdovirus, an oleavirus, an ophiovirus, an oryzavirus, a panicovirus, a pecluvirus, a petuvirus, a phytoreovirus, a polerovirus, a pomovirus, a pospiviroid, a potexvirus, a potyvirus, a reovirus, a rhabdovirus, a rymovirus, a sadwavirus, a SbCMV-like virus, a sequivirus, a sobemovirus, a tenuivirus, a TNsatV-like satellite virus, a tobamovirus, a topocuvirus, a tospovirus, a trichovirus, a tritimovirus, a tungrovirus, a tymovirus, an umbravirus, a varicosavirus, a vitivirus, or a waikavirus.

In certain embodiments, this disclosure provides a transgenic plant or plant tissue or plant cell resistant to a plant pathogenic fungus, wherein the transgenic plant or plant tissue or plant cell comprises at least one polynucleotide comprising at least one sequence encoding a VHH specifically binding to a sphingolipid of a fungus.

In certain embodiments, this disclosure provides a transgenic plant or plant tissue or plant cell resistant to an infection or other biological inter-reaction with a plant pathogenic fungus, wherein the transgenic plant or plant tissue or plant cell comprises at least one polynucleotide comprising at least one sequence encoding a VHH specifically binding to a sphingolipid of a fungus.

Methods and Uses

A further aspect provides a method for protecting at least part of a plant or plant tissue or plant cell from an infection with a plant pathogen, for inhibiting the growth of a plant pathogen on at least part of a plant or plant tissue or plant cell, and/or for increasing pathogen resistance of at least part of a plant or plant tissue or plant cell, comprising expressing in at least part of the plant or plant tissue or plant cell at least one polynucleotide encoding a VHH specifically binding to a pathogen.

In certain embodiments, this disclosure provides methods for protecting or treating a plant or a part of a plant from an infection or other biological interaction with a plant pathogen, at least comprising the step of expressing in the plant or plant tissue or plant cell or in at least part of the plant or plant tissue or plant cell (i.e., in planta) a polynucleotide comprising at least one sequence encoding a VHH specifically binding to a pathogen, in particular, to a sphingolipid of a fungus. In certain embodiments, the polynucleotide may be expressed in the plant or plant tissue or plant cell or in at least part of the plant or plant tissue or plant cell (i.e., in planta) under conditions effective to protect or treat at least part of the plant or plant tissue or plant cell against that infection or biological interaction with the plant pathogen, in particular, with a plant pathogenic fungus.

In certain particular embodiments, this disclosure provides methods of inhibiting, preventing, reducing or controlling the growth of a plant pathogen, in particular, a plant pathogenic fungus, comprising at least the step of expressing in at least part of the plant or plant tissue or plant cell at least one polynucleotide encoding a VHH specifically binding to a pathogen, in particular, to a sphingolipid of a fungus.

In certain other embodiments, this disclosure provides methods for killing a plant pathogen, in particular, a plant pathogenic fungus, comprising at least the step of expressing in at least part of the plant or plant tissue or plant cell at least one polynucleotide encoding a VHH specifically binding to a pathogen, in particular, to a sphingolipid of a fungus.

In certain embodiments, this disclosure provides the use of at least one variable domain of a heavy-chain antibody (VHH) specifically binding to a pathogen, as a antimicrobial agent, preferably as a microbiostatic agent, wherein the VHH is encoded by a polynucleotide that is expressed in at least part of the plant or plant tissue.

In certain embodiments, this disclosure provides the use of the polynucleotides of SEQ ID NO:336 and/or SEQ ID NO:337 for protecting a transgenic plant or plant tissue or plant cell against a plant pathogen, preferably a plant pathogenic fungus.

In certain embodiments, this disclosure provides the use of the polynucleotides of SEQ ID NO:336 and/or SEQ ID NO:337 for improving the yield of a transgenic plant or plant tissue.

The disclosure further provides methods for preparing or generating the VHH as taught herein, as well as methods for producing polynucleotides encoding these. Some preferred but non-limiting examples of such methods will become clear from the further description herein.

As will be clear to the skilled person, one particularly useful method for preparing VHH sequences as disclosed herein generally comprises the steps of:

a) expressing a nucleotide sequence encoding a heavy chain variable domain sequence as disclosed herein or a vector or genetic construct a nucleotide sequence encoding that heavy chain variable domain sequence; and
b) optionally isolating and/or purifying the VHH sequence.

In particular embodiments envisaged herein, the pest-specific a VHH sequences can be obtained by methods that involve generating a random library of amino acid sequences and screening this library for an amino acid sequence capable of specifically binding to a sphingolipid target.

Accordingly, in particular embodiments, methods for preparing a heavy chain variable domain sequence as disclosed herein comprise the steps of a) providing a set, collection or library of amino acid sequences of a heavy chain variable domain sequences;
b) screening the set, collection or library of amino acid sequences for amino acid sequences that can bind to and/or have affinity for the sphingolipid target; and
c) isolating the amino acid sequence(s) that can bind to and/or have affinity for the sphingolipid target.

In such a method, the set, collection or library of amino acid sequences may be any suitable set, collection or library of amino acid sequences. For example, the set, collection or library of amino acid sequences may be a set, collection or library of immunoglobulin fragment sequences (as described herein), such as a naïve set, collection or library of immunoglobulin fragment sequences; a synthetic or semi-synthetic set, collection or library of immunoglobulin fragment sequences; and/or a set, collection or library of immunoglobulin fragment sequences that have been subjected to affinity maturation.

In particular embodiments of this method, the set, collection or library of amino acid sequences may be an immune set, collection or library of immunoglobulin fragment sequences, for example, derived from a mammal that has been suitably immunized with a sphingolipid target or with a suitable antigenic determinant based thereon or derived therefrom, such as an antigenic part, fragment, region, domain, loop or other epitope thereof. In one particular aspect, the antigenic determinant may be an extracellular part, region, domain, loop or other extracellular epitope(s).

In the above methods, the set, collection or library of amino acid sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art, for example, on the basis of the further disclosure herein. Reference is also made to the review by Hoogenboom in *Nature Biotechnology* 23, 9:1105-1116 (2005).

In other embodiments, the methods for generating the VHH sequences as disclosed herein comprise at least the steps of:

a) providing a collection or sample of cells expressing heavy chain variable domain amino acid sequences;
b) screening the collection or sample of cells for cells that express an amino acid sequence that can bind to and/or have affinity for a sphingolipid target; and
c) either (i) isolating the amino acid sequence; or (ii) isolating from the cell a nucleic acid sequence that encodes the amino acid sequence, followed by expressing the amino acid sequence.

The collection or sample of cells may, for example, be a collection or sample of B-cells. Also, in this method, the sample of cells may be derived from a mammal that has been suitably immunized with a fungal target or with a suitable antigenic determinant based thereon or derived therefrom, such as an antigenic part, fragment, region, domain, loop or other epitope thereof. In one particular embodiment, the antigenic determinant may be an extracellular part, region, domain, loop or other extracellular epitope(s).

In other embodiments, the method for generating a heavy chain variable domain sequence directed against a sphingolipid target may comprise at least the steps of:

a) providing a set, collection or library of nucleic acid sequences encoding a heavy chain variable domain amino acid sequence;
b) screening the set, collection or library of nucleic acid sequences for nucleic acid sequences that encode an amino acid sequence that can bind to and/or has affinity for the sphingolipid target; and
c) isolating the nucleic acid sequence, followed by expressing the amino acid sequence.

In the above methods, the set, collection or library of nucleic acid sequences encoding amino acid sequences may, for example, be a set, collection or library of nucleic acid sequences encoding a naïve set, collection or library of immunoglobulin fragment sequences; a set, collection or library of nucleic acid sequences encoding a synthetic or semi-synthetic set, collection or library of immunoglobulin fragment sequences; and/or a set, collection or library of nucleic acid sequences encoding a set, collection or library of immunoglobulin fragment sequences that have been subjected to affinity maturation.

In particular, in such a method, the set, collection or library of nucleic acid sequences encodes a set, collection, or library of VHHs. For example, the set, collection or library of nucleic acid sequences may encode a set, collection or library of domain antibodies or single domain antibodies, or a set, collection or library of amino acid sequences that are capable of functioning as a domain antibody or single domain antibody. In specific embodiments, the set, collection or library of nucleotide sequences encodes a set, collection or library of VHH sequences.

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, for example, on the basis of the further disclosure herein. Reference is also made to the review by Hoogenboom in *Nature Biotechnology* 23, 9:1105-1116 (2005).

The disclosure also relates to amino acid sequences that are obtainable or obtained by the above methods, or alternatively by a method that comprises one of the above methods and in addition at least the steps of determining the nucleotide sequence or amino acid sequence of the immunoglobulin sequence; and of expressing or synthesizing the amino acid sequence in a manner known per se, such as by expression in a suitable host cell or host organism or by chemical synthesis.

In some cases, the methods for producing the amino acid sequences binding specifically to a fungal target as envisaged herein may further comprise the step of isolating from the amino acid sequence library at least one heavy chain variable domain having detectable binding affinity for, or detectable in vitro effect on a sphingolipid target.

These methods may further comprise the step of amplifying a sequence encoding at least one heavy chain variable domain having detectable binding affinity for, or detectable in vitro effect on the activity of a sphingolipid target. For example, a phage clone displaying a particular amino acid sequence, obtained from a selection step of a method described herein, may be amplified by reinfection of a host bacteria and incubation in a growth medium.

In particular embodiments, these methods may encompass determining the sequence of the one or more amino acid sequences capable of binding to a sphingolipid target.

Where a heavy chain variable domain sequence, comprised in a set, collection or library of amino acid sequences, is displayed on a suitable cell or phage or particle, it is possible to isolate from the cell or phage or particle, the nucleotide sequence that encodes that amino acid sequence. In this way, the nucleotide sequence of the selected amino acid sequence library member(s) can be determined by a routine sequencing method.

In further particular embodiments, the methods for producing a heavy chain variable domain as envisaged herein comprise the step of expressing the nucleotide sequence(s) in a host organism under suitable conditions, so as to obtain the actual desired amino acid sequence. This step can be performed by methods known to the person skilled in the art.

In addition, the obtained heavy chain variable domain sequences having detectable binding affinity for, or detectable in vitro effect on the activity of a sphingolipid target, may be synthesized as soluble protein construct, optionally after their sequence has been identified.

For instance, the heavy chain variable domain sequences obtained, obtainable or selected by the above methods can be synthesized using recombinant or chemical synthesis methods known in the art. Also, the amino acid sequences obtained, obtainable or selected by the above methods can be produced by genetic engineering techniques. Thus, methods for synthesizing the heavy chain variable domain sequences obtained, obtainable or selected by the above methods may comprise transforming or infecting a host cell with a nucleic acid or a vector encoding an amino acid sequence having detectable binding affinity for, or detectable in vitro effect on the activity of a sphingolipid target. Accordingly, the amino acid sequences having detectable binding affinity for, or detectable in vitro effect on the activity of a sphingolipid target can be made by recombinant DNA methods. DNA encoding the amino acid sequences can be readily synthesized using conventional procedures. Once prepared, the DNA can be introduced into expression vectors, which can then be transformed or transfected into host cells such as *E. coli* or any suitable expression system, in order to obtain the expression of amino acid sequences in the recombinant host cells and/or in the medium in which these recombinant host cells reside.

It should be understood, as known by someone skilled in the art of protein expression and purification, that the VHH as taught herein produced from an expression vector using a suitable expression system may be tagged (typically at the N-terminal or C-terminal end of the amino acid sequence) with, e.g., a His-tag or other sequence tag for easy purification.

Transformation or transfection of nucleic acids or vectors into host cells may be accomplished by a variety of means known to the person skilled in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Suitable host cells for the expression of the desired heavy chain variable domain sequences may be any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic plant.

Thus, the application also provides methods for the production of heavy chain variable domain sequences having detectable binding affinity for, or detectable in vitro effect on the activity of a sphingolipid target comprising transforming, transfecting or infecting a host cell with nucleic acid sequences or vectors encoding such amino acid sequences and expressing the amino acid sequences under suitable conditions.

In other particular embodiments of these methods, the step of obtaining at least one heavy chain variable domain or functional fragment thereof, which specifically binds to a sphingolipid of a plant pathogen comprises:

a) providing a set, collection or library of VHHs or functional variants thereof, b) screening the set, collection or library of VHHs or functional variants thereof for sequences that specifically bind to and/or have affinity for a sphingolipid of a plant pathogen, and optionally c) isolating the VHHs or functional variants thereof that specifically bind to and/or have affinity for a sphingolipid of a plant pathogen.

The following non-limiting Examples describe methods and means according to the disclosure. Unless stated otherwise in the Examples, all techniques are carried out according to protocols standard in the art. The following examples are included to illustrate embodiments of the disclosure. Those of skill in the art should, in light of the present disclosure, appreciate that many changes can be made in the specific embodiments that are disclosed and still obtain a like or similar result without departing from the concept, spirit and scope of the disclosure. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

Thus, the Figures, Sequence Listing and the Experimental Part/Examples are only given to further illustrate the disclosure and should not be interpreted or construed as limiting the scope of the disclosure and/or of the appended claims in any way, unless explicitly indicated otherwise herein.

The above disclosure will now be further described by means of the following non-limiting Examples.

EXAMPLES

Example 1

Isolation of Nucleic Acid Sequences Encoding Peptides with Affinity for Fungal Glucosylceramide Animal Immunizations:

VHHs were generated from llamas immunized with fungal glucosylceramide (GlcCer). Llamas were immunized according to standard protocols with 6 boosts of thin Layer Chromatography (TLC)-purified (99%) glucosylceramide (GlcCer) from *Pleurotus citrinopileatus* (Nacalai Tesque). Purified GlcCer was dissolved in a water:methanol:chloroform mixture and spotted on a TLC silica glass plate. Silica with adsorbed GlcCer was scraped from the plate and suspended in phosphate buffer. The suspension was sonicated, mixed with Freund incomplete adjuvant, and used for subcutaneous injections. VHH were also generated from llamas immunized with native germinated fungal or oomycete spores. Llamas were immunized according to standard protocols with 6 boosts of native germinated spores of *Botrytis cinerea* or *Phytophthora infestans* by subcutaneous injections. All llamas remained healthy throughout the immunization process and blood samples were taken before and after immunizations.

Library Construction:

A phage library of antibodies is a phage population in which each individual phage exposes a unique antigen-binding antibody domain on its surface as a part of a chimeric pIII protein. Peripheral blood mononuclear cells were prepared from blood samples of the immunized llamas using Ficoll-Hypaque according to the manufacturer's instructions. Total RNA was extracted from these cells and used as starting material for RT-PCR to amplify VHH encoding gene fragments. These fragments were cloned into phagemid vector pASF20. pASF20 is an expression vector that is derived from pUC119, which contains the lacZ promotor, a synthetic leader sequence, a multiple cloning site, a coliphage pIII protein coding sequence, a resistance gene for ampicillin, and an M13 phage origin for single strand production. In frame with the VHH coding sequence, the vector codes for a C-terminal (His)6 peptide tag and c-myc peptide tag. Phages were prepared according to standard methods (*Phage Display of Peptides and Proteins: A Laboratory Manual*; Brian K. Kay, Jill Winter, Dr. John McCafferty). Four libraries, each with a clonal diversity equal to or greater than 1E+08, were obtained and phage were produced ensuring presentation of the antibody diversity.

VHH Selections by Phage Display:

Phage expressing antigen-binding antibody domains specific for a particular antigen were isolated by selecting the phage in the library for binding to the antigen. Fungal GlcCer were immobilized on polystyrene Maxisorp multiwell plates by dissolving fungal GlcCer in a water:methanol:chloroform mixture or methanol at different concentrations, adding dissolved fungal GlcCer to wells of the multiwell plate, and allowing to dry overnight at room temperature. Wells with coated fungal GlcCer were washed and blocked with 1% fish gelatin in preparation of VHH selections by phage display. VHH library phages were allowed to bind for two hours at room temperature to wells of 96-well plate coated with fungal GlcCer. To specifically select for phage binding to fungal GlcCer phage were pre-incubated with 1% fish gelatin and/or BSA and/or skimmed milk and/or plant GlcCer and/or mammalian GlcCer. Non-bound phage were removed by extensive washing and bound phage were eluted by competitive elution with RsAFP2 (Osborn et al., 1995) or with trypsin. One to three consecutive rounds of selection were performed, and the titers of phage from fungal GlcCer-coated wells were compared to titers of phage from blank wells and non-target pathogen sphingolipids for enrichment and specificity, respectively. Enrichments were observed in first and subsequent rounds of selection, and phage populations after one or more selection rounds already showed specificity for fungal GlcCer in ELISA (not shown). Individual clones were picked from first, second and/or third round selections for further characterization by sequence analysis and primary binding assays.

VHH Characterization by Sequencing and Binding Assays:

The diversity of the obtained antibody or antibody domain population can be rapidly determined using high-throughput DNA sequencing and allows precise quantification of clonal diversity. Antibody or antibody domain binding and specificity of binding to an antigen can be analyzed in assays for binding to that antigen and compared to related and unrelated controls. Each antibody or antibody domain can bind to a specific antigen and possibly to antigenic variants of that antigen. Specificity is the degree to which the binding of an antibody or antibody domain discriminates between antigenic variants. From individual VHH clones that were picked from first, second or third round phage display selections the DNA was amplified in a colony PCR and PCR products were sequenced by Sanger-sequencing. After sequence analysis and based on sequence diversity, VHH were selected for further characterization. To check for species specificity, fungal and non-fungal GlcCer from target and non-target species were used in binding assays. Primary binding assays to identify which clones were functionally selected from the libraries were performed with TLC-purified (99%) GlcCer or GlcCer-enriched Glycosphingolipids (GSL) fractions from *A. brassicicola, B. cinerea, C. beticola, F. culmorum, F. graminearum, F. oxysporum, P. citrinopileatus P. digitatum, P. expansum*, or *V. dahlia* (prepared as described in Ternes et al., 2011 *JBC* 286:11401-14). GlcCer from soybean and porcine GlcCer were purchased from Avanti Polar Lipids. VHH were produced in 96-well deep-well plates and the binding profile of diluted crude VHH-containing periplasmic extracts was assessed in ELISA format. In the same way, binding assays were performed with purified VHH.

Figure 1:
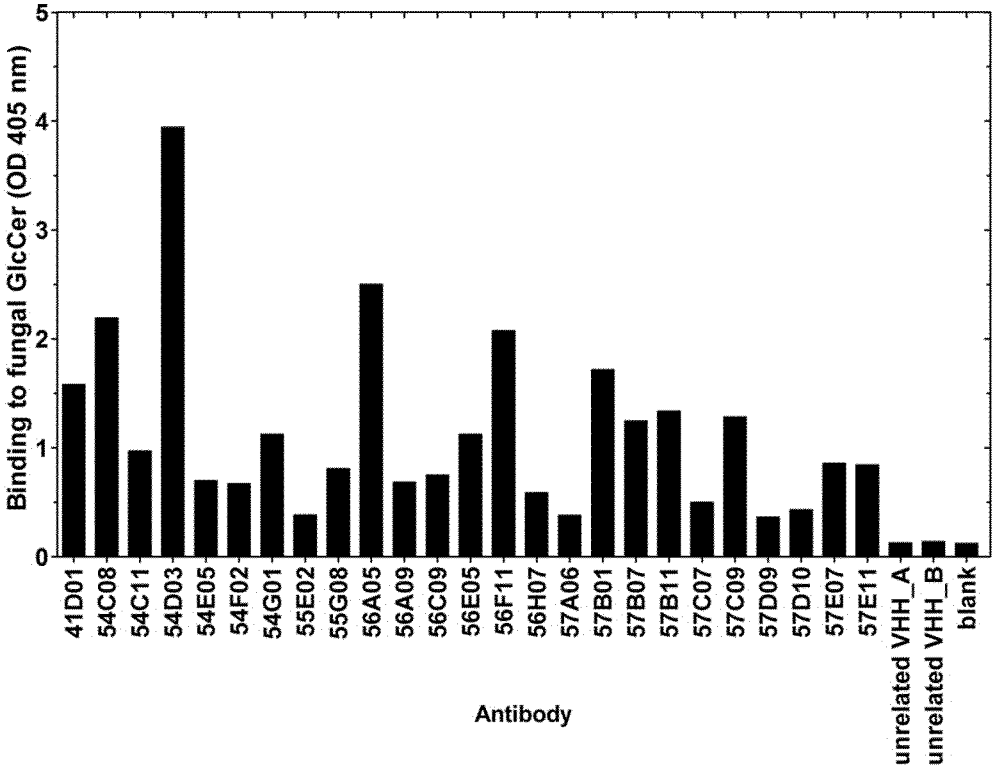
FIG. 1: Binding of VHH as crude VHH-containing periplasmic extracts to coated fungal GlcCer from *Pleurotus citrinopileatus*. Anti-GlcCer VHH bind to fungal GlcCer, no binding is observed for unrelated VHH.

From the primary binding assays 130 VHH-containing periplasmic extracts showed to bind fungal GlcCer with higher OD 405 nm values than the unrelated VHH_A, unrelated VHH_B and blank. OD 405 nm values demonstrating the specific binding of several of these fungal GlcCer binding VHHs are shown in FIG. 1. Sequence analysis revealed 84 unique sequences from the identified set of anti-GlcCer VHH.

Further Characterization by Differential Binding Screens:

For further characterization, VHH belonging to the abovementioned lead panel were produced in *E. coli* in culture flasks according to standard procedures. Hexahistidine-tagged VHH were purified from the periplasmic extract with TALON metal affinity resin (Clontech), according to the manufacturer's instructions. Purified VHH were concentrated and dialyzed to PBS. VHH were also purified using automated purification systems using a combination of immobilized Nickel IMAC and desalting columns. VHH of the lead panel that scored positively in primary binding assays, were subsequently tested for their specificity towards GlcCer or cell wall fractions from different fungal phytopathogens.

As demonstrated in FIGS. 2, 3A, 3B and 3C, GlcCer-specific VHH showed specific binding to fungal GlcCer (*Pleurotus citrinopileatus, Fusarium oxysporum*) and not to other non-fungal GlcCer or blank non-coated well.

Surface Plasmon Resonance:

Binding of VHH to fungal GlcCer was characterized by surface plasmon resonance in a BIACORE® 3000 instrument. Anti-GlcCer VHH 41D01 or unrelated VHH_A were covalently bound to CM5 sensor chips surface via amine coupling until an increase of 1000 response units was reached. Remaining reactive groups were inactivated. A range of concentrations of in solution *Fusarium oxysporum* GlcCer prepared according to Salio et al., 2013 *PNAS* 110, E4753-E4761 was injected for 2 minutes at a flow rate of 30 μl/minute to allow for binding to chip-bound VHH. Running buffer without GlcCer was injected over the chip at the same flow rate to allow spontaneous dissociation of bound fungal GlcCer for 10 minutes. A $K_{off}$-value was calculated from the sensorgrams obtained for the different fungal GlcCer concentrations with 1:1 Langmuir dissociation global fitting model.

Figure 4:
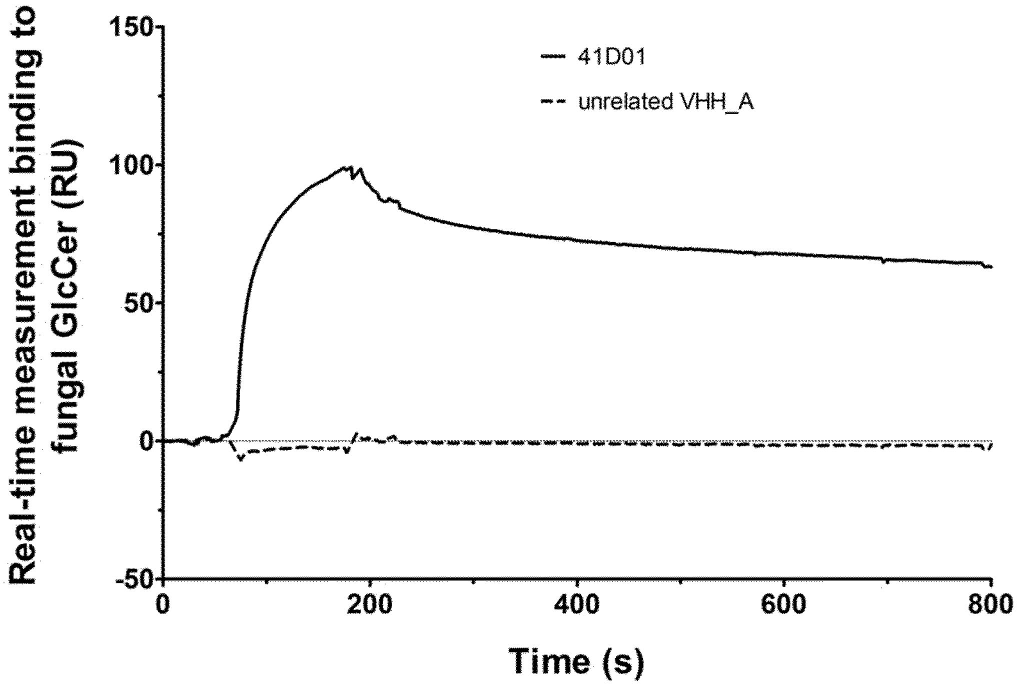
FIG. 4: Real-time measurement of the antibody-antigen interaction between VHH 41D01 and fungal GlcCer. VHH 41D01 binds fungal GlcCer. A slow dissociation of GlcCer from VHH 41D01 is observed. Unrelated VHH_A does not bind fungal GlcCer.

For anti-GlcCer VHH a slow off-rate of 4.86*1E−4/s was calculated. As shown in FIG. 4, an unrelated VHH did not bind fungal GlcCer.

Plant (soy), mammalian (pork) and fungal (*Fusarim oxysporum*) GlcCer in solution were sequentially injected for 2 minutes at a flow rate of 30 μl/minute to allow for binding to chip-bound VHH (anti-GlcCer VHH 41D01 or unrelated VHH_A). Running buffer without GlcCer was injected over the chip between each injection at the same flow rate to allow spontaneous dissociation of bound GlcCer.

No plant or mammalian GlcCer binding to anti-GlcCer VHH 41D01 or unrelated VHH_A was observed. Specific binding of fungal GlcCer was observed for anti-GlcCer VHH 41D01 and not for unrelated VHH_A.

Differential Binding to Different Fungal Lipid Extracts:

The binding of anti-GlcCer VHH compositions to different fungal lipid extracts compared to unrelated compounds.

Fungal extracts were prepared according to Rodrigues et al. 2000 *Infection and Immunity* 68 (12):7049-60. Briefly, mycelium from *Botrytis cinerea* B05-10, *Botrytis cinerea* MUCL401, *Botrytis cinerea* R16, *Botrytis cinerea* (own pear isolate), *Fusarium culmorum* MUCL555, *Fusarium graminearum* MUCL53451, *Penicillium digitatum* MUCL43-410, *Penicillium digitatum* (own lemon isolate) or *Penicillium expansum* CBS 146.45 were harvested from fungi grown in agar plates and lipids were extracted with chloroform/methanol 2:1 (vol/vol) and 1:2 (vol/vol); crude lipid extract was partitioned according to Folch et al. 1957, *Journal of Biological Chemistry* 226 (1):497-509. Fungal lipid extracts were recovered from Folch's lower phase. Binding of anti-GlcCer VHH 41D01 (0.1 μg/ml) and anti-GlcCer VHH 56F11 (1 μg/ml) was evaluated to wells coated with the extracted fungal lipids (each in 1/20 dilution), purified *Fusarium oxysporum* GlcCer, purified *Pleurotus citrinopileatus* GlcCer and unrelated compounds: apple pectin (Apple pectin high esterified 70-75%, Sigma, cat #: 76282), citrus pectin (Citrus pectin low esterified 20-34%, Sigma, cat #P9311) or potato lectin (Solanum Tuberosum Lectin, Vector labs, cat #: L-1160) or a blank non-coated well. Binding was measured after consecutive incubation with enzyme-conjugated detection antibodies, adding substrate, and measuring absorbance at 405 nm. Bars represent average OD 405 nm values, error bars represent standard errors of the mean of n=2.

Figure 5:
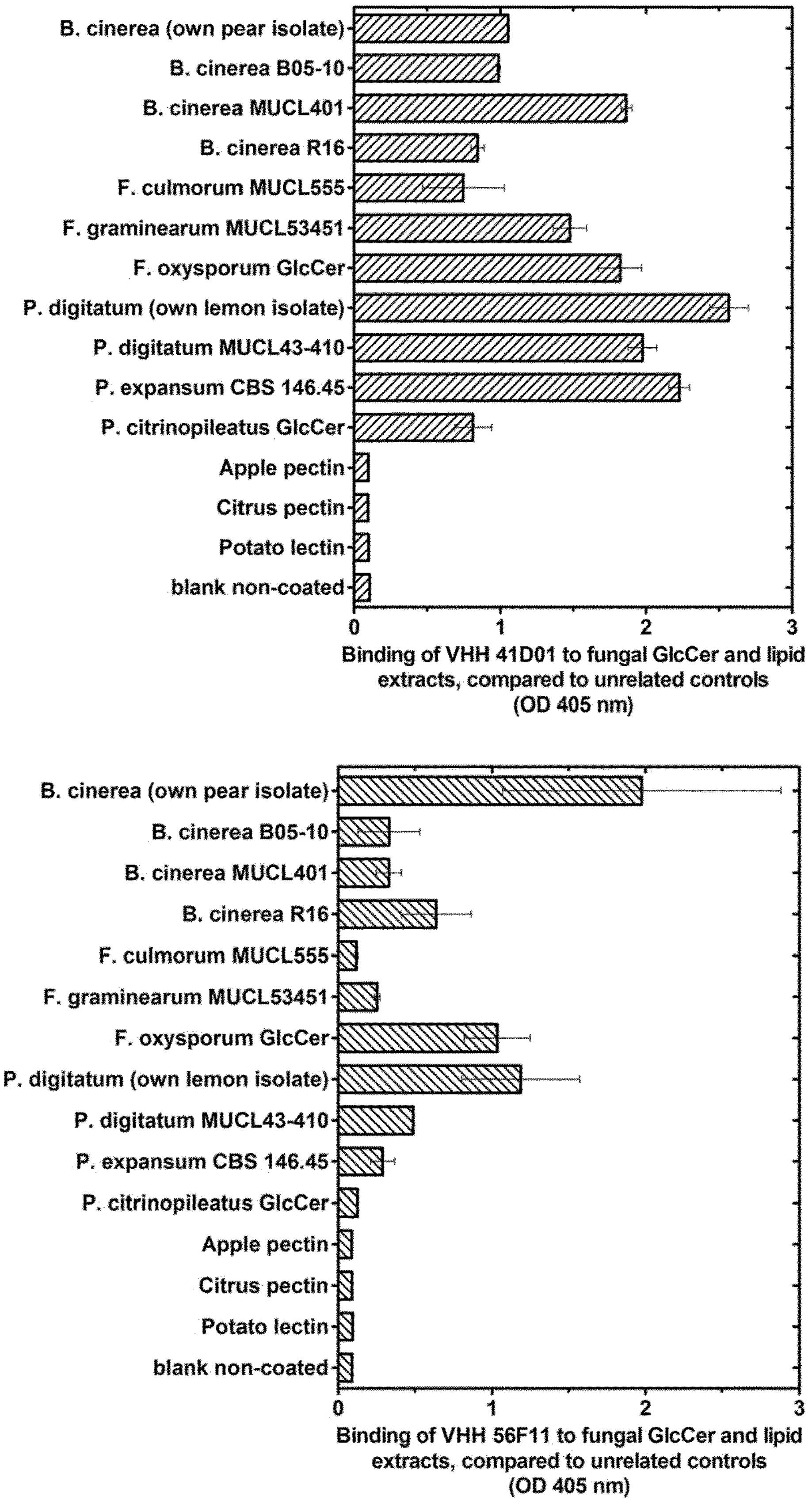
FIG. 5: Cross-reactivity and specificity of VHH 41D01 and VHH 56F11. Binding of purified VHH 41D01 at 0.1 μg/ml and VHH 56F11 at 1 μg/ml to coated fungal lipid extracts, GlcCer from *Pleurotus citrinopileatus*, and unrelated compounds: apple pectin, citrus pectin, or potato lectin. Bars represent average OD 405 nm values, error bars represent standard errors of the mean of n=2. Anti-GlcCer VHH 41D01 and VHH 56F11 specifically bind each of the fungal lipid extracts tested. Anti-GlcCer VHH 41D01 and VHH 56F11 do not show binding to unrelated coated compounds or non-coated wells.

As shown in FIG. 5, anti-GlcCer VHH 41D01 and 56F11 specifically recognized all the fungi lipid extracts tested. Anti-GlcCer VHH 41D01 and 56F11 did not show binding to unrelated coated compounds or non-coated wells. The binding of the anti-GlcCer VHH compositions to a wide array of fungal lipids extracts potentiates a variety of applications for the anti-GlcCer VHH compositions as disclosed herein against different fungi.

Binding of anti-GlcCer VHH to fungal GlcCer in different aqueous compositions:

Aqueous compositions containing anti-GlcCer VHH 41D01 and/or protease inhibitors and/or non-ionic surfactants and/or preservatives were prepared. Composition A1 (protease inhibitors: 0.06 μg/ml aprotinin (Roche, cat #: 10236624001), 0.5 μg/ml leupeptin (Roche, cat #: 11017101001), 24 μg/ml 4-benzenesulfonyl fluoride hydrochloride (Sigma, A8456), 1 mM EDTA (Carl-Roth, cat #8040.1) and non-ionic surfactant: 0.00001% Polysorbate 20 (TWEEN®20, Sigma, cat #P2287); Composition A2 (protease inhibitors: 1 μg/ml aprotinin, 2.5 μg/ml leupeptin, 100 μg/ml 4-benzenesulfonyl fluoride hydrochloride, 1 mM EDTA and non-ionic surfactant: 0.05% Polysorbate 20); Composition A3 (protease inhibitors: 2 μg/ml aprotinin, 5 μg/ml leupeptin, 240 μg/ml 4-benzenesulfonyl fluoride hydrochloride, 1 mM EDTA and non-ionic surfactant: 5% Polysorbate 20), Composition B1 (non-ionic surfactant: 0.0001%% Polysorbate 20), Composition B2 (non-ionic surfactant: 0.05% Polysorbate 20), Composition B3 (non-ionic surfactant: 5% Polysorbate 20) and Composition C1 (preservative: 0.05% sodium benzoate (Sigma, cat #B3420)). Binding of anti-GlcCer VHH (at 0.1 μg/ml) to fungal GlcCer in different aqueous compositions was tested in ELISA with coated GlcCer from *F. oxysporum* and compared to blank non-coated wells. Binding was measured after consecutive incubation with enzyme-conjugated detection antibodies, adding substrate and measuring absorbance at 405 nm.

Figure 6:
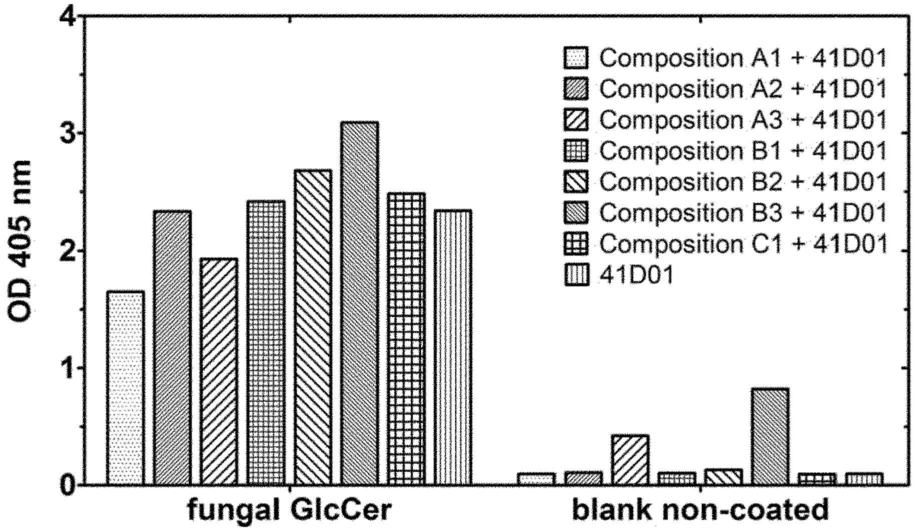
FIG. 6: Binding of VHH 41D01 in different compositions to fungal GlcCer from *Fusarium oxysporum*. Aqueous compositions containing anti-GlcCer VHH 41D01 at 0.1 μg/ml and protease inhibitors and/or non-ionic surfactant and/or preservative were tested for binding to fungal GlcCer. GlcCer-specific VHH 41D01 binds to fungal GlcCer in all compositions tested without adverse effects of any of the additives.

In FIG. 6, values of GlcCer-specific VHH 41D01 in the different compositions were compared with 41D01 in solution without other additives. It is shown in FIG. 6 that GlcCer-specific VHH 41D01 was capable of specifically binding to fungal GlcCer in all tested compositions.

Example 2

Generation of Transgenic Plants According to Embodiments of this Disclosure

Figure 7:
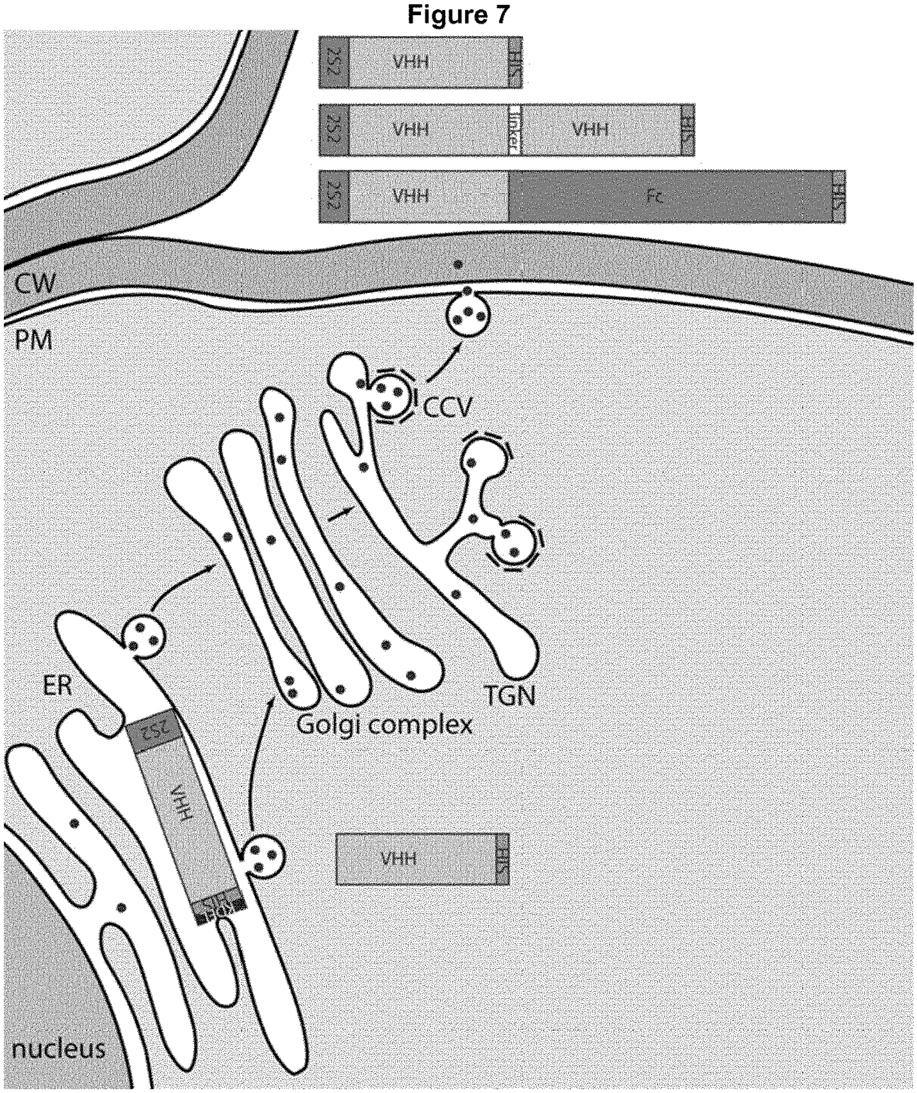
FIG. 7: Schematic representation of localization and protein expression of VHH constructs as taught herein. VHH.

*Arabidopsis* has been transformed with different vectors for the expression of polynucleotides encoding VHH specifically binding to a sphingolipid of a plant pathogenic fungus. The polynucleotides comprise at least one sequence encoding a targeting signal for secretion (e.g., 2S2), for localization to the cytoplasm (e.g., start codon), or for location to the endoplasmatic reticulum (e.g., KDEL (SEQ ID NO:349)), as schematically illustrated in FIG. 7. The transgenic *Arabidopsis* plants are analyzed in bioassays with different plant pathogenic fungi.

Transgenic plants comprising a polynucleotide encoding VHH 41D01 were made. Also, transgenic plants comprising a polynucleotide encoding VHH 56F11 were made. The nucleotide sequence of the polynucleotides encoding VHH 41D01 and VHH 56F11 are respectively represented by SEQ ID NO:336 and SEQ ID NO:337.

Different chimeric constructs were made comprising each of the polynucleotides encoding VHH 41D01 and 56F11 and polynucleotides encoding various tag sequences, signal sequences, spacer sequences, hinge sequence, and/or Fc sequences. These different chimeric constructs are listed in Table 4.

TABLE 4

Chimeric constructs for generating transgenic plants according to embodiments of this disclosure

| Construct name | Targeting | SEQ ID NO |
|---|---|---|
| 41D01_His_KDEL | ER | 338 |
| sec_41D01_hinge_Fc_His | secreted | 339 |
| sec_41D01-9GS-41D01_His | secreted | 340 |
| sec_41D01_His | secreted | 341 |
| cyto_41D01_His | cytoplasmatic | 342 |
| 56F11_His_KDEL | ER | 343 |
| sec_56F11_hinge_Fc_His | secreted | 344 |
| sec_56F11-9GS-56F11_His | secreted | 345 |
| sec_56F11_His | secreted | 346 |
| cyto_56F11_His | cytoplasmatic | 347 |

41D01: VHH1 (SEQ ID NO:336); His: His6 tag, consists of 6 His repeats (SEQ ID NO:348); KDEL: ER retention signal (SEQ ID NO:349); sec: 2S2 seed storage protein gene signal peptide (SEQ ID NO:350); Fc: Fc from mouse IgG3 (SEQ ID NO:351); 9GS: spacer, consisting of GGGGSGGGS (SEQ ID NO:352); hinge: mouse IgG3 hinge (SEQ ID NO:353); cyto: addition of an ATG start codon; 56F11: VHH2 (SEQ ID NO:337); ER: endoplasmatic reticulum.

Table 5 lists the protein sequence of the various tags, signal sequences, spacers, hinge regions, or Fc used to generate the different chimeric constructs.

TABLE 5

Protein sequence of the elements used to generate chimeric constructs

| Sequence elements | SEQ ID NO |
|---|---|
| His6 | 348 |
| ER retention signal | 349 |
| 2S2 seed storage protein gene signal peptide | 350 |
| Fc of mouse IgG3 | 351 |
| 9GS | 352 |
| Mouse IgG3 hinge | 353 |

The chimeric constructs of Table 4 were placed under transcriptional control of the 35S CaMV promoter (SEQ ID NO:354) in the pK7WG2 destination vector (see further below).

Generation of Entry Vectors

The vectors listed in Table 6 were ordered at GENEART® Gene Synthesis (Life technologies).

TABLE 6

Vectors used to generate entry vectors

| Vector number | Vector name |
|---|---|
| 1 | pMA_56F11-KDEL |
| 2 | pMA_sec-bi56F11 |
| 3 | pMA_sec-56F11Fc |
| 4 | pMA_sec-56F11 |
| 5 | pMA_41D01-KDEL |
| 6 | pMA_sec-bi41D01 |

TABLE 6-continued

| Vectors used to generate entry vectors | |
|---|---|
| Vector number | Vector name |
| 7 | pMA_sec-41D01Fc |
| 8 | pMA_sec-41D01 |

KDEL (SEQ ID NO:349): 4 amino acid sequence (K, D, E, and L) to retain the expressed VHH in the endoplasmic reticulum (ER); sec: 2S2 signal peptide (to target the expressed VHH to the secretory pathway); bi: indicates that the VHH is expressed as a bivalent; Fc: "fragment crystallizable" chain of the mouse IgG3 antibody PCR amplification of these sequences was done using specific primers (pMA_FW and pMA_REV) to introduce restriction sites (EcoRI+BamHI). A second set of primers (pCYTO_FW and pMA_REV) was used to introduce a cytoplasmic targeting signal. For this, sequence 4 and 8 were used as a template. The sequences of pMA_FW, pMA_REV, and pCYTO_FW are listed in Table 7.

TABLE 7

| Nucleic acid sequences of the primers used for PCR amplification | | |
|---|---|---|
| Primer | Nucleic acid sequence | SEQ ID NO |
| pMA_FW | TTGTAAAACGACGGCCAG | 355 |
| pMA_REV | GGAAACAGCTATGACCATGT | 356 |
| pMA_CYTO | CCGGAATTCCCACCATGCAGGTTCAGCTGCAGGAAT (underlined section overlaps with N-terminal VHH ends) | 357 |

Restriction digest was performed on both amplified fragments and the entry vector E-IgG3-GmR. This vector introduces AttL1 and AttL2 sites for further downstream Gateway-compatible cloning. Digested sequence fragments and vector fragment were purified (using a purification kit for the sequence fragments and in-gel purification for the vector fragment).

Digested sequence fragments were ligated into the digested E-IgG3-GmR vector.

Next, the obtained entry clones (10 in total: 2× VHH-KDEL, 2× sec-VHH, 2× sec-biVHH, 2× sec-VHH-Fc and 2× cyto-VHH) were used for transformation of DH5α *E. coli* cells.

Per entry clone, 10 colonies were checked via colony-PCR. Of each construct, up to 4 positive clones were plated again, to screen for single colonies. Next, colony-PCR was performed on the generated single colonies using a high-fidelity polymerase (Phusion PCR, New England Biolabs).

The PCR products resulting from this Phusion PCR (35 in total) were sent to LGC Genomics for sequence analysis.

Generation of Expression Vectors

All 35 entry vectors (representing 10 different entry vector constructs in total) that were sent for sequencing, were initially continued with. DNA was purified of each construct, and used for LR reaction (Gateway cloning) to the pK7WG2 destination vector (Plant Systems Biology (Karimi et al., "Gateway vectors for *Agrobacterium*-mediated plant transformation," *Trends Plant. Sci.* 2002 May; 7 (5): 193-195); SEQ ID NO:358).

The obtained expression clones were used for transformation of DH5α *E. coli* cells.

Based on the obtained sequencing results from the 35 entry clones, a positive candidate for each of the ten different entry vector constructs was selected.

Per expression clone, two colonies were checked via colony-PCR. From one positive clone per expression clone, plasmid was prepared and sent for sequence analysis (VIB sequence service facility).

A glycerol bank of DH5α *E. coli* cells containing each of the ten entry clones and each of the ten expression clones was established (20 entries in total). The ten expression vectors are listed in Table 8.

TABLE 8

| Expression vectors for generating plants according to embodiments of this disclosure | | |
|---|---|---|
| Construct name | Targeting | SEQ ID NO |
| pK7WG2-41D01_His_KDEL | ER | 359 |
| pK7WG2-sec_41D01_hinge_Fc_His | secreted | 360 |
| pK7WG2-sec_41D01-9GS-41D01_His | secreted | 361 |
| pK7WG2-sec_41D01_His | secreted | 362 |
| pK7WG2-cyto_41D01_His | cytoplasmatic | 363 |
| pK7WG2-56F11_His_KDEL | ER | 364 |
| pK7WG2-sec_56F11_hinge_Fc_His | secreted | 365 |
| pK7WG2-sec_56F11-9GS-56F11_His | secreted | 366 |
| pK7WG2-sec_56F11_His | secreted | 367 |
| pK7WG2-cyto_56F11_His | cytoplasmatic | 368 |

Transformation of Expression Vectors into *Agrobacterium* and *Arabidopsis* Transformation Each of the 10 expression constructs (SEQ ID NOS:359-368) was transformed into *Agrobacterium* strain C58C1 Rif® (pMP90); (Koncz and Schell (1986) Mol. Gen. Genet. 204:383-396). Colonies were checked for the presence of the expression vector via colony-PCR. For each of the 10 expression constructs, a positive strain was identified.

Of these positive strains, a glycerol bank was established.

The same positive strains were used for the transformation of *Arabidopsis* Col-0 WT plants using floral dipping. Five plants were dipped per construct. The floral dip transformation protocol is described in S. J. Clough and A. F. Bent (1998), "Floral dip: a simplified method for *Agrobacterium*-mediated transformation of *Arabidopsis thaliana," Plant J.* 16:735-743.

Floral dip transformation of *Arabidopsis* generated T1 seeds after 6 weeks. Per construct, 300-400 mg of T1 seed was obtained.

T1 seeds were sterilized by bleach and ethanol, and sown on K1 medium, supplemented with kanamycin (50 mg/L), nystatin (50 mg/L) and vancomycin (750 mg/L). After sowing with 7 ml of 0.1% agarose, plates were first incubated for 4 nights at 4° C., then transferred to the growth chamber. For each construct, 30 kanamycin-resistant T1 plants were transferred to soil and further allowed to set seed.

VHH Expression Analysis

T1 Plants—Confirmation of VHH Expression:

VHH Expression Analysis (Protein Level) in Isolated Leaves from T1 Plants by Western Blotting For each construct (10 in total), VHH protein expression analysis was performed for 30 T1 plants. From each T1 plant, 2 leaves were cut and harvested in 2-ml Eppendorfs, cooled in liquid nitrogen and crushed for 2 minutes at 20 Hz with two steel, 4-mm balls. The powder was dissolved in 100 μl extraction buffer (20 mM Pi, 300 mM NaCl, 0.1% CHAPS, pH 7.8, COMPLETE® protease inhibitor) and centrifuged (10 minutes, max speed, 4° C.) to spin down the cell debris. The supernatant was transferred to a fresh Eppendorf and centrifuged again (10 minutes, max speed, 4° C.). Ninety μl of final supernatant was kept, 22.5 μl of glycerol was added and the extract was stored at −20° C. Total protein content of each extract was determined by Bradford analysis. The total protein concentrations ranged from 0.5 to 4 mg/ml.

Protein extracts were analyzed by SDS-PAGE (12% TGX gels; Bio-Rad) followed by Western blotting (WB). For SDS-PAGE analysis, a volume corresponding with 10 μg of total protein content of each extract was loaded onto gel. WB detection was performed in 2 steps: the primary antibody was a mouse anti-His (Serotec; 1/1000 dilution). The secondary antibody comprised a mixture of 2 antibodies: sheep anti-mIgG-HRP (GE; 1/5000 dilution) and anti-IgG1-HRP (Sigma; 1/1000 dilution). For the constructs that contain the Fc fragment, detection was performed in a single step using goat anti-mouse IgG3-HRP (Sigma; 1/5000 dilution). All events for which a band appeared that corresponded with the appropriate size of the VHH-construct were considered as events in which the VHH-construct was expressed.

From the WB analysis, it became clear that expression was highest for VHHs fused to an Fc fragment. It was decided to continue analysis with the constructs sec_41D01_hinge_Fc_HIS and sec_56F11_hinge_Fc_HIS.

T1 plants that showed expression of VHH on WB were further allowed to set seed and T2 seed were harvested for segregation analysis.

T2 Plants—Segregation Analysis

T2 seeds were sterilized by bleach and ethanol, and sown on K1 medium, supplemented with kanamycin (50 mg/L), nystatin (50 mg/L) and vancomycin (750 mg/L). After sowing with 7 ml of 0.1% agarose, plates were first incubated for 4 nights at 4° C., and then transferred to the growth chamber. To identify lines containing the expression construct at a single locus in the genome, plates were scored for the ratio of the number of kanamycin-sensitive to resistant seedlings, and plates for which this ratio diverged from 1:3 were discarded. For the single-copy lines that showed the highest VHH expression, 10 plants were transferred to soil and further allowed to set seed. T3 seed were harvested for zygosity analysis.

T3 Plants—Zygosity Analysis

T3 seeds were sterilized by bleach and ethanol, and sown on K1 medium, supplemented with kanamycin (50 mg/L), nystatin (50 mg/L) and vancomycin (750 mg/L). After sowing with 7 ml of 0.1% agarose, plates were first incubated for 4 nights at 4° C., and then transferred to the growth chamber. Plates were scored for the number of kanamycin-resistant seedlings, and plates for which not all seedlings were resistant were discarded. For the remaining homozygous lines, plants were transferred to soil for seed propagation.

Example 3

Functional Assays

Glucosylceramide Binding Assay

Leaf extract from a homozygous single-copy event of *Arabidopsis* overexpressing sec_56F11_hinge_Fc_HIS was tested in an ELISA for binding of glucosylceramide (GlcCer). For this, wells of a multi-well plate (Greiner Bio-one, Clear, black, half area, high bind) was coated with 250 ng (50 μl of a 5 μg/ml solution) of GlcCer purified from *Fusarium oxysporum*. After coating, the plate was blocked with 1% gelatin in PBS for 1 hour. The blocking agent was removed and the plate incubated with 50 μl of (diluted) leaf extract for 1 hour. Next, the plate is washed 3 times with PBS. The plate is incubated with mouse anti-His (Serotec) for 1 hour. After washing the plate 3 times with PBS, the plate was incubated with anti-mouse IgG/alkaline phosphatase antibody (Sigma) for 1 hour. After washing three times with PBS, the plate was developed by adding ELISA buffer (100 mM Tris-HCl; 100 mM NaCl; 5 mM MgCl; pH 9.5; containing 2 mg/ml PNPP ELISA substrate (Sigma)) in each well. After 5 minutes, the absorbance at 405 nm was measured. As a control, uncoated wells were used. FIG. 8 shows the specific binding of sec_56F11_hinge_Fc_HIS in leaf extract to fungal GlcCer.

*Botrytis cinerea* Infection Assay

*A. thaliana* wild-type (Col-0) and plants overexpressing sec_41D01_hinge_Fc_HIS and sec_56F11_hinge_Fc_HIS were grown for five weeks in soil ("DCM potgrond voor Zaaien en Stekken," DCM, Sint-Katelijne-Waver, Belgium) in a growth chamber with 21° C., 75% humidity and a 12-hour day-light cycle with a light intensity of approximately 120 $\mu mol/m^2s$. A 5 μL drop of a *B. cinerea* spore suspension (B05.10, $5\times10^4$/mL in ½ PDB) was inoculated onto three leaves per plant. Plants were kept in transparent sealed boxes to retain almost 100% humidity after inoculation. Disease symptoms were scored by measuring the diameters of the necrotic lesions on 3, 4 and 7 days post inoculation (dpi). Twenty plants per line and condition, divided over 5 boxes, were analyzed.

FIG. 9A shows increased resistance against *B. cinerea* in plants expressing VHH against fungal GlcCer as compared to wild-type plants.

A further infection assay was performed under identical conditions using twenty four plants per line and condition, divided over 6 boxes. A different line of plants overexpressing sec_41D01_hinge_Fc_HIS was used than in the first bioassay. FIG. 9B confirms increased resistance against *B. cinerea* in plants expressing VHH against fungal GlcCer as compared to wild-type plants.

Example 4

In Vitro Evaluation of the Antifungal Activity of Anti-GlcCer VHH-Containing Leaf Extract From a homozygous single-copy event of *Arabidopsis* overexpressing anti-GlcCer VHH, 2 leaves are cut and harvested in 2-ml Eppendorfs, cooled in liquid nitrogen and crushed for 2 minutes at 20 Hz with two steel, 4-mm balls. The powder is dissolved in 100 extraction buffer (20 mM Pi, 300 mM NaCl, 0.1% CHAPS, pH 7.8, COMPLETE® protease inhibitor) and centrifuged (10 minutes, max speed, 4° C.) to spin down the cell debris. The supernatant is transferred to a fresh Eppendorf and centrifuged again (10 minutes, max speed, 4° C.). This final supernatant is used in the antifungal bioassay.

The antifungal activity of anti-GlcCer VHH-containing leaf extract is tested using antifungal assays in liquid media and on agar plates as described in Thevissen et al., 2011, *Bioorg. Med. Chem. Lett.* 21 (12):3686-92; Frangois et al., 2009, *J. Biol. Chem.* 284 (47):32680-5; Aerts et al., 2009, *FEBS Lett.* 583 (15):25143-6. The inhibitory action is determined for the anti-GlcCer VHH-containing leaf extract on in vitro growth of *Botrytis cinerea* and *Phytophthora infestans.*

Two-fold dilutions of the anti-GlcCer VHH-containing leaf extract in water are prepared in 96-well microtiter plates. To 20 μl of these dilutions and to 20 μl of water as a control, 80 μl of fungal spores suspension (1E+05 spores/ml in half strength potato dextrose broth (PDB)) are added. The fungal test strains are *Alternaria brassicicola* MUCL20297, *Botrytis cinerea* R16, *Cercospora beticola* (own sugar beet isolate), *Fusarium culmorum* MUCL555 and *Verticillium dahliae* MUCL6963. The test plates are incubated for 72 hours at room temperature in the dark and the antifungal activity of the test compounds is scored microscopically and quantified based on photographic standards, whereby a score of 0 or 100 refers to no or maximal fungal growth, respectively. All tests are performed in at least 2 replicas.

The results of the antifungal activity assays, indicate a clear difference between the growth inhibition pattern, expressed as the % fungal growth in function of dilution of the anti-GlcCer VHH-containing leaf extract. This difference is clear irrespective of the species of the test fungus.

The results show the antifungal potency of anti-GlcCer VHH-containing leaf extract. Moreover, the results reveal a broad-spectrum of antifungal activity of anti-GlcCer VHH-containing leaf extract towards at least 5 different fungal plant pathogens and indicate that the spectrum of antifungal activity of the selected anti-GlcCer VHH-containing leaf extract can be broadened to other plant pathogenic fungi.

Example 5

In Planta Evaluation of the Antifungal Activity of Leaf Extracts Containing Anti-GlcCer VHH to Protect Crops Against Fungal Infection Efficacy of leaf extracts containing anti-GlcCer VHH on tomato leaves inoculated with *Botrytis cinerea*: preventive treatment.

Leaf extract from homozygous single-copy event of *Arabidopsis* overexpressing anti-GlcCer VHH is tested in a *Botrytis cinerea* infection assay on tomato. The effect of a preventive treatment with plant extracts containing anti-GlcCer VHH on the disease severity of *Botryts cinerea* B05-10 inoculated tomato leaves is evaluated and compared with the effect of water.

Leaves from greenhouse grown tomato plants are treated with 10 μl of VHH-containing leaf extract and water. Upon drying of the applied compositions, 10 μl drops of a *Botrytis cinerea* spores suspension (6E+06 spores/ml in 4-fold diluted PDB) are applied on the treated surfaces. Treated and inoculated leaves are incubated at high relative humidity and at room temperature in small plant propagators. Disease severity is scored measuring the bidirectional diameter at 6 days post inoculation (dpi).

Preventive treatment with the anti-GlcCer VHH composition results in a smaller average lesion diameter than treatment with water. Preventive treatment of tomato leaves with the application of the anti-GlcCer VHH-containing leaf extract clearly results in a reduction of disease severity compared with the treatment with water. Therefore, anti-GlcCer VHH-containing leaf extracts show the potency to be used as antifungal compounds to protect crops against fungal pathogens in agricultural applications.

Efficacy of Anti-GlcCer VHH Compositions on Tomato Leaves Inoculated with *Botrytis cinerea*: Curative Treatment.

The effect of a curative treatment with anti-GlcCer VHH-containing leaf extract on the disease severity of *Botrytis cinerea* B05-10 inoculated tomato leaves is evaluated and compared with the effect of water.

Leaves from greenhouse-grown tomato plants are inoculated with 10 μl drops of a *Botrytis cinerea* spores suspension ((6E+06 spores/ml) in 4-fold diluted PDB). One hour after inoculation, the inoculated spots on the leaves are treated with 10 μl of VHH-containing leaf extract and water. Inoculated and treated leaves are incubated at high relative humidity and at room temperature in small plant propagators. Disease severity is scored measuring the bidirectional diameter at 5 dpi.

Curative treatment with anti-GlcCer VHH-containing leaf extract results in a smaller average lesion diameter than treatment with water. Curative treatment of tomato leaves with the application of anti-GlcCer VHH-containing leaf extract clearly results in a reduction of disease severity compared with the treatment with water Therefore, anti-GlcCer VHH-containing leaf extracts show the potency to be used as antifungal compounds to protect crops against fungal pathogens in agricultural applications.

The invention claimed is:

1. A transgenic plant or plant tissue or plant cell comprising:

at least one polynucleotide encoding a polypeptide comprising a variable domain of a heavy-chain antibody (VHH) that specifically binds to a glucosylceramide of a fungus;

wherein the at least one polynucleotide is operably linked to a promoter suitable for expression in plants;

wherein the transgenic plant or plant tissue or plant cell expresses the polypeptide; and wherein the VHH comprises any one of SEQ ID NOs: 1 to 84.

2. The transgenic plant or plant tissue or plant cell according to claim 1, wherein the expression of the at least one polynucleotide in at least part of the transgenic plant or plant tissue or plant cell (i) protects at least part of the transgenic plant or plant tissue or plant cell from an infection with a plant pathogenic fungus, (ii) inhibits the growth of a plant pathogenic fungus on at least part of the transgenic plant or plant tissue or plant cell, and/or (iii) increases the resistance of at least part of the transgenic plant or plant tissue or plant cell against a plant pathogenic fungus.

3. The transgenic plant or plant tissue or plant cell according to claim 1, wherein the promoter suitable for expression in plants is a plant tissue or plant cell specific promoter, or an inducible promoter.

4. The transgenic plant or plant tissue or plant cell of claim 1, wherein the polypeptide further comprises, fused to the VHH, a targeting signal for secretion of the VHH or for locating the VHH to cellular compartments or organelles.

5. The transgenic plant or plant tissue or plant cell of claim 1, wherein the polypeptide further comprises (i) one or more identical or different VHHs, or (ii) a fragment crystallizable region (Fc region);

wherein, optionally, the VHH and one or more identical or different VHHs or the VHH and Fc regions are separated by a spacer peptide.

6. The transgenic plant or plant tissue or plant cell of claim 1, wherein the plant is a plant selected from the group consisting of corn, rice, wheat, barley, sorghum, millet oats, rye, triticale and other cereals, soybean, alfalfa and other leguminous crops, sugar beet, fodder beet, papaya, banana and plantains and other fruits, grapevines, nuts, oilseed rape, sunflower and other oil crops, squash cucumber, melons and other cucurbits, cotton and other fiber plants, sugarcane, palm, jatropha and other fuel crops, cabbages, tomato, pepper and other vegetables, ornamentals, shrubs, poplar, eucalyptus and other trees, evergreens, grasses, coffee plants, tea plants, tobacco plants, hop plants, rubber plants, and latex plants.

7. A harvestable part or propagation material of the transgenic plant or plant tissue or plant cell of claim 1, the harvestable part or propagation material comprising:

at least one polynucleotide encoding the polypeptide comprising a variable domain of a heavy-chain antibody (VHH) that specifically binds to a glucosylceramide of a fungus.

8. The harvestable part or propagation material according to claim 7, wherein the harvestable part or propagation material is selected from the group consisting of seeds, fruits, grains, bulbs, bolls, and tubers.

9. A method for producing the transgenic plant or plant tissue or plant cell of claim 1, the method comprising:

introducing the at least one polynucleotide into the genome of a plant or plant tissue.

10. A method for protecting at least part of a plant or plant tissue or plant cell from an infection with a plant fungus, for inhibiting the growth of a plant fungus on at least part of a plant or plant tissue or plant cell, and/or for increasing fungal resistance of at least part of a plant or plant tissue or plant cell, the method comprising:

expressing in the at least part of the plant or plant tissue or plant cell of claim 1 the at least one polynucleotide.

11. An extract of the transgenic plant or plant tissue or plant cell of claim 1, said extract comprising said VHH.

12. A composition comprising the extract of claim 11.

13. A method for protecting at least part of a plant or plant tissue or plant cell from an infection with a plant pathogen, for inhibiting the growth of a plant pathogen on at least part of a plant or plant tissue or plant cell, and/or for increasing pathogen resistance of at least part of a plant or plant tissue or plant cell, the method comprising:

treating said at least part of a plant or plant tissue or plant cell with the extract of claim 11.

14. The transgenic plant or plant tissue or plant cell of claim 4, wherein the polypeptide further comprises, fused to the VHH, a targeting signal for locating the VHH to a cellular part selected from the group consisting of the endoplasmatic reticulum (ER) lumen, the apoplast, the vacuole, intra-membranes, and exterior membranes.

15. The transgenic plant or plant tissue or plant cell of claim 1, wherein the VHH comprises SEQ ID NO: 1.

16. The transgenic plant or plant tissue or plant cell of claim 1, wherein the VHH comprises SEQ ID NO: 2.

17. The transgenic plant or plant tissue or plant cell of claim 1, wherein the VHH comprises SEQ ID NO: 70.

18. A transgenic plant or plant tissue or plant cell comprising:

at least one polynucleotide encoding a polypeptide comprising a variable domain of a heavy-chain antibody (VHH) that specifically binds to a glucosylceramide of a fungus;

wherein the at least one polynucleotide is operably linked to a promoter suitable for expression in plants;

wherein the transgenic plant or plant tissue or plant cell expresses the polypeptide; and wherein the VHH comprises:

a CDR1 region having SEQ ID NO: 85, a CDR2 region having has SEQ ID NO: 169, and a CDR3 region having SEQ ID NO: 253, or a CDR1 region having SEQ ID NO: 86, a CDR2 region having has SEQ ID NO: 170, and a CDR3 region having SEQ ID NO: 254, or a CDR1 region having SEQ ID NO: 87, a CDR2 region having has SEQ ID NO: 171, and a CDR3 region having SEQ ID NO: 255, or a CDR1 region having SEQ ID NO: 88, a CDR2 region having has SEQ ID NO: 172, and a CDR3 region having SEQ ID NO: 256, or a CDR1 region having SEQ ID NO: 89, a CDR2 region having has SEQ ID NO: 173, and a CDR3 region having SEQ ID NO: 257, or a CDR1 region having SEQ ID NO: 90, a CDR2 region having has SEQ ID NO: 174, and a CDR3 region having SEQ ID NO: 258, or a CDR1 region having SEQ ID NO: 91, a CDR2 region having has SEQ ID NO: 175, and a CDR3 region having SEQ ID NO: 259, or a CDR1 region having SEQ ID NO: 92, a CDR2 region having has SEQ ID NO: 176, and a CDR3 region having SEQ ID NO: 260, or a CDR1 region having SEQ ID NO: 93, a CDR2 region having has SEQ ID NO: 177, and a CDR3 region having SEQ ID NO: 261, or a CDR1 region having SEQ ID NO: 94, a CDR2 region having has SEQ ID NO: 178, and a CDR3 region having SEQ ID NO: 262, or a CDR1 region having SEQ ID NO: 95, a CDR2 region having has SEQ ID NO: 179, and a CDR3 region having SEQ ID NO: 263, or a CDR1 region having SEQ ID NO: 96, a CDR2 region having has SEQ ID NO: 180, and a CDR3 region having SEQ ID NO: 264, or a CDR1 region having SEQ ID NO: 97, a CDR2 region having has SEQ ID NO: 181, and a CDR3 region having SEQ ID NO: 265, or a CDR1 region having SEQ ID NO: 98, a CDR2 region having has SEQ ID NO: 182, and a CDR3 region having SEQ ID NO: 266, or a CDR1 region having SEQ ID NO: 99, a CDR2 region having has SEQ ID NO: 183, and a CDR3 region having SEQ ID NO: 267, or a CDR1 region having SEQ ID NO: 100, a CDR2 region having has SEQ ID NO: 184, and a CDR3 region having SEQ ID NO: 268, or a CDR1 region having SEQ ID NO: 101, a CDR2 region having has SEQ ID NO: 185, and a CDR3 region having SEQ ID NO: 269, or a CDR1 region having SEQ ID NO: 102, a CDR2 region having has SEQ ID NO: 186, and a CDR3 region having SEQ ID NO: 270, or a CDR1 region having SEQ ID NO: 103, a CDR2 region having has SEQ ID NO: 187, and a CDR3 region having SEQ ID NO: 271, or a CDR1 region having SEQ ID NO: 104, a CDR2 region having has SEQ ID NO: 188, and a CDR3 region having SEQ ID NO: 272, or a CDR1 region having SEQ ID NO: 105, a CDR2 region having has SEQ ID NO: 189, and a CDR3 region having SEQ ID NO: 273, or a CDR1 region having SEQ ID NO: 106, a CDR2 region having has SEQ ID NO: 190, and a CDR3 region having SEQ ID NO: 274, or a CDR1 region having SEQ ID NO: 107, a CDR2 region having has SEQ ID NO: 191, and a CDR3 region having SEQ ID NO: 275, or a CDR1 region having SEQ ID NO: 108, a CDR2 region having has SEQ ID NO: 192, and a CDR3 region having SEQ ID NO: 276, or a CDR1 region having SEQ ID NO: 109, a CDR2 region having has SEQ ID NO: 193, and a CDR3 region having SEQ ID NO: 277, or a CDR1 region having SEQ ID NO: 110, a CDR2 region having has SEQ ID NO: 194, and a CDR3 region having SEQ ID NO: 278, or a CDR1 region having SEQ ID NO: 111, a CDR2 region having has SEQ ID NO: 195, and a CDR3 region having SEQ ID NO: 279, or a CDR1 region having SEQ ID NO: 112, a CDR2 region having has SEQ ID NO: 196, and a CDR3 region having SEQ ID NO: 280, or a CDR1 region having SEQ ID NO: 113, a CDR2 region having has SEQ ID NO: 197, and a CDR3 region having SEQ ID NO: 281, or a CDR1 region having SEQ ID NO: 114, a CDR2 region having has SEQ ID NO: 198, and a CDR3 region having SEQ ID NO: 282, or a CDR1 region having SEQ ID NO: 115, a CDR2 region having has SEQ ID NO: 199, and a CDR3 region having SEQ ID NO: 283, or a CDR1 region having SEQ ID NO: 116, a CDR2 region having has SEQ ID NO: 200, and a CDR3 region having SEQ ID NO: 284, or a CDR1 region having SEQ ID NO: 117, a CDR2 region having has SEQ ID NO: 201, and a CDR3 region having SEQ ID NO: 285, or a CDR1 region having SEQ ID NO: 118, a CDR2 region having has SEQ ID NO: 202, and a CDR3 region having SEQ ID NO: 286, or a CDR1 region having SEQ ID NO: 119, a CDR2 region having has SEQ ID NO: 203, and a CDR3 region having SEQ ID NO: 287, or a CDR1 region having SEQ ID NO: 120, a CDR2 region having has SEQ ID NO: 204, and a CDR3 region having SEQ ID NO: 288, or a CDR1 region having SEQ ID NO: 121, a CDR2 region having has SEQ ID NO: 205, and a CDR3 region having SEQ ID NO: 289, or a CDR1 region having SEQ ID NO: 122, a CDR2 region having has SEQ ID NO: 206, and a CDR3 region having SEQ ID NO: 290, or a CDR1 region having SEQ ID NO: 123, a CDR2 region having has SEQ ID NO: 207, and a CDR3 region having SEQ ID NO: 291, or a CDR1 region having SEQ ID NO: 124, a CDR2 region having has SEQ ID NO: 208, and a CDR3 region having SEQ ID NO: 292, or a CDR1 region having SEQ ID NO: 125, a CDR2 region having has SEQ ID NO: 209, and a CDR3 region having SEQ ID NO: 293, or a CDR1 region having SEQ ID NO: 126, a CDR2 region having has SEQ ID NO: 210, and a CDR3 region having SEQ ID NO: 294, or a CDR1 region having SEQ ID NO: 127, a CDR2 region having has SEQ ID NO: 211, and a CDR3 region having SEQ ID NO: 295, or a CDR1 region having SEQ ID NO: 128, a CDR2 region having has SEQ ID NO: 212, and a CDR3 region having SEQ ID NO: 296, or a CDR1 region having SEQ ID NO: 129, a CDR2 region having has SEQ ID NO: 213, and a CDR3 region having SEQ ID NO: 297, or a CDR1 region having SEQ ID NO: 130, a CDR2 region having has SEQ ID NO: 214, and a CDR3 region having SEQ ID NO: 298, or a CDR1 region having SEQ ID NO: 131, a CDR2 region having has SEQ ID NO: 215, and a CDR3 region having SEQ ID NO: 299, or a CDR1 region having SEQ ID NO: 132, a CDR2 region having has SEQ ID NO: 216, and a CDR3 region having SEQ ID NO: 300, or a CDR1 region having SEQ ID NO: 133, a CDR2 region having has SEQ ID NO: 217, and a CDR3 region having SEQ ID NO: 301, or a CDR1 region having SEQ ID NO: 134, a CDR2 region having has SEQ ID NO: 218, and a CDR3 region having SEQ ID NO: 302, or a CDR1 region having SEQ ID NO: 135, a CDR2 region having has SEQ ID NO: 219, and a CDR3 region having SEQ ID NO: 303, or a CDR1 region having SEQ ID NO: 136, a CDR2 region having has SEQ ID NO: 220, and a CDR3 region having SEQ ID NO: 304, or a CDR1 region having SEQ ID NO: 137, a CDR2 region having has SEQ ID NO: 221, and a CDR3 region having SEQ ID NO: 305, or a CDR1 region having SEQ ID NO: 138, a CDR2 region having has SEQ ID NO: 222, and a CDR3 region having the amino acid sequence NRY, or a CDR1 region having SEQ ID NO: 139, a CDR2 region having has SEQ ID NO: 223, and a CDR3 region having SEQ ID NO: 306, or a CDR1 region having SEQ ID NO: 140, a CDR2 region having has SEQ ID NO: 224, and a CDR3 region having SEQ ID NO: 307, or a CDR1 region having SEQ ID NO: 141, a CDR2 region having has SEQ ID NO: 225, and a CDR3 region having SEQ ID NO: 308, or
a CDR1 region having SEQ ID NO: 142, a CDR2 region having has SEQ ID NO: 226, and a CDR3 region having SEQ ID NO: 309, or
a CDR1 region having SEQ ID NO: 143, a CDR2 region having has SEQ ID NO: 227, and a CDR3 region having SEQ ID NO: 310, or
a CDR1 region having SEQ ID NO: 144, a CDR2 region having has SEQ ID NO: 228, and a CDR3 region having SEQ ID NO: 311, or
a CDR1 region having SEQ ID NO: 145, a CDR2 region having has SEQ ID NO: 229, and a CDR3 region having SEQ ID NO: 312, or
a CDR1 region having SEQ ID NO: 146, a CDR2 region having has SEQ ID NO: 230, and a CDR3 region having SEQ ID NO: 313, or
a CDR1 region having SEQ ID NO: 147, a CDR2 region having has SEQ ID NO: 231, and a CDR3 region having SEQ ID NO: 314, or
a CDR1 region having SEQ ID NO: 148, a CDR2 region having has SEQ ID NO: 232, and a CDR3 region having SEQ ID NO: 315, or
a CDR1 region having SEQ ID NO: 149, a CDR2 region having has SEQ ID NO: 233, and a CDR3 region having SEQ ID NO: 316, or
a CDR1 region having SEQ ID NO: 150, a CDR2 region having has SEQ ID NO: 234, and a CDR3 region having SEQ ID NO: 317, or
a CDR1 region having SEQ ID NO: 151, a CDR2 region having has SEQ ID NO: 235, and a CDR3 region having SEQ ID NO: 318, or
a CDR1 region having SEQ ID NO: 152, a CDR2 region having has SEQ ID NO: 236, and a CDR3 region having SEQ ID NO: 319, or
a CDR1 region having SEQ ID NO: 153, a CDR2 region having has SEQ ID NO: 237, and a CDR3 region having SEQ ID NO: 320, or
a CDR1 region having SEQ ID NO: 154, a CDR2 region having has SEQ ID NO: 238, and a CDR3 region having SEQ ID NO: 321, or
a CDR1 region having SEQ ID NO: 155, a CDR2 region having has SEQ ID NO: 239, and a CDR3 region having SEQ ID NO: 322, or
a CDR1 region having SEQ ID NO: 156, a CDR2 region having has SEQ ID NO: 240, and a CDR3 region having SEQ ID NO: 323, or
a CDR1 region having SEQ ID NO: 157, a CDR2 region having has SEQ ID NO: 241, and a CDR3 region having SEQ ID NO: 324, or
a CDR1 region having SEQ ID NO: 158, a CDR2 region having has SEQ ID NO: 242, and a CDR3 region having SEQ ID NO: 325, or
a CDR1 region having SEQ ID NO: 159, a CDR2 region having has SEQ ID NO: 243, and a CDR3 region having SEQ ID NO: 326, or
a CDR1 region having SEQ ID NO: 160, a CDR2 region having has SEQ ID NO: 244, and a CDR3 region having SEQ ID NO: 327, or
a CDR1 region having SEQ ID NO: 161, a CDR2 region having has SEQ ID NO: 245, and a CDR3 region having SEQ ID NO: 328, or
a CDR1 region having SEQ ID NO: 162, a CDR2 region having has SEQ ID NO: 246, and a CDR3 region having SEQ ID NO: 329, or
a CDR1 region having SEQ ID NO: 163, a CDR2 region having has SEQ ID NO: 247, and a CDR3 region having SEQ ID NO: 330, or
a CDR1 region having SEQ ID NO: 164, a CDR2 region having has SEQ ID NO: 248, and a CDR3 region having SEQ ID NO: 331, or
a CDR1 region having SEQ ID NO: 165, a CDR2 region having has SEQ ID NO: 249, and a CDR3 region having SEQ ID NO: 332, or
a CDR1 region having SEQ ID NO: 166, a CDR2 region having has SEQ ID NO: 250, and a CDR3 region having SEQ ID NO: 333, or
a CDR1 region having SEQ ID NO: 167, a CDR2 region having has SEQ ID NO: 251, and a CDR3 region having SEQ ID NO: 334, or
a CDR1 region having SEQ ID NO: 168, a CDR2 region having has SEQ ID NO: 252, and a CDR3 region having SEQ ID NO: 335.

19. The transgenic plant or plant tissue or plant cell of claim 1, wherein the plant is a hybrid.

* * * * *

SEQUENCE LISTING

```
<160> NUMBER OF SEQ ID NOS: 368

<210> SEQ ID NO 1
<211> LENGTH: 115
<212> TYPE: PRT
<213> ORGANISM: Artificial Sequence
<220> FEATURE:
<223> OTHER INFORMATION: VHH sequence 41D01

<400> SEQUENCE: 1

Gln Val Gln Leu Gln Glu Ser Gly Gly Gly Leu Val Gln Ala Gly Gly
1               5                   10                  15
```

```
Ser Leu Arg Leu Ser Cys Ala Ala Ser Gly Arg Thr Phe Ser Arg Tyr
            20                  25                  30

Gly Met Gly Trp Phe Arg Gln Leu Pro Gly Lys Gln Arg Glu Leu Val
        35                  40                  45

Thr Ser Ile Thr Arg Gly Gly Thr Thr Thr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Arg Ser Ile Trp Arg Asp Tyr Trp Gly Gln Gly Thr Gln Val Thr
            100                 105                 110

Val Ser Ser
        115


<210> SEQ ID NO 2
<211> LENGTH: 121
<212> TYPE: PRT
<213> ORGANISM: Artificial Sequence
<220> FEATURE:
<223> OTHER INFORMATION: VHH sequence 56F11

<400> SEQUENCE: 2

Gln Val Gln Leu Gln Glu Ser Gly Gly Gly Leu Val Gln Ser Gly Gly
1               5                   10                  15

Ser Leu Arg Leu Ser Cys Val His Ser Lys Thr Thr Phe Thr Arg Asn
            20                  25                  30

Ala Met Gly Trp Tyr Arg Gln Ala Leu Gly Lys Glu Arg Glu Leu Val
        35                  40                  45

Ala Thr Ile Thr Ser Gly Gly Thr Thr Asn Tyr Ala Asp Ser Val Lys
    50                  55                  60

Gly Arg Phe Thr Ile Ser Met Asp Ser Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Asn Thr Arg Arg Ile Phe Gly Gly Thr Val Arg Glu Tyr Trp Gly
            100                 105                 110

Gln Gly Thr Gln Val Thr Val Ser Ser
        115                 120


<210> SEQ ID NO 3
<211> LENGTH: 118
<212> TYPE: PRT
<213> ORGANISM: Artificial Sequence
<220> FEATURE:
<223> OTHER INFORMATION: VHH sequence 40F07

<400> SEQUENCE: 3

Gln Val Gln Leu Gln Glu Ser Gly Gly Gly Leu Val Gln Ala Gly Gly
1               5                   10                  15

Ser Leu Arg Leu Ser Cys Val Ala Ser Gly Thr Thr Phe Ser Ser Tyr
            20                  25                  30

Thr Met Gly Trp Tyr Arg Gln Ala Pro Gly Lys Gln Arg Glu Leu Leu
        35                  40                  45

Ala Ser Ile Glu Gly Gly Gly Asn Thr Asp Tyr Ala Asp Ser Val Lys
    50                  55                  60

Gly Arg Phe Thr Ile Ser Arg Asp Asn Ala Arg Asn Thr Val Tyr Leu
```

```
65                  70                  75                  80

Gln Met Asn Ser Leu Lys Thr Glu Asp Thr Ala Val Tyr Tyr Cys Asn
                85                  90                  95

Ala Ala Arg Thr Trp Ser Ile Phe Arg Asn Tyr Trp Gly Gln Gly Thr
            100                 105                 110

Gln Val Thr Val Ser Ser
        115


<210> SEQ ID NO 4
<211> LENGTH: 116
<212> TYPE: PRT
<213> ORGANISM: Artificial Sequence
<220> FEATURE:
<223> OTHER INFORMATION: VHH sequence 41D06

<400> SEQUENCE: 4

Gln Val Gln Leu Gln Glu Ser Gly Gly Gly Leu Val Gln Ala Gly Gly
1               5                   10                  15

Ser Leu Arg Leu Ser Cys Ala Ala Ser Gly Gly Ile Phe Gly Ile Asn
            20                  25                  30

Ala Met Arg Trp Tyr Arg Gln Ala Pro Gly Lys Gln Arg Glu Leu Val
        35                  40                  45

Ala Ser Ile Ser Ser Gly Gly Asn Thr Asn Tyr Ser Glu Ser Val Lys
    50                  55                  60

Gly Arg Phe Thr Ile Ser Arg Asp Asp Ala Asn Tyr Thr Val Tyr Leu
65                  70                  75                  80

Gln Met Asn Ser Leu Lys Pro Glu Asp Thr Ala Val Tyr Tyr Cys Asn
                85                  90                  95

Phe Val Arg Leu Trp Phe Pro Asp Tyr Trp Gly Gln Gly Thr Gln Val
            100                 105                 110

Thr Val Ser Ser
        115


<210> SEQ ID NO 5
<211> LENGTH: 121
<212> TYPE: PRT
<213> ORGANISM: Artificial Sequence
<220> FEATURE:
<223> OTHER INFORMATION: VHH sequence 41G10

<400> SEQUENCE: 5

Gln Val Gln Leu Gln Glu Ser Gly Gly Gly Leu Val Gln Pro Gly Gly
1               5                   10                  15

Ser Leu Thr Leu Ser Cys Ala Ala Thr Lys Thr Gly Phe Ser Ile Asn
            20                  25                  30

Ala Met Gly Trp Tyr Arg Gln Ala Pro Gly Lys Gln Arg Glu Met Val
        35                  40                  45

Ala Thr Ile Thr Ser Gly Gly Thr Thr Asn Tyr Ala Asp Ser Val Lys
    50                  55                  60

Gly Arg Phe Ala Ile Ser Arg Asp Asn Ala Lys Asn Thr Val Ser Leu
65                  70                  75                  80

Gln Met Asn Thr Leu Lys Pro Glu Asp Thr Ala Leu Tyr Tyr Cys Asn
                85                  90                  95

Thr Glu Ala Arg Arg Tyr Phe Thr Arg Ala Ser Gln Val Tyr Trp Gly
            100                 105                 110

Gln Gly Thr Gln Val Thr Val Ser Ser
        115                 120
```

<210> SEQ ID NO 6
<211> LENGTH: 120
<212> TYPE: PRT
<213> ORGANISM: Artificial Sequence
<220> FEATURE:
<223> OTHER INFORMATION: VHH sequence 41H05

<400> SEQUENCE: 6

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Gly Ile Phe Ser Ile Asn
            20                  25                  30

Ala Met Gly Trp Tyr Arg Gln Asp Pro Gly Lys Gln Arg Glu Met Val
        35                  40                  45

Ala Thr Ile Thr Ser Gly Ala Asn Thr Asn Tyr Thr Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Val Gly Arg Arg Trp Tyr Gly Gly Tyr Val Glu Leu Trp Gly Gln
            100                 105                 110

Gly Thr Gln Val Thr Val Ser Ser
        115                 120
```

<210> SEQ ID NO 7
<211> LENGTH: 119
<212> TYPE: PRT
<213> ORGANISM: Artificial Sequence
<220> FEATURE:
<223> OTHER INFORMATION: VHH sequence 42C11

<400> SEQUENCE: 7

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Thr Tyr
            20                  25                  30

Val Met Gly Trp Tyr Arg Gln Ala Ile Gly Lys Gln Arg Glu Leu Val
        35                  40                  45

Ala Thr Ile Thr Ser Ser Gly Lys Thr Asn Tyr Ala Ala Ser Val Lys
    50                  55                  60

Gly Arg Phe Thr Val Ser Arg Asp Ile Thr Lys Asn Thr Met Tyr Leu
65                  70                  75                  80

Gln Met Asn Ser Leu Lys Pro Glu Asp Thr Ala Val Tyr Tyr Cys Gly
                85                  90                  95

Ala Asp Arg Trp Val Leu Thr Arg Trp Ser Asn Tyr Trp Gly Gln Gly
            100                 105                 110

Thr Gln Val Thr Val Ser Ser
        115
```

<210> SEQ ID NO 8
<211> LENGTH: 116
<212> TYPE: PRT
<213> ORGANISM: Artificial Sequence
<220> FEATURE:
<223> OTHER INFORMATION: VHH sequence 42C12

<400> SEQUENCE: 8

```
Gln Val Gln Leu Gln Glu Ser Gly Gly Gly Leu Val Gln Pro Gly Gly
```

-continued

```
1               5                   10                  15

Ser Leu Arg Leu Ser Cys Ala Ala Ser Gly Ser Ile Ser Ser Leu Gly
            20                  25                  30

Trp Tyr Arg Gln Ala Pro Gly Lys Gln Arg Glu Phe Val Ala Ser Ala
        35                  40                  45

Thr Ser Gly Gly Asp Thr Thr Tyr Ala Asp Ser Val Lys Gly Arg Phe
    50                  55                  60

Thr Ile Ser Arg Asp Asn Ser Lys Asn Thr Val Tyr Leu Gln Met Asn
65                  70                  75                  80

Ser Leu Lys Pro Glu Asp Thr Ala Val Tyr Tyr Cys Lys Gly Gln Arg
                85                  90                  95

Gly Val Ala Trp Thr Arg Lys Glu Tyr Trp Gly Gln Gly Thr Gln Val
            100                 105                 110

Thr Val Ser Ser
        115


<210> SEQ ID NO 9
<211> LENGTH: 119
<212> TYPE: PRT
<213> ORGANISM: Artificial Sequence
<220> FEATURE:
<223> OTHER INFORMATION: VHH sequence 50D03

<400> SEQUENCE: 9

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Thr Tyr
            20                  25                  30

Ala Met Gly Trp Tyr Arg Gln Ala Ile Gly Lys Gln Arg Glu Leu Val
        35                  40                  45

Ala Thr Ile Thr Ser Ser Gly Lys Thr Asn Tyr Ala Ala Ser Val Lys
    50                  55                  60

Gly Arg Phe Thr Ile Ser Arg Asp Ile Thr Lys Asn Thr Met Tyr Leu
65                  70                  75                  80

Gln Met Asn Ser Leu Lys Pro Glu Asp Thr Ala Val Tyr Tyr Cys Gly
                85                  90                  95

Ala Asp Arg Trp Val Leu Thr Arg Trp Ser Asn Tyr Trp Gly Gln Gly
            100                 105                 110

Thr Gln Val Thr Val Ser Ser
        115


<210> SEQ ID NO 10
<211> LENGTH: 120
<212> TYPE: PRT
<213> ORGANISM: Artificial Sequence
<220> FEATURE:
<223> OTHER INFORMATION: VHH sequence 50D07

<400> SEQUENCE: 10

Gln Val Gln Leu Gln Glu Ser Gly Gly Gly Leu Val Gln Pro Gly Gly
1               5                   10                  15

Ser Leu Arg Leu Ser Cys Thr Ala Ser Gly Asn Ile Val Asn Ile Arg
            20                  25                  30

Asp Met Gly Trp Tyr Arg Gln Val Pro Gly Lys Gln Arg Glu Leu Val
        35                  40                  45

Ala Thr Ile Thr Ser Asp Gln Ser Thr Asn Tyr Ala Asp Ser Val Lys
    50                  55                  60
```

```
Gly Arg Phe Thr Thr Thr Arg Asp Asn Ala Lys Lys Thr Val Tyr Leu
65                  70                  75                  80

Gln Met Asp Ser Leu Lys Pro Glu Asp Thr Ala Gly Tyr Tyr Cys Asn
                85                  90                  95

Ala Arg Val Arg Thr Val Leu Arg Gly Trp Arg Asp Tyr Trp Gly Gln
            100                 105                 110

Gly Thr Gln Val Thr Val Ser Ser
        115                 120
```

<210> SEQ ID NO 11
<211> LENGTH: 119
<212> TYPE: PRT
<213> ORGANISM: Artificial Sequence
<220> FEATURE:
<223> OTHER INFORMATION: VHH sequence 50E02

<400> SEQUENCE: 11

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Thr Ser Asp Gly Ser Thr Asn Tyr Ala Asp Ser Val Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Asn
                85                  90                  95

Leu Arg Arg Arg Thr Phe Leu Lys Ser Ser Asp Tyr Trp Gly Gln Gly
            100                 105                 110

Thr Gln Val Thr Val Ser Ser
        115
```

<210> SEQ ID NO 12
<211> LENGTH: 123
<212> TYPE: PRT
<213> ORGANISM: Artificial Sequence
<220> FEATURE:
<223> OTHER INFORMATION: VHH sequence 51B08

<400> SEQUENCE: 12

```
Gln Val Gln Leu Gln Glu Ser Gly Gly Gly Leu Val Gln Ala Gly Asp
1               5                   10                  15

Ser Leu Arg Leu Ser Cys Ala Ala Ser Gly Arg Arg Phe Gly Ser Tyr
            20                  25                  30

Ala Met Gly Trp Phe Arg Gln Val Pro Gly Lys Glu Arg Glu Leu Val
        35                  40                  45

Ala Gly Ile Ser Ser Gly Gly Ser Thr Lys Tyr Ala Asp Ser Val Arg
    50                  55                  60

Gly Arg Phe Thr Ile Ser Arg Asp Asn Ala Lys Asn Thr Val Ser Leu
65                  70                  75                  80

Gln Met Lys Ser Leu Lys Pro Glu Asp Thr Ala Val Tyr Tyr Cys Asn
                85                  90                  95

Ala Lys Tyr Gly Arg Trp Thr Tyr Thr Gly Arg Pro Glu Tyr Asp Ser
            100                 105                 110

Trp Gly Gln Gly Thr Gln Val Thr Val Ser Ser
        115                 120
```

-continued

<210> SEQ ID NO 13
<211> LENGTH: 116
<212> TYPE: PRT
<213> ORGANISM: Artificial Sequence
<220> FEATURE:
<223> OTHER INFORMATION: VHH sequence 51C06

<400> SEQUENCE: 13

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ser Asp
            20                  25                  30

Thr Met Gly Trp Tyr Arg Arg Ala Pro Gly Lys Gln Arg Glu Leu Val
        35                  40                  45

Ala Ala Ile Thr Thr Gly Gly Asn Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Gln Pro Glu Asp Thr Ala Val Tyr Tyr Cys Asn
                85                  90                  95

Cys Arg Arg Arg Trp Ser Arg Asp Phe Trp Gly Gln Gly Thr Gln Val
            100                 105                 110

Thr Val Ser Ser
        115
```

<210> SEQ ID NO 14
<211> LENGTH: 119
<212> TYPE: PRT
<213> ORGANISM: Artificial Sequence
<220> FEATURE:
<223> OTHER INFORMATION: VHH sequence 51C08

<400> SEQUENCE: 14

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Thr Ile Phe Ser Ile Lys
            20                  25                  30

Thr Met Gly Trp Tyr Arg Gln Ala Pro Gly Lys Gln Arg Glu Leu Val
        35                  40                  45

Ala Thr Ile Ser Asn Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Arg Gln Gln Phe Ile Gly Ala Pro Tyr Glu Tyr Trp Gly Gln Gly
            100                 105                 110

Thr Gln Val Thr Val Ser Ser
        115
```

<210> SEQ ID NO 15
<211> LENGTH: 115
<212> TYPE: PRT
<213> ORGANISM: Artificial Sequence
<220> FEATURE:
<223> OTHER INFORMATION: VHH sequence 52A01

<400> SEQUENCE: 15

```
Gln Val Gln Leu Gln Glu Ser Gly Gly Gly Leu Val Gln Ala Gly Gly
1               5                   10                  15

Ser Leu Arg Leu Ser Cys Thr Ala Ser Gly Ala Ile Thr Phe Ser Leu
            20                  25                  30

Gly Thr Met Gly Trp Tyr Arg Gln Ala Pro Gly Lys Gln Arg Glu Leu
        35                  40                  45

Val Ala Ser Ile Ser Thr Gly Ser Thr Asn Tyr Ala Asp Ser Val Lys
    50                  55                  60

Gly Arg Phe Thr Ile Ser Arg Asp Ile Ile Lys Asn Ile Leu Tyr Leu
65                  70                  75                  80

Gln Met Asn Ser Leu Lys Pro Glu Asp Thr Ala Val Tyr Ser Cys Asn
                85                  90                  95

Ala Arg Leu Leu Trp Ser Asn Tyr Trp Gly Gln Gly Thr Gln Val Thr
            100                 105                 110

Val Ser Ser
        115
```

<210> SEQ ID NO 16
<211> LENGTH: 117
<212> TYPE: PRT
<213> ORGANISM: Artificial Sequence
<220> FEATURE:
<223> OTHER INFORMATION: VHH sequence 52B01

<400> SEQUENCE: 16

```
Gln Val Gln Leu Gln Glu Ser Gly Gly Gly Leu Val Gln Ala Gly Glu
1               5                   10                  15

Ser Leu Arg Leu Ser Cys Ala Ala Ser Gly Ser Thr Phe Ser Ile Asn
            20                  25                  30

Val Met Gly Trp Tyr Arg Gln Ala Pro Gly Glu Gln Arg Glu Leu Val
        35                  40                  45

Ala Thr Ile Ser Arg Gly Gly Ser Thr Asn Tyr Ala Asp Ser Val Lys
    50                  55                  60

Gly Arg Phe Thr Ile Ser Arg Asp Asn Ala Lys Val Thr Val Tyr Leu
65                  70                  75                  80

Gln Met Asp Ser Leu Lys Pro Glu Asp Thr Ala Val Tyr Tyr Cys Asn
                85                  90                  95

Ala Ala Gly Trp Val Gly Val Thr Asn Tyr Trp Gly Gln Gly Thr Gln
            100                 105                 110

Val Thr Val Ser Ser
        115
```

<210> SEQ ID NO 17
<211> LENGTH: 117
<212> TYPE: PRT
<213> ORGANISM: Artificial Sequence
<220> FEATURE:
<223> OTHER INFORMATION: VHH sequence 52G05

<400> SEQUENCE: 17

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Gly Ser Ile Ser
            20                  25                  30

Ala Met Gly Trp Tyr Arg Gln Ala Pro Gly Lys Gln Arg Glu Leu Val
        35                  40                  45

Ala Ser Ile Thr Arg Arg Gly Ser Thr Asn Tyr Ala Asp Ser Val Lys
    50                  55                  60
```

Asp Arg Phe Thr Ile Ser Arg Asp Asn Ala Trp Asn Thr Val Tyr Leu
65 70 75 80

Gln Met Asn Ser Leu Lys Pro Glu Asp Thr Ala Val Tyr Tyr Cys Asn
85 90 95

Ala Arg Arg Tyr Tyr Thr Arg Asn Asp Tyr Trp Gly Gln Gly Thr Gln
100 105 110

Val Thr Val Ser Ser
115

<210> SEQ ID NO 18
<211> LENGTH: 114
<212> TYPE: PRT
<213> ORGANISM: Artificial Sequence
<220> FEATURE:
<223> OTHER INFORMATION: VHH sequence 53A01

<400> SEQUENCE: 18

Gln Val Gln Leu Gln Glu Ser Gly Gly Gly Leu Gly Gln Ala Gly Gly
1 5 10 15

Ser Leu Arg Leu Ser Cys Glu Val Ser Gly Thr Thr Phe Ser Ile Asn
20 25 30

Thr Met Gly Trp His Arg Gln Ala Pro Gly Lys Gln Arg Glu Leu Val
35 40 45

Ala Ser Ile Ser Ser Gly Gly Trp Thr Asn Tyr Ala Asp Ser Val Lys
50 55 60

Gly Arg Phe Thr Ile Ser Arg Asp Asn Ala Lys Lys Thr Val Tyr Leu
65 70 75 80

Gln Met Asn Asn Leu Lys Pro Glu Asp Thr Ala Val Tyr Tyr Cys Arg
85 90 95

Trp Gly Ala Ile Gly Asn Trp Tyr Gly Gln Gly Thr Gln Val Thr Val
100 105 110

Ser Ser

<210> SEQ ID NO 19
<211> LENGTH: 117
<212> TYPE: PRT
<213> ORGANISM: Artificial Sequence
<220> FEATURE:
<223> OTHER INFORMATION: VHH sequence 53F05

<400> SEQUENCE: 19

Gln Val Gln Leu Gln Glu Ser Gly Gly Gly Leu Val Gln Pro Gly Gly
1 5 10 15

Ser Leu Arg Leu Ser Cys Ala Ala Ser Val Arg Ile Phe Gly Leu Asn
20 25 30

Ala Met Gly Trp Tyr Arg Gln Gly Pro Gly Lys Gln Arg Glu Leu Val
35 40 45

Ala Ser Ile Thr Thr Gly Gly Ser Thr Asn Tyr Ala Glu Pro Val Lys
50 55 60

Gly Arg Phe Thr Ile Ser Arg Asp Asn Ala Asn Asn Thr Val Tyr Leu
65 70 75 80

Gln Met Asn Asn Leu Lys Pro Glu Asp Thr Ala Val Tyr Tyr Cys Asn
85 90 95

Ala Glu Arg Arg Trp Gly Leu Pro Asn Tyr Trp Gly Gln Gly Thr Gln
100 105 110

Val Thr Val Ser Ser
115

<210> SEQ ID NO 20
<211> LENGTH: 126
<212> TYPE: PRT
<213> ORGANISM: Artificial Sequence
<220> FEATURE:
<223> OTHER INFORMATION: VHH sequence 54A02

<400> SEQUENCE: 20

```
Gln Val Gln Leu Gln Glu Ser Gly Gly Gly Leu Val Glu Ala Gly Gly
1               5                   10                  15

Ser Leu Arg Leu Ser Cys Ala Ala Ser Gly Arg Thr Phe Ser Arg Tyr
            20                  25                  30

Gly Met Gly Trp Phe Arg Gln Ala Pro Gly Lys Glu Arg Glu Phe Val
        35                  40                  45

Ala Ala Asn Arg Trp Ser Gly Gly Ser Thr Tyr Tyr Ala Asp Ser Val
    50                  55                  60

Arg Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Tyr Ala His Ile Thr Ala Trp Gly Met Arg Asn Asp Tyr Glu
            100                 105                 110

Tyr Asp Tyr Trp Gly Gln Gly Thr Gln Val Thr Val Ser Ser
        115                 120                 125
```

<210> SEQ ID NO 21
<211> LENGTH: 125
<212> TYPE: PRT
<213> ORGANISM: Artificial Sequence
<220> FEATURE:
<223> OTHER INFORMATION: VHH sequence 54B01

<400> SEQUENCE: 21

```
Gln Val Gln Leu Gln Glu Ser Gly Gly Gly Leu Val Gln Ala Gly Gly
1               5                   10                  15

Ser Leu Arg Leu Ser Cys Ala Ala Thr Gly Arg Thr Phe Ser Arg Tyr
            20                  25                  30

Thr Met Gly Trp Phe Arg Gln Ala Pro Gly Lys Glu Arg Asp Phe Val
        35                  40                  45

Ala Gly Ile Thr Trp Thr Gly Gly Ser Thr Asp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Asn Leu Leu Arg Leu Ala Gly Gln Leu Arg Arg Gly Tyr
            100                 105                 110

Asp Ser Trp Gly Gln Gly Thr Gln Val Thr Val Ser Ser
        115                 120                 125
```

<210> SEQ ID NO 22
<211> LENGTH: 129
<212> TYPE: PRT
<213> ORGANISM: Artificial Sequence
<220> FEATURE:
<223> OTHER INFORMATION: VHH sequence 54C01

<400> SEQUENCE: 22

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Gly Ser Arg Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Gly Ser Thr Tyr Tyr Ala Asp Ser Val
    50                  55                  60

Lys Asp Arg Phe Thr Ile Ser Arg Asp Asn Ala Lys Asn Thr Val Tyr
65                  70                  75                  80

Leu Gln Met His Ser Leu Lys Pro Glu Asp Thr Ala Val Tyr Tyr Cys
                85                  90                  95

Ala Thr Arg Asn Arg Ala Gly Pro His Tyr Ser Arg Gly Tyr Thr Ala
            100                 105                 110

Gly Gln Glu Tyr Asp Tyr Trp Gly Gln Gly Thr Gln Val Thr Val Ser
        115                 120                 125

Ser


<210> SEQ ID NO 23
<211> LENGTH: 121
<212> TYPE: PRT
<213> ORGANISM: Artificial Sequence
<220> FEATURE:
<223> OTHER INFORMATION: VHH sequence 54C04

<400> SEQUENCE: 23

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Ile Phe Ser Ile Asn
            20                  25                  30

Ala Met Gly Trp Tyr Arg Gln Gly Pro Gly Lys Glu Arg Glu Leu Val
        35                  40                  45

Val Asp Met Thr Ser Gly Gly Ser Ile Asn Tyr Ala Asp Ser Val Ser
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys His
                85                  90                  95

Ala Asn Leu Arg Thr Ala Phe Trp Arg Asn Gly Asn Asp Tyr Trp Gly
            100                 105                 110

Gln Gly Thr Gln Val Thr Val Ser Ser
        115                 120


<210> SEQ ID NO 24
<211> LENGTH: 115
<212> TYPE: PRT
<213> ORGANISM: Artificial Sequence
<220> FEATURE:
<223> OTHER INFORMATION: VHH sequence 54C08

<400> SEQUENCE: 24

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Ser Ser Ile Asn
            20                  25                  30

Ala Met Gly Trp Tyr Arg Gln Ala Pro Gly Lys Gln Arg Glu Leu Val
        35                  40                  45
```

-continued

```
Ala Ser Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Asn Leu
65                  70                  75                  80

Gln Met Asn Ser Leu Lys Pro Glu Asp Thr Ala Val Tyr Tyr Cys Ser
                85                  90                  95

Ala Gly Pro Trp Tyr Arg Arg Ser Trp Gly Arg Gly Thr Gln Val Thr
            100                 105                 110

Val Ser Ser
        115
```

<210> SEQ ID NO 25
<211> LENGTH: 116
<212> TYPE: PRT
<213> ORGANISM: Artificial Sequence
<220> FEATURE:
<223> OTHER INFORMATION: VHH sequence 54C10

<400> SEQUENCE: 25

```
Gln Val Gln Leu Gln Glu Ser Gly Gly Gly Leu Val Gln Pro Gly Glu
1               5                   10                  15

Ser Leu Arg Leu Ser Cys Ala Ala Ser Ala Ser Ile Phe Trp Val Asn
            20                  25                  30

Asp Met Gly Trp Tyr Arg Gln Ala Pro Gly Lys Gln Arg Glu Leu Val
        35                  40                  45

Ala Gln Ile Thr Arg Arg Gly Ser Thr Asn Tyr Ala Asp Ser Val Lys
    50                  55                  60

Gly Arg Phe Thr Ile Ser Arg Asp Asn Ala Lys Asp Glu Val Tyr Leu
65                  70                  75                  80

Gln Met Asn Ser Leu Lys Pro Glu Asp Thr Ala Val Tyr Tyr Cys Asn
                85                  90                  95

Ala Asp Leu Ala Val Arg Gly Arg Tyr Trp Gly Gln Gly Thr Gln Val
            100                 105                 110

Thr Val Ser Ser
        115
```

<210> SEQ ID NO 26
<211> LENGTH: 119
<212> TYPE: PRT
<213> ORGANISM: Artificial Sequence
<220> FEATURE:
<223> OTHER INFORMATION: VHH sequence 54C11

<400> SEQUENCE: 26

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Phe Phe Pro Val Asn
            20                  25                  30

Asp Met Ala Trp Tyr Arg Gln Ala Leu Gly Asn Glu Arg Glu Leu Val
        35                  40                  45

Ala Asn Ile Thr Arg Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Thr Leu Lys Pro Glu Asp Thr Ala Val Tyr Tyr Cys Asn
                85                  90                  95

Val Arg Ile Gly Phe Gly Trp Thr Ala Lys Ala Tyr Trp Gly Gln Gly
            100                 105                 110
```

Thr Gln Val Thr Val Ser Ser
115

<210> SEQ ID NO 27
<211> LENGTH: 116
<212> TYPE: PRT
<213> ORGANISM: Artificial Sequence
<220> FEATURE:
<223> OTHER INFORMATION: VHH sequence 54D03

<400> SEQUENCE: 27

Gln Val Gln Leu Gln Glu Ser Gly Gly Gly Leu Val Gln Pro Gly Gly
1 5 10 15

Ser Leu Arg Leu Ser Cys Ala Ala Ser Gly Gly Ile Phe Gly Ile Asn
20 25 30

Ala Met Arg Trp Tyr Arg Gln Ala Pro Gly Lys Gln Arg Glu Leu Val
35 40 45

Ala Ser Ile Ser Ser Gly Gly Asn Thr Asn Tyr Ser Glu Ser Val Lys
50 55 60

Gly Arg Phe Thr Ile Ser Arg Asp Asp Ala Asn Tyr Thr Val Tyr Leu
65 70 75 80

Gln Met Asn Ser Leu Lys Pro Glu Asp Thr Ala Val Tyr Tyr Cys Asn
85 90 95

Phe Val Arg Leu Trp Phe Pro Asp Tyr Trp Gly Gln Gly Thr Gln Val
100 105 110

Thr Val Ser Ser
115

<210> SEQ ID NO 28
<211> LENGTH: 116
<212> TYPE: PRT
<213> ORGANISM: Artificial Sequence
<220> FEATURE:
<223> OTHER INFORMATION: VHH sequence 54D06

<400> SEQUENCE: 28

Gln Val Gln Leu Gln Glu Ser Gly Gly Gly Leu Val Gln Pro Gly Gly
1 5 10 15

Ser Leu Arg Leu Ser Cys Ala Ala Ser Gly Ser Thr Ile Arg Ile Asn
20 25 30

Ala Met Gly Trp Tyr Arg Gln Ala Pro Gly Lys Gln Arg Glu Leu Val
35 40 45

Ala Thr Ile Thr Arg Gly Gly Ile Thr Asn Tyr Ala Asp Ser Val Lys
50 55 60

Gly Arg Phe Thr Ile Ser Arg Asp Asn Ala Lys Phe Thr Val Tyr Leu
65 70 75 80

Gln Met Asn Ser Leu Lys Pro Glu Asp Thr Ala Val Tyr Tyr Cys Asn
85 90 95

Ala Arg Ser Trp Val Gly Pro Glu Tyr Trp Gly Gln Gly Thr Gln Val
100 105 110

Thr Val Ser Ser
115

<210> SEQ ID NO 29
<211> LENGTH: 120
<212> TYPE: PRT
<213> ORGANISM: Artificial Sequence
<220> FEATURE:
<223> OTHER INFORMATION: VHH sequence 54D10

<400> SEQUENCE: 29

Gln Val Gln Leu Gln Glu Ser Gly Gly Gly Leu Val Gln Pro Gly Gly
1               5                   10                  15

Ser Leu Arg Leu Ser Cys Ala Ala Ser Gly Met Thr Tyr Ser Ile His
            20                  25                  30

Ala Met Gly Trp Tyr Arg Gln Ala Pro Gly Lys Glu Arg Glu Leu Val
        35                  40                  45

Ala Ile Thr Ser Thr Ser Gly Thr Thr Asp Tyr Thr Asp Ser Val Lys
    50                  55                  60

Gly Arg Phe Thr Ile Ser Arg Asp Gly Ala Asn Asn Thr Val Tyr Leu
65                  70                  75                  80

Gln Met Asn Ser Leu Lys Ser Glu Asp Thr Ala Val Tyr Tyr Cys His
                85                  90                  95

Val Lys Thr Arg Thr Trp Tyr Asn Gly Lys Tyr Asp Tyr Trp Gly Gln
            100                 105                 110

Gly Thr Gln Val Thr Val Ser Ser
        115                 120

<210> SEQ ID NO 30
<211> LENGTH: 117
<212> TYPE: PRT
<213> ORGANISM: Artificial Sequence
<220> FEATURE:
<223> OTHER INFORMATION: VHH sequence 54E01

<400> SEQUENCE: 30

Gln Val Gln Leu Gln Glu Ser Gly Gly Gly Leu Val Gln Pro Gly Gly
1               5                   10                  15

Ser Leu Arg Leu Ser Cys Thr Ala Ser Gly Ser Ile Phe Ser Ile Asn
            20                  25                  30

Pro Met Gly Trp Tyr Arg Gln Ala Pro Gly Lys Gln Arg Glu Leu Val
        35                  40                  45

Ala Ala Ile Thr Ser Gly Gly Ser Thr Asn Tyr Ala Asp Tyr Val Lys
    50                  55                  60

Gly Arg Phe Thr Ile Ser Arg Asp Asn Ala Lys Asn Val Val Tyr Leu
65                  70                  75                  80

Gln Met Asn Ser Leu Lys Pro Glu Asp Thr Ala Val Tyr Tyr Cys Asn
                85                  90                  95

Gly Arg Ser Thr Leu Trp Arg Arg Asp Tyr Trp Gly Gln Gly Thr Gln
            100                 105                 110

Val Thr Val Ser Ser
        115

<210> SEQ ID NO 31
<211> LENGTH: 117
<212> TYPE: PRT
<213> ORGANISM: Artificial Sequence
<220> FEATURE:
<223> OTHER INFORMATION: VHH sequence 54E05

<400> SEQUENCE: 31

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Thr Met Gly Trp Tyr Arg Gln Ala Pro Gly Lys Gln Arg Glu Leu Val
        35                  40                  45

```
Ala Ala Ile Thr Asn Arg Gly Ser Thr Asn Tyr Ala Asp Phe Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Asp Asp Thr Ala Val Tyr Tyr Cys Asn
                85                  90                  95

Ala His Arg Ser Trp Pro Arg Tyr Asp Ser Trp Gly Gln Gly Thr Gln
            100                 105                 110

Val Thr Val Ser Ser
        115


<210> SEQ ID NO 32
<211> LENGTH: 118
<212> TYPE: PRT
<213> ORGANISM: Artificial Sequence
<220> FEATURE:
<223> OTHER INFORMATION: VHH sequence 54E10

<400> SEQUENCE: 32

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Phe Asn
            20                  25                  30

Ala Met Gly Trp Tyr Arg Gln Ala Pro Gly Lys Gln Arg Glu Leu Val
        35                  40                  45

Ala Ala Ile Thr Arg Gly Gly Ser Thr Asn Tyr Ala Asp Ser Val Lys
    50                  55                  60

Gly Arg Phe Thr Ile Ser Arg Asp Asn Ala Asn Asn Thr Val Tyr Leu
65                  70                  75                  80

Gln Met Asn Ser Leu Lys Pro Glu Asp Thr Ala Val Tyr Tyr Cys Asn
                85                  90                  95

Ala Glu Ser Arg Ile Phe Arg Arg Tyr Asp Tyr Trp Gly Pro Gly Thr
            100                 105                 110

Gln Val Thr Val Ser Ser
        115


<210> SEQ ID NO 33
<211> LENGTH: 115
<212> TYPE: PRT
<213> ORGANISM: Artificial Sequence
<220> FEATURE:
<223> OTHER INFORMATION: VHH sequence 54F01

<400> SEQUENCE: 33

Gln Val Gln Leu Gln Glu Ser Gly Gly Gly Leu Val Gln Pro Gly Gly
1               5                   10                  15

Ser Leu Arg Leu Ser Cys Val Thr Ser Gly Ser Ile Phe Gly Leu Asn
            20                  25                  30

Leu Met Gly Trp Tyr Arg Gln Ala Pro Gly Lys Gln Arg Glu Leu Val
        35                  40                  45

Ala Thr Ile Thr Arg Gly Gly Ser Thr Asn Tyr Ala Asp Ser Val Lys
    50                  55                  60

Gly Arg Phe Thr Ile Ser Arg Asp Asn Ala Lys Lys Thr Val Tyr Leu
65                  70                  75                  80

Gln Met Asn Ser Leu Lys Pro Glu Asp Thr Ala Val Tyr Tyr Cys Asn
                85                  90                  95

Val Asp Arg Gly Trp Ser Ser Tyr Trp Gly Gln Gly Thr Gln Val Thr
```

```
            100                 105                 110

Val Ser Ser
        115


<210> SEQ ID NO 34
<211> LENGTH: 119
<212> TYPE: PRT
<213> ORGANISM: Artificial Sequence
<220> FEATURE:
<223> OTHER INFORMATION: VHH sequence 54F02

<400> SEQUENCE: 34

Gln Val Gln Leu Gln Glu Ser Gly Gly Gly Leu Val Gln Pro Gly Gly
1               5                   10                  15

Ser Leu Arg Leu Ser Cys Val Thr Ser Gly Ser Ile Arg Ser Ile Asn
            20                  25                  30

Thr Met Gly Trp Tyr Arg Gln Ala Pro Gly Asn Glu Arg Glu Leu Val
        35                  40                  45

Ala Thr Ile Thr Ser Gly Gly Thr Thr Asn Tyr Ala Asp Ser Val Lys
    50                  55                  60

Asn Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Leu His Gln Arg Ala Trp Ala Arg Ser Tyr Val Tyr Trp Gly Gln Gly
            100                 105                 110

Thr Gln Val Thr Val Ser Ser
        115


<210> SEQ ID NO 35
<211> LENGTH: 117
<212> TYPE: PRT
<213> ORGANISM: Artificial Sequence
<220> FEATURE:
<223> OTHER INFORMATION: VHH sequence 54G01

<400> SEQUENCE: 35

Gln Val Gln Leu Gln Glu Ser Gly Gly Gly Ser Val Gln Pro Gly Gly
1               5                   10                  15

Ser Leu Arg Leu Ser Cys Ala Ala Ser Gly Ser Ile Phe Ala Val Asn
            20                  25                  30

Ala Met Gly Trp Tyr Arg Gln Ala Pro Gly His Gln Arg Glu Leu Val
        35                  40                  45

Ala Ile Ile Ser Ser Asn Ser Thr Ser Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Phe Cys Tyr
                85                  90                  95

Ala Lys Arg Ser Trp Phe Ser Gln Glu Tyr Trp Gly Gln Gly Thr Gln
            100                 105                 110

Val Thr Val Ser Ser
        115


<210> SEQ ID NO 36
<211> LENGTH: 121
<212> TYPE: PRT
<213> ORGANISM: Artificial Sequence
<220> FEATURE:
```

<223> OTHER INFORMATION: VHH sequence 54G08

<400> SEQUENCE: 36

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Phe Asn
            20                  25                  30

Leu Met Gly Trp Tyr Arg Gln Ala Pro Gly Lys Gln Arg Glu Leu Val
        35                  40                  45

Ala Ala Ile Thr Ser Ser Ser Asn Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Gln Tyr Thr Ile Thr Pro Trp Gly Ile Lys Lys Asp Tyr Trp Gly
            100                 105                 110

Gln Gly Thr Gln Val Thr Val Ser Ser
        115                 120

<210> SEQ ID NO 37
<211> LENGTH: 120
<212> TYPE: PRT
<213> ORGANISM: Artificial Sequence
<220> FEATURE:
<223> OTHER INFORMATION: VHH sequence 54G09

<400> SEQUENCE: 37

Gln Val Gln Leu Gln Glu Ser Gly Gly Gly Leu Met Gln Pro Gly Gly
1               5                   10                  15

Ser Leu Arg Leu Ser Cys Thr Ala Ser Gly Asn Ile Val Asn Ile Arg
            20                  25                  30

Asp Met Gly Trp Tyr Arg Gln Val Pro Gly Lys Gln Arg Glu Leu Val
        35                  40                  45

Ala Thr Ile Thr Ser Asp Gln Ser Thr Asn Tyr Ala Asp Ser Val Lys
    50                  55                  60

Gly Arg Phe Thr Thr Thr Arg Asp Asn Ala Lys Lys Thr Val Tyr Leu
65                  70                  75                  80

Gln Met Asp Ser Leu Lys Pro Glu Asp Thr Ala Gly Tyr Tyr Cys Asn
                85                  90                  95

Ala Arg Val Arg Thr Val Leu Arg Gly Trp Arg Asp Tyr Trp Gly Gln
            100                 105                 110

Gly Thr Gln Val Thr Val Ser Ser
        115                 120

<210> SEQ ID NO 38
<211> LENGTH: 117
<212> TYPE: PRT
<213> ORGANISM: Artificial Sequence
<220> FEATURE:
<223> OTHER INFORMATION: VHH sequence 55B02

<400> SEQUENCE: 38

Gln Val Gln Leu Gln Glu Ser Gly Gly Gly Leu Val Gln Pro Gly Glu
1               5                   10                  15

Ser Leu Arg Leu Ser Cys Val Gly Ser Gly Ser Ile Phe Asn Ile Asn
            20                  25                  30

Ser Met Asn Trp Tyr Arg Gln Ala Ser Gly Lys Gln Arg Glu Leu Val

```
        35                  40                  45

Ala Asp Met Arg Ser Asp Gly Ser Thr Asn Tyr Ala Asp Ser Val Lys
    50                  55                  60

Gly Arg Phe Thr Ile Ser Arg Asp Asn Ala Arg Lys Thr Val Tyr Leu
65                  70                  75                  80

Gln Met Asn Ser Leu Lys Pro Glu Asp Thr Ala Val Tyr Tyr Cys His
                85                  90                  95

Ala Asn Ser Ile Phe Arg Ser Arg Asp Tyr Trp Gly Gln Gly Thr Gln
            100                 105                 110

Val Thr Val Ser Ser
        115


<210> SEQ ID NO 39
<211> LENGTH: 125
<212> TYPE: PRT
<213> ORGANISM: Artificial Sequence
<220> FEATURE:
<223> OTHER INFORMATION: VHH sequence 55B05

<400> SEQUENCE: 39

Gln Val Gln Leu Gln Glu Ser Gly Gly Gly Val Val Gln Ala Gly Asp
1               5                   10                  15

Ser Leu Arg Leu Ser Cys Ala Ala Ser Gly Arg Thr Phe Gly Gly Tyr
            20                  25                  30

Thr Val Ala Trp Phe Arg Gln Ala Pro Gly Lys Glu Arg Glu Phe Val
        35                  40                  45

Ala Arg Ile Ser Trp Ser Gly Ile Met Ala Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ser Arg Ser Gln Ile Arg Ser Pro Trp Ser Ser Leu Asp Asp Tyr
            100                 105                 110

Asp Arg Trp Gly Gln Gly Thr Gln Val Thr Val Ser Ser
        115                 120                 125


<210> SEQ ID NO 40
<211> LENGTH: 116
<212> TYPE: PRT
<213> ORGANISM: Artificial Sequence
<220> FEATURE:
<223> OTHER INFORMATION: VHH sequence 55C05

<400> SEQUENCE: 40

Gln Val Gln Leu Gln Glu Ser Gly Gly Gly Leu Val Gln Pro Gly Gly
1               5                   10                  15

Ser Leu Arg Leu Ser Cys Val Val Ser Gly Ser Ile Ser Ser Met Lys
            20                  25                  30

Ala Met Gly Trp His Arg Gln Ala Pro Gly Lys Glu Arg Glu Leu Val
        35                  40                  45

Ala Gln Ile Thr Arg Gly Asp Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Asp Asp Thr Gly Val Tyr Tyr Cys Asn
                85                  90                  95
```

```
Ala Asp Arg Phe Phe Gly Arg Asp Tyr Trp Gly Lys Gly Thr Gln Val
            100                 105                 110

Thr Val Ser Ser
        115


<210> SEQ ID NO 41
<211> LENGTH: 120
<212> TYPE: PRT
<213> ORGANISM: Artificial Sequence
<220> FEATURE:
<223> OTHER INFORMATION: VHH sequence 55D08

<400> SEQUENCE: 41

Gln Val Gln Leu Gln Glu Ser Gly Gly Gly Leu Val Gln Pro Gly Gly
1               5                   10                  15

Ser Leu Arg Leu Ser Cys Ala Ala Ser Arg Ser Ile Leu Ser Ile Ser
            20                  25                  30

Ala Met Gly Trp Tyr Arg Gln Gly Pro Gly Lys Gln Arg Glu Pro Val
        35                  40                  45

Ala Thr Ile Thr Ser Ala Gly Ser Ser Asn Tyr Ser Asp Ser Val Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Lys
                85                  90                  95

Thr Val Tyr Ser Arg Pro Leu Leu Gly Pro Leu Glu Val Trp Gly Gln
            100                 105                 110

Gly Thr Gln Val Thr Val Ser Ser
        115                 120


<210> SEQ ID NO 42
<211> LENGTH: 115
<212> TYPE: PRT
<213> ORGANISM: Artificial Sequence
<220> FEATURE:
<223> OTHER INFORMATION: VHH sequence 55E02

<400> SEQUENCE: 42

Gln Val Gln Leu Gln Glu Ser Gly Gly Gly Leu Val Gln Thr Gly Gly
1               5                   10                  15

Ser Leu Arg Leu Ser Cys Val Ala Ser Gly Ser Met Phe Ser Ser Asn
            20                  25                  30

Ala Met Ala Trp Tyr Arg Gln Ala Pro Gly Lys Gln Arg Glu Leu Val
        35                  40                  45

Ala Arg Ile Leu Ser Gly Gly Ser Thr Asn Tyr Ala Asp Ser Val Lys
    50                  55                  60

Gly Arg Phe Thr Ile Ser Arg Gly Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Val Arg Tyr Leu Val Asn Tyr Trp Gly Gln Gly Thr Gln Val Thr
            100                 105                 110

Val Ser Ser
        115


<210> SEQ ID NO 43
<211> LENGTH: 121
<212> TYPE: PRT
<213> ORGANISM: Artificial Sequence
```

```
<220> FEATURE:
<223> OTHER INFORMATION: VHH sequence 55E07

<400> SEQUENCE: 43

Gln Val Gln Leu Gln Glu Ser Gly Gly Gly Ser Val Gln Val Gly Asp
1               5                   10                  15

Ser Leu Thr Leu Ser Cys Val Ala Ser Gly Arg Ser Leu Asp Ile Tyr
            20                  25                  30

Gly Met Gly Trp Phe Arg Gln Ala Pro Gly Lys Glu Arg Glu Phe Val
        35                  40                  45

Ala Arg Ile Thr Ser Gly Gly Ser Thr Tyr Tyr Ala Asp Ser Val Lys
    50                  55                  60

Gly Arg Phe Thr Leu Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Ala Gly Val Val Val Ala Thr Ser Pro Lys Phe Tyr Ala Tyr Trp Gly
            100                 105                 110

Gln Gly Thr Gln Val Thr Val Ser Ser
        115                 120


<210> SEQ ID NO 44
<211> LENGTH: 116
<212> TYPE: PRT
<213> ORGANISM: Artificial Sequence
<220> FEATURE:
<223> OTHER INFORMATION: VHH sequence 55E09

<400> SEQUENCE: 44

Gln Val Gln Leu Gln Glu Ser Gly Gly Gly Leu Val Gln Ala Gly Gly
1               5                   10                  15

Ser Leu Arg Leu Ser Cys Ala Ala Ser Lys Arg Ile Phe Ser Thr Tyr
            20                  25                  30

Thr Met Gly Trp Phe Arg Gln Ala Pro Gly Lys Glu Arg Glu Phe Val
        35                  40                  45

Ala Ala Ile Ile Trp Ser Gly Gly Arg Thr Arg Tyr Ala Asp Ser Val
    50                  55                  60

Lys Gly Arg Phe Thr Ile Ser Arg Asp Asn Ala Arg Asn Thr Val His
65                  70                  75                  80

Leu Gln Met Asn Ser Leu Glu Pro Glu Asp Thr Ala Val Tyr Tyr Cys
                85                  90                  95

Tyr Thr Arg Arg Leu Gly Thr Gly Tyr Trp Gly Gln Gly Thr Gln Val
            100                 105                 110

Thr Val Ser Ser
        115


<210> SEQ ID NO 45
<211> LENGTH: 115
<212> TYPE: PRT
<213> ORGANISM: Artificial Sequence
<220> FEATURE:
<223> OTHER INFORMATION: VHH sequence 55E10

<400> SEQUENCE: 45

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Phe Ser Ile Gln
            20                  25                  30
```

-continued

```
Thr Ile Gly Trp Tyr Arg Gln Ala Pro Gly Lys Gln Arg Asp Arg Val
        35                  40                  45

Ala Thr Ile Ser Ser Gly Gly Ser Thr Asn Tyr Ala Asp Ser Val Lys
    50                  55                  60

Gly Arg Phe Thr Ile Ser Arg Asp Asn Ala Lys Lys Thr Val Tyr Leu
65                  70                  75                  80

Gln Met Asn Asn Leu Lys Pro Glu Asp Thr Ala Val Tyr Tyr Cys Asn
                85                  90                  95

Leu Arg Tyr Trp Phe Arg Asp Tyr Trp Gly Gln Gly Thr Gln Val Thr
            100                 105                 110

Val Ser Ser
        115


<210> SEQ ID NO 46
<211> LENGTH: 115
<212> TYPE: PRT
<213> ORGANISM: Artificial Sequence
<220> FEATURE:
<223> OTHER INFORMATION: VHH sequence 55F04

<400> SEQUENCE: 46

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Thr Phe Ser Ile Asn
            20                  25                  30

Val Arg Gly Trp Tyr Arg Gln Ala Pro Gly Lys Gln Arg Glu Leu Val
        35                  40                  45

Ala Thr Ile Thr Ser Asp Gly Ser Thr Asn Tyr Ala Asp Ser Val Lys
    50                  55                  60

Gly Arg Phe Thr Ile Ser Arg Asp Asn Ala Lys Asn Thr Ala Tyr Leu
65                  70                  75                  80

Gln Met Asn Ser Leu Lys Pro Glu Asp Thr Ala Val Tyr Tyr Cys Asn
                85                  90                  95

Ala Val Arg Leu Phe Arg Gln Tyr Trp Gly Gln Gly Thr Gln Val Thr
            100                 105                 110

Val Ser Ser
        115


<210> SEQ ID NO 47
<211> LENGTH: 125
<212> TYPE: PRT
<213> ORGANISM: Artificial Sequence
<220> FEATURE:
<223> OTHER INFORMATION: VHH sequence 55F09

<400> SEQUENCE: 47

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Arg Leu Asn
            20                  25                  30

Ala Met Gly Trp Tyr Arg Gln Ala Pro Gly Lys Gln Arg Glu Leu Val
        35                  40                  45

Ala Ala Ile Thr Pro Gly Gly Gly Asn Thr Thr Tyr Ala Asp Ser Val
    50                  55                  60

Lys Gly Arg Phe Thr Ile Ser Arg Asp Asn Ala Leu Asn Thr Ile Tyr
65                  70                  75                  80

Leu Gln Met Asn Ser Leu Lys Pro Glu Asp Thr Ala Val Tyr Tyr Cys
                85                  90                  95
```

```
Asn Ala Gly Gly Ser Ser Arg Trp Tyr Ser Ser Arg Tyr Tyr Pro Gly
            100                 105                 110

Gly Tyr Trp Gly Gln Gly Thr Gln Val Thr Val Ser Ser
        115                 120                 125


<210> SEQ ID NO 48
<211> LENGTH: 126
<212> TYPE: PRT
<213> ORGANISM: Artificial Sequence
<220> FEATURE:
<223> OTHER INFORMATION: VHH sequence 55F10

<400> SEQUENCE: 48

Gln Val Gln Leu Gln Glu Ser Gly Gly Gly Leu Val Gln Ala Gly Gly
1               5                   10                  15

Ser Leu Arg Leu Ser Cys Ala Thr Ser Gly Gly Thr Phe Ser Arg Tyr
            20                  25                  30

Ala Met Gly Trp Phe Arg Gln Ala Pro Gly Lys Glu Arg Glu Leu Val
        35                  40                  45

Ala Thr Ile Arg Arg Ser Gly Ser Ser Thr Tyr Tyr Leu Asp Ser Thr
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Leu Glu Asp Thr Ala Val Tyr Tyr Cys
                85                  90                  95

Ala Ala Asp Ser Ser Ala Arg Ala Leu Val Gly Gly Pro Gly Asn Arg
            100                 105                 110

Trp Asp Tyr Trp Gly Gln Gly Thr Gln Val Thr Val Ser Ser
        115                 120                 125


<210> SEQ ID NO 49
<211> LENGTH: 118
<212> TYPE: PRT
<213> ORGANISM: Artificial Sequence
<220> FEATURE:
<223> OTHER INFORMATION: VHH sequence 55G02

<400> SEQUENCE: 49

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Gly Ser Ile Asn
            20                  25                  30

Val Met Gly Trp Tyr Arg Gln Tyr Pro Gly Lys Gln Arg Glu Leu Val
        35                  40                  45

Ala Phe Ile Thr Ser Gly Gly Ile Thr Asn Tyr Thr Asp Ser Val Lys
    50                  55                  60

Gly Arg Phe Ala Ile Ser Arg Asp Asn Ala Gln Asn Thr Val Tyr Leu
65                  70                  75                  80

Gln Met Asn Ser Leu Thr Pro Glu Asp Thr Ala Val Tyr Tyr Cys His
                85                  90                  95

Leu Lys Asn Ala Lys Asn Val Arg Pro Gly Tyr Trp Gly Gln Gly Thr
            100                 105                 110

Gln Val Thr Val Ser Ser
        115


<210> SEQ ID NO 50
<211> LENGTH: 116
<212> TYPE: PRT
```

```
<213> ORGANISM: Artificial Sequence
<220> FEATURE:
<223> OTHER INFORMATION: VHH sequence 55G08

<400> SEQUENCE: 50

Gln Val Gln Leu Gln Glu Ser Gly Gly Gly Leu Val Gln Pro Gly Gly
1               5                   10                  15

Ser Leu Arg Leu Ser Cys Arg Ala Ser Gly Gly Ile Phe Gly Ile Asn
            20                  25                  30

Ala Met Arg Trp Tyr Arg Gln Ala Pro Gly Lys Gln Arg Glu Leu Val
        35                  40                  45

Ala Ser Ile Ser Ser Gly Gly Thr Thr Asp Tyr Val Glu Ser Val Lys
    50                  55                  60

Gly Arg Phe Thr Ile Ser Arg Asp Asn Ala Thr Asn Thr Val Asp Leu
65                  70                  75                  80

Gln Met Ser Ala Leu Lys Pro Glu Asp Thr Ala Val Tyr Tyr Cys Asn
                85                  90                  95

Phe Val Arg Phe Trp Phe Pro Asp Tyr Trp Gly Gln Gly Thr Gln Val
            100                 105                 110

Thr Val Ser Ser
        115


<210> SEQ ID NO 51
<211> LENGTH: 116
<212> TYPE: PRT
<213> ORGANISM: Artificial Sequence
<220> FEATURE:
<223> OTHER INFORMATION: VHH sequence 56A05

<400> SEQUENCE: 51

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ile Thr Phe Met Ser Asn
            20                  25                  30

Thr Met Gly Trp Tyr Arg Gln Ala Pro Gly Lys Gln Arg Glu Leu Val
        35                  40                  45

Ala Ser Ile Ser Ser Gly Gly Ser Thr Asn Tyr Ala Asp Ser Val Lys
    50                  55                  60

Gly Arg Phe Thr Ile Ser Arg Asp Asn Ala Lys Lys Thr Val Tyr Leu
65                  70                  75                  80

Gln Met Asn Ser Leu Lys Pro Glu Asp Thr Ala Val Tyr Tyr Cys Asn
                85                  90                  95

Ala Arg Arg Asn Val Phe Ile Ser Ser Trp Gly Gln Gly Thr Gln Val
            100                 105                 110

Thr Val Ser Ser
        115


<210> SEQ ID NO 52
<211> LENGTH: 114
<212> TYPE: PRT
<213> ORGANISM: Artificial Sequence
<220> FEATURE:
<223> OTHER INFORMATION: VHH sequence 56A06

<400> SEQUENCE: 52

Gln Val Gln Leu Gln Glu Ser Gly Gly Gly Leu Val Gln Pro Gly Gly
1               5                   10                  15

Ser Leu Arg Leu Ser Cys Val Ala Ser Gly Ser Ile Ser Val Tyr Gly
            20                  25                  30
```

```
Met Gly Trp Tyr Arg Gln Ala Pro Gly Lys Gln Arg Glu Leu Val Ala
        35                  40                  45

Arg Ile Thr Asn Ile Gly Thr Thr Asn Tyr Ala Asp Ser Val Lys Gly
    50                  55                  60

Arg Phe Thr Ile Ser Arg Asp Asn Ala Lys Asn Thr Val Tyr Leu Gln
65                  70                  75                  80

Met Asn Ser Leu Gln Pro Glu Asp Thr Ala Val Tyr Tyr Cys Asn Leu
                85                  90                  95

Arg Arg Leu Gly Arg Asp Tyr Trp Gly Gln Gly Thr Gln Val Thr Val
            100                 105                 110

Ser Ser
```

<210> SEQ ID NO 53
<211> LENGTH: 118
<212> TYPE: PRT
<213> ORGANISM: Artificial Sequence
<220> FEATURE:
<223> OTHER INFORMATION: VHH sequence 56A09

<400> SEQUENCE: 53

```
Gln Val Gln Leu Gln Glu Ser Gly Gly Gly Leu Val Gln Pro Gly Gly
1               5                   10                  15

Ser Leu Arg Leu Ser Cys Ala Ala Ser Arg Thr Ala Leu Arg Leu Asn
            20                  25                  30

Ser Met Gly Trp Tyr Arg Gln Ala Pro Gly Ser Gln Arg Glu Leu Val
        35                  40                  45

Ala Thr Ile Thr Arg Gly Gly Thr Thr Asn Tyr Ala Asp Ser Val Lys
    50                  55                  60

Gly Arg Phe Thr Ile Ser Arg Glu Ile Gly Asn Asn Thr Val Tyr Leu
65                  70                  75                  80

Gln Met Asn Ser Leu Glu Pro Glu Asp Thr Ala Val Tyr Tyr Cys Asn
                85                  90                  95

Ala Asn Phe Gly Ile Leu Val Gly Arg Glu Tyr Trp Gly Lys Gly Thr
            100                 105                 110

Gln Val Thr Val Ser Ser
        115
```

<210> SEQ ID NO 54
<211> LENGTH: 116
<212> TYPE: PRT
<213> ORGANISM: Artificial Sequence
<220> FEATURE:
<223> OTHER INFORMATION: VHH sequence 56C09

<400> SEQUENCE: 54

```
Gln Val Gln Leu Gln Glu Ser Gly Gly Gly Leu Val Gln Ala Gly Gly
1               5                   10                  15

Ser Leu Arg Leu Ser Cys Ala Val Ser Gly Ser Ile Phe Ser Ile Leu
            20                  25                  30

Ser Met Ala Trp Tyr Arg Gln Thr Pro Gly Lys Gln Arg Glu Leu Val
        35                  40                  45

Ala Asn Ile Thr Ser Val Gly Ser Thr Asn Tyr Ala Asp Ser Val Lys
    50                  55                  60

Gly Arg Phe Thr Ile Ser Arg Asp Ile Ala Lys Lys Thr Leu Tyr Leu
65                  70                  75                  80

Gln Met Asn Asn Leu Lys Pro Glu Asp Thr Ala Ile Tyr Tyr Cys Asn
                85                  90                  95
```

```
Thr Arg Met Pro Phe Leu Gly Asp Ser Trp Gly Gln Gly Thr Gln Val
            100                 105                 110

Thr Val Ser Ser
        115


<210> SEQ ID NO 55
<211> LENGTH: 111
<212> TYPE: PRT
<213> ORGANISM: Artificial Sequence
<220> FEATURE:
<223> OTHER INFORMATION: VHH sequence 56C12

<400> SEQUENCE: 55

Gln Val Gln Leu Gln Glu Ser Gly Gly Gly Leu Val Gln Ala Gly Gly
1               5                   10                  15

Ser Leu Arg Leu Ser Cys Ala Val Ser Ala Phe Ser Phe Ser Asn Arg
            20                  25                  30

Ala Val Ser Trp Tyr Arg Gln Ala Pro Gly Lys Ser Arg Glu Trp Val
        35                  40                  45

Ala Ser Ile Ser Gly Ile Arg Ile Thr Thr Tyr Thr Asn Ser Val Lys
    50                  55                  60

Gly Arg Phe Ile Ile Ser Arg Asp Asn Ala Lys Lys Thr Val Tyr Leu
65                  70                  75                  80

Gln Met Asn Asp Leu Arg Pro Glu Asp Thr Gly Val Tyr Arg Cys Tyr
                85                  90                  95

Met Asn Arg Tyr Ser Gly Gln Gly Thr Gln Val Thr Val Ser Ser
            100                 105                 110


<210> SEQ ID NO 56
<211> LENGTH: 117
<212> TYPE: PRT
<213> ORGANISM: Artificial Sequence
<220> FEATURE:
<223> OTHER INFORMATION: VHH sequence 56D06

<400> SEQUENCE: 56

Gln Val Gln Leu Gln Glu Ser Gly Gly Gly Ser Val Gln Pro Gly Gly
1               5                   10                  15

Ser Leu Arg Leu Ser Cys Ala Ala Ser Gly Thr Val Phe Phe Ser Ile
            20                  25                  30

Ser Ala Met Gly Trp Tyr Arg Gln Ala Pro Gly Lys Gln Arg Glu Leu
        35                  40                  45

Val Ala Gly Ile Ser Arg Gly Gly Ser Thr Lys Tyr Gly Asp Phe Val
    50                  55                  60

Lys Gly Arg Phe Thr Ile Ser Arg Asp Asn Gly Lys Lys Thr Ile Trp
65                  70                  75                  80

Leu Gln Met Asn Asn Leu Gln Pro Glu Asp Thr Ala Ile Tyr Tyr Cys
                85                  90                  95

Arg Leu Thr Ser Ile Thr Gly Thr Tyr Leu Trp Gly Gln Gly Thr Gln
            100                 105                 110

Val Thr Val Ser Ser
        115


<210> SEQ ID NO 57
<211> LENGTH: 114
<212> TYPE: PRT
<213> ORGANISM: Artificial Sequence
<220> FEATURE:
<223> OTHER INFORMATION: VHH sequence 56D07
```

<400> SEQUENCE: 57

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Met Lys
            20                  25                  30

Val Met Gly Trp Tyr Arg Gln Gly Pro Gly Lys Leu Arg Glu Leu Val
        35                  40                  45

Ala Val Ile Thr Ser Gly Gly Arg Thr Asn Tyr Ala Glu Ser Val Lys
    50                  55                  60

Gly Arg Phe Thr Ile Ser Arg Asp Asn Ala Lys Asn Thr Val Ser Leu
65                  70                  75                  80

Gln Met Asn Ser Leu Gln Pro Glu Asp Thr Ala Val Tyr Tyr Cys Tyr
                85                  90                  95

Tyr Lys Thr Ile Arg Pro Tyr Trp Gly Gln Gly Thr Gln Val Thr Val
            100                 105                 110

Ser Ser

<210> SEQ ID NO 58
<211> LENGTH: 120
<212> TYPE: PRT
<213> ORGANISM: Artificial Sequence
<220> FEATURE:
<223> OTHER INFORMATION: VHH sequence 56D10

<400> SEQUENCE: 58

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ile Thr Phe Arg Ile Thr
            20                  25                  30

Thr Met Gly Trp Tyr Arg Gln Ala Pro Gly Lys Gln Arg Glu Leu Val
        35                  40                  45

Ala Ser Ser Ser Ser Gly Gly Thr Thr Asn Tyr Ala Ser Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Asn
                85                  90                  95

Ala Arg Lys Phe Ile Thr Thr Pro Trp Ser Thr Asp Tyr Trp Gly Gln
            100                 105                 110

Gly Thr Gln Val Thr Val Ser Ser
        115                 120

<210> SEQ ID NO 59
<211> LENGTH: 116
<212> TYPE: PRT
<213> ORGANISM: Artificial Sequence
<220> FEATURE:
<223> OTHER INFORMATION: VHH sequence 56E04

<400> SEQUENCE: 59

Gln Val Gln Leu Gln Glu Ser Gly Gly Gly Leu Val Gln Pro Gly Asp
1               5                   10                  15

Ser Leu Arg Leu Ser Cys Thr Pro Ser Gly Ser Ile Phe Asn His Lys
            20                  25                  30

Ala Thr Gly Trp Tyr Arg Gln Ala Pro Gly Ser Gln Arg Glu Leu Val
        35                  40                  45

```
Ala Lys Ile Thr Thr Gly Gly Thr Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Lys Pro Glu Asp Thr Ala Val Tyr Tyr Cys Asn
                85                  90                  95

Ala Glu Arg Tyr Phe Ala Thr Thr Leu Trp Gly Gln Gly Thr Gln Val
            100                 105                 110

Thr Val Ser Ser
        115


<210> SEQ ID NO 60
<211> LENGTH: 119
<212> TYPE: PRT
<213> ORGANISM: Artificial Sequence
<220> FEATURE:
<223> OTHER INFORMATION: VHH sequence 56E05

<400> SEQUENCE: 60

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ile Thr Phe Ser Asn Asn
            20                  25                  30

Ala Gly Gly Trp Tyr Arg Gln Ala Pro Gly Gln Gln Arg Glu Leu Val
        35                  40                  45

Ala Arg Ile Ser Ser Gly Gly Asn Thr Asn Tyr Thr Asp Ser Val Lys
    50                  55                  60

Gly Arg Phe Thr Ile Ser Arg Asp Ile Thr Lys Asn Thr Leu Ser Leu
65                  70                  75                  80

Gln Met Asn Asn Leu Lys Pro Glu Asp Ser Ala Val Tyr Tyr Cys Asn
                85                  90                  95

Ala Gln Arg Arg Val Ile Leu Gly Pro Arg Asn Tyr Trp Gly Gln Gly
            100                 105                 110

Thr Gln Val Thr Val Ser Ser
        115


<210> SEQ ID NO 61
<211> LENGTH: 121
<212> TYPE: PRT
<213> ORGANISM: Artificial Sequence
<220> FEATURE:
<223> OTHER INFORMATION: VHH sequence 56E08

<400> SEQUENCE: 61

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Phe Arg Ile Asn
            20                  25                  30

Asp Met Gly Trp Tyr Arg Gln Ala Pro Gly Asn Gln Arg Glu Leu Val
        35                  40                  45

Ala Thr Ile Thr Ser Ala Asn Ile Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Asn Pro Glu Asp Thr Ala Val Tyr Tyr Cys Thr
                85                  90                  95

Ala Gln Ala Lys Lys Trp Arg Ile Gly Pro Trp Ser Asp Tyr Trp Gly
            100                 105                 110
```

```
Gln Gly Thr Gln Val Thr Val Ser Ser
        115                 120


<210> SEQ ID NO 62
<211> LENGTH: 119
<212> TYPE: PRT
<213> ORGANISM: Artificial Sequence
<220> FEATURE:
<223> OTHER INFORMATION: VHH sequence 56F07

<400> SEQUENCE: 62

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Ile Phe Ser Ile Asn
            20                  25                  30

Asp Met Ala Trp Tyr Arg Gln Ala Pro Gly Lys Gln Arg Glu Leu Val
        35                  40                  45

Ala Ile Ile Thr Asn Asp Asp Ser Thr Thr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Ile Asn Thr Ala Ile Trp Arg Arg Lys Tyr Trp Gly Gln Gly
            100                 105                 110

Thr Gln Val Thr Val Ser Ser
        115


<210> SEQ ID NO 63
<211> LENGTH: 115
<212> TYPE: PRT
<213> ORGANISM: Artificial Sequence
<220> FEATURE:
<223> OTHER INFORMATION: VHH sequence 56G07

<400> SEQUENCE: 63

Gln Val Gln Leu Gln Glu Ser Gly Gly Gly Leu Val Gln Pro Gly Gly
1               5                   10                  15

Ser Leu Arg Leu Ser Cys Ala Val Ser Gly Ser Arg Ile Phe Ile His
            20                  25                  30

Asp Met Gly Trp His Arg Gln Ala Pro Gly Glu Pro Arg Glu Leu Val
        35                  40                  45

Ala Thr Ile Thr Pro Phe Gly Arg Arg Asn Tyr Ser Glu Tyr Val Lys
    50                  55                  60

Gly Arg Phe Thr Val Ser Arg Asp Ile Ala Arg Asn Thr Met Ser Leu
65                  70                  75                  80

Gln Met Ser Asn Leu Lys Ala Glu Asp Thr Gly Met Tyr Tyr Cys Asn
                85                  90                  95

Val Arg Val Asn Gly Val Asp Tyr Trp Gly Gln Gly Thr Gln Val Thr
            100                 105                 110

Val Ser Ser
        115


<210> SEQ ID NO 64
<211> LENGTH: 119
<212> TYPE: PRT
<213> ORGANISM: Artificial Sequence
<220> FEATURE:
<223> OTHER INFORMATION: VHH sequence 56G08
```

<400> SEQUENCE: 64

Gln Val Gln Leu Gln Glu Ser Gly Gly Gly Leu Val Gln Ala Gly Gly
1 5 10 15

Ser Leu Arg Leu Ser Cys Ala Ile Ser Gly Ile Thr Phe Arg Arg Pro
20 25 30

Phe Gly Ile Ser Arg Met Gly Trp Tyr Arg Gln Ala Pro Gly Lys Glu
35 40 45

Arg Glu Leu Val Ala Thr Leu Ser Arg Ala Gly Thr Ser Arg Tyr Val
50 55 60

Asp Ser Val Lys Gly Arg Phe Thr Ile Ser Arg Asp Asp Ala Lys Asn
65 70 75 80

Thr Leu Tyr Leu Gln Met Val Ser Leu Asn Pro Glu Asp Thr Ala Val
85 90 95

Tyr Tyr Cys Tyr Ile Ala Gln Leu Gly Thr Asp Tyr Trp Gly Gln Gly
100 105 110

Thr Gln Val Thr Val Ser Ser
115

<210> SEQ ID NO 65
<211> LENGTH: 117
<212> TYPE: PRT
<213> ORGANISM: Artificial Sequence
<220> FEATURE:
<223> OTHER INFORMATION: VHH sequence 56G10

<400> SEQUENCE: 65

Gln Val Gln Leu Gln Glu Ser Gly Gly Gly Leu Val Gln Ala Gly Gly
1 5 10 15

Ser Leu Arg Leu Ser Cys Val Ala Ser Gly Ile Thr Leu Arg Met Tyr
20 25 30

Gln Val Gly Trp Tyr Arg Gln Ala Pro Gly Lys Gln Arg Glu Leu Val
35 40 45

Ala Glu Ile Ser Ser Arg Gly Thr Thr Met Tyr Ala Asp Ser Val Lys
50 55 60

Gly Arg Phe Thr Ile Ser Arg Asp Gly Ala Lys Asn Ile Val Tyr Leu
65 70 75 80

Gln Met Asn Ser Leu Glu Pro Glu Asp Thr Ala Val Tyr Tyr Cys Asn
85 90 95

Ala Arg Ala Phe Ala Phe Gly Arg Asn Ser Trp Gly Gln Gly Thr Gln
100 105 110

Val Thr Val Ser Ser
115

<210> SEQ ID NO 66
<211> LENGTH: 118
<212> TYPE: PRT
<213> ORGANISM: Artificial Sequence
<220> FEATURE:
<223> OTHER INFORMATION: VHH sequence 56H04

<400> SEQUENCE: 66

Gln Val Gln Leu Gln Glu Ser Gly Gly Gly Ser Val Gln Ala Gly Gly
1 5 10 15

Ser Leu Arg Leu Ser Cys Ala Val Ser Gly Gly Thr Phe Ser Asn Lys
20 25 30

Ala Met Gly Trp Tyr Arg Gln Ser Ser Gly Lys Gln Arg Ala Leu Val
35 40 45

```
Ala Arg Ile Ser Thr Val Gly Thr Ala His Tyr Ala Asp Ser Val Lys
    50                  55                  60

Gly Arg Phe Thr Val Ser Lys Asp Asn Ala Gly Asn Thr Leu Tyr Leu
65                  70                  75                  80

Gln Met Asn Ser Leu Lys Pro Glu Asp Thr Ala Val Tyr Tyr Cys Asn
                85                  90                  95

Ala Gln Ala Gly Arg Leu Tyr Leu Arg Asn Tyr Trp Gly Gln Gly Thr
            100                 105                 110

Gln Val Thr Val Ser Ser
        115
```

<210> SEQ ID NO 67
<211> LENGTH: 119
<212> TYPE: PRT
<213> ORGANISM: Artificial Sequence
<220> FEATURE:
<223> OTHER INFORMATION: VHH sequence 56H05

<400> SEQUENCE: 67

```
Gln Val Gln Leu Gln Glu Ser Gly Gly Gly Leu Val Gln Pro Gly Glu
1               5                   10                  15

Ser Leu Arg Leu Ser Cys Val Ala Ala Ala Ser Thr Ser Ile Thr Thr
            20                  25                  30

Phe Asn Thr Met Ala Trp Tyr Arg Gln Ala Pro Gly Lys Gln Arg Glu
        35                  40                  45

Leu Val Ala Gln Ile Asn Asn Arg Asp Asn Thr Glu Tyr Ala Asp Ser
    50                  55                  60

Val Lys Gly Arg Phe Ile Ile Ser Arg Gly Asn Ala Lys Asn Thr Ser
65                  70                  75                  80

Asn Leu Gln Met Asn Asp Leu Lys Ser Glu Asp Thr Gly Ile Tyr Tyr
                85                  90                  95

Cys Asn Ala Lys Arg Trp Ser Trp Ser Thr Gly Phe Trp Gly Gln Gly
            100                 105                 110

Thr Gln Val Thr Val Ser Ser
        115
```

<210> SEQ ID NO 68
<211> LENGTH: 114
<212> TYPE: PRT
<213> ORGANISM: Artificial Sequence
<220> FEATURE:
<223> OTHER INFORMATION: VHH sequence 56H07

<400> SEQUENCE: 68

```
Gln Val Gln Leu Gln Glu Ser Gly Gly Gly Leu Val Gln Ala Gly Gly
1               5                   10                  15

Ser Leu Arg Leu Ser Cys Thr Ala Ser Gly Leu Thr Phe Ala Leu Gly
            20                  25                  30

Thr Met Gly Trp Tyr Arg Gln Ala Pro Gly Lys Gln Arg Glu Leu Val
        35                  40                  45

Ala Ser Ile Ser Thr Gly Ser Thr Asn Tyr Ala Asp Ser Val Lys Gly
    50                  55                  60

Arg Phe Thr Ile Ser Arg Asp Ile Ile Lys Asn Ile Leu Tyr Leu Gln
65                  70                  75                  80

Met Asn Ser Leu Lys Pro Glu Asp Thr Ala Val Tyr Ser Cys Asn Ala
                85                  90                  95

Arg Leu Trp Trp Ser Asn Tyr Trp Gly Gln Gly Thr Gln Val Thr Val
```

```
            100                 105                 110

Ser Ser


<210> SEQ ID NO 69
<211> LENGTH: 118
<212> TYPE: PRT
<213> ORGANISM: Artificial Sequence
<220> FEATURE:
<223> OTHER INFORMATION: VHH sequence 56H08

<400> SEQUENCE: 69

Gln Val Gln Leu Gln Glu Ser Gly Gly Gly Leu Val Gln Ala Gly Gly
1               5                   10                  15

Ser Leu Arg Leu Ser Cys Thr Ala Ser Gly Arg Thr Ser Ser Val Asn
            20                  25                  30

Pro Met Gly Trp Tyr Arg Gln Ala Pro Gly Lys Gln Arg Glu Leu Val
        35                  40                  45

Ala Val Ile Ser Ser Asp Gly Ser Thr Asn Tyr Ala Asp Ser Val Lys
    50                  55                  60

Gly Arg Phe Thr Val Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asn
                85                  90                  95

Ala Asn Arg Arg Trp Ser Trp Gly Ser Glu Tyr Trp Gly Gln Gly Thr
            100                 105                 110

Gln Val Thr Val Ser Ser
        115


<210> SEQ ID NO 70
<211> LENGTH: 119
<212> TYPE: PRT
<213> ORGANISM: Artificial Sequence
<220> FEATURE:
<223> OTHER INFORMATION: VHH sequence 57A06

<400> SEQUENCE: 70

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ile Thr Phe Thr Asn Asn
            20                  25                  30

Ala Gly Gly Trp Tyr Arg Gln Ala Pro Gly Gln Gln Arg Glu Leu Val
        35                  40                  45

Ala Arg Ile Ser Ser Gly Gly Asn Thr Asn Tyr Thr Asp Ser Val Lys
    50                  55                  60

Gly Arg Phe Thr Ile Ser Arg Asp Ile Thr Lys Asn Thr Leu Ser Leu
65                  70                  75                  80

Gln Met Asn Asn Leu Lys Pro Glu Asp Ser Ala Val Tyr Tyr Cys Asn
                85                  90                  95

Ala Gln Arg Arg Val Ile Leu Gly Pro Arg Asn Tyr Trp Gly Gln Gly
            100                 105                 110

Thr Gln Val Thr Val Ser Ser
        115


<210> SEQ ID NO 71
<211> LENGTH: 116
<212> TYPE: PRT
<213> ORGANISM: Artificial Sequence
<220> FEATURE:
<223> OTHER INFORMATION: VHH sequence 57B01
```

<400> SEQUENCE: 71

```
Gln Val Gln Leu Gln Glu Ser Gly Gly Gly Leu Val Gln Ala Gly Gly
1               5                   10                  15

Ser Leu Arg Leu Ser Cys Glu Ala Pro Val Ser Thr Phe Asn Ile Asn
            20                  25                  30

Ala Met Ala Trp Tyr Arg Gln Ala Pro Gly Lys Ser Arg Glu Leu Val
        35                  40                  45

Ala Arg Ile Ser Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Ile Cys Tyr
                85                  90                  95

Val Asn Arg His Trp Gly Trp Asp Tyr Trp Gly Gln Gly Thr Gln Val
            100                 105                 110

Thr Val Ser Ser
        115
```

<210> SEQ ID NO 72
<211> LENGTH: 122
<212> TYPE: PRT
<213> ORGANISM: Artificial Sequence
<220> FEATURE:
<223> OTHER INFORMATION: VHH sequence 57B07

<400> SEQUENCE: 72

```
Gln Val Gln Leu Gln Glu Ser Gly Gly Gly Leu Val Gln Pro Gly Gly
1               5                   10                  15

Thr Leu Arg Leu Ser Cys Val Ala Ser Gly Ser Phe Arg Ser Ile Asn
            20                  25                  30

Ala Met Gly Trp Tyr Arg Gln Ala Pro Gly Lys Gln Arg Glu Leu Val
        35                  40                  45

Ala Thr Val Asp Ser Gly Gly Tyr Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Thr Pro Glu Asp Thr Ala Val Tyr Tyr Cys Tyr
                85                  90                  95

Ala Gly Ile Tyr Lys Trp Pro Trp Ser Val Asp Ala Arg Asp Tyr Trp
            100                 105                 110

Gly Gln Gly Thr Gln Val Thr Val Ser Ser
        115                 120
```

<210> SEQ ID NO 73
<211> LENGTH: 117
<212> TYPE: PRT
<213> ORGANISM: Artificial Sequence
<220> FEATURE:
<223> OTHER INFORMATION: VHH sequence 57B11

<400> SEQUENCE: 73

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ser Ile Ser Met Asn
            20                  25                  30

Ser Met Gly Trp Tyr Arg Gln Ala Pro Gly Lys Glu Arg Glu Arg Val
        35                  40                  45
```

```
Ala Leu Ile Arg Ser Ser Gly Gly Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Asn Leu Lys Pro Glu Asp Thr Ala Val Tyr Tyr Cys Gln
                85                  90                  95

Ala Arg Arg Thr Trp Leu Ser Ser Glu Ser Trp Gly Gln Gly Thr Gln
            100                 105                 110

Val Thr Val Ser Ser
        115


<210> SEQ ID NO 74
<211> LENGTH: 122
<212> TYPE: PRT
<213> ORGANISM: Artificial Sequence
<220> FEATURE:
<223> OTHER INFORMATION: VHH sequence 57C07

<400> SEQUENCE: 74

Gln Val Gln Leu Gln Glu Ser Gly Gly Gly Leu Val Gln Ala Gly Gly
1               5                   10                  15

Ser Leu Arg Leu Ser Cys Ala Val Ser Gly Ser Thr Phe Gly Ile Asn
            20                  25                  30

Thr Met Gly Trp Tyr Arg Gln Ala Pro Glu Lys Gln Arg Glu Leu Val
        35                  40                  45

Ala Ser Ile Ser Arg Gly Gly Met Thr Asn Tyr Ala Asp Ser Val Lys
    50                  55                  60

Gly Arg Phe Ile Ile Ser Arg Asp Asn Ala Lys Asn Thr Val Tyr Leu
65                  70                  75                  80

Gln Met Asn Ser Leu Lys Pro Glu Asp Thr Ala Val Tyr Val Cys Asn
                85                  90                  95

Ala Gly Ile Arg Ser Arg Trp Tyr Gly Gly Pro Ile Thr Thr Tyr Trp
            100                 105                 110

Gly Gln Gly Thr Gln Val Thr Val Ser Ser
        115                 120


<210> SEQ ID NO 75
<211> LENGTH: 121
<212> TYPE: PRT
<213> ORGANISM: Artificial Sequence
<220> FEATURE:
<223> OTHER INFORMATION: VHH sequence 57C09

<400> SEQUENCE: 75

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Thr Gly Ser Ile Asn
            20                  25                  30

Ala Met Gly Trp Tyr Arg Gln Gly Pro Gly Lys Gln Arg Asp Leu Val
        35                  40                  45

Ala Ser Ile Ser Ser Gly Gly Ala Thr Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Ser Ser Leu Lys Pro Glu Asp Thr Ala Val Tyr Tyr Cys Asn
                85                  90                  95

Ala Lys Lys Ser Arg Trp Ser Trp Ser Ile Val His Asp Tyr Trp Gly
```

```
            100                 105                 110

Gln Gly Thr Gln Val Thr Val Ser Ser
        115                 120


<210> SEQ ID NO 76
<211> LENGTH: 118
<212> TYPE: PRT
<213> ORGANISM: Artificial Sequence
<220> FEATURE:
<223> OTHER INFORMATION: VHH sequence 57D02

<400> SEQUENCE: 76

Gln Val Gln Leu Gln Glu Ser Gly Gly Gly Ser Val Gln Thr Gly Gly
1               5                   10                  15

Ser Leu Thr Leu Ser Cys Thr Thr Ser Gly Ser Ile Phe Gly Arg Ser
            20                  25                  30

Asp Met Gly Trp Tyr Arg Gln Ala Pro Gly Lys Gln Arg Glu Leu Val
        35                  40                  45

Ala Thr Ile Thr Arg Arg Ser Arg Thr Asn Tyr Ala Glu Phe Val Lys
    50                  55                  60

Gly Arg Phe Thr Ile Ser Arg Asp Ser Ala Lys Asn Leu Val Thr Leu
65                  70                  75                  80

Gln Met Asn Ser Leu Lys Pro Glu Asp Thr Asn Val Tyr Tyr Cys Asn
                85                  90                  95

Ala Arg Trp Gly Ala Gly Gly Ile Phe Ser Thr Trp Gly Gln Gly Thr
            100                 105                 110

Gln Val Thr Val Ser Ser
        115


<210> SEQ ID NO 77
<211> LENGTH: 120
<212> TYPE: PRT
<213> ORGANISM: Artificial Sequence
<220> FEATURE:
<223> OTHER INFORMATION: VHH sequence 57D09

<400> SEQUENCE: 77

Gln Val Gln Leu Gln Glu Ser Gly Gly Gly Leu Val Gln Pro Gly Glu
1               5                   10                  15

Ser Leu Arg Leu Ser Cys Ala Ala Ser Gly Ser Met Ser Ile Asp Ala
            20                  25                  30

Met Gly Trp Tyr Arg Gln Ala Pro Gly Asp Gln Arg Glu Leu Val Ala
        35                  40                  45

Ser Ile Thr Thr Gly Gly Ser Thr Asn Tyr Ala Asp Ser Val Lys Gly
    50                  55                  60

Arg Phe Thr Ile Ser Arg Asp Asn Ala Lys Asn Thr Val Trp Leu Gln
65                  70                  75                  80

Met Asn Ser Leu Lys Pro Glu Asp Thr Ala Val Tyr Tyr Cys Asn Ala
                85                  90                  95

Lys Val Arg Leu Arg Trp Phe Arg Pro Pro Ser Asp Tyr Trp Gly Gln
            100                 105                 110

Gly Thr Gln Val Thr Val Ser Ser
        115                 120


<210> SEQ ID NO 78
<211> LENGTH: 122
<212> TYPE: PRT
<213> ORGANISM: Artificial Sequence
<220> FEATURE:
```

<223> OTHER INFORMATION: VHH sequence 57D10

<400> SEQUENCE: 78

Gln Val Gln Leu Gln Glu Ser Gly Gly Gly Leu Val Gln Pro Gly Gly
1 5 10 15

Ser Leu Arg Leu Ser Cys Ala Ala Ser Gly Arg Leu Leu Ser Ile Ser
20 25 30

Thr Met Gly Trp Tyr Arg Arg Thr Pro Glu Asp Gln Arg Glu Met Val
35 40 45

Ala Ser Ile Thr Lys Asp Gly Thr Thr Asn Tyr Ala Asp Ser Val Lys
50 55 60

Gly Arg Leu Thr Ile Ser Arg Asp Asn Ala Lys Asn Thr Val Tyr Leu
65 70 75 80

Gln Met Asn Ser Leu Lys Pro Asp Asp Thr Ala Val Tyr Val Cys Asn
85 90 95

Ala Arg Ala Thr Thr Trp Val Pro Tyr Arg Arg Asp Ala Glu Phe Trp
100 105 110

Gly Gln Gly Thr Gln Val Thr Val Ser Ser
115 120

<210> SEQ ID NO 79
<211> LENGTH: 120
<212> TYPE: PRT
<213> ORGANISM: Artificial Sequence
<220> FEATURE:
<223> OTHER INFORMATION: VHH sequence 57E07

<400> SEQUENCE: 79

Gln Val Gln Leu Gln Glu Ser Gly Gly Gly Leu Val Gln Ala Gly Gly
1 5 10 15

Ser Leu Arg Leu Ser Cys Ala Ala Ser Gly Ser Ile Phe Gly Ile Asn
20 25 30

Asp Met Gly Trp Tyr Arg Gln Ala Pro Gly Lys Gln Arg Asp Leu Val
35 40 45

Ala Asp Ile Thr Arg Ser Gly Ser Thr His Tyr Val Asp Ser Val Lys
50 55 60

Gly Arg Phe Thr Ile Ser Arg Asp Asn Ala Lys Asn Thr Val Tyr Leu
65 70 75 80

Gln Met Asn Ser Leu Lys Pro Glu Asp Thr Ala Val Tyr Tyr Cys Asn
85 90 95

Ala Asp Ser Gly Ser His Trp Trp Asn Arg Arg Asp Tyr Trp Gly Gln
100 105 110

Gly Thr Gln Val Thr Val Ser Ser
115 120

<210> SEQ ID NO 80
<211> LENGTH: 118
<212> TYPE: PRT
<213> ORGANISM: Artificial Sequence
<220> FEATURE:
<223> OTHER INFORMATION: VHH sequence 57E11

<400> SEQUENCE: 80

Gln Val Gln Leu Gln Glu Ser Gly Gly Gly Leu Val Gln Pro Gly Gly
1 5 10 15

Ser Leu Lys Leu Ser Cys Ala Ala Ser Gly Phe Thr Phe Ser Ile Asn
20 25 30

Thr Met Gly Trp Tyr Arg Gln Ala Pro Gly Lys Gln Arg Glu Leu Val

```
        35                  40                  45

Ala Arg Ile Ser Arg Leu Arg Val Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Ala Asn Trp Gly Leu Ala Gly Asn Glu Tyr Trp Gly Gln Gly Thr
            100                 105                 110

Gln Val Thr Val Ser Ser
        115


<210> SEQ ID NO 81
<211> LENGTH: 116
<212> TYPE: PRT
<213> ORGANISM: Artificial Sequence
<220> FEATURE:
<223> OTHER INFORMATION: VHH sequence 57G01

<400> SEQUENCE: 81

Gln Val Gln Leu Gln Glu Ser Gly Gly Gly Leu Val Gln Ala Gly Gly
1               5                   10                  15

Ser Leu Arg Pro Ser Cys Thr Ala Ser Gly Ser Thr Leu Leu Ile Asn
            20                  25                  30

Ser Met Gly Trp Tyr Arg Gln Ala Pro Gly Lys Gln Arg Glu Leu Val
        35                  40                  45

Ala Thr Ile Ser Asn Ser Gly Thr Thr Asn Tyr Val Asp Ala Val Lys
    50                  55                  60

Gly Arg Phe Ala Ile Ser Arg Asp Asn Ala Asn His Thr Val Tyr Leu
65                  70                  75                  80

Gln Met Asn Ser Leu Glu Pro Glu Asp Thr Ala Val Tyr Tyr Cys Asn
                85                  90                  95

Ala Gln Thr Phe Trp Arg Arg Asn Tyr Trp Gly Gln Gly Thr Gln Val
            100                 105                 110

Thr Val Ser Ser
        115


<210> SEQ ID NO 82
<211> LENGTH: 116
<212> TYPE: PRT
<213> ORGANISM: Artificial Sequence
<220> FEATURE:
<223> OTHER INFORMATION: VHH sequence 57G07

<400> SEQUENCE: 82

Gln Val Gln Leu Gln Glu Ser Gly Gly Gly Leu Val Gln Ala Gly Gly
1               5                   10                  15

Ser Leu Arg Leu Ser Cys Ala Val Ser Gly Ser Thr Ser Arg Ile Asn
            20                  25                  30

Ala Met Gly Trp Tyr Arg Gln Ala Pro Gly Lys Lys Arg Glu Ser Val
        35                  40                  45

Ala Thr Ile Arg Arg Gly Gly Asn Thr Lys Tyr Ala Asp Ser Val Lys
    50                  55                  60

Gly Arg Phe Thr Ile Ser Arg Asp Asn Ala Asn Asn Thr Val Tyr Leu
65                  70                  75                  80

Gln Leu Asn Ser Leu Lys Pro Glu Asp Thr Ala Val Tyr Tyr Cys Asn
                85                  90                  95
```

-continued

```
Ala His Ser Trp Leu Asp Tyr Asp Tyr Trp Gly Arg Gly Thr Gln Val
            100                 105                 110

Thr Val Ser Ser
        115


<210> SEQ ID NO 83
<211> LENGTH: 114
<212> TYPE: PRT
<213> ORGANISM: Artificial Sequence
<220> FEATURE:
<223> OTHER INFORMATION: VHH sequence 57G08

<400> SEQUENCE: 83

Gln Val Gln Leu Gln Glu Ser Gly Gly Gly Leu Val Gln Ala Gly Gly
1               5                   10                  15

Ser Leu Arg Leu Ser Cys Ala Ser Arg Arg Arg Ile Asn Gly Ile Thr
            20                  25                  30

Met Gly Trp Tyr Arg Gln Ala Pro Gly Lys Gln Arg Glu Leu Val Ala
        35                  40                  45

Thr Ile Asp Ile His Asn Ser Thr Lys Tyr Ala Asp Ser Val Lys Gly
    50                  55                  60

Arg Phe Ile Ile Ser Arg Asp Asn Gly Lys Ser Met Leu Tyr Leu Gln
65                  70                  75                  80

Met Asn Ser Leu Lys Pro Glu Asp Thr Ala Val Tyr Tyr Cys Asn Arg
                85                  90                  95

Ile Pro Thr Phe Gly Arg Tyr Trp Gly Gln Gly Thr Gln Val Thr Val
            100                 105                 110

Ser Ser


<210> SEQ ID NO 84
<211> LENGTH: 118
<212> TYPE: PRT
<213> ORGANISM: Artificial Sequence
<220> FEATURE:
<223> OTHER INFORMATION: VHH sequence 57H08

<400> SEQUENCE: 84

Gln Val Gln Leu Gln Glu Ser Gly Gly Gly Leu Val Gln Ala Gly Gly
1               5                   10                  15

Ser Leu Arg Leu Ser Cys Val Ala Ser Gly Ser Thr Phe Tyr Thr Phe
            20                  25                  30

Ser Thr Lys Asn Val Gly Trp Tyr Arg Gln Ala Pro Gly Lys Gln Arg
        35                  40                  45

Glu Leu Val Ala Gln Gln Arg Tyr Asp Gly Ser Thr Asn Tyr Ala Asp
    50                  55                  60

Ser Leu Gln Gly Arg Phe Thr Ile Ser Arg Asp Asn Ala Lys Arg Thr
65                  70                  75                  80

Val Tyr Leu Gln Met Asn Ser Leu Lys Pro Glu Asp Thr Ala Val Tyr
                85                  90                  95

Ile Cys Asn Val Asn Arg Gly Phe Ile Ser Tyr Trp Gly Gln Gly Thr
            100                 105                 110

Gln Val Thr Val Ser Ser
        115


<210> SEQ ID NO 85
<211> LENGTH: 5
<212> TYPE: PRT
<213> ORGANISM: Artificial Sequence
<220> FEATURE:
```

-continued

<223> OTHER INFORMATION: CDR1 of VHH sequence 41D01

<400> SEQUENCE: 85

Arg Tyr Gly Met Gly
1 5

<210> SEQ ID NO 86
<211> LENGTH: 5
<212> TYPE: PRT
<213> ORGANISM: Artificial Sequence
<220> FEATURE:
<223> OTHER INFORMATION: CDR1 of VHH sequence 56F11

<400> SEQUENCE: 86

Arg Asn Ala Met Gly
1 5

<210> SEQ ID NO 87
<211> LENGTH: 5
<212> TYPE: PRT
<213> ORGANISM: Artificial Sequence
<220> FEATURE:
<223> OTHER INFORMATION: CDR1 of VHH sequence 40F07

<400> SEQUENCE: 87

Ser Tyr Thr Met Gly
1 5

<210> SEQ ID NO 88
<211> LENGTH: 5
<212> TYPE: PRT
<213> ORGANISM: Artificial Sequence
<220> FEATURE:
<223> OTHER INFORMATION: CDR1 of VHH sequence 41D06

<400> SEQUENCE: 88

Ile Asn Ala Met Arg
1 5

<210> SEQ ID NO 89
<211> LENGTH: 5
<212> TYPE: PRT
<213> ORGANISM: Artificial Sequence
<220> FEATURE:
<223> OTHER INFORMATION: CDR1 of VHH sequence 41G10

<400> SEQUENCE: 89

Ile Asn Ala Met Gly
1 5

<210> SEQ ID NO 90
<211> LENGTH: 5
<212> TYPE: PRT
<213> ORGANISM: Artificial Sequence
<220> FEATURE:
<223> OTHER INFORMATION: CDR1 of VHH sequence 41H05

<400> SEQUENCE: 90

Ile Asn Ala Met Gly
1 5

<210> SEQ ID NO 91
<211> LENGTH: 5
<212> TYPE: PRT
<213> ORGANISM: Artificial Sequence
<220> FEATURE:
<223> OTHER INFORMATION: CDR1 of VHH sequence 42C11

<400> SEQUENCE: 91

Thr Tyr Val Met Gly
1 5

<210> SEQ ID NO 92
<211> LENGTH: 5
<212> TYPE: PRT
<213> ORGANISM: Artificial Sequence
<220> FEATURE:
<223> OTHER INFORMATION: CDR1 of VHH sequence 42C12

<400> SEQUENCE: 92

Ile Ser Ser Leu Gly
1 5

<210> SEQ ID NO 93
<211> LENGTH: 5
<212> TYPE: PRT
<213> ORGANISM: Artificial Sequence
<220> FEATURE:
<223> OTHER INFORMATION: CDR1 of VHH sequence 50D03

<400> SEQUENCE: 93

Thr Tyr Ala Met Gly
1 5

<210> SEQ ID NO 94
<211> LENGTH: 5
<212> TYPE: PRT
<213> ORGANISM: Artificial Sequence
<220> FEATURE:
<223> OTHER INFORMATION: CDR1 of VHH sequence 50D07

<400> SEQUENCE: 94

Ile Arg Asp Met Gly
1 5

<210> SEQ ID NO 95
<211> LENGTH: 5
<212> TYPE: PRT
<213> ORGANISM: Artificial Sequence
<220> FEATURE:
<223> OTHER INFORMATION: CDR1 of VHH sequence 50E02

<400> SEQUENCE: 95

Ile Asn Ala Met Gly
1 5

<210> SEQ ID NO 96
<211> LENGTH: 5
<212> TYPE: PRT
<213> ORGANISM: Artificial Sequence
<220> FEATURE:
<223> OTHER INFORMATION: CDR1 of VHH sequence 51B08

<400> SEQUENCE: 96

Ser Tyr Ala Met Gly
1 5

<210> SEQ ID NO 97
<211> LENGTH: 5
<212> TYPE: PRT
<213> ORGANISM: Artificial Sequence
<220> FEATURE:
<223> OTHER INFORMATION: CDR1 of VHH sequence 51C06

<400> SEQUENCE: 97

Ser Asp Thr Met Gly
1 5

<210> SEQ ID NO 98
<211> LENGTH: 5
<212> TYPE: PRT
<213> ORGANISM: Artificial Sequence
<220> FEATURE:
<223> OTHER INFORMATION: CDR1 of VHH sequence 51C08

<400> SEQUENCE: 98

Ile Lys Thr Met Gly
1 5

<210> SEQ ID NO 99
<211> LENGTH: 5
<212> TYPE: PRT
<213> ORGANISM: Artificial Sequence
<220> FEATURE:
<223> OTHER INFORMATION: CDR1 of VHH sequence 52A01

<400> SEQUENCE: 99

Leu Gly Thr Met Gly
1 5

<210> SEQ ID NO 100
<211> LENGTH: 5
<212> TYPE: PRT
<213> ORGANISM: Artificial Sequence
<220> FEATURE:
<223> OTHER INFORMATION: CDR1 of VHH sequence 52B01

<400> SEQUENCE: 100

Ile Asn Val Met Gly
1 5

<210> SEQ ID NO 101
<211> LENGTH: 5
<212> TYPE: PRT
<213> ORGANISM: Artificial Sequence
<220> FEATURE:
<223> OTHER INFORMATION: CDR1 of VHH sequence 52G05

<400> SEQUENCE: 101

Ile Ser Ala Met Gly
1 5

<210> SEQ ID NO 102
<211> LENGTH: 5
<212> TYPE: PRT
<213> ORGANISM: Artificial Sequence
<220> FEATURE:
<223> OTHER INFORMATION: CDR1 of VHH sequence 53A01

<400> SEQUENCE: 102

Ile Asn Thr Met Gly
1 5

<210> SEQ ID NO 103
<211> LENGTH: 5
<212> TYPE: PRT
<213> ORGANISM: Artificial Sequence
<220> FEATURE:
<223> OTHER INFORMATION: CDR1 of VHH sequence 53F05

<400> SEQUENCE: 103

Leu Asn Ala Met Gly
1 5

<210> SEQ ID NO 104
<211> LENGTH: 5
<212> TYPE: PRT
<213> ORGANISM: Artificial Sequence
<220> FEATURE:
<223> OTHER INFORMATION: CDR1 of VHH sequence 54A02

<400> SEQUENCE: 104

Arg Tyr Gly Met Gly
1 5

<210> SEQ ID NO 105
<211> LENGTH: 5
<212> TYPE: PRT
<213> ORGANISM: Artificial Sequence
<220> FEATURE:
<223> OTHER INFORMATION: CDR1 of VHH sequence 54B01

<400> SEQUENCE: 105

Arg Tyr Thr Met Gly
1 5

<210> SEQ ID NO 106
<211> LENGTH: 5
<212> TYPE: PRT
<213> ORGANISM: Artificial Sequence
<220> FEATURE:
<223> OTHER INFORMATION: CDR1 of VHH sequence 54C01

<400> SEQUENCE: 106

Arg Tyr Ala Met Gly
1 5

<210> SEQ ID NO 107
<211> LENGTH: 5
<212> TYPE: PRT
<213> ORGANISM: Artificial Sequence
<220> FEATURE:
<223> OTHER INFORMATION: CDR1 of VHH sequence 54C04

<400> SEQUENCE: 107

Ile Asn Ala Met Gly
1 5

<210> SEQ ID NO 108
<211> LENGTH: 5
<212> TYPE: PRT
<213> ORGANISM: Artificial Sequence
<220> FEATURE:
<223> OTHER INFORMATION: CDR1 of VHH sequence 54C08

<400> SEQUENCE: 108

Ile Asn Ala Met Gly
1 5

<210> SEQ ID NO 109
<211> LENGTH: 5
<212> TYPE: PRT
<213> ORGANISM: Artificial Sequence
<220> FEATURE:
<223> OTHER INFORMATION: CDR1 of VHH sequence 54C10

<400> SEQUENCE: 109

Val Asn Asp Met Gly
1 5

<210> SEQ ID NO 110
<211> LENGTH: 5
<212> TYPE: PRT
<213> ORGANISM: Artificial Sequence
<220> FEATURE:
<223> OTHER INFORMATION: CDR1 of VHH sequence 54C11

<400> SEQUENCE: 110

Val Asn Asp Met Ala
1 5

<210> SEQ ID NO 111
<211> LENGTH: 5
<212> TYPE: PRT
<213> ORGANISM: Artificial Sequence
<220> FEATURE:
<223> OTHER INFORMATION: CDR1 of VHH sequence 54D03

<400> SEQUENCE: 111

Ile Asn Ala Met Arg
1 5

<210> SEQ ID NO 112
<211> LENGTH: 5
<212> TYPE: PRT
<213> ORGANISM: Artificial Sequence
<220> FEATURE:
<223> OTHER INFORMATION: CDR1 of VHH sequence 54D06

<400> SEQUENCE: 112

Ile Asn Ala Met Gly
1 5

<210> SEQ ID NO 113
<211> LENGTH: 5
<212> TYPE: PRT
<213> ORGANISM: Artificial Sequence
<220> FEATURE:
<223> OTHER INFORMATION: CDR1 of VHH sequence 54D10

<400> SEQUENCE: 113

Ile His Ala Met Gly
1 5

<210> SEQ ID NO 114
<211> LENGTH: 5
<212> TYPE: PRT
<213> ORGANISM: Artificial Sequence
<220> FEATURE:
<223> OTHER INFORMATION: CDR1 of VHH sequence 54E01

<400> SEQUENCE: 114

Ile Asn Pro Met Gly
1 5

<210> SEQ ID NO 115
<211> LENGTH: 5
<212> TYPE: PRT
<213> ORGANISM: Artificial Sequence
<220> FEATURE:
<223> OTHER INFORMATION: CDR1 of VHH sequence 54E05

<400> SEQUENCE: 115

Ile Asn Thr Met Gly 1 5

<210> SEQ ID NO 116
<211> LENGTH: 5
<212> TYPE: PRT
<213> ORGANISM: Artificial Sequence
<220> FEATURE:
<223> OTHER INFORMATION: CDR1 of VHH sequence 54E10

<400> SEQUENCE: 116

Phe Asn Ala Met Gly
1 5

<210> SEQ ID NO 117
<211> LENGTH: 5
<212> TYPE: PRT
<213> ORGANISM: Artificial Sequence
<220> FEATURE:
<223> OTHER INFORMATION: CDR1 of VHH sequence 54F01

<400> SEQUENCE: 117

Leu Asn Leu Met Gly
1 5

<210> SEQ ID NO 118
<211> LENGTH: 5
<212> TYPE: PRT
<213> ORGANISM: Artificial Sequence
<220> FEATURE:
<223> OTHER INFORMATION: CDR1 of VHH sequence 54F02

<400> SEQUENCE: 118

Ile Asn Thr Met Gly
1 5

<210> SEQ ID NO 119
<211> LENGTH: 5
<212> TYPE: PRT
<213> ORGANISM: Artificial Sequence
<220> FEATURE:
<223> OTHER INFORMATION: CDR1 of VHH sequence 54G01

<400> SEQUENCE: 119

Val Asn Ala Met Gly
1 5

<210> SEQ ID NO 120
<211> LENGTH: 5
<212> TYPE: PRT
<213> ORGANISM: Artificial Sequence
<220> FEATURE:
<223> OTHER INFORMATION: CDR1 of VHH sequence 54G08

<400> SEQUENCE: 120

Phe Asn Leu Met Gly
1 5

<210> SEQ ID NO 121
<211> LENGTH: 5
<212> TYPE: PRT
<213> ORGANISM: Artificial Sequence
<220> FEATURE:
<223> OTHER INFORMATION: CDR1 of VHH sequence 54G09

<400> SEQUENCE: 121

Ile Arg Asp Met Gly
1 5

<210> SEQ ID NO 122
<211> LENGTH: 5
<212> TYPE: PRT
<213> ORGANISM: Artificial Sequence
<220> FEATURE:
<223> OTHER INFORMATION: CDR1 of VHH sequence 55B02

<400> SEQUENCE: 122

Ile Asn Ser Met Asn
1 5

<210> SEQ ID NO 123
<211> LENGTH: 5
<212> TYPE: PRT
<213> ORGANISM: Artificial Sequence
<220> FEATURE:
<223> OTHER INFORMATION: CDR1 of VHH sequence 55B05

<400> SEQUENCE: 123

Gly Tyr Thr Val Ala
1 5

<210> SEQ ID NO 124
<211> LENGTH: 5
<212> TYPE: PRT
<213> ORGANISM: Artificial Sequence
<220> FEATURE:
<223> OTHER INFORMATION: CDR1 of VHH sequence 55C05

<400> SEQUENCE: 124

Met Lys Ala Met Gly
1 5

<210> SEQ ID NO 125
<211> LENGTH: 5
<212> TYPE: PRT
<213> ORGANISM: Artificial Sequence
<220> FEATURE:
<223> OTHER INFORMATION: CDR1 of VHH sequence 55D08

<400> SEQUENCE: 125

Ile Ser Ala Met Gly
1 5

<210> SEQ ID NO 126
<211> LENGTH: 5
<212> TYPE: PRT
<213> ORGANISM: Artificial Sequence
<220> FEATURE:
<223> OTHER INFORMATION: CDR1 of VHH sequence 55E02

<400> SEQUENCE: 126

Ser Asn Ala Met Ala
1 5

<210> SEQ ID NO 127
<211> LENGTH: 5
<212> TYPE: PRT
<213> ORGANISM: Artificial Sequence
<220> FEATURE:
<223> OTHER INFORMATION: CDR1 of VHH sequence 55E07

<400> SEQUENCE: 127

Ile Tyr Gly Met Gly
1 5

<210> SEQ ID NO 128
<211> LENGTH: 5
<212> TYPE: PRT
<213> ORGANISM: Artificial Sequence
<220> FEATURE:
<223> OTHER INFORMATION: CDR1 of VHH sequence 55E09

<400> SEQUENCE: 128

Thr Tyr Thr Met Gly
1               5

<210> SEQ ID NO 129
<211> LENGTH: 5
<212> TYPE: PRT
<213> ORGANISM: Artificial Sequence
<220> FEATURE:
<223> OTHER INFORMATION: CDR1 of VHH sequence 55E10

<400> SEQUENCE: 129

Ile Gln Thr Ile Gly
1               5

<210> SEQ ID NO 130
<211> LENGTH: 5
<212> TYPE: PRT
<213> ORGANISM: Artificial Sequence
<220> FEATURE:
<223> OTHER INFORMATION: CDR1 of VHH sequence 55F04

<400> SEQUENCE: 130

Ile Asn Val Arg Gly
1               5

<210> SEQ ID NO 131
<211> LENGTH: 5
<212> TYPE: PRT
<213> ORGANISM: Artificial Sequence
<220> FEATURE:
<223> OTHER INFORMATION: CDR1 of VHH sequence 55F09

<400> SEQUENCE: 131

Leu Asn Ala Met Gly
1               5

<210> SEQ ID NO 132
<211> LENGTH: 5
<212> TYPE: PRT
<213> ORGANISM: Artificial Sequence
<220> FEATURE:
<223> OTHER INFORMATION: CDR1 of VHH sequence 55F10

<400> SEQUENCE: 132

Arg Tyr Ala Met Gly
1               5

<210> SEQ ID NO 133
<211> LENGTH: 5
<212> TYPE: PRT
<213> ORGANISM: Artificial Sequence
<220> FEATURE:
<223> OTHER INFORMATION: CDR1 of VHH sequence 55G02

<400> SEQUENCE: 133

Ile Asn Val Met Gly
1               5

<210> SEQ ID NO 134
<211> LENGTH: 5
<212> TYPE: PRT
<213> ORGANISM: Artificial Sequence
<220> FEATURE:
<223> OTHER INFORMATION: CDR1 of VHH sequence 55G08

<400> SEQUENCE: 134

Ile Asn Ala Met Arg
1 5

<210> SEQ ID NO 135
<211> LENGTH: 5
<212> TYPE: PRT
<213> ORGANISM: Artificial Sequence
<220> FEATURE:
<223> OTHER INFORMATION: CDR1 of VHH sequence 56A05

<400> SEQUENCE: 135

Ser Asn Thr Met Gly
1 5

<210> SEQ ID NO 136
<211> LENGTH: 5
<212> TYPE: PRT
<213> ORGANISM: Artificial Sequence
<220> FEATURE:
<223> OTHER INFORMATION: CDR1 of VHH sequence 56A06

<400> SEQUENCE: 136

Val Tyr Gly Met Gly
1 5

<210> SEQ ID NO 137
<211> LENGTH: 5
<212> TYPE: PRT
<213> ORGANISM: Artificial Sequence
<220> FEATURE:
<223> OTHER INFORMATION: CDR1 of VHH sequence 56A09

<400> SEQUENCE: 137

Leu Asn Ser Met Gly
1 5

<210> SEQ ID NO 138
<211> LENGTH: 5
<212> TYPE: PRT
<213> ORGANISM: Artificial Sequence
<220> FEATURE:
<223> OTHER INFORMATION: CDR1 of VHH sequence 56C09

<400> SEQUENCE: 138

Ile Leu Ser Met Ala
1 5

<210> SEQ ID NO 139
<211> LENGTH: 5
<212> TYPE: PRT
<213> ORGANISM: Artificial Sequence
<220> FEATURE:
<223> OTHER INFORMATION: CDR1 of VHH sequence 56C12

<400> SEQUENCE: 139

Asn Arg Ala Val Ser
1 5

<210> SEQ ID NO 140

-continued

<211> LENGTH: 5
<212> TYPE: PRT
<213> ORGANISM: Artificial Sequence
<220> FEATURE:
<223> OTHER INFORMATION: CDR1 of VHH sequence 56D06

<400> SEQUENCE: 140

Ile Ser Ala Met Gly
1 5

<210> SEQ ID NO 141
<211> LENGTH: 5
<212> TYPE: PRT
<213> ORGANISM: Artificial Sequence
<220> FEATURE:
<223> OTHER INFORMATION: CDR1 of VHH sequence 56D07

<400> SEQUENCE: 141

Met Lys Val Met Gly
1 5

<210> SEQ ID NO 142
<211> LENGTH: 5
<212> TYPE: PRT
<213> ORGANISM: Artificial Sequence
<220> FEATURE:
<223> OTHER INFORMATION: CDR1 of VHH sequence 56D10

<400> SEQUENCE: 142

Ile Thr Thr Met Gly
1 5

<210> SEQ ID NO 143
<211> LENGTH: 5
<212> TYPE: PRT
<213> ORGANISM: Artificial Sequence
<220> FEATURE:
<223> OTHER INFORMATION: CDR1 of VHH sequence 56E04

<400> SEQUENCE: 143

His Lys Ala Thr Gly
1 5

<210> SEQ ID NO 144
<211> LENGTH: 5
<212> TYPE: PRT
<213> ORGANISM: Artificial Sequence
<220> FEATURE:
<223> OTHER INFORMATION: CDR1 of VHH sequence 56E05

<400> SEQUENCE: 144

Asn Asn Ala Gly Gly
1 5

<210> SEQ ID NO 145
<211> LENGTH: 5
<212> TYPE: PRT
<213> ORGANISM: Artificial Sequence
<220> FEATURE:
<223> OTHER INFORMATION: CDR1 of VHH sequence 56E08

<400> SEQUENCE: 145

Ile Asn Asp Met Gly
1 5

<210> SEQ ID NO 146
<211> LENGTH: 5

<212> TYPE: PRT
<213> ORGANISM: Artificial Sequence
<220> FEATURE:
<223> OTHER INFORMATION: CDR1 of VHH sequence 56F07

<400> SEQUENCE: 146

Ile Asn Asp Met Ala
1 5

<210> SEQ ID NO 147
<211> LENGTH: 5
<212> TYPE: PRT
<213> ORGANISM: Artificial Sequence
<220> FEATURE:
<223> OTHER INFORMATION: CDR1 of VHH sequence 56G07

<400> SEQUENCE: 147

Ile His Asp Met Gly
1 5

<210> SEQ ID NO 148
<211> LENGTH: 5
<212> TYPE: PRT
<213> ORGANISM: Artificial Sequence
<220> FEATURE:
<223> OTHER INFORMATION: CDR1 of VHH sequence 56G08

<400> SEQUENCE: 148

Ile Ser Arg Met Gly
1 5

<210> SEQ ID NO 149
<211> LENGTH: 5
<212> TYPE: PRT
<213> ORGANISM: Artificial Sequence
<220> FEATURE:
<223> OTHER INFORMATION: CDR1 of VHH sequence 56G10

<400> SEQUENCE: 149

Met Tyr Gln Val Gly
1 5

<210> SEQ ID NO 150
<211> LENGTH: 5
<212> TYPE: PRT
<213> ORGANISM: Artificial Sequence
<220> FEATURE:
<223> OTHER INFORMATION: CDR1 of VHH sequence 56H04

<400> SEQUENCE: 150

Asn Lys Ala Met Gly
1 5

<210> SEQ ID NO 151
<211> LENGTH: 5
<212> TYPE: PRT
<213> ORGANISM: Artificial Sequence
<220> FEATURE:
<223> OTHER INFORMATION: CDR1 of VHH sequence 56H05

<400> SEQUENCE: 151

Phe Asn Thr Met Ala
1 5

<210> SEQ ID NO 152
<211> LENGTH: 5
<212> TYPE: PRT

<213> ORGANISM: Artificial Sequence
<220> FEATURE:
<223> OTHER INFORMATION: CDR1 of VHH sequence 56H07

<400> SEQUENCE: 152

Leu Gly Thr Met Gly
1 5

<210> SEQ ID NO 153
<211> LENGTH: 5
<212> TYPE: PRT
<213> ORGANISM: Artificial Sequence
<220> FEATURE:
<223> OTHER INFORMATION: CDR1 of VHH sequence 56H08

<400> SEQUENCE: 153

Val Asn Pro Met Gly
1 5

<210> SEQ ID NO 154
<211> LENGTH: 5
<212> TYPE: PRT
<213> ORGANISM: Artificial Sequence
<220> FEATURE:
<223> OTHER INFORMATION: CDR1 of VHH sequence 57A06

<400> SEQUENCE: 154

Asn Asn Ala Gly Gly
1 5

<210> SEQ ID NO 155
<211> LENGTH: 5
<212> TYPE: PRT
<213> ORGANISM: Artificial Sequence
<220> FEATURE:
<223> OTHER INFORMATION: CDR1 of VHH sequence 57B01

<400> SEQUENCE: 155

Ile Asn Ala Met Ala
1 5

<210> SEQ ID NO 156
<211> LENGTH: 5
<212> TYPE: PRT
<213> ORGANISM: Artificial Sequence
<220> FEATURE:
<223> OTHER INFORMATION: CDR1 of VHH sequence 57B07

<400> SEQUENCE: 156

Ile Asn Ala Met Gly
1 5

<210> SEQ ID NO 157
<211> LENGTH: 5
<212> TYPE: PRT
<213> ORGANISM: Artificial Sequence
<220> FEATURE:
<223> OTHER INFORMATION: CDR1 of VHH sequence 57B11

<400> SEQUENCE: 157

Met Asn Ser Met Gly
1 5

<210> SEQ ID NO 158
<211> LENGTH: 5
<212> TYPE: PRT
<213> ORGANISM: Artificial Sequence -continued
<220> FEATURE:
<223> OTHER INFORMATION: CDR1 of VHH sequence 57C07

<400> SEQUENCE: 158

Ile Asn Thr Met Gly
1 5

<210> SEQ ID NO 159
<211> LENGTH: 5
<212> TYPE: PRT
<213> ORGANISM: Artificial Sequence
<220> FEATURE:
<223> OTHER INFORMATION: CDR1 of VHH sequence 57C09

<400> SEQUENCE: 159

Ile Asn Ala Met Gly
1 5

<210> SEQ ID NO 160
<211> LENGTH: 5
<212> TYPE: PRT
<213> ORGANISM: Artificial Sequence
<220> FEATURE:
<223> OTHER INFORMATION: CDR1 of VHH sequence 57D02

<400> SEQUENCE: 160

Arg Ser Asp Met Gly
1 5

<210> SEQ ID NO 161
<211> LENGTH: 5
<212> TYPE: PRT
<213> ORGANISM: Artificial Sequence
<220> FEATURE:
<223> OTHER INFORMATION: CDR1 of VHH sequence 57D09

<400> SEQUENCE: 161

Ile Asp Ala Met Gly
1 5

<210> SEQ ID NO 162
<211> LENGTH: 5
<212> TYPE: PRT
<213> ORGANISM: Artificial Sequence
<220> FEATURE:
<223> OTHER INFORMATION: CDR1 of VHH sequence 57D10

<400> SEQUENCE: 162

Ile Ser Thr Met Gly
1 5

<210> SEQ ID NO 163
<211> LENGTH: 5
<212> TYPE: PRT
<213> ORGANISM: Artificial Sequence
<220> FEATURE:
<223> OTHER INFORMATION: CDR1 of VHH sequence 57E07

<400> SEQUENCE: 163

Ile Asn Asp Met Gly
1 5

<210> SEQ ID NO 164
<211> LENGTH: 5
<212> TYPE: PRT
<213> ORGANISM: Artificial Sequence
<220> FEATURE:

<223> OTHER INFORMATION: CDR1 of VHH sequence 57E11

<400> SEQUENCE: 164

Ile Asn Thr Met Gly
1 5

<210> SEQ ID NO 165
<211> LENGTH: 5
<212> TYPE: PRT
<213> ORGANISM: Artificial Sequence
<220> FEATURE:
<223> OTHER INFORMATION: CDR1 of VHH sequence 57G01

<400> SEQUENCE: 165

Ile Asn Ser Met Gly
1 5

<210> SEQ ID NO 166
<211> LENGTH: 5
<212> TYPE: PRT
<213> ORGANISM: Artificial Sequence
<220> FEATURE:
<223> OTHER INFORMATION: CDR1 of VHH sequence 57G07

<400> SEQUENCE: 166

Ile Asn Ala Met Gly
1 5

<210> SEQ ID NO 167
<211> LENGTH: 5
<212> TYPE: PRT
<213> ORGANISM: Artificial Sequence
<220> FEATURE:
<223> OTHER INFORMATION: CDR1 of VHH sequence 57G08

<400> SEQUENCE: 167

Gly Ile Thr Met Gly
1 5

<210> SEQ ID NO 168
<211> LENGTH: 5
<212> TYPE: PRT
<213> ORGANISM: Artificial Sequence
<220> FEATURE:
<223> OTHER INFORMATION: CDR1 of VHH sequence 57H08

<400> SEQUENCE: 168

Thr Lys Asn Val Gly
1 5

<210> SEQ ID NO 169
<211> LENGTH: 16
<212> TYPE: PRT
<213> ORGANISM: Artificial Sequence
<220> FEATURE:
<223> OTHER INFORMATION: CDR2 of VHH sequence 41D01

<400> SEQUENCE: 169

Ser Ile Thr Arg Gly Gly Thr Thr Thr Tyr Ala Asp Ser Val Lys Gly
1 5 10 15

<210> SEQ ID NO 170
<211> LENGTH: 16
<212> TYPE: PRT
<213> ORGANISM: Artificial Sequence
<220> FEATURE:
<223> OTHER INFORMATION: CDR2 of VHH sequence 56F11

<400> SEQUENCE: 170

Thr Ile Thr Ser Gly Gly Thr Thr Asn Tyr Ala Asp Ser Val Lys Gly
1 5 10 15

<210> SEQ ID NO 171
<211> LENGTH: 16
<212> TYPE: PRT
<213> ORGANISM: Artificial Sequence
<220> FEATURE:
<223> OTHER INFORMATION: CDR2 of VHH sequence 40F07

<400> SEQUENCE: 171

Ser Ile Glu Gly Gly Gly Asn Thr Asp Tyr Ala Asp Ser Val Lys Gly
1 5 10 15

<210> SEQ ID NO 172
<211> LENGTH: 16
<212> TYPE: PRT
<213> ORGANISM: Artificial Sequence
<220> FEATURE:
<223> OTHER INFORMATION: CDR2 of VHH sequence 41D06

<400> SEQUENCE: 172

Ser Ile Ser Ser Gly Gly Asn Thr Asn Tyr Ser Glu Ser Val Lys Gly
1 5 10 15

<210> SEQ ID NO 173
<211> LENGTH: 16
<212> TYPE: PRT
<213> ORGANISM: Artificial Sequence
<220> FEATURE:
<223> OTHER INFORMATION: CDR2 of VHH sequence 41G10

<400> SEQUENCE: 173

Thr Ile Thr Ser Gly Gly Thr Thr Asn Tyr Ala Asp Ser Val Lys Gly
1 5 10 15

<210> SEQ ID NO 174
<211> LENGTH: 16
<212> TYPE: PRT
<213> ORGANISM: Artificial Sequence
<220> FEATURE:
<223> OTHER INFORMATION: CDR2 of VHH sequence 41H05

<400> SEQUENCE: 174

Thr Ile Thr Ser Gly Ala Asn Thr Asn Tyr Thr Asp Ser Val Lys Gly
1 5 10 15

<210> SEQ ID NO 175
<211> LENGTH: 16
<212> TYPE: PRT
<213> ORGANISM: Artificial Sequence
<220> FEATURE:
<223> OTHER INFORMATION: CDR2 of VHH sequence 42C11

<400> SEQUENCE: 175

Thr Ile Thr Ser Ser Gly Lys Thr Asn Tyr Ala Ala Ser Val Lys Gly
1 5 10 15

<210> SEQ ID NO 176
<211> LENGTH: 16
<212> TYPE: PRT
<213> ORGANISM: Artificial Sequence
<220> FEATURE:
<223> OTHER INFORMATION: CDR2 of VHH sequence 42C12

<400> SEQUENCE: 176

Ser Ala Thr Ser Gly Gly Asp Thr Thr Tyr Ala Asp Ser Val Lys Gly
1 5 10 15

<210> SEQ ID NO 177
<211> LENGTH: 16
<212> TYPE: PRT
<213> ORGANISM: Artificial Sequence
<220> FEATURE:
<223> OTHER INFORMATION: CDR2 of VHH sequence 50D03

<400> SEQUENCE: 177

Thr Ile Thr Ser Ser Gly Lys Thr Asn Tyr Ala Ala Ser Val Lys Gly
1 5 10 15

<210> SEQ ID NO 178
<211> LENGTH: 16
<212> TYPE: PRT
<213> ORGANISM: Artificial Sequence
<220> FEATURE:
<223> OTHER INFORMATION: CDR2 of VHH sequence 50D07

<400> SEQUENCE: 178

Thr Ile Thr Ser Asp Gln Ser Thr Asn Tyr Ala Asp Ser Val Lys Gly
1 5 10 15

<210> SEQ ID NO 179
<211> LENGTH: 16
<212> TYPE: PRT
<213> ORGANISM: Artificial Sequence
<220> FEATURE:
<223> OTHER INFORMATION: CDR2 of VHH sequence 50E02

<400> SEQUENCE: 179

Ala Ile Thr Ser Asp Gly Ser Thr Asn Tyr Ala Asp Ser Val Lys Gly
1 5 10 15

<210> SEQ ID NO 180
<211> LENGTH: 16
<212> TYPE: PRT
<213> ORGANISM: Artificial Sequence
<220> FEATURE:
<223> OTHER INFORMATION: CDR2 of VHH sequence 51B08

<400> SEQUENCE: 180

Gly Ile Ser Ser Gly Gly Ser Thr Lys Tyr Ala Asp Ser Val Arg Gly
1 5 10 15

<210> SEQ ID NO 181
<211> LENGTH: 16
<212> TYPE: PRT
<213> ORGANISM: Artificial Sequence
<220> FEATURE:
<223> OTHER INFORMATION: CDR2 of VHH sequence 51C06

<400> SEQUENCE: 181

Ala Ile Thr Thr Gly Gly Asn Thr Asn Tyr Ala Asp Ser Val Lys Gly
1 5 10 15

<210> SEQ ID NO 182
<211> LENGTH: 16
<212> TYPE: PRT
<213> ORGANISM: Artificial Sequence
<220> FEATURE:
<223> OTHER INFORMATION: CDR2 of VHH sequence 51C08

<400> SEQUENCE: 182

```
Thr Ile Ser Asn Gly Gly Ser Thr Asn Tyr Ala Asp Ser Val Lys Gly
1               5                   10                  15


<210> SEQ ID NO 183
<211> LENGTH: 15
<212> TYPE: PRT
<213> ORGANISM: Artificial Sequence
<220> FEATURE:
<223> OTHER INFORMATION: CDR2 of VHH sequence 52A01

<400> SEQUENCE: 183

Ser Ile Ser Thr Gly Ser Thr Asn Tyr Ala Asp Ser Val Lys Gly
1               5                   10                  15


<210> SEQ ID NO 184
<211> LENGTH: 16
<212> TYPE: PRT
<213> ORGANISM: Artificial Sequence
<220> FEATURE:
<223> OTHER INFORMATION: CDR2 of VHH sequence 52B01

<400> SEQUENCE: 184

Thr Ile Ser Arg Gly Gly Ser Thr Asn Tyr Ala Asp Ser Val Lys Gly
1               5                   10                  15


<210> SEQ ID NO 185
<211> LENGTH: 16
<212> TYPE: PRT
<213> ORGANISM: Artificial Sequence
<220> FEATURE:
<223> OTHER INFORMATION: CDR2 of VHH sequence 52G05

<400> SEQUENCE: 185

Ser Ile Thr Arg Arg Gly Ser Thr Asn Tyr Ala Asp Ser Val Lys Asp
1               5                   10                  15


<210> SEQ ID NO 186
<211> LENGTH: 16
<212> TYPE: PRT
<213> ORGANISM: Artificial Sequence
<220> FEATURE:
<223> OTHER INFORMATION: CDR2 of VHH sequence 53A01

<400> SEQUENCE: 186

Ser Ile Ser Ser Gly Gly Trp Thr Asn Tyr Ala Asp Ser Val Lys Gly
1               5                   10                  15


<210> SEQ ID NO 187
<211> LENGTH: 16
<212> TYPE: PRT
<213> ORGANISM: Artificial Sequence
<220> FEATURE:
<223> OTHER INFORMATION: CDR2 of VHH sequence 53F05

<400> SEQUENCE: 187

Ser Ile Thr Thr Gly Gly Ser Thr Asn Tyr Ala Glu Pro Val Lys Gly
1               5                   10                  15


<210> SEQ ID NO 188
<211> LENGTH: 17
<212> TYPE: PRT
<213> ORGANISM: Artificial Sequence
<220> FEATURE:
<223> OTHER INFORMATION: CDR2 of VHH sequence 54A02

<400> SEQUENCE: 188
```

-continued

Ala Asn Arg Trp Ser Gly Gly Ser Thr Tyr Tyr Ala Asp Ser Val Arg
1 5 10 15

Gly

<210> SEQ ID NO 189
<211> LENGTH: 17
<212> TYPE: PRT
<213> ORGANISM: Artificial Sequence
<220> FEATURE:
<223> OTHER INFORMATION: CDR2 of VHH sequence 54B01

<400> SEQUENCE: 189

Gly Ile Thr Trp Thr Gly Gly Ser Thr Asp Tyr Ala Asp Ser Val Lys
1 5 10 15

Gly

<210> SEQ ID NO 190
<211> LENGTH: 17
<212> TYPE: PRT
<213> ORGANISM: Artificial Sequence
<220> FEATURE:
<223> OTHER INFORMATION: CDR2 of VHH sequence 54C01

<400> SEQUENCE: 190

Ala Ile Ser Trp Ser Gly Gly Ser Thr Tyr Tyr Ala Asp Ser Val Lys
1 5 10 15

Asp

<210> SEQ ID NO 191
<211> LENGTH: 16
<212> TYPE: PRT
<213> ORGANISM: Artificial Sequence
<220> FEATURE:
<223> OTHER INFORMATION: CDR2 of VHH sequence 54C04

<400> SEQUENCE: 191

Asp Met Thr Ser Gly Gly Ser Ile Asn Tyr Ala Asp Ser Val Ser Gly
1 5 10 15

<210> SEQ ID NO 192
<211> LENGTH: 16
<212> TYPE: PRT
<213> ORGANISM: Artificial Sequence
<220> FEATURE:
<223> OTHER INFORMATION: CDR2 of VHH sequence 54C08

<400> SEQUENCE: 192

Ser Ile Thr Ser Gly Gly Ser Thr Asn Tyr Ala Asp Ser Val Lys Gly
1 5 10 15

<210> SEQ ID NO 193
<211> LENGTH: 16
<212> TYPE: PRT
<213> ORGANISM: Artificial Sequence
<220> FEATURE:
<223> OTHER INFORMATION: CDR2 of VHH sequence 54C10

<400> SEQUENCE: 193

Gln Ile Thr Arg Arg Gly Ser Thr Asn Tyr Ala Asp Ser Val Lys Gly
1 5 10 15

<210> SEQ ID NO 194
<211> LENGTH: 16
<212> TYPE: PRT
<213> ORGANISM: Artificial Sequence
<220> FEATURE:
<223> OTHER INFORMATION: CDR2 of VHH sequence 54C11

<400> SEQUENCE: 194

Asn Ile Thr Arg Gly Gly Ser Thr Asn Tyr Ala Asp Ser Val Lys Gly
1 5 10 15

<210> SEQ ID NO 195
<211> LENGTH: 16
<212> TYPE: PRT
<213> ORGANISM: Artificial Sequence
<220> FEATURE:
<223> OTHER INFORMATION: CDR2 of VHH sequence 54D03

<400> SEQUENCE: 195

Ser Ile Ser Ser Gly Gly Asn Thr Asn Tyr Ser Glu Ser Val Lys Gly
1 5 10 15

<210> SEQ ID NO 196
<211> LENGTH: 16
<212> TYPE: PRT
<213> ORGANISM: Artificial Sequence
<220> FEATURE:
<223> OTHER INFORMATION: CDR2 of VHH sequence 54D06

<400> SEQUENCE: 196

Thr Ile Thr Arg Gly Gly Ile Thr Asn Tyr Ala Asp Ser Val Lys Gly
1 5 10 15

<210> SEQ ID NO 197
<211> LENGTH: 16
<212> TYPE: PRT
<213> ORGANISM: Artificial Sequence
<220> FEATURE:
<223> OTHER INFORMATION: CDR2 of VHH sequence 54D10

<400> SEQUENCE: 197

Ile Thr Ser Thr Ser Gly Thr Thr Asp Tyr Thr Asp Ser Val Lys Gly
1 5 10 15

<210> SEQ ID NO 198
<211> LENGTH: 16
<212> TYPE: PRT
<213> ORGANISM: Artificial Sequence
<220> FEATURE:
<223> OTHER INFORMATION: CDR2 of VHH sequence 54E01

<400> SEQUENCE: 198

Ala Ile Thr Ser Gly Gly Ser Thr Asn Tyr Ala Asp Tyr Val Lys Gly
1 5 10 15

<210> SEQ ID NO 199
<211> LENGTH: 16
<212> TYPE: PRT
<213> ORGANISM: Artificial Sequence
<220> FEATURE:
<223> OTHER INFORMATION: CDR2 of VHH sequence 54E05

<400> SEQUENCE: 199

Ala Ile Thr Asn Arg Gly Ser Thr Asn Tyr Ala Asp Phe Val Lys Gly
1 5 10 15

<210> SEQ ID NO 200
<211> LENGTH: 16
<212> TYPE: PRT
<213> ORGANISM: Artificial Sequence
<220> FEATURE:

<223> OTHER INFORMATION: CDR2 of VHH sequence 54E10

<400> SEQUENCE: 200

Ala Ile Thr Arg Gly Gly Ser Thr Asn Tyr Ala Asp Ser Val Lys Gly
1 5 10 15

<210> SEQ ID NO 201
<211> LENGTH: 16
<212> TYPE: PRT
<213> ORGANISM: Artificial Sequence
<220> FEATURE:
<223> OTHER INFORMATION: CDR2 of VHH sequence 54F01

<400> SEQUENCE: 201

Thr Ile Thr Arg Gly Gly Ser Thr Asn Tyr Ala Asp Ser Val Lys Gly
1 5 10 15

<210> SEQ ID NO 202
<211> LENGTH: 16
<212> TYPE: PRT
<213> ORGANISM: Artificial Sequence
<220> FEATURE:
<223> OTHER INFORMATION: CDR2 of VHH sequence 54F02

<400> SEQUENCE: 202

Thr Ile Thr Ser Gly Gly Thr Thr Asn Tyr Ala Asp Ser Val Lys Asn
1 5 10 15

<210> SEQ ID NO 203
<211> LENGTH: 16
<212> TYPE: PRT
<213> ORGANISM: Artificial Sequence
<220> FEATURE:
<223> OTHER INFORMATION: CDR2 of VHH sequence 54G01

<400> SEQUENCE: 203

Ile Ile Ser Ser Asn Ser Thr Ser Asn Tyr Ala Asp Ser Val Lys Gly
1 5 10 15

<210> SEQ ID NO 204
<211> LENGTH: 16
<212> TYPE: PRT
<213> ORGANISM: Artificial Sequence
<220> FEATURE:
<223> OTHER INFORMATION: CDR2 of VHH sequence 54G08

<400> SEQUENCE: 204

Ala Ile Thr Ser Ser Ser Asn Thr Asn Tyr Ala Asp Ser Val Lys Gly
1 5 10 15

<210> SEQ ID NO 205
<211> LENGTH: 16
<212> TYPE: PRT
<213> ORGANISM: Artificial Sequence
<220> FEATURE:
<223> OTHER INFORMATION: CDR2 of VHH sequence 54G09

<400> SEQUENCE: 205

Thr Ile Thr Ser Asp Gln Ser Thr Asn Tyr Ala Asp Ser Val Lys Gly
1 5 10 15

<210> SEQ ID NO 206
<211> LENGTH: 16
<212> TYPE: PRT
<213> ORGANISM: Artificial Sequence
<220> FEATURE:
<223> OTHER INFORMATION: CDR2 of VHH sequence 55B02

<400> SEQUENCE: 206

Asp Met Arg Ser Asp Gly Ser Thr Asn Tyr Ala Asp Ser Val Lys Gly
1               5                   10                  15

<210> SEQ ID NO 207
<211> LENGTH: 17
<212> TYPE: PRT
<213> ORGANISM: Artificial Sequence
<220> FEATURE:
<223> OTHER INFORMATION: CDR2 of VHH sequence 55B05

<400> SEQUENCE: 207

Arg Ile Ser Trp Ser Gly Ile Met Ala Tyr Tyr Ala Glu Ser Val Lys
1               5                   10                  15

Gly

<210> SEQ ID NO 208
<211> LENGTH: 16
<212> TYPE: PRT
<213> ORGANISM: Artificial Sequence
<220> FEATURE:
<223> OTHER INFORMATION: CDR2 of VHH sequence 55C05

<400> SEQUENCE: 208

Gln Ile Thr Arg Gly Asp Ser Thr Asn Tyr Ala Asp Ser Val Lys Gly
1               5                   10                  15

<210> SEQ ID NO 209
<211> LENGTH: 16
<212> TYPE: PRT
<213> ORGANISM: Artificial Sequence
<220> FEATURE:
<223> OTHER INFORMATION: CDR2 of VHH sequence 55D08

<400> SEQUENCE: 209

Thr Ile Thr Ser Ala Gly Ser Ser Asn Tyr Ser Asp Ser Val Lys Gly
1               5                   10                  15

<210> SEQ ID NO 210
<211> LENGTH: 16
<212> TYPE: PRT
<213> ORGANISM: Artificial Sequence
<220> FEATURE:
<223> OTHER INFORMATION: CDR2 of VHH sequence 55E02

<400> SEQUENCE: 210

Arg Ile Leu Ser Gly Gly Ser Thr Asn Tyr Ala Asp Ser Val Lys Gly
1               5                   10                  15

<210> SEQ ID NO 211
<211> LENGTH: 16
<212> TYPE: PRT
<213> ORGANISM: Artificial Sequence
<220> FEATURE:
<223> OTHER INFORMATION: CDR2 of VHH sequence 55E07

<400> SEQUENCE: 211

Arg Ile Thr Ser Gly Gly Ser Thr Tyr Tyr Ala Asp Ser Val Lys Gly
1               5                   10                  15

<210> SEQ ID NO 212
<211> LENGTH: 17
<212> TYPE: PRT
<213> ORGANISM: Artificial Sequence
<220> FEATURE:

<223> OTHER INFORMATION: CDR2 of VHH sequence 55E09

<400> SEQUENCE: 212

Ala Ile Ile Trp Ser Gly Gly Arg Thr Arg Tyr Ala Asp Ser Val Lys
1 5 10 15

Gly

<210> SEQ ID NO 213
<211> LENGTH: 16
<212> TYPE: PRT
<213> ORGANISM: Artificial Sequence
<220> FEATURE:
<223> OTHER INFORMATION: CDR2 of VHH sequence 55E10

<400> SEQUENCE: 213

Thr Ile Ser Ser Gly Gly Ser Thr Asn Tyr Ala Asp Ser Val Lys Gly
1 5 10 15

<210> SEQ ID NO 214
<211> LENGTH: 16
<212> TYPE: PRT
<213> ORGANISM: Artificial Sequence
<220> FEATURE:
<223> OTHER INFORMATION: CDR2 of VHH sequence 55F04

<400> SEQUENCE: 214

Thr Ile Thr Ser Asp Gly Ser Thr Asn Tyr Ala Asp Ser Val Lys Gly
1 5 10 15

<210> SEQ ID NO 215
<211> LENGTH: 17
<212> TYPE: PRT
<213> ORGANISM: Artificial Sequence
<220> FEATURE:
<223> OTHER INFORMATION: CDR2 of VHH sequence 55F09

<400> SEQUENCE: 215

Ala Ile Thr Pro Gly Gly Gly Asn Thr Thr Tyr Ala Asp Ser Val Lys
1 5 10 15

Gly

<210> SEQ ID NO 216
<211> LENGTH: 17
<212> TYPE: PRT
<213> ORGANISM: Artificial Sequence
<220> FEATURE:
<223> OTHER INFORMATION: CDR2 of VHH sequence 55F10

<400> SEQUENCE: 216

Thr Ile Arg Arg Ser Gly Ser Ser Thr Tyr Tyr Leu Asp Ser Thr Lys
1 5 10 15

Gly

<210> SEQ ID NO 217
<211> LENGTH: 16
<212> TYPE: PRT
<213> ORGANISM: Artificial Sequence
<220> FEATURE:
<223> OTHER INFORMATION: CDR2 of VHH sequence 55G02

<400> SEQUENCE: 217

Phe Ile Thr Ser Gly Gly Ile Thr Asn Tyr Thr Asp Ser Val Lys Gly
1 5 10 15

-continued

<210> SEQ ID NO 218
<211> LENGTH: 16
<212> TYPE: PRT
<213> ORGANISM: Artificial Sequence
<220> FEATURE:
<223> OTHER INFORMATION: CDR2 of VHH sequence 55G08

<400> SEQUENCE: 218

Ser Ile Ser Ser Gly Gly Thr Thr Asp Tyr Val Glu Ser Val Lys Gly
1 5 10 15

<210> SEQ ID NO 219
<211> LENGTH: 16
<212> TYPE: PRT
<213> ORGANISM: Artificial Sequence
<220> FEATURE:
<223> OTHER INFORMATION: CDR2 of VHH sequence 56A05

<400> SEQUENCE: 219

Ser Ile Ser Ser Gly Gly Ser Thr Asn Tyr Ala Asp Ser Val Lys Gly
1 5 10 15

<210> SEQ ID NO 220
<211> LENGTH: 16
<212> TYPE: PRT
<213> ORGANISM: Artificial Sequence
<220> FEATURE:
<223> OTHER INFORMATION: CDR2 of VHH sequence 56A06

<400> SEQUENCE: 220

Arg Ile Thr Asn Ile Gly Thr Thr Asn Tyr Ala Asp Ser Val Lys Gly
1 5 10 15

<210> SEQ ID NO 221
<211> LENGTH: 16
<212> TYPE: PRT
<213> ORGANISM: Artificial Sequence
<220> FEATURE:
<223> OTHER INFORMATION: CDR2 of VHH sequence 56A09

<400> SEQUENCE: 221

Thr Ile Thr Arg Gly Gly Thr Thr Asn Tyr Ala Asp Ser Val Lys Gly
1 5 10 15

<210> SEQ ID NO 222
<211> LENGTH: 16
<212> TYPE: PRT
<213> ORGANISM: Artificial Sequence
<220> FEATURE:
<223> OTHER INFORMATION: CDR2 of VHH sequence 56C09

<400> SEQUENCE: 222

Asn Ile Thr Ser Val Gly Ser Thr Asn Tyr Ala Asp Ser Val Lys Gly
1 5 10 15

<210> SEQ ID NO 223
<211> LENGTH: 16
<212> TYPE: PRT
<213> ORGANISM: Artificial Sequence
<220> FEATURE:
<223> OTHER INFORMATION: CDR2 of VHH sequence 56C12

<400> SEQUENCE: 223

Ser Ile Ser Gly Ile Arg Ile Thr Thr Tyr Thr Asn Ser Val Lys Gly
1 5 10 15

<210> SEQ ID NO 224

-continued

<211> LENGTH: 16
<212> TYPE: PRT
<213> ORGANISM: Artificial Sequence
<220> FEATURE:
<223> OTHER INFORMATION: CDR2 of VHH sequence 56D07

<400> SEQUENCE: 224

Val Ile Thr Ser Gly Gly Arg Thr Asn Tyr Ala Glu Ser Val Lys Gly
1 5 10 15

<210> SEQ ID NO 225
<211> LENGTH: 16
<212> TYPE: PRT
<213> ORGANISM: Artificial Sequence
<220> FEATURE:
<223> OTHER INFORMATION: CDR2 of VHH sequence 56D07

<400> SEQUENCE: 225

Val Ile Thr Ser Gly Gly Arg Thr Asn Tyr Ala Glu Ser Val Lys Gly
1 5 10 15

<210> SEQ ID NO 226
<211> LENGTH: 16
<212> TYPE: PRT
<213> ORGANISM: Artificial Sequence
<220> FEATURE:
<223> OTHER INFORMATION: CDR2 of VHH sequence 56D10

<400> SEQUENCE: 226

Ser Ser Ser Ser Gly Gly Thr Thr Asn Tyr Ala Ser Ser Val Lys Gly
1 5 10 15

<210> SEQ ID NO 227
<211> LENGTH: 16
<212> TYPE: PRT
<213> ORGANISM: Artificial Sequence
<220> FEATURE:
<223> OTHER INFORMATION: CDR2 of VHH sequence 56E04

<400> SEQUENCE: 227

Lys Ile Thr Thr Gly Gly Thr Thr Asn Tyr Ala Asp Ser Val Lys Gly
1 5 10 15

<210> SEQ ID NO 228
<211> LENGTH: 16
<212> TYPE: PRT
<213> ORGANISM: Artificial Sequence
<220> FEATURE:
<223> OTHER INFORMATION: CDR2 of VHH sequence 56E05

<400> SEQUENCE: 228

Arg Ile Ser Ser Gly Gly Asn Thr Asn Tyr Thr Asp Ser Val Lys Gly
1 5 10 15

<210> SEQ ID NO 229
<211> LENGTH: 16
<212> TYPE: PRT
<213> ORGANISM: Artificial Sequence
<220> FEATURE:
<223> OTHER INFORMATION: CDR2 of VHH sequence 56E08

<400> SEQUENCE: 229

Thr Ile Thr Ser Ala Asn Ile Thr Asn Tyr Ala Asp Ser Val Lys Gly
1 5 10 15

<210> SEQ ID NO 230
<211> LENGTH: 16

<212> TYPE: PRT
<213> ORGANISM: Artificial Sequence
<220> FEATURE:
<223> OTHER INFORMATION: CDR2 of VHH sequence 56F07

<400> SEQUENCE: 230

Ile Ile Thr Asn Asp Asp Ser Thr Thr Tyr Ala Asp Ser Val Lys Gly
1 5 10 15

<210> SEQ ID NO 231
<211> LENGTH: 16
<212> TYPE: PRT
<213> ORGANISM: Artificial Sequence
<220> FEATURE:
<223> OTHER INFORMATION: CDR2 of VHH sequence 56G07

<400> SEQUENCE: 231

Thr Ile Thr Pro Phe Gly Arg Arg Asn Tyr Ser Glu Tyr Val Lys Gly
1 5 10 15

<210> SEQ ID NO 232
<211> LENGTH: 16
<212> TYPE: PRT
<213> ORGANISM: Artificial Sequence
<220> FEATURE:
<223> OTHER INFORMATION: CDR2 of VHH sequence 56G08

<400> SEQUENCE: 232

Thr Leu Ser Arg Ala Gly Thr Ser Arg Tyr Val Asp Ser Val Lys Gly
1 5 10 15

<210> SEQ ID NO 233
<211> LENGTH: 16
<212> TYPE: PRT
<213> ORGANISM: Artificial Sequence
<220> FEATURE:
<223> OTHER INFORMATION: CDR2 of VHH sequence 56G10

<400> SEQUENCE: 233

Glu Ile Ser Ser Arg Gly Thr Thr Met Tyr Ala Asp Ser Val Lys Gly
1 5 10 15

<210> SEQ ID NO 234
<211> LENGTH: 16
<212> TYPE: PRT
<213> ORGANISM: Artificial Sequence
<220> FEATURE:
<223> OTHER INFORMATION: CDR2 of VHH sequence 56H04

<400> SEQUENCE: 234

Arg Ile Ser Thr Val Gly Thr Ala His Tyr Ala Asp Ser Val Lys Gly
1 5 10 15

<210> SEQ ID NO 235
<211> LENGTH: 16
<212> TYPE: PRT
<213> ORGANISM: Artificial Sequence
<220> FEATURE:
<223> OTHER INFORMATION: CDR2 of VHH sequence 56H05

<400> SEQUENCE: 235

Gln Ile Asn Asn Arg Asp Asn Thr Glu Tyr Ala Asp Ser Val Lys Gly
1 5 10 15

<210> SEQ ID NO 236
<211> LENGTH: 15
<212> TYPE: PRT

<213> ORGANISM: Artificial Sequence
<220> FEATURE:
<223> OTHER INFORMATION: CDR2 of VHH sequence 56H07

<400> SEQUENCE: 236

Ser Ile Ser Thr Gly Ser Thr Asn Tyr Ala Asp Ser Val Lys Gly
1 5 10 15

<210> SEQ ID NO 237
<211> LENGTH: 16
<212> TYPE: PRT
<213> ORGANISM: Artificial Sequence
<220> FEATURE:
<223> OTHER INFORMATION: CDR2 of VHH sequence 56H08

<400> SEQUENCE: 237

Val Ile Ser Ser Asp Gly Ser Thr Asn Tyr Ala Asp Ser Val Lys Gly
1 5 10 15

<210> SEQ ID NO 238
<211> LENGTH: 16
<212> TYPE: PRT
<213> ORGANISM: Artificial Sequence
<220> FEATURE:
<223> OTHER INFORMATION: CDR2 of VHH sequence 57A06

<400> SEQUENCE: 238

Arg Ile Ser Ser Gly Gly Asn Thr Asn Tyr Thr Asp Ser Val Lys Gly
1 5 10 15

<210> SEQ ID NO 239
<211> LENGTH: 16
<212> TYPE: PRT
<213> ORGANISM: Artificial Sequence
<220> FEATURE:
<223> OTHER INFORMATION: CDR2 of VHH sequence 57B01

<400> SEQUENCE: 239

Arg Ile Ser Ser Gly Gly Ser Thr Asn Tyr Ala Asp Ser Val Lys Gly
1 5 10 15

<210> SEQ ID NO 240
<211> LENGTH: 16
<212> TYPE: PRT
<213> ORGANISM: Artificial Sequence
<220> FEATURE:
<223> OTHER INFORMATION: CDR2 of VHH sequence 57B07

<400> SEQUENCE: 240

Thr Val Asp Ser Gly Gly Tyr Thr Asn Tyr Ala Asp Ser Val Lys Gly
1 5 10 15

<210> SEQ ID NO 241
<211> LENGTH: 16
<212> TYPE: PRT
<213> ORGANISM: Artificial Sequence
<220> FEATURE:
<223> OTHER INFORMATION: CDR2 of VHH sequence 57B11

<400> SEQUENCE: 241

Leu Ile Arg Ser Ser Gly Gly Thr Tyr Tyr Ala Asp Ser Val Lys Gly
1 5 10 15

<210> SEQ ID NO 242
<211> LENGTH: 16
<212> TYPE: PRT
<213> ORGANISM: Artificial Sequence
<220> FEATURE:
<223> OTHER INFORMATION: CDR2 of VHH sequence 57C07

<400> SEQUENCE: 242

Ser Ile Ser Arg Gly Gly Met Thr Asn Tyr Ala Asp Ser Val Lys Gly
1 5 10 15

<210> SEQ ID NO 243
<211> LENGTH: 16
<212> TYPE: PRT
<213> ORGANISM: Artificial Sequence
<220> FEATURE:
<223> OTHER INFORMATION: CDR2 of VHH sequence 57C09

<400> SEQUENCE: 243

Ser Ile Ser Ser Gly Gly Ala Thr Asn Tyr Ala Asp Ser Val Lys Gly
1 5 10 15

<210> SEQ ID NO 244
<211> LENGTH: 16
<212> TYPE: PRT
<213> ORGANISM: Artificial Sequence
<220> FEATURE:
<223> OTHER INFORMATION: CDR2 of VHH sequence 57D02

<400> SEQUENCE: 244

Thr Ile Thr Arg Arg Ser Arg Thr Asn Tyr Ala Glu Phe Val Lys Gly
1 5 10 15

<210> SEQ ID NO 245
<211> LENGTH: 16
<212> TYPE: PRT
<213> ORGANISM: Artificial Sequence
<220> FEATURE:
<223> OTHER INFORMATION: CDR2 of VHH sequence 57D09

<400> SEQUENCE: 245

Ser Ile Thr Thr Gly Gly Ser Thr Asn Tyr Ala Asp Ser Val Lys Gly
1 5 10 15

<210> SEQ ID NO 246
<211> LENGTH: 16
<212> TYPE: PRT
<213> ORGANISM: Artificial Sequence
<220> FEATURE:
<223> OTHER INFORMATION: CDR2 of VHH sequence 57D10

<400> SEQUENCE: 246

Ser Ile Thr Lys Asp Gly Thr Thr Asn Tyr Ala Asp Ser Val Lys Gly
1 5 10 15

<210> SEQ ID NO 247
<211> LENGTH: 16
<212> TYPE: PRT
<213> ORGANISM: Artificial Sequence
<220> FEATURE:
<223> OTHER INFORMATION: CDR2 of VHH sequence 57E07

<400> SEQUENCE: 247

Asp Ile Thr Arg Ser Gly Ser Thr His Tyr Val Asp Ser Val Lys Gly
1 5 10 15

<210> SEQ ID NO 248
<211> LENGTH: 16
<212> TYPE: PRT
<213> ORGANISM: Artificial Sequence
<220> FEATURE:

<223> OTHER INFORMATION: CDR2 of VHH sequence 57E11

<400> SEQUENCE: 248

Arg Ile Ser Arg Leu Arg Val Thr Asn Tyr Ala Asp Ser Val Lys Gly
1 5 10 15

<210> SEQ ID NO 249
<211> LENGTH: 16
<212> TYPE: PRT
<213> ORGANISM: Artificial Sequence
<220> FEATURE:
<223> OTHER INFORMATION: CDR2 of VHH sequence 57G01

<400> SEQUENCE: 249

Thr Ile Ser Asn Ser Gly Thr Thr Asn Tyr Val Asp Ala Val Lys Gly
1 5 10 15

<210> SEQ ID NO 250
<211> LENGTH: 16
<212> TYPE: PRT
<213> ORGANISM: Artificial Sequence
<220> FEATURE:
<223> OTHER INFORMATION: CDR2 of VHH sequence 57G07

<400> SEQUENCE: 250

Thr Ile Arg Arg Gly Gly Asn Thr Lys Tyr Ala Asp Ser Val Lys Gly
1 5 10 15

<210> SEQ ID NO 251
<211> LENGTH: 16
<212> TYPE: PRT
<213> ORGANISM: Artificial Sequence
<220> FEATURE:
<223> OTHER INFORMATION: CDR2 of VHH sequence 57G08

<400> SEQUENCE: 251

Thr Ile Asp Ile His Asn Ser Thr Lys Tyr Ala Asp Ser Val Lys Gly
1 5 10 15

<210> SEQ ID NO 252
<211> LENGTH: 16
<212> TYPE: PRT
<213> ORGANISM: Artificial Sequence
<220> FEATURE:
<223> OTHER INFORMATION: CDR2 of VHH sequence 57H08

<400> SEQUENCE: 252

Gln Gln Arg Tyr Asp Gly Ser Thr Asn Tyr Ala Asp Ser Leu Gln Gly
1 5 10 15

<210> SEQ ID NO 253
<211> LENGTH: 7
<212> TYPE: PRT
<213> ORGANISM: Artificial Sequence
<220> FEATURE:
<223> OTHER INFORMATION: CDR3 of VHH sequence 41D01

<400> SEQUENCE: 253

Arg Ser Ile Trp Arg Asp Tyr
1 5

<210> SEQ ID NO 254
<211> LENGTH: 11
<212> TYPE: PRT
<213> ORGANISM: Artificial Sequence
<220> FEATURE:
<223> OTHER INFORMATION: CDR3 of VHH sequence 56F07

<400> SEQUENCE: 254

Asp Ile Asn Thr Ala Ile Trp Arg Arg Lys Tyr
1 5 10

<210> SEQ ID NO 255
<211> LENGTH: 10
<212> TYPE: PRT
<213> ORGANISM: Artificial Sequence
<220> FEATURE:
<223> OTHER INFORMATION: CDR3 of VHH sequence 40F07

<400> SEQUENCE: 255

Ala Arg Thr Trp Ser Ile Phe Arg Asn Tyr
1 5 10

<210> SEQ ID NO 256
<211> LENGTH: 8
<212> TYPE: PRT
<213> ORGANISM: Artificial Sequence
<220> FEATURE:
<223> OTHER INFORMATION: CDR3 of VHH sequence 41D06

<400> SEQUENCE: 256

Val Arg Leu Trp Phe Pro Asp Tyr
1 5

<210> SEQ ID NO 257
<211> LENGTH: 13
<212> TYPE: PRT
<213> ORGANISM: Artificial Sequence
<220> FEATURE:
<223> OTHER INFORMATION: CDR3 of VHH sequence 41G10

<400> SEQUENCE: 257

Glu Ala Arg Arg Tyr Phe Thr Arg Ala Ser Gln Val Tyr
1 5 10

<210> SEQ ID NO 258
<211> LENGTH: 12
<212> TYPE: PRT
<213> ORGANISM: Artificial Sequence
<220> FEATURE:
<223> OTHER INFORMATION: CDR3 of VHH sequence 41H05

<400> SEQUENCE: 258

Val Gly Arg Arg Trp Tyr Gly Gly Tyr Val Glu Leu
1 5 10

<210> SEQ ID NO 259
<211> LENGTH: 11
<212> TYPE: PRT
<213> ORGANISM: Artificial Sequence
<220> FEATURE:
<223> OTHER INFORMATION: CDR3 of VHH sequence 42C11

<400> SEQUENCE: 259

Asp Arg Trp Val Leu Thr Arg Trp Ser Asn Tyr
1 5 10

<210> SEQ ID NO 260
<211> LENGTH: 11
<212> TYPE: PRT
<213> ORGANISM: Artificial Sequence
<220> FEATURE:
<223> OTHER INFORMATION: CDR3 of VHH sequence 42C12

<400> SEQUENCE: 260

Gln Arg Gly Val Ala Trp Thr Arg Lys Glu Tyr
1 5 10

<210> SEQ ID NO 261
<211> LENGTH: 11
<212> TYPE: PRT
<213> ORGANISM: Artificial Sequence
<220> FEATURE:
<223> OTHER INFORMATION: CDR3 of VHH sequence 50D03

<400> SEQUENCE: 261

Asp Arg Trp Val Leu Thr Arg Trp Ser Asn Tyr
1 5 10

<210> SEQ ID NO 262
<211> LENGTH: 12
<212> TYPE: PRT
<213> ORGANISM: Artificial Sequence
<220> FEATURE:
<223> OTHER INFORMATION: CDR3 of VHH sequence 50D07

<400> SEQUENCE: 262

Arg Val Arg Thr Val Leu Arg Gly Trp Arg Asp Tyr
1 5 10

<210> SEQ ID NO 263
<211> LENGTH: 11
<212> TYPE: PRT
<213> ORGANISM: Artificial Sequence
<220> FEATURE:
<223> OTHER INFORMATION: CDR3 of VHH sequence 50E02

<400> SEQUENCE: 263

Arg Arg Arg Thr Phe Leu Lys Ser Ser Asp Tyr
1 5 10

<210> SEQ ID NO 264
<211> LENGTH: 15
<212> TYPE: PRT
<213> ORGANISM: Artificial Sequence
<220> FEATURE:
<223> OTHER INFORMATION: CDR3 of VHH sequence 51B08

<400> SEQUENCE: 264

Lys Tyr Gly Arg Trp Thr Tyr Thr Gly Arg Pro Glu Tyr Asp Ser
1 5 10 15

<210> SEQ ID NO 265
<211> LENGTH: 8
<212> TYPE: PRT
<213> ORGANISM: Artificial Sequence
<220> FEATURE:
<223> OTHER INFORMATION: CDR3 of VHH sequence 51C06

<400> SEQUENCE: 265

Arg Arg Arg Trp Ser Arg Asp Phe
1 5

<210> SEQ ID NO 266
<211> LENGTH: 11
<212> TYPE: PRT
<213> ORGANISM: Artificial Sequence
<220> FEATURE:
<223> OTHER INFORMATION: CDR3 of VHH sequence 51C08

<400> SEQUENCE: 266

Arg Gln Gln Phe Ile Gly Ala Pro Tyr Glu Tyr
1 5 10

<210> SEQ ID NO 267
<211> LENGTH: 7
<212> TYPE: PRT
<213> ORGANISM: Artificial Sequence
<220> FEATURE:
<223> OTHER INFORMATION: CDR3 of VHH sequence 52A01

<400> SEQUENCE: 267

Arg Leu Leu Trp Ser Asn Tyr
1 5

<210> SEQ ID NO 268
<211> LENGTH: 9
<212> TYPE: PRT
<213> ORGANISM: Artificial Sequence
<220> FEATURE:
<223> OTHER INFORMATION: CDR3 of VHH sequence 52B01

<400> SEQUENCE: 268

Ala Gly Trp Val Gly Val Thr Asn Tyr
1 5

<210> SEQ ID NO 269
<211> LENGTH: 9
<212> TYPE: PRT
<213> ORGANISM: Artificial Sequence
<220> FEATURE:
<223> OTHER INFORMATION: CDR3 of VHH sequence 52G05

<400> SEQUENCE: 269

Arg Arg Tyr Tyr Thr Arg Asn Asp Tyr
1 5

<210> SEQ ID NO 270
<211> LENGTH: 6
<212> TYPE: PRT
<213> ORGANISM: Artificial Sequence
<220> FEATURE:
<223> OTHER INFORMATION: CDR3 of VHH sequence 53A01

<400> SEQUENCE: 270

Gly Ala Ile Gly Asn Trp
1 5

<210> SEQ ID NO 271
<211> LENGTH: 9
<212> TYPE: PRT
<213> ORGANISM: Artificial Sequence
<220> FEATURE:
<223> OTHER INFORMATION: CDR3 of VHH sequence 53F05

<400> SEQUENCE: 271

Glu Arg Arg Trp Gly Leu Pro Asn Tyr
1 5

<210> SEQ ID NO 272
<211> LENGTH: 17
<212> TYPE: PRT
<213> ORGANISM: Artificial Sequence
<220> FEATURE:
<223> OTHER INFORMATION: CDR3 of VHH sequence 54A02

<400> SEQUENCE: 272

Tyr Ala His Ile Thr Ala Trp Gly Met Arg Asn Asp Tyr Glu Tyr Asp
1 5 10 15

Tyr

<210> SEQ ID NO 273
<211> LENGTH: 16
<212> TYPE: PRT
<213> ORGANISM: Artificial Sequence
<220> FEATURE:
<223> OTHER INFORMATION: CDR3 of VHH sequence 54B01

<400> SEQUENCE: 273

Gly Asn Leu Leu Arg Leu Ala Gly Gln Leu Arg Arg Gly Tyr Asp Ser
1 5 10 15

<210> SEQ ID NO 274
<211> LENGTH: 20
<212> TYPE: PRT
<213> ORGANISM: Artificial Sequence
<220> FEATURE:
<223> OTHER INFORMATION: CDR3 of VHH sequence 54C01

<400> SEQUENCE: 274

Arg Asn Arg Ala Gly Pro His Tyr Ser Arg Gly Tyr Thr Ala Gly Gln
1 5 10 15

Glu Tyr Asp Tyr
20

<210> SEQ ID NO 275
<211> LENGTH: 13
<212> TYPE: PRT
<213> ORGANISM: Artificial Sequence
<220> FEATURE:
<223> OTHER INFORMATION: CDR3 of VHH sequence 54C04

<400> SEQUENCE: 275

Asn Leu Arg Thr Ala Phe Trp Arg Asn Gly Asn Asp Tyr
1 5 10

<210> SEQ ID NO 276
<211> LENGTH: 7
<212> TYPE: PRT
<213> ORGANISM: Artificial Sequence
<220> FEATURE:
<223> OTHER INFORMATION: CDR3 of VHH sequence 54C08

<400> SEQUENCE: 276

Gly Pro Trp Tyr Arg Arg Ser
1 5

<210> SEQ ID NO 277
<211> LENGTH: 8
<212> TYPE: PRT
<213> ORGANISM: Artificial Sequence
<220> FEATURE:
<223> OTHER INFORMATION: CDR3 of VHH sequence 54C10

<400> SEQUENCE: 277

Asp Leu Ala Val Arg Gly Arg Tyr
1 5

<210> SEQ ID NO 278
<211> LENGTH: 11
<212> TYPE: PRT
<213> ORGANISM: Artificial Sequence
<220> FEATURE:

<223> OTHER INFORMATION: CDR3 of VHH sequence 54C11

<400> SEQUENCE: 278

Arg Ile Gly Phe Gly Trp Thr Ala Lys Ala Tyr
1 5 10

<210> SEQ ID NO 279
<211> LENGTH: 8
<212> TYPE: PRT
<213> ORGANISM: Artificial Sequence
<220> FEATURE:
<223> OTHER INFORMATION: CDR3 of VHH sequence 54D03

<400> SEQUENCE: 279

Val Arg Leu Trp Phe Pro Asp Tyr
1 5

<210> SEQ ID NO 280
<211> LENGTH: 8
<212> TYPE: PRT
<213> ORGANISM: Artificial Sequence
<220> FEATURE:
<223> OTHER INFORMATION: CDR3 of VHH sequence 54D06

<400> SEQUENCE: 280

Arg Ser Trp Val Gly Pro Glu Tyr
1 5

<210> SEQ ID NO 281
<211> LENGTH: 12
<212> TYPE: PRT
<213> ORGANISM: Artificial Sequence
<220> FEATURE:
<223> OTHER INFORMATION: CDR3 of VHH sequence 54D10

<400> SEQUENCE: 281

Lys Thr Arg Thr Trp Tyr Asn Gly Lys Tyr Asp Tyr
1 5 10

<210> SEQ ID NO 282
<211> LENGTH: 9
<212> TYPE: PRT
<213> ORGANISM: Artificial Sequence
<220> FEATURE:
<223> OTHER INFORMATION: CDR3 of VHH sequence 54E01

<400> SEQUENCE: 282

Arg Ser Thr Leu Trp Arg Arg Asp Tyr
1 5

<210> SEQ ID NO 283
<211> LENGTH: 9
<212> TYPE: PRT
<213> ORGANISM: Artificial Sequence
<220> FEATURE:
<223> OTHER INFORMATION: CDR3 of VHH sequence 54E05

<400> SEQUENCE: 283

His Arg Ser Trp Pro Arg Tyr Asp Ser
1 5

<210> SEQ ID NO 284
<211> LENGTH: 10
<212> TYPE: PRT
<213> ORGANISM: Artificial Sequence
<220> FEATURE:
<223> OTHER INFORMATION: CDR3 of VHH sequence 54E10

<400> SEQUENCE: 284

Glu Ser Arg Ile Phe Arg Arg Tyr Asp Tyr
1 5 10

<210> SEQ ID NO 285
<211> LENGTH: 7
<212> TYPE: PRT
<213> ORGANISM: Artificial Sequence
<220> FEATURE:
<223> OTHER INFORMATION: CDR3 of VHH sequence 54F01

<400> SEQUENCE: 285

Asp Arg Gly Trp Ser Ser Tyr
1 5

<210> SEQ ID NO 286
<211> LENGTH: 11
<212> TYPE: PRT
<213> ORGANISM: Artificial Sequence
<220> FEATURE:
<223> OTHER INFORMATION: CDR3 of VHH sequence 54F02

<400> SEQUENCE: 286

His Gln Arg Ala Trp Ala Arg Ser Tyr Val Tyr
1 5 10

<210> SEQ ID NO 287
<211> LENGTH: 9
<212> TYPE: PRT
<213> ORGANISM: Artificial Sequence
<220> FEATURE:
<223> OTHER INFORMATION: CDR3 of VHH sequence 54G01

<400> SEQUENCE: 287

Lys Arg Ser Trp Phe Ser Gln Glu Tyr
1 5

<210> SEQ ID NO 288
<211> LENGTH: 13
<212> TYPE: PRT
<213> ORGANISM: Artificial Sequence
<220> FEATURE:
<223> OTHER INFORMATION: CDR3 of VHH sequence 54G08

<400> SEQUENCE: 288

Gln Tyr Thr Ile Thr Pro Trp Gly Ile Lys Lys Asp Tyr
1 5 10

<210> SEQ ID NO 289
<211> LENGTH: 12
<212> TYPE: PRT
<213> ORGANISM: Artificial Sequence
<220> FEATURE:
<223> OTHER INFORMATION: CDR3 of VHH sequence 54G09

<400> SEQUENCE: 289

Arg Val Arg Thr Val Leu Arg Gly Trp Arg Asp Tyr
1 5 10

<210> SEQ ID NO 290
<211> LENGTH: 9
<212> TYPE: PRT
<213> ORGANISM: Artificial Sequence
<220> FEATURE:
<223> OTHER INFORMATION: CDR3 of VHH sequence 55B02

<400> SEQUENCE: 290

Asn Ser Ile Phe Arg Ser Arg Asp Tyr
1 5

<210> SEQ ID NO 291
<211> LENGTH: 16
<212> TYPE: PRT
<213> ORGANISM: Artificial Sequence
<220> FEATURE:
<223> OTHER INFORMATION: CDR3 of VHH sequence 55B05

<400> SEQUENCE: 291

Arg Ser Gln Ile Arg Ser Pro Trp Ser Ser Leu Asp Asp Tyr Asp Arg
1 5 10 15

<210> SEQ ID NO 292
<211> LENGTH: 8
<212> TYPE: PRT
<213> ORGANISM: Artificial Sequence
<220> FEATURE:
<223> OTHER INFORMATION: CDR3 of VHH sequence 55C05

<400> SEQUENCE: 292

Asp Arg Phe Phe Gly Arg Asp Tyr
1 5

<210> SEQ ID NO 293
<211> LENGTH: 12
<212> TYPE: PRT
<213> ORGANISM: Artificial Sequence
<220> FEATURE:
<223> OTHER INFORMATION: CDR3 of VHH sequence 55D08

<400> SEQUENCE: 293

Val Tyr Ser Arg Pro Leu Leu Gly Pro Leu Glu Val
1 5 10

<210> SEQ ID NO 294
<211> LENGTH: 7
<212> TYPE: PRT
<213> ORGANISM: Artificial Sequence
<220> FEATURE:
<223> OTHER INFORMATION: CDR3 of VHH sequence 55E02

<400> SEQUENCE: 294

Val Arg Tyr Leu Val Asn Tyr
1 5

<210> SEQ ID NO 295
<211> LENGTH: 13
<212> TYPE: PRT
<213> ORGANISM: Artificial Sequence
<220> FEATURE:
<223> OTHER INFORMATION: CDR3 of VHH sequence 55E07

<400> SEQUENCE: 295

Gly Val Val Val Ala Thr Ser Pro Lys Phe Tyr Ala Tyr
1 5 10

<210> SEQ ID NO 296
<211> LENGTH: 7
<212> TYPE: PRT
<213> ORGANISM: Artificial Sequence
<220> FEATURE:
<223> OTHER INFORMATION: CDR3 of VHH sequence 55E09

<400> SEQUENCE: 296

Arg Arg Leu Gly Thr Gly Tyr
1               5

<210> SEQ ID NO 297
<211> LENGTH: 7
<212> TYPE: PRT
<213> ORGANISM: Artificial Sequence
<220> FEATURE:
<223> OTHER INFORMATION: CDR3 of VHH sequence 55E10

<400> SEQUENCE: 297

Arg Tyr Trp Phe Arg Asp Tyr
1               5

<210> SEQ ID NO 298
<211> LENGTH: 7
<212> TYPE: PRT
<213> ORGANISM: Artificial Sequence
<220> FEATURE:
<223> OTHER INFORMATION: CDR3 of VHH sequence 55F04

<400> SEQUENCE: 298

Val Arg Leu Phe Arg Gln Tyr
1               5

<210> SEQ ID NO 299
<211> LENGTH: 16
<212> TYPE: PRT
<213> ORGANISM: Artificial Sequence
<220> FEATURE:
<223> OTHER INFORMATION: CDR3 of VHH sequence 55F09

<400> SEQUENCE: 299

Gly Gly Ser Ser Arg Trp Tyr Ser Ser Arg Tyr Tyr Pro Gly Gly Tyr
1               5                   10                  15

<210> SEQ ID NO 300
<211> LENGTH: 17
<212> TYPE: PRT
<213> ORGANISM: Artificial Sequence
<220> FEATURE:
<223> OTHER INFORMATION: CDR3 of VHH sequence 55F10

<400> SEQUENCE: 300

Asp Ser Ser Ala Arg Ala Leu Val Gly Gly Pro Gly Asn Arg Trp Asp
1               5                   10                  15

Tyr

<210> SEQ ID NO 301
<211> LENGTH: 10
<212> TYPE: PRT
<213> ORGANISM: Artificial Sequence
<220> FEATURE:
<223> OTHER INFORMATION: CDR3 of VHH sequence 55G02

<400> SEQUENCE: 301

Lys Asn Ala Lys Asn Val Arg Pro Gly Tyr
1               5                   10

<210> SEQ ID NO 302
<211> LENGTH: 8
<212> TYPE: PRT
<213> ORGANISM: Artificial Sequence
<220> FEATURE:
<223> OTHER INFORMATION: CDR3 of VHH sequence 55G08

<400> SEQUENCE: 302

Val Arg Phe Trp Phe Pro Asp Tyr
1 5

<210> SEQ ID NO 303
<211> LENGTH: 8
<212> TYPE: PRT
<213> ORGANISM: Artificial Sequence
<220> FEATURE:
<223> OTHER INFORMATION: CDR3 of VHH sequence 56A05

<400> SEQUENCE: 303

Arg Arg Asn Val Phe Ile Ser Ser
1 5

<210> SEQ ID NO 304
<211> LENGTH: 7
<212> TYPE: PRT
<213> ORGANISM: Artificial Sequence
<220> FEATURE:
<223> OTHER INFORMATION: CDR3 of VHH sequence 56A06

<400> SEQUENCE: 304

Arg Arg Leu Gly Arg Asp Tyr
1 5

<210> SEQ ID NO 305
<211> LENGTH: 10
<212> TYPE: PRT
<213> ORGANISM: Artificial Sequence
<220> FEATURE:
<223> OTHER INFORMATION: CDR3 of VHH sequence 56A09

<400> SEQUENCE: 305

Asn Phe Gly Ile Leu Val Gly Arg Glu Tyr
1 5 10

<210> SEQ ID NO 306
<211> LENGTH: 8
<212> TYPE: PRT
<213> ORGANISM: Artificial Sequence
<220> FEATURE:
<223> OTHER INFORMATION: CDR3 of VHH sequence 56C09

<400> SEQUENCE: 306

Arg Met Pro Phe Leu Gly Asp Ser
1 5

<210> SEQ ID NO 307
<211> LENGTH: 8
<212> TYPE: PRT
<213> ORGANISM: Artificial Sequence
<220> FEATURE:
<223> OTHER INFORMATION: CDR3 of VHH sequence 56D06

<400> SEQUENCE: 307

Thr Ser Ile Thr Gly Thr Tyr Leu
1 5

<210> SEQ ID NO 308
<211> LENGTH: 6
<212> TYPE: PRT
<213> ORGANISM: Artificial Sequence
<220> FEATURE:
<223> OTHER INFORMATION: CDR3 of VHH sequence 56D07

<400> SEQUENCE: 308

Lys Thr Ile Arg Pro Tyr
1 5

<210> SEQ ID NO 309
<211> LENGTH: 12
<212> TYPE: PRT
<213> ORGANISM: Artificial Sequence
<220> FEATURE:
<223> OTHER INFORMATION: CDR3 of VHH sequence 56D10

<400> SEQUENCE: 309

Arg Lys Phe Ile Thr Thr Pro Trp Ser Thr Asp Tyr
1 5 10

<210> SEQ ID NO 310
<211> LENGTH: 8
<212> TYPE: PRT
<213> ORGANISM: Artificial Sequence
<220> FEATURE:
<223> OTHER INFORMATION: CDR3 of VHH sequence 56E04

<400> SEQUENCE: 310

Glu Arg Tyr Phe Ala Thr Thr Leu
1 5

<210> SEQ ID NO 311
<211> LENGTH: 11
<212> TYPE: PRT
<213> ORGANISM: Artificial Sequence
<220> FEATURE:
<223> OTHER INFORMATION: CDR3 of VHH sequence 56E05

<400> SEQUENCE: 311

Gln Arg Arg Val Ile Leu Gly Pro Arg Asn Tyr
1 5 10

<210> SEQ ID NO 312
<211> LENGTH: 13
<212> TYPE: PRT
<213> ORGANISM: Artificial Sequence
<220> FEATURE:
<223> OTHER INFORMATION: CDR3 of VHH sequence 56E08

<400> SEQUENCE: 312

Gln Ala Lys Lys Trp Arg Ile Gly Pro Trp Ser Asp Tyr
1 5 10

<210> SEQ ID NO 313
<211> LENGTH: 13
<212> TYPE: PRT
<213> ORGANISM: Artificial Sequence
<220> FEATURE:
<223> OTHER INFORMATION: CDR3 of VHH sequence 56F11

<400> SEQUENCE: 313

Asn Thr Arg Arg Ile Phe Gly Gly Thr Val Arg Glu Tyr
1 5 10

<210> SEQ ID NO 314
<211> LENGTH: 7
<212> TYPE: PRT
<213> ORGANISM: Artificial Sequence
<220> FEATURE:
<223> OTHER INFORMATION: CDR3 of VHH sequence 56G07

<400> SEQUENCE: 314

Arg Val Asn Gly Val Asp Tyr
1 5

<210> SEQ ID NO 315
<211> LENGTH: 7
<212> TYPE: PRT
<213> ORGANISM: Artificial Sequence
<220> FEATURE:
<223> OTHER INFORMATION: CDR3 of VHH sequence 56G08

<400> SEQUENCE: 315

Ala Gln Leu Gly Thr Asp Tyr
1 5

<210> SEQ ID NO 316
<211> LENGTH: 9
<212> TYPE: PRT
<213> ORGANISM: Artificial Sequence
<220> FEATURE:
<223> OTHER INFORMATION: CDR3 of VHH sequence 56G10

<400> SEQUENCE: 316

Arg Ala Phe Ala Phe Gly Arg Asn Ser
1 5

<210> SEQ ID NO 317
<211> LENGTH: 10
<212> TYPE: PRT
<213> ORGANISM: Artificial Sequence
<220> FEATURE:
<223> OTHER INFORMATION: CDR3 of VHH sequence 56H04

<400> SEQUENCE: 317

Gln Ala Gly Arg Leu Tyr Leu Arg Asn Tyr
1 5 10

<210> SEQ ID NO 318
<211> LENGTH: 9
<212> TYPE: PRT
<213> ORGANISM: Artificial Sequence
<220> FEATURE:
<223> OTHER INFORMATION: CDR3 of VHH sequence 56H05

<400> SEQUENCE: 318

Lys Arg Trp Ser Trp Ser Thr Gly Phe
1 5

<210> SEQ ID NO 319
<211> LENGTH: 7
<212> TYPE: PRT
<213> ORGANISM: Artificial Sequence
<220> FEATURE:
<223> OTHER INFORMATION: CDR3 of VHH sequence 56H07

<400> SEQUENCE: 319

Arg Leu Trp Trp Ser Asn Tyr
1 5

<210> SEQ ID NO 320
<211> LENGTH: 10
<212> TYPE: PRT
<213> ORGANISM: Artificial Sequence
<220> FEATURE:
<223> OTHER INFORMATION: CDR3 of VHH sequence 56H08

<400> SEQUENCE: 320

Asn Arg Arg Trp Ser Trp Gly Ser Glu Tyr

-continued 1 5 10

<210> SEQ ID NO 321
<211> LENGTH: 11
<212> TYPE: PRT
<213> ORGANISM: Artificial Sequence
<220> FEATURE:
<223> OTHER INFORMATION: CDR3 of VHH sequence 57A06

<400> SEQUENCE: 321

Gln Arg Arg Val Ile Leu Gly Pro Arg Asn Tyr
1 5 10

<210> SEQ ID NO 322
<211> LENGTH: 8
<212> TYPE: PRT
<213> ORGANISM: Artificial Sequence
<220> FEATURE:
<223> OTHER INFORMATION: CDR3 of VHH sequence 57B01

<400> SEQUENCE: 322

Asn Arg His Trp Gly Trp Asp Tyr
1 5

<210> SEQ ID NO 323
<211> LENGTH: 14
<212> TYPE: PRT
<213> ORGANISM: Artificial Sequence
<220> FEATURE:
<223> OTHER INFORMATION: CDR3 of VHH sequence 57B07

<400> SEQUENCE: 323

Gly Ile Tyr Lys Trp Pro Trp Ser Val Asp Ala Arg Asp Tyr
1 5 10

<210> SEQ ID NO 324
<211> LENGTH: 9
<212> TYPE: PRT
<213> ORGANISM: Artificial Sequence
<220> FEATURE:
<223> OTHER INFORMATION: CDR3 of VHH sequence 57B11

<400> SEQUENCE: 324

Arg Arg Thr Trp Leu Ser Ser Glu Ser
1 5

<210> SEQ ID NO 325
<211> LENGTH: 14
<212> TYPE: PRT
<213> ORGANISM: Artificial Sequence
<220> FEATURE:
<223> OTHER INFORMATION: CDR3 of VHH sequence 57C07

<400> SEQUENCE: 325

Gly Ile Arg Ser Arg Trp Tyr Gly Gly Pro Ile Thr Thr Tyr
1 5 10

<210> SEQ ID NO 326
<211> LENGTH: 13
<212> TYPE: PRT
<213> ORGANISM: Artificial Sequence
<220> FEATURE:
<223> OTHER INFORMATION: CDR3 of VHH sequence 57C09

<400> SEQUENCE: 326

Lys Lys Ser Arg Trp Ser Trp Ser Ile Val His Asp Tyr
1 5 10

-continued

<210> SEQ ID NO 327
<211> LENGTH: 10
<212> TYPE: PRT
<213> ORGANISM: Artificial Sequence
<220> FEATURE:
<223> OTHER INFORMATION: CDR3 of VHH sequence 57D02

<400> SEQUENCE: 327

Arg Trp Gly Ala Gly Gly Ile Phe Ser Thr
1 5 10

<210> SEQ ID NO 328
<211> LENGTH: 13
<212> TYPE: PRT
<213> ORGANISM: Artificial Sequence
<220> FEATURE:
<223> OTHER INFORMATION: CDR3 of VHH sequence 57D09

<400> SEQUENCE: 328

Lys Val Arg Leu Arg Trp Phe Arg Pro Pro Ser Asp Tyr
1 5 10

<210> SEQ ID NO 329
<211> LENGTH: 14
<212> TYPE: PRT
<213> ORGANISM: Artificial Sequence
<220> FEATURE:
<223> OTHER INFORMATION: CDR3 of VHH sequence 57D10

<400> SEQUENCE: 329

Arg Ala Thr Thr Trp Val Pro Tyr Arg Arg Asp Ala Glu Phe
1 5 10

<210> SEQ ID NO 330
<211> LENGTH: 12
<212> TYPE: PRT
<213> ORGANISM: Artificial Sequence
<220> FEATURE:
<223> OTHER INFORMATION: CDR3 of VHH sequence 57E07

<400> SEQUENCE: 330

Asp Ser Gly Ser His Trp Trp Asn Arg Arg Asp Tyr
1 5 10

<210> SEQ ID NO 331
<211> LENGTH: 10
<212> TYPE: PRT
<213> ORGANISM: Artificial Sequence
<220> FEATURE:
<223> OTHER INFORMATION: CDR3 of VHH sequence 57E11

<400> SEQUENCE: 331

Ala Asn Trp Gly Leu Ala Gly Asn Glu Tyr
1 5 10

<210> SEQ ID NO 332
<211> LENGTH: 8
<212> TYPE: PRT
<213> ORGANISM: Artificial Sequence
<220> FEATURE:
<223> OTHER INFORMATION: CDR3 of VHH sequence 57G01

<400> SEQUENCE: 332

Gln Thr Phe Trp Arg Arg Asn Tyr
1 5

<210> SEQ ID NO 333
<211> LENGTH: 8
<212> TYPE: PRT
<213> ORGANISM: Artificial Sequence
<220> FEATURE:
<223> OTHER INFORMATION: CDR3 of VHH sequence 57G07

<400> SEQUENCE: 333

His Ser Trp Leu Asp Tyr Asp Tyr
1               5

<210> SEQ ID NO 334
<211> LENGTH: 7
<212> TYPE: PRT
<213> ORGANISM: Artificial Sequence
<220> FEATURE:
<223> OTHER INFORMATION: CDR3 of VHH sequence 57G08

<400> SEQUENCE: 334

Ile Pro Thr Phe Gly Arg Tyr
1               5

<210> SEQ ID NO 335
<211> LENGTH: 7
<212> TYPE: PRT
<213> ORGANISM: Artificial Sequence
<220> FEATURE:
<223> OTHER INFORMATION: CDR3 of VHH sequence 57H08

<400> SEQUENCE: 335

Asn Arg Gly Phe Ile Ser Tyr
1               5

<210> SEQ ID NO 336
<211> LENGTH: 345
<212> TYPE: DNA
<213> ORGANISM: Artificial Sequence
<220> FEATURE:
<223> OTHER INFORMATION: VHH 41D01

<400> SEQUENCE: 336
caggttcagc tgcaggaatc tggtggtgga cttgttcaag ctggtggatc tcttagactc 60
tcttgcgctg cttctggaag gaccttctct agatatggaa tgggatggtt caggcagctc 120
cctggaaaac agagagagct tgttacctct atcaccaggg gtggaactac cacctacgct 180
gattctgtga agggaaggtt caccatctct agggataacg ctaagaacac cgtgtacctc 240
cagatgaact ctctcaagcc tgaggatacc gctgtgtact actgcaacgc tagatctatt 300
tggagggatt actggggaca gggaactcag gtcaccgttt cttca 345

<210> SEQ ID NO 337
<211> LENGTH: 363
<212> TYPE: DNA
<213> ORGANISM: Artificial Sequence
<220> FEATURE:
<223> OTHER INFORMATION: VHH 56F11

<400> SEQUENCE: 337
caggttcagc tgcaggaatc tggtggtgga cttgttcagt ctggtggatc tctcagactc 60
tcttgcgtgc actctaagac caccttcacc agaaatgcta tgggatggta cagacaggct 120
ctcggaaaag agagagagct tgttgctacc atcacctctg gtggaactac caactacgct 180
gattctgtga agggaaggtt caccatctct atggattctg ctaagaacac cgtgtacctc 240

-continued

```
cagatgaact ctctcaagcc tgaggatacc gctgtgtact actgcaacgt gaacaccaga    300

aggatcttcg gaggaaccgt tagagaatac tggggacaag gtactcaggt caccgtttct    360

tca                                                                  363
```

<210> SEQ ID NO 338
<211> LENGTH: 456
<212> TYPE: DNA
<213> ORGANISM: Artificial Sequence
<220> FEATURE:
<223> OTHER INFORMATION: 41D01_His_KDEL

<400> SEQUENCE: 338

```
atggcaaaca agcttttctt ggtgtgcgct accttcgctc tttgcttcct tttgactaac     60

gctcaggttc agctgcagga atctggtggt ggacttgttc aagctggtgg atctcttaga    120

ctctcttgcg ctgcttctgg aaggaccttc tctagatatg gaatgggatg gttcaggcag    180

ctccctggaa aacagagaga gcttgttacc tctatcacca ggggtggaac taccacctac    240

gctgattctg tgaagggaag gttcaccatc tctagggata acgctaagaa caccgtgtac    300

ctccagatga actctctcaa gcctgaggat accgctgtgt actactgcaa cgctagatct    360

atttggaggg attactgggg acagggaact caggtcaccg tttcttcagc ggccgcacat    420

catcatcacc atcatggtgc tgctaaggat gagctt                              456
```

<210> SEQ ID NO 339
<211> LENGTH: 1131
<212> TYPE: DNA
<213> ORGANISM: Artificial Sequence
<220> FEATURE:
<223> OTHER INFORMATION: sec_41D01_hinge_Fc_His

<400> SEQUENCE: 339

```
atggcaaaca agcttttctt ggtgtgcgct accttcgctc tttgcttcct tttgactaac     60

gctcaggttc agctgcagga atctggtggt ggacttgttc aagctggtgg atctcttaga    120

ctctcttgcg ctgcttctgg aaggaccttc tctagatatg gaatgggatg gttcaggcag    180

ctccctggaa aacagagaga gcttgttacc tctatcacca ggggtggaac taccacctac    240

gctgattctg tgaagggaag gttcaccatc tctagggata acgctaagaa caccgtgtac    300

ctccagatga actctctcaa gcctgaggat accgctgtgt actactgcaa cgctagatct    360

atttggaggg attactgggg acagggaact caggtcaccg tttcttcacc tagaatccct    420

aagccttcta cccctcctgg atcttcttgt cctcctggaa atatcctcgg tggaccttct    480

gtgttcatct tcccacctaa gcctaaggat gctctcatga tctcactcac ccctaaggtt    540

acatgcgttg tggtggatgt gtctgaggat gatcctgatg tgcacgtgtc atggttcgtg    600

gataacaaag aggtgcacac tgcttggact cagcctagag aagctcagta caactctacc    660

ttcagggtgg tgtctgctct ccctatccaa caccaagatt ggatgagggg taaagagttc    720

aagtgcaagg tgaacaacaa ggctctccct gctcctatcg agaggactat ctctaaacct    780

aagggaaggg ctcagacccc tcaagtgtat acaattcctc cacctaggga acagatgtct    840

aagaagaagg tttcactcac ttgcctcgtg accaacttct tcagtgaggc tatctctgtt    900

gagtgggaga ggaatggtga gcttgagcag gattacaaga acacccctcc tatcctcgat    960

tctgatggaa cctacttcct ctactctaag ctcaccgtgg ataccgattc ttggttgcag   1020

ggtgagatct tcacttgctc tgttgtgcat gaggctctcc acaaccatca cacccagaag   1080

aacctcagta gatctcctgg taaagcggcc gcacatcatc atcaccatca t            1131
```

<210> SEQ ID NO 340
<211> LENGTH: 807
<212> TYPE: DNA
<213> ORGANISM: Artificial Sequence
<220> FEATURE:
<223> OTHER INFORMATION: sec_41D01-9GS-41D01_His

<400> SEQUENCE: 340
atggcaaaca agcttttctt ggtgtgcgct accttcgctc tttgcttcct tttgactaac 60
gctcaggttc aattgcaaga gtctggtggt ggacttgttc aggctggtgg atctcttaga 120
ctttcttgcg ctgcttctgg aaggaccttc tctagatatg gaatgggatg gttcaggcag 180
ctccctggaa aacagagaga gcttgttacc tctatcacca ggggtggaac taccacctac 240
gctgattctg tgaagggaag gttcaccatc tctagggata acgctaagaa caccgtgtac 300
ctccagatga actctctcaa gcctgaggat accgctgtgt actactgcaa cgctagatct 360
atttggaggg attactgggg acagggaact caggtcaccg tttcttcagg tggtggtgga 420
agtggtggtg gttctcaagt tcaactgcag gaatcaggtg gtggattggt gcaagctggt 480
ggttctttga ggttgtcatg tgctgctagt ggtaggacct tcagtaggta cggtatggga 540
tggtttagac agttgcctgg taagcagagg gaactcgtga cttcaatcac tagaggtgga 600
accactactt acgcagatag tgttaaggga agattcacta tcagtagaga taatgcaaag 660
aacactgttt acttgcaaat gaactcattg aagccagagg atacagcagt ttattactgt 720
aacgcaagaa gtatttggag agattattgg ggtcaaggta ctcaagtgac cgttagttca 780
gcggccgcac atcatcatca ccatcat 807

<210> SEQ ID NO 341
<211> LENGTH: 435
<212> TYPE: DNA
<213> ORGANISM: Artificial Sequence
<220> FEATURE:
<223> OTHER INFORMATION: sec_41D01_His

<400> SEQUENCE: 341
atggcaaaca agcttttctt ggtgtgcgct accttcgctc tttgcttcct tttgactaac 60
gctcaggttc agctgcagga atctggtggt ggacttgttc aagctggtgg atctcttaga 120
ctctcttgcg ctgcttctgg aaggaccttc tctagatatg gaatgggatg gttcaggcag 180
ctccctggaa aacagagaga gcttgttacc tctatcacca ggggtggaac taccacctac 240
gctgattctg tgaagggaag gttcaccatc tctagggata acgctaagaa caccgtgtac 300
ctccagatga actctctcaa gcctgaggat accgctgtgt actactgcaa cgctagatct 360
atttggaggg attactgggg acagggaact caggtcaccg tttcttcagc ggccgcacat 420
catcatcacc atcat 435

<210> SEQ ID NO 342
<211> LENGTH: 375
<212> TYPE: DNA
<213> ORGANISM: Artificial Sequence
<220> FEATURE:
<223> OTHER INFORMATION: cyto_41D01_His

<400> SEQUENCE: 342
atgcaggttc agctgcagga atctggtggt ggacttgttc aagctggtgg atctcttaga 60
ctctcttgcg ctgcttctgg aaggaccttc tctagatatg gaatgggatg gttcaggcag 120

-continued

```
ctccctggaa aacagagaga gcttgttacc tctatcacca ggggtggaac taccacctac    180

gctgattctg tgaagggaag gttcaccatc tctagggata acgctaagaa caccgtgtac    240

ctccagatga actctctcaa gcctgaggat accgctgtgt actactgcaa cgctagatct    300

atttggaggg attactgggg acagggaact caggtcaccg tttcttcagc ggccgcacat    360

catcatcacc atcat                                                     375


<210> SEQ ID NO 343
<211> LENGTH: 474
<212> TYPE: DNA
<213> ORGANISM: Artificial Sequence
<220> FEATURE:
<223> OTHER INFORMATION: 56F11_His_KDEL

<400> SEQUENCE: 343

atggcaaaca agcttttctt ggtgtgcgct accttcgctc tttgcttcct tttgactaac     60

gctcaggttc agctgcagga atctggtggt ggacttgttc agtctggtgg atctctcaga    120

ctctcttgcg tgcactctaa gaccaccttc accagaaatg ctatgggatg gtacagacag    180

gctctcggaa aagagagaga gcttgttgct accatcacct ctggtggaac taccaactac    240

gctgattctg tgaagggaag gttcaccatc tctatggatt ctgctaagaa caccgtgtac    300

ctccagatga actctctcaa gcctgaggat accgctgtgt actactgcaa cgtgaacacc    360

agaaggatct tcggaggaac cgttagagaa tactggggac aaggtactca ggtcaccgtt    420

tcttcagcgg ccgcacatca tcatcaccat catggtgctg ctaaggatga gctt          474


<210> SEQ ID NO 344
<211> LENGTH: 1149
<212> TYPE: DNA
<213> ORGANISM: Artificial Sequence
<220> FEATURE:
<223> OTHER INFORMATION: sec_56F11_hinge_Fc_His

<400> SEQUENCE: 344

atggcaaaca agcttttctt ggtgtgcgct accttcgctc tttgcttcct tttgactaac     60

gctcaggttc agctgcagga atctggtggt ggacttgttc agtctggtgg atctctcaga    120

ctctcttgcg tgcactctaa gaccaccttc accagaaatg ctatgggatg gtacagacag    180

gctctcggaa aagagagaga gcttgttgct accatcacct ctggtggaac taccaactac    240

gctgattctg tgaagggaag gttcaccatc tctatggatt ctgctaagaa caccgtgtac    300

ctccagatga actctctcaa gcctgaggat accgctgtgt actactgcaa cgtgaacacc    360

agaaggatct tcggaggaac cgttagagaa tactggggac aaggtactca ggtcaccgtt    420

tcttcaccta gaatccctaa gccttctacc cctcctggat cttcttgtcc tcctggaaat    480

atcctcggag gaccttcagt gttcatcttc ccacctaagc ctaaggatgc tctcatgatc    540

tcactcaccc ctaaggttac atgcgttgtg gtggatgtgt ctgaggatga tcctgatgtg    600

cacgtgtcat ggttcgtgga taacaaagag gtgcacactg cttggactca gcctagagaa    660

gctcagtaca actctacctt cagggtggtg tctgctctcc ctatccaaca ccaagattgg    720

atgaggggta aagagttcaa gtgcaaggtg aacaacaagg ctctccctgc tcctatcgag    780

aggactatct ctaaacctaa gggaagggct cagacccctc aagtgtatac aattcctcca    840

cctagggaac agatgtctaa gaagaaggtt tcactcactt gcctcgtgac caacttcttc    900

agtgaggcta tctctgttga gtgggagagg aatggtgagc ttgagcagga ttacaagaac    960

acccctccta tcctcgattc tgatggaacc tacttcctct actctaagct caccgtggat   1020
```

accgattctt ggttgcaggg tgagatcttc acttgctctg ttgtgcatga ggctctccac 1080
aaccatcaca cccagaagaa cctcagtaga tctcctggta aagcggccgc acatcatcat 1140
caccatcat 1149

<210> SEQ ID NO 345
<211> LENGTH: 843
<212> TYPE: DNA
<213> ORGANISM: Artificial Sequence
<220> FEATURE:
<223> OTHER INFORMATION: sec_56F11-9GS-56F11_His

<400> SEQUENCE: 345
atggcaaaca agcttttctt ggtgtgcgct accttcgctc tttgcttcct tttgactaac 60
gctcaggttc aattgcaaga gtctggtggt ggactcgtgc aatctggtgg atctcttaga 120
ctctcttgcg tgcactctaa gaccaccttc accagaaatg ctatgggatg gtacagacag 180
gctctcggaa aagagagaga gcttgttgct accatcacct ctggtggaac taccaactac 240
gctgattctg tgaagggaag gttcaccatc tctatggatt ctgctaagaa caccgtgtac 300
ctccagatga actctctcaa gcctgaggat accgctgtgt actactgcaa cgtgaacacc 360
agaaggatct tcggaggaac cgttagagaa tactggggac aaggtactca ggtcaccgtt 420
tcttcaggtg gtggtggaag tggtggtggt tctcaagttc aactgcagga atcaggtggt 480
ggattggttc agtctggtgg ttctctcagg ttgtcatgcg ttcacagtaa gactactttc 540
actaggaacg caatgggatg gtataggcaa gcacttggta aagagaggga actcgttgca 600
actatcacaa gtggtggaac cactaattac gcagatagtg ttaagggaag attcactatt 660
agtatggata gtgcaaagaa cactgtttac ttgcaaatga actcattgaa gccagaggat 720
acagcagttt attactgtaa tgttaacact agaagaattt tcggtggtac tgtgagagag 780
tattggggac agggaaccca ggttacagtt agttcagcgg ccgcacatca tcaccatcac 840
cat 843

<210> SEQ ID NO 346
<211> LENGTH: 453
<212> TYPE: DNA
<213> ORGANISM: Artificial Sequence
<220> FEATURE:
<223> OTHER INFORMATION: sec_56F11_His

<400> SEQUENCE: 346
atggcaaaca agcttttctt ggtgtgcgct accttcgctc tttgcttcct tttgactaac 60
gctcaggttc agctgcagga atctggtggt ggacttgttc agtctggtgg atctctcaga 120
ctctcttgcg tgcactctaa gaccaccttc accagaaatg ctatgggatg gtacagacag 180
gctctcggaa aagagagaga gcttgttgct accatcacct ctggtggaac taccaactac 240
gctgattctg tgaagggaag gttcaccatc tctatggatt ctgctaagaa caccgtgtac 300
ctccagatga actctctcaa gcctgaggat accgctgtgt actactgcaa cgtgaacacc 360
agaaggatct tcggaggaac cgttagagaa tactggggac aaggtactca ggtcaccgtt 420
tcttcagcgg ccgcacatca tcatcaccat cat 453

<210> SEQ ID NO 347
<211> LENGTH: 393
<212> TYPE: DNA
<213> ORGANISM: Artificial Sequence
<220> FEATURE:

<223> OTHER INFORMATION: cyto_56F11_His

<400> SEQUENCE: 347
atgcaggttc agctgcagga atctggtggt ggacttgttc agtctggtgg atctctcaga 60
ctctcttgcg tgcactctaa gaccaccttc accagaaatg ctatgggatg gtacagacag 120
gctctcggaa aagagagaga gcttgttgct accatcacct ctggtggaac taccaactac 180
gctgattctg tgaagggaag gttcaccatc tctatggatt ctgctaagaa caccgtgtac 240
ctccagatga actctctcaa gcctgaggat accgctgtgt actactgcaa cgtgaacacc 300
agaaggatct tcggaggaac cgttagagaa tactggggac aaggtactca ggtcaccgtt 360
tcttcagcgg ccgcacatca tcatcaccat cat 393

<210> SEQ ID NO 348
<211> LENGTH: 6
<212> TYPE: PRT
<213> ORGANISM: Artificial Sequence
<220> FEATURE:
<223> OTHER INFORMATION: His

<400> SEQUENCE: 348

His His His His His His
1 5

<210> SEQ ID NO 349
<211> LENGTH: 4
<212> TYPE: PRT
<213> ORGANISM: Artificial Sequence
<220> FEATURE:
<223> OTHER INFORMATION: ER retention signal

<400> SEQUENCE: 349

Lys Asp Glu Leu
1

<210> SEQ ID NO 350
<211> LENGTH: 21
<212> TYPE: PRT
<213> ORGANISM: Artificial Sequence
<220> FEATURE:
<223> OTHER INFORMATION: 2S2 secretion signal

<400> SEQUENCE: 350

Met Ala Asn Lys Leu Phe Leu Val Cys Ala Thr Phe Ala Leu Cys Phe
1 5 10 15

Leu Leu Thr Asn Ala
20

<210> SEQ ID NO 351
<211> LENGTH: 217
<212> TYPE: PRT
<213> ORGANISM: Artificial Sequence
<220> FEATURE:
<223> OTHER INFORMATION: Fc region

<400> SEQUENCE: 351

Pro Gly Asn Ile Leu Gly Gly Pro Ser Val Phe Ile Phe Pro Pro Lys
1 5 10 15

Pro Lys Asp Ala Leu Met Ile Ser Leu Thr Pro Lys Val Thr Cys Val
20 25 30

Val Val Asp Val Ser Glu Asp Asp Pro Asp Val His Val Ser Trp Phe
35 40 45

Val Asp Asn Lys Glu Val His Thr Ala Trp Thr Gln Pro Arg Glu Ala
    50                  55                  60

Gln Tyr Asn Ser Thr Phe Arg Val Val Ser Ala Leu Pro Ile Gln His
65                  70                  75                  80

Gln Asp Trp Met Arg Gly Lys Glu Phe Lys Cys Lys Val Asn Asn Lys
                85                  90                  95

Ala Leu Pro Ala Pro Ile Glu Arg Thr Ile Ser Lys Pro Lys Gly Arg
            100                 105                 110

Ala Gln Thr Pro Gln Val Tyr Thr Ile Pro Pro Pro Arg Glu Gln Met
        115                 120                 125

Ser Lys Lys Lys Val Ser Leu Thr Cys Leu Val Thr Asn Phe Phe Ser
    130                 135                 140

Glu Ala Ile Ser Val Glu Trp Glu Arg Asn Gly Glu Leu Glu Gln Asp
145                 150                 155                 160

Tyr Lys Asn Thr Pro Pro Ile Leu Asp Ser Asp Gly Thr Tyr Phe Leu
                165                 170                 175

Tyr Ser Lys Leu Thr Val Asp Thr Asp Ser Trp Leu Gln Gly Glu Ile
            180                 185                 190

Phe Thr Cys Ser Val Val His Glu Ala Leu His Asn His His Thr Gln
        195                 200                 205

Lys Asn Leu Ser Arg Ser Pro Gly Lys
    210                 215

<210> SEQ ID NO 352
<211> LENGTH: 9
<212> TYPE: PRT
<213> ORGANISM: Artificial Sequence
<220> FEATURE:
<223> OTHER INFORMATION: 9GS spacer

<400> SEQUENCE: 352

Gly Gly Gly Gly Ser Gly Gly Gly Ser
1               5

<210> SEQ ID NO 353
<211> LENGTH: 15
<212> TYPE: PRT
<213> ORGANISM: Artificial Sequence
<220> FEATURE:
<223> OTHER INFORMATION: hinge

<400> SEQUENCE: 353

Pro Arg Ile Pro Lys Pro Ser Thr Pro Pro Gly Ser Ser Cys Pro
1               5                   10                  15

<210> SEQ ID NO 354
<211> LENGTH: 1027
<212> TYPE: DNA
<213> ORGANISM: Artificial Sequence
<220> FEATURE:
<223> OTHER INFORMATION: CaMV 35S promoter

<400> SEQUENCE: 354
actagagcca agctgatctc ctttgccccg gagatcacca tggacgactt tctctatctc      60
tacgatctag gaagaaagtt cgacggagaa ggtgacgata ccatgttcac caccgataat     120
gagaagatta gcctcttcaa tttcagaaag aatgctgacc cacagatggt tagagaggcc     180
tacgcggcag gtctcatcaa gacgatctac ccgagtaata atctccagga gatcaaatac     240
cttcccaaga aggttaaaga tgcagtcaaa agattcagga ctaactgcat caagaacaca     300

-continued gagaaagata tatttctcaa gatcagaagt actattccag tatggacgat tcaaggcttg 360
cttcataaac caaggcaagt aatagagatt ggagtctcta agaaagtagt tcctactgaa 420
tcaaaggcca tggagtcaaa aattcagatc gaggatctaa cagaactcgc cgtgaagact 480
ggcgaacagt tcatacagag tcttttacga ctcaatgaca agaagaaaat cttcgtcaac 540
atggtggagc acgacactct cgtctactcc aagaatatca aagatacagt ctcagaagac 600
caaagggcta ttgagacttt tcaacaaagg gtaatatcgg gaaacctcct cggattccat 660
tgcccagcta tctgtcactt catcaaaagg acagtagaaa aggaaggtgg cacctacaaa 720
tgccatcatt gcgataaagg aaaggctatc gttcaagatg cctctgccga cagtggtccc 780
aaagatggac ccccacccac gaggagcatc gtggaaaaag aagacgttcc aaccacgtct 840
tcaaagcaag tggattgatg tgatatctcc actgacgtaa gggatgacgc acaatcccac 900
tatccttcgc aagacccttc ctctatataa ggaagttcat ttcatttgga gaggactccg 960
gtatttttac aacaatacca caacaaaaca aacaacaaac aacattacaa tttactattc 1020
tagtcga 1027

<210> SEQ ID NO 355
<211> LENGTH: 18
<212> TYPE: DNA
<213> ORGANISM: Artificial Sequence
<220> FEATURE:
<223> OTHER INFORMATION: pMA_FW primer

<400> SEQUENCE: 355
ttgtaaaacg acggccag 18

<210> SEQ ID NO 356
<211> LENGTH: 20
<212> TYPE: DNA
<213> ORGANISM: Artificial Sequence
<220> FEATURE:
<223> OTHER INFORMATION: pMA_REV primer

<400> SEQUENCE: 356
ggaaacagct atgaccatgt 20

<210> SEQ ID NO 357
<211> LENGTH: 36
<212> TYPE: DNA
<213> ORGANISM: Artificial Sequence
<220> FEATURE:
<223> OTHER INFORMATION: pMA_CYTO primer

<400> SEQUENCE: 357
ccggaattcc caccatgcag gttcagctgc aggaat 36

<210> SEQ ID NO 358
<211> LENGTH: 11159
<212> TYPE: DNA
<213> ORGANISM: Artificial Sequence
<220> FEATURE:
<223> OTHER INFORMATION: pK7WG2

<400> SEQUENCE: 358
ggccctctag aggatccccg ggtaccctcg aattatcata catgagaatt aagggagtca 60
cgttatgacc cccgccgatg acgcgggaca agccgtttta cgtttggaac tgacagaacc 120
gcaacgttga aggagccact cagccgcggg tttctggagt ttaatgagct aagcacatac 180
gtcagaaacc attattgcgc gttcaaaagt cgcctaaggt cactatcagc tagcaaatat 240

-continued

```
ttcttgtcaa aaatgctcca ctgacgttcc ataaattccc ctcggtatcc aattagagtc    300
tcatattcac tctcaactcg atcgaggcat gattgaacaa gatggattgc acgcaggttc    360
tccggccgct tgggtggaga ggctattcgg ctatgactgg gcacaacaga caatcggctg    420
ctctgatgcc gccgtgttcc ggctgtcagc gcaggggcgc ccggttcttt ttgtcaagac    480
cgacctgtcc ggtgccctga atgaactcca agacgaggca gcgcggctat cgtggctggc    540
cacgacgggc gttccttgcg cagctgtgct cgacgttgtc actgaagcgg gaagggactg    600
gctgctattg ggcgaagtgc cggggcagga tctcctgtca tctcaccttg ctcctgccga    660
gaaagtatcc atcatggctg atgcaatgcg gcggctgcat acgcttgatc cggctacctg    720
cccattcgac caccaagcga aacatcgcat cgagcgagca cgtactcgga tggaagccgg    780
tcttgtcgat caggatgatc tggacgaaga gcatcagggg ctcgcgccag ccgaactgtt    840
cgccaggctc aaggcgcgga tgcccgacgg cgaggatctc gtcgtgaccc acggcgatgc    900
ctgcttgccg aatatcatgg tggaaaatgg ccgcttttct ggattcatcg actgtggccg    960
gctgggtgtg gcggaccgct atcaggacat agcgttggct acccgtgata ttgctgaaga   1020
gcttggcggc gaatgggctg accgcttcct cgtgctttac ggtatcgccg ctcccgattc   1080
gcagcgcatc gccttctatc gccttcttga cgagttcttc tgagcgggac tctggggttc   1140
ggactctagc tagagtcaag cagatcgttc aaacatttgg caataaagtt tcttaagatt   1200
gaatcctgtt gccggtcttg cgatgattat catataattt ctgttgaatt acgttaagca   1260
tgtaataatt aacatgtaat gcatgacgtt atttatgaga tgggttttta tgattagagt   1320
cccgcaatta tacatttaat acgcgataga aaacaaaata tagcgcgcaa actaggataa   1380
attatcgcgc gcggtgtcat ctatgttact agatcgaccg gcatgcaagc tgataattca   1440
attcggcgtt aattcagtac attaaaaacg tccgcaatgt gttattaagt tgtctaagcg   1500
tcaatttgtt tacaccacaa tatatcctgc caccagccag ccaacagctc cccgaccggc   1560
agctcggcac aaaatcacca ctcgatacag gcagcccatc agtccgggac ggcgtcagcg   1620
ggagagccgt tgtaaggcgg cagactttgc tcatgttacc gatgctattc ggaagaacgg   1680
caactaagct gccgggtttg aaacacggat gatctcgcgg agggtagcat gttgattgta   1740
acgatgacag agcgttgctg cctgtgatca attcgggcac gaacccagtg gacataagcc   1800
tcgttcggtt cgtaagctgt aatgcaagta gcgtaactgc cgtcacgcaa ctggtccaga   1860
accttgaccg aacgcagcgg tggtaacggc gcagtggcgg ttttcatggc ttcttgttat   1920
gacatgtttt tttggggtac agtctatgcc tcgggcatcc aagcagcaag cgcgttacgc   1980
cgtgggtcga tgtttgatgt tatggagcag caacgatgtt acgcagcagg gcagtcgccc   2040
taaaacaaag ttaaacatca tgggggaagc ggtgatcgcc gaagtatcga ctcaactatc   2100
agaggtagtt ggcgtcatcg agcgccatct cgaaccgacg ttgctggccg tacatttgta   2160
cggctccgca gtggatggcg gcctgaagcc acacagtgat attgatttgc tggttacggt   2220
gaccgtaagg cttgatgaaa caacgcggcg agctttgatc aacgaccttt tggaaacttc   2280
ggcttcccct ggagagagcg agattctccg cgctgtagaa gtcaccattg ttgtgcacga   2340
cgacatcatt ccgtggcgtt atccagctaa gcgcgaactg caatttggag aatggcagcg   2400
caatgacatt cttgcaggta tcttcgagcc agccacgatc gacattgatc tggctatctt   2460
gctgacaaaa gcaagagaac atagcgttgc cttggtaggt ccagcggcgg aggaactctt   2520
tgatccggtt cctgaacagg atctatttga ggcgctaaat gaaaccttaa cgctatggaa   2580
```

-continued

```
ctcgccgccc gactgggctg gcgatgagcg aaatgtagtg cttacgttgt cccgcatttg   2640
gtacagcgca gtaaccggca aaatcgcgcc gaaggatgtc gctgccgact gggcaatgga   2700
gcgcctgccg gcccagtatc agcccgtcat acttgaagct agacaggctt atcttggaca   2760
agaagaagat cgcttggcct cgcgcgcaga tcagttggaa gaatttgtcc actacgtgaa   2820
aggcgagatc accaaggtag tcggcaaata atgtctagct agaaattcgt tcaagccgac   2880
gccgcttcgc cggcgttaac tcaagcgatt agatgcacta agcacataat tgctcacagc   2940
caaactatca ggtcaagtct gcttttatta tttttaagcg tgcataataa gccctacaca   3000
aattgggaga tatatcatgc atgaccaaaa tcccttaacg tgagttttcg ttccactgag   3060
cgtcagaccc cgtagaaaag atcaaaggat cttcttgaga tccttttttt ctgcgcgtaa   3120
tctgctgctt gcaaacaaaa aaaccaccgc taccagcggt ggtttgtttg ccggatcaag   3180
agctaccaac tctttttccg aaggtaactg gcttcagcag agcgcagata ccaaatactg   3240
tccttctagt gtagccgtag ttaggccacc acttcaagaa ctctgtagca ccgcctacat   3300
acctcgctct gctaatcctg ttaccagtgg ctgctgccag tggcgataag tcgtgtctta   3360
ccgggttgga ctcaagacga tagttaccgg ataaggcgca gcggtcgggc tgaacggggg   3420
gttcgtgcac acagcccagc ttggagcgaa cgacctacac cgaactgaga tacctacagc   3480
gtgagctatg agaaagcgcc acgcttcccg aagggagaaa ggcggacagg tatccggtaa   3540
gcggcagggt cggaacagga gagcgcacga gggagcttcc agggggaaac gcctggtatc   3600
tttatagtcc tgtcgggttt cgccacctct gacttgagcg tcgatttttg tgatgctcgt   3660
caggggggcg gagcctatgg aaaaacgcca gcaacgcggc ctttttacgg ttcctggcct   3720
tttgctggcc ttttgctcac atgttctttc ctgcgttatc ccctgattct gtggataacc   3780
gtattaccgc ctttgagtga gctgataccg ctcgccgcag ccgaacgacc gagcgcagcg   3840
agtcagtgag cgaggaagcg gaagagcgcc tgatgcggta ttttctcctt acgcatctgt   3900
gcggtatttc acaccgcata tggtgcactc tcagtacaat ctgctctgat gccgcatagt   3960
taagccagta tacactccgc tatcgctacg tgactgggtc atggctgcgc cccgacaccc   4020
gccaacaccc gctgacgcgc cctgacgggc ttgtctgctc ccggcatccg cttacagaca   4080
agctgtgacc gtctccggga gctgcatgtg tcagaggttt tcaccgtcat caccgaaacg   4140
cgcgaggcag ggtgccttga tgtgggcgcc ggcggtcgag tggcgacggc gcggcttgtc   4200
cgcgccctgg tagattgcct ggccgtaggc cagccatttt tgagcggcca gcggccgcga   4260
taggccgacg cgaagcggcg gggcgtaggg agcgcagcga ccgaagggta ggcgcttttt   4320
gcagctcttc ggctgtgcgc tggccagaca gttatgcaca ggccaggcgg gttttaagag   4380
ttttaataag ttttaaagag ttttaggcgg aaaaatcgcc tttttctct tttatatcag   4440
tcacttacat gtgtgaccgg ttcccaatgt acggctttgg gttcccaatg tacgggttcc   4500
ggttcccaat gtacggcttt gggttcccaa tgtacgtgct atccacagga aagagacctt   4560
ttcgaccttt ttcccctgct agggcaattt gccctagcat ctgctccgta cattaggaac   4620
cggcggatgc ttcgccctcg atcaggttgc ggtagcgcat gactaggatc gggccagcct   4680
gccccgcctc ctccttcaaa tcgtactccg gcaggtcatt tgacccgatc agcttgcgca   4740
cggtgaaaca gaacttcttg aactctccgg cgctgccact gcgttcgtag atcgtcttga   4800
acaaccatct ggcttctgcc ttgcctgcgg cgcggcgtgc caggcggtag agaaaacggc   4860
cgatgccggg atcgatcaaa aagtaatcgg ggtgaaccgt cagcacgtcc gggttcttgc   4920
cttctgtgat ctcgcggtac atccaatcag ctagctcgat ctcgatgtac tccggccgcc   4980
```

-continued

```
cggtttcgct ctttacgatc ttgtagcggc taatcaaggc ttcaccctcg gataccgtca   5040
ccaggcggcc gttcttggcc ttcttcgtac gctgcatggc aacgtgcgtg gtgtttaacc   5100
gaatgcaggt ttctaccagg tcgtctttct gctttccgcc atcggctcgc cggcagaact   5160
tgagtacgtc cgcaacgtgt ggacggaaca cgcggccggg cttgtctccc ttcccttccc   5220
ggtatcggtt catggattcg gttagatggg aaaccgccat cagtaccagg tcgtaatccc   5280
acacactggc catgccggcc ggccctgcgg aaacctctac gtgcccgtct ggaagctcgt   5340
agcggatcac ctcgccagct cgtcggtcac gcttcgacag acggaaaacg gccacgtcca   5400
tgatgctgcg actatcgcgg gtgcccacgt catagagcat cggaacgaaa aaatctggtt   5460
gctcgtcgcc cttgggcggc ttcctaatcg acggcgcacc ggctgccggc ggttgccggg   5520
attctttgcg gattcgatca gcggccgctt gccacgattc accggggcgt gcttctgcct   5580
cgatgcgttg ccgctgggcg gcctgcgcgg ccttcaactt ctccaccagg tcatcaccca   5640
gcgccgcgcc gatttgtacc gggccggatg gtttgcgacc gtcacgccga ttcctcgggc   5700
ttgggggttc cagtgccatt gcagggccgg cagacaaccc agccgcttac gcctggccaa   5760
ccgcccgttc ctccacacat ggggcattcc acggcgtcgg tgcctggttg ttcttgattt   5820
tccatgccgc ctcctttagc cgctaaaatt catctactca tttattcatt tgctcattta   5880
ctctggtagc tgcgcgatgt attcagatag cagctcggta atggtcttgc cttggcgtac   5940
cgcgtacatc ttcagcttgg tgtgatcctc cgccggcaac tgaaagttga cccgcttcat   6000
ggctggcgtg tctgccaggc tggccaacgt tgcagccttg ctgctgcgtg cgctcggacg   6060
gccggcactt agcgtgtttg tgcttttgct catttttctct ttacctcatt aactcaaatg   6120
agttttgatt taatttcagc ggccagcgcc tggacctcgc gggcagcgtc gccctcgggt   6180
tctgattcaa gaacggttgt gccggcggcg gcagtgcctg ggtagctcac gcgctgcgtg   6240
atacgggact caagaatggg cagctcgtac ccggccagcg cctcggcaac ctcaccgccg   6300
atgcgcgtgc ctttgatcgc ccgcgacacg acaaaggccg cttgtagcct tccatccgtg   6360
acctcaatgc gctgcttaac cagctccacc aggtcggcgg tggcccatat gtcgtaaggg   6420
cttggctgca ccggaatcag cacgaagtcg gctgccttga tcgcggacac agccaagtcc   6480
gccgcctggg gcgctccgtc gatcactacg aagtcgcgcc ggccgatggc cttcacgtcg   6540
cggtcaatcg tcgggcggtc gatgccgaca acggttagcg gttgatcttc ccgcacggcc   6600
gcccaatcgc gggcactgcc ctggggatcg gaatcgacta acagaacatc ggccccggcg   6660
agttgcaggg cgcgggctag atgggttgcg atggtcgtct tgcctgaccc gcctttctgg   6720
ttaagtacag cgataacctt catgcgttcc ccttgcgtat ttgtttattt actcatcgca   6780
tcatatacgc agcgaccgca tgacgcaagc tgttttactc aaatacacat caccttttta   6840
gacggcggcg ctcggtttct tcagcggcca agctggccgg ccaggccgcc agcttggcat   6900
cagacaaacc ggccaggatt tcatgcagcc gcacggttga gacgtgcgcg ggcggctcga   6960
acacgtaccc ggccgcgatc atctccgcct cgatctcttc ggtaatgaaa aacggttcgt   7020
cctggccgtc ctggtgcggt ttcatgcttg ttcctcttgg cgttcattct cggcggccgc   7080
cagggcgtcg gcctcggtca atgcgtcctc acggaaggca ccgcgccgcc tggcctcggt   7140
gggcgtcact tcctcgctgc gctcaagtgc gcggtacagg gtcgagcgat gcacgccaag   7200
cagtgcagcc gcctctttca cggtgcggcc ttcctggtcg atcagctcgc gggcgtgcgc   7260
gatctgtgcc ggggtgaggg tagggcgggg gccaaacttc acgcctcggg ccttggcggc   7320
```

ctcgcgcccg ctccgggtgc ggtcgatgat tagggaacgc tcgaactcgg caatgccggc 7380
gaacacggtc aacaccatgc ggccggccgg cgtggtggtg tcggcccacg gctctgccag 7440
gctacgcagg cccgcgccgg cctcctggat gcgctcggca atgtccagta ggtcgcgggt 7500
gctgcgggcc aggcggtcta gcctggtcac tgtcacaacg tcgccagggc gtaggtggtc 7560
aagcatcctg gccagctccg ggcggtcgcg cctggtgccg gtgatcttct cggaaaacag 7620
cttggtgcag ccggccgcgt gcagttcggc ccgttggttg gtcaagtcct ggtcgtcggt 7680
gctgacgcgg gcatagccca gcaggccagc ggcggcgctc ttgttcatgg cgtaatgtct 7740
ccggttctag tcgcaagtat tctactttat gcgactaaaa cacgcgacaa gaaaacgcca 7800
ggaaaagggc agggcggcag cctgtcgcgt aacttaggac ttgtgcgaca tgtcgttttc 7860
agaagacggc tgcactgaac gtcagaagcc gactgcacta tagcagcgga ggggttggat 7920
caaagtactt tgatcccgag gggaaccctg tggttggcat gcacatacaa atggacgaac 7980
ggataaacct tttcacgccc ttttaaatat ccgttattct aataaacgct cttttctctt 8040
aggtttaccc gccaatatat cctgtcaaac actgatagtt taaactgaag gcgggaaacg 8100
acaatctgat ccaagctcaa gctaagcttg agctctccca tatggtcgac tagagccaag 8160
ctgatctcct ttgccccgga gatcaccatg gacgactttc tctatctcta cgatctagga 8220
agaaagttcg acggagaagg tgacgatacc atgttcacca ccgataatga gaagattagc 8280
ctcttcaatt tcagaaagaa tgctgaccca cagatggtta gagaggccta cgcggcaggt 8340
ctcatcaaga cgatctaccc gagtaataat ctccaggaga tcaaatacct tcccaagaag 8400
gttaaagatg cagtcaaaag attcaggact aactgcatca agaacacaga gaaagatata 8460
tttctcaaga tcagaagtac tattccagta tggacgattc aaggcttgct tcataaacca 8520
aggcaagtaa tagagattgg agtctctaag aaagtagttc ctactgaatc aaaggccatg 8580
gagtcaaaaa ttcagatcga ggatctaaca gaactcgccg tgaagactgg cgaacagttc 8640
atacagagtc ttttacgact caatgacaag aagaaaatct tcgtcaacat ggtggagcac 8700
gacactctcg tctactccaa gaatatcaaa gatacagtct cagaagacca aagggctatt 8760
gagacttttc aacaaagggt aatatcggga aacctcctcg gattccattg cccagctatc 8820
tgtcacttca tcaaaaggac agtagaaaag gaaggtggca cctacaaatg ccatcattgc 8880
gataaaggaa aggctatcgt tcaagatgcc tctgccgaca gtggtcccaa agatggaccc 8940
ccacccacga ggagcatcgt ggaaaaagaa gacgttccaa ccacgtcttc aaagcaagtg 9000
gattgatgtg atatctccac tgacgtaagg gatgacgcac aatcccacta tccttcgcaa 9060
gacccttcct ctatataagg aagttcattt catttggaga ggactccggt atttttacaa 9120
caataccaca acaaaacaaa caacaaacaa cattacaatt tactattcta gtcgacctgc 9180
aggcggccgc actagtgata tcacaagttt gtacaaaaaa gctgaacgag aaacgtaaaa 9240
tgatataaat atcaatatat taaattagat tttgcataaa aaacagacta cataatactg 9300
taaaacacaa catatccagt cactatggcg gccgcattag gcaccccagg ctttacactt 9360
tatgcttccg gctcgtataa tgtgtggatt ttgagttagg atccggcgag attttcagga 9420
gctaaggaag ctaaaatgga gaaaaaaatc actggatata ccaccgttga tatatcccaa 9480
tggcatcgta aagaacattt tgaggcattt cagtcagttg ctcaatgtac ctataaccag 9540
accgttcagc tggatattac ggccttttta aagaccgtaa agaaaaataa gcacaagttt 9600
tatccggcct ttattcacat tcttgcccgc ctgatgaatg ctcatccgga attccgtatg 9660
gcaatgaaag acggtgagct ggtgatatgg gatagtgttc acccttgtta caccgttttc 9720

```
catgagcaaa ctgaaacgtt ttcatcgctc tggagtgaat accacgacga tttccggcag   9780
tttctacaca tatattcgca agatgtggcg tgttacggtg aaaacctggc ctatttccct   9840
aaagggttta ttgagaatat gtttttcgtc tcagccaatc cctgggtgag tttcaccagt   9900
tttgatttaa acgtggccaa tatggacaac ttcttcgccc ccgttttcac catgggcaaa   9960
tattatacgc aaggcgacaa ggtgctgatg ccgctggcga ttcaggttca tcatgccgtc  10020
tgtgatggct tccatgtcgg cagaatgctt aatgaattac aacagtactg cgatgagtgg  10080
cagggcgggg cgtaaacgcg tggatccggc ttactaaaag ccagataaca gtatgcgtat  10140
ttgcgcgctg atttttgcgg tataagaata tatactgata tgtatacccg aagtatgtca  10200
aaaagaggtg tgctatgaag cagcgtatta cagtgacagt tgacagcgac agctatcagt  10260
tgctcaaggc atatatgatg tcaatatctc cggtctggta agcacaacca tgcagaatga  10320
agcccgtcgt ctgcgtgccg aacgctggaa agcggaaaat caggaaggga tggctgaggt  10380
cgcccggttt attgaaatga acggctcttt tgctgacgag aacagggact ggtgaaatgc  10440
agtttaaggt ttacacctat aaaagagaga gccgttatcg tctgtttgtg gatgtacaga  10500
gtgatattat tgacacgccc gggcgacgga tggtgatccc cctggccagt gcacgtctgc  10560
tgtcagataa agtctcccgt gaactttacc cggtggtgca tatcggggat gaaagctggc  10620
gcatgatgac caccgatatg gccagtgtgc cggtctccgt tatcggggaa gaagtggctg  10680
atctcagcca ccgcgaaaat gacatcaaaa acgccattaa cctgatgttc tggggaatat  10740
aaatgtcagg ctcccttata cacagccagt ctgcaggtcg accatagtga ctggatatgt  10800
tgtgttttac agtattatgt agtctgtttt ttatgcaaaa tctaatttaa tatattgata  10860
tttatatcat tttacgtttc tcgttcagct ttcttgtaca aagtggtgat atcccgcggc  10920
catgctagag tccgcaaaaa tcaccagtct ctctctacaa atctatctct ctctattttt  10980
ctccagaata atgtgtgagt agttcccaga taagggaatt agggttctta tagggtttcg  11040
ctcatgtgtt gagcatataa gaaaccctta gtatgtattt gtatttgtaa aatacttcta  11100
tcaataaaat ttctaattcc taaaaccaaa atccagtgac ctgcaggcat gcgacgtcg   11159
```

<210> SEQ ID NO 359
<211> LENGTH: 9966
<212> TYPE: DNA
<213> ORGANISM: Artificial Sequence
<220> FEATURE:
<223> OTHER INFORMATION: pK7WG2-35S:41D01_His_KDEL

<400> SEQUENCE: 359

```
ggccctctag aggatccccg ggtaccgcga attatcatac atgagaatta agggagtcac     60
gttatgaccc ccgccgatga cgcgggacaa gccgttttac gtttggaact gacagaaccg    120
caacgttgaa ggagccactc agccgcgggt ttctggagtt taatgagcta agcacatacg    180
tcagaaacca ttattgcgcg ttcaaaagtc gcctaaggtc actatcagct agcaaatatt    240
tcttgtcaaa aatgctccac tgacgttcca taaattcccc tcggtatcca attagagtct    300
catattcact ctcaactcga tcgaggcatg attgaacaag atggattgca cgcaggttct    360
ccggccgctt gggtggagag gctattcggc tatgactggg cacaacagac aatcggctgc    420
tctgatgccg ccgtgttccg gctgtcagcg caggggcgcc cggttctttt tgtcaagacc    480
gacctgtccg gtgccctgaa tgaactccaa gacgaggcag cgcggctatc gtggctggcc    540
acgacgggcg ttccttgcgc agctgtgctc gacgttgtca ctgaagcggg aagggactgg    600
```

-continued

```
ctgctattgg gcgaagtgcc ggggcaggat ctcctgtcat ctcaccttgc tcctgccgag    660
aaagtatcca tcatggctga tgcaatgcgg cggctgcata cgcttgatcc ggctacctgc    720
ccattcgacc accaagcgaa acatcgcatc gagcgaggac gtactcggat ggaagccggt    780
cttgtcgatc aggatgatct ggacgaagag catcaggggc tcgcgccagc cgaactgttc    840
gccaggctca aggcgcggat gcccgacggc gaggatctcg tcgtgaccca gggcgatgcc    900
tgcttgccga atatcatggt ggaaaatggc cgcttttctg gattcatcga ctgtggccgg    960
ctgggtgtgg cggaccgcta tcaggacata gcgttggcta cccgtgatat tgctgaagag   1020
cttggcggcg aatgggctga ccgcttcctc gtgctttacg gtatcgccgc tcccgattcg   1080
cagcgcatcg ccttctatcg ccttcttgac gagttcttct gagcgggact ctggggttcg   1140
gactctagct agagtcaagc agatcgttca aacatttggc aataaagttt cttaagattg   1200
aatcctgttg ccggtcttgc gatgattatc atataatttc tgttgaatta cgttaagcat   1260
gtaataatta acatgtaatg catgacgtta tttatgagat gggtttttg attagagtcc    1320
cgcaattata catttaatac gcgatagaaa acaaaatata gcgcgcaaac taggataaat   1380
tatcgcgcgc ggtgtcatct atgttactag atcgaccggc atgcaagctg ataattcaat   1440
tcggcgttaa ttcagtacat taaaaacgtc cgcaatgtgt tattaagttg tctaagcgtc   1500
aatttgttta caccacaata tatcctgcca ccagccagcc aacagctccc cgaccggcag   1560
ctcggcacaa aatcaccact cgatacaggc agcccatcag tccgggacgg cgtcagcggg   1620
agagccgttg taaggcggca gactttgctc atgttaccga tgctattcgg aagaacggca   1680
actaagctgc cgggtttgaa acacggatga tctcgcggag ggtagcatgt tgattgtaac   1740
gatgacagag cgttgctgcc tgtgatcaat tcgggcacga acccagtgga cataagcctc   1800
gttcggttcg taagctgtaa tgcaagtagc gtaactgccg tcacgcaact ggtccagaac   1860
cttgaccgaa cgcagcggtg gtaacggcgc agtggcggtt ttcatggctt cttgttatga   1920
catgtttttt tggggtacag tctatgcctc gggcatccaa gcagcaagcg cgttacgccg   1980
tgggtcgatg tttgatgtta tggagcagca acgatgttac gcagcagggc agtcgcccta   2040
aaacaaagtt aaacatcatg ggggaagcgg tgatcgccga agtatcgact caactatcag   2100
aggtagttgg cgtcatcgag cgccatctcg aaccgacgtt gctggccgta catttgtacg   2160
gctccgcagt ggatggcggc ctgaagccac acagtgatat tgatttgctg gttacggtga   2220
ccgtaaggct tgatgaaaca acgcggcgag ctttgatcaa cgaccttttg gaaacttcgg   2280
cttcccctgg agagagcgag attctccgcg ctgtagaagt caccattgtt gtgcacgacg   2340
acatcattcc gtggcgttat ccagctaagc gcgaactgca atttggagaa tggcagcgca   2400
atgacattct tgcaggtatc ttcgagccag ccacgatcga cattgatctg gctatcttgc   2460
tgacaaaagc aagagaacat agcgttgcct tggtaggtcc agcggcggag gaactctttg   2520
atccggttcc tgaacaggat ctatttgagg cgctaaatga aaccttaacg ctatggaact   2580
cgccgcccga ctgggctggc gatgagcgaa atgtagtgct tacgttgtcc cgcatttggt   2640
acagcgcagt aaccggcaaa atcgcgccga aggatgtcgc tgccgactgg gcaatggagc   2700
gcctgccggc ccagtatcag cccgtcatac ttgaagctag acaggcttat cttggacaag   2760
aagaagatcg cttggcctcg cgcgcagatc agttggaaga atttgtccac tacgtgaaag   2820
gcgagatcac caaggtagtc ggcaaataat gtctagctag aaattcgttc aagccgacgc   2880
cgcttcgccg gcgttaactc aagcgattag atgcactaag cacataattg ctcacagcca   2940
aactatcagg tcaagtctgc ttttattatt tttaagcgtg cataataagc cctacacaaa   3000
```

-continued

```
ttgggagata tatcatgcat gaccaaaatc ccttaacgtg agttttcgtt ccactgagcg   3060
tcagaccccg tagaaaagat caaaggatct tcttgagatc cttttttct gcgcgtaatc   3120
tgctgcttgc aaacaaaaaa accaccgcta ccagcggtgg tttgtttgcc ggatcaagag   3180
ctaccaactc tttttccgaa ggtaactggc ttcagcagag cgcagatacc aaatactgtc   3240
cttctagtgt agccgtagtt aggccaccac ttcaagaact ctgtagcacc gcctacatac   3300
ctcgctctgc taatcctgtt accagtggct gctgccagtg gcgataagtc gtgtcttacc   3360
gggttggact caagacgata gttaccggat aaggcgcagc ggtcgggctg aacggggggt   3420
tcgtgcacac agcccagctt ggagcgaacg acctacaccg aactgagata cctacagcgt   3480
gagctatgag aaagcgccac gcttcccgaa gggagaaagg cggacaggta tccggtaagc   3540
ggcagggtcg gaacaggaga gcgcacgagg gagcttccag ggggaaacgc ctggtatctt   3600
tatagtcctg tcgggtttcg ccacctctga cttgagcgtc gatttttgtg atgctcgtca   3660
gggggcgga gcctatggaa aaacgccagc aacgcggcct ttttacggtt cctggccttt   3720
tgctggcctt ttgctcacat gttctttcct gcgttatccc ctgattctgt ggataaccgt   3780
attaccgcct ttgagtgagc tgataccgct cgccgcagcc gaacgaccga gcgcagcgag   3840
tcagtgagcg aggaagcgga agagcgcctg atgcggtatt ttctccttac gcatctgtgc   3900
ggtatttcac accgcatatg gtgcactctc agtacaatct gctctgatgc cgcatagtta   3960
agccagtata cactccgcta tcgctacgtg actgggtcat ggctgcgccc cgacacccgc   4020
caacacccgc tgacgcgccc tgacgggctt gtctgctccc ggcatccgct tacagacaag   4080
ctgtgaccgt ctccgggagc tgcatgtgtc agaggttttc accgtcatca ccgaaacgcg   4140
cgaggcaggg tgccttgatg tgggcgccgg cggtcgagtg gcgacggcgc ggcttgtccg   4200
cgccctggta gattgcctgg ccgtaggcca gccatttttg agcggccagc ggccgcgata   4260
ggccgacgcg aagcggcggg gcgtagggag cgcagcgacc gaagggtagg cgctttttgc   4320
agctcttcgg ctgtgcgctg gccagacagt tatgcacagg ccaggcgggt tttaagagtt   4380
ttaataagtt ttaaagagtt ttaggcggaa aaatcgcctt ttttctcttt tatatcagtc   4440
acttacatgt gtgaccggtt cccaatgtac ggctttgggt tcccaatgta cgggttccgg   4500
ttcccaatgt acggctttgg gttcccaatg tacgtgctat ccacaggaaa gagacctttt   4560
cgaccttttt cccctgctag ggcaatttgc cctagcatct gctccgtaca ttaggaaccg   4620
gcggatgctt cgccctcgat caggttgcgg tagcgcatga ctaggatcgg gccagcctgc   4680
cccgcctcct ccttcaaatc gtactccggc aggtcatttg acccgatcag cttgcgcacg   4740
gtgaaacaga acttcttgaa ctctccggcg ctgccactgc gttcgtagat cgtcttgaac   4800
aaccatctgg cttctgcctt gcctgcggcg cggcgtgcca ggcggtagag aaaacggccg   4860
atgccgggat cgatcaaaaa gtaatcgggg tgaaccgtca gcacgtccgg gttcttgcct   4920
tctgtgatct cgcggtacat ccaatcagct agctcgatct cgatgtactc cggccgcccg   4980
gtttcgctct ttacgatctt gtagcggcta atcaaggctt caccctcgga taccgtcacc   5040
aggcggccgt tcttggcctt cttcgtacgc tgcatggcaa cgtgcgtggt gtttaaccga   5100
atgcaggttt ctaccaggtc gtctttctgc tttccgccat cggctcgccg gcagaacttg   5160
agtacgtccg caacgtgtgg acggaacacg cggccgggct tgtctccctt cccttcccgg   5220
tatcggttca tggattcggt tagatgggaa accgccatca gtaccaggtc gtaatcccac   5280
acactggcca tgccggccgg ccctgcggaa acctctacgt gcccgtctgg aagctcgtag   5340
```

-continued cggatcacct cgccagctcg tcggtcacgc ttcgacagac ggaaaacggc cacgtccatg 5400
atgctgcgac tatcgcgggt gcccacgtca tagagcatcg gaacgaaaaa atctggttgc 5460
tcgtcgccct tgggcggctt cctaatcgac ggcgcaccgg ctgccggcgg ttgccgggat 5520
tctttgcgga ttcgatcagc ggccgcttgc cacgattcac cggggcgtgc ttctgcctcg 5580
atgcgttgcc gctgggcggc ctgcgcggcc ttcaacttct ccaccaggtc atcacccagc 5640
gccgcgccga tttgtaccgg gccggatggt ttgcgaccgt cacgccgatt cctcgggctt 5700
gggggttcca gtgccattgc agggccggca gacaacccag ccgcttacgc ctggccaacc 5760
gcccgttcct ccacacatgg ggcattccac ggcgtcggtg cctggttgtt cttgattttc 5820
catgccgcct cctttagccg ctaaaattca tctactcatt tattcatttg ctcatttact 5880
ctggtagctg cgcgatgtat tcagatagca gctcggtaat ggtcttgcct tggcgtaccg 5940
cgtacatctt cagcttggtg tgatcctccg ccggcaactg aaagttgacc cgcttcatgg 6000
ctggcgtgtc tgccaggctg gccaacgttg cagccttgct gctgcgtgcg ctcggacggc 6060
cggcacttag cgtgtttgtg cttttgctca ttttctcttt acctcattaa ctcaaatgag 6120
ttttgattta atttcagcgg ccagcgcctg gacctcgcgg gcagcgtcgc cctcgggttc 6180
tgattcaaga acggttgtgc cggcggcggc agtgcctggg tagctcacgc gctgcgtgat 6240
acgggactca agaatgggca gctcgtaccc ggccagcgcc tcggcaacct caccgccgat 6300
gcgcgtgcct ttgatcgccc gcgacacgac aaaggccgct tgtagccttc catccgtgac 6360
ctcaatgcgc tgcttaacca gctccaccag gtcggcggtg gcccatatgt cgtaagggct 6420
tggctgcacc ggaatcagca cgaagtcggc tgccttgatc gcggacacag ccaagtccgc 6480
cgcctggggc gctccgtcga tcactacgaa gtcgcgccgg ccgatggcct tcacgtcgcg 6540
gtcaatcgtc gggcggtcga tgccgacaac ggttagcggt tgatcttccc gcacggccgc 6600
ccaatcgcgg gcactgccct ggggatcgga atcgactaac agaacatcgg ccccggcgag 6660
ttgcagggcg cgggctagat gggttgcgat ggtcgtcttg cctgacccgc ctttctggtt 6720
aagtacagcg ataaccttca tgcgttcccc ttgcgtattt gtttatttac tcatcgcatc 6780
atatacgcag cgaccgcatg acgcaagctg ttttactcaa atacacatca cctttttaga 6840
cggcggcgct cggtttcttc agcggccaag ctggccggcc aggccgccag cttggcatca 6900
gacaaaccgg ccaggatttc atgcagccgc acggttgaga cgtgcgcggg cggctcgaac 6960
acgtacccgg ccgcgatcat ctccgcctcg atctcttcgg taatgaaaaa cggttcgtcc 7020
tggccgtcct ggtgcggttt catgcttgtt cctcttggcg ttcattctcg gcggccgcca 7080
gggcgtcggc ctcggtcaat gcgtcctcac ggaaggcacc gcgccgcctg gcctcggtgg 7140
gcgtcacttc ctcgctgcgc tcaagtgcgc ggtacagggt cgagcgatgc acgccaagca 7200
gtgcagccgc ctctttcacg gtgcggcctt cctggtcgat cagctcgcgg gcgtgcgcga 7260
tctgtgccgg ggtgagggta gggcgggggc caaacttcac gcctcgggcc ttggcggcct 7320
cgcgcccgct ccgggtgcgg tcgatgatta gggaacgctc gaactcggca atgccggcga 7380
acacggtcaa caccatgcgg ccggccggcg tggtggtgtc ggcccacggc tctgccaggc 7440
tacgcaggcc cgcgccggcc tcctggatgc gctcggcaat gtccagtagg tcgcgggtgc 7500
tgcgggccag gcggtctagc ctggtcactg tcacaacgtc gccagggcgt aggtggtcaa 7560
gcatcctggc cagctccggg cggtcgcgcc tggtgccggt gatcttctcg gaaaacagct 7620
tggtgcagcc ggccgcgtgc agttcggccc gttggttggt caagtcctgg tcgtcggtgc 7680
tgacgcgggc atagcccagc aggccagcgg cggcgctctt gttcatggcg taatgtctcc 7740

```
ggttctagtc gcaagtattc tactttatgc gactaaaaca cgcgacaaga aaacgccagg   7800
aaaagggcag ggcggcagcc tgtcgcgtaa cttaggactt gtgcgacatg tcgttttcag   7860
aagacggctg cactgaacgt cagaagccga ctgcactata gcagcggagg ggttggatca   7920
aagtactttg atcccgaggg gaaccctgtg gttggcatgc acatacaaat ggacgaacgg   7980
ataaaccttt tcacgccctt ttaaatatcc gttattctaa taaacgctct tttctcttag   8040
gtttacccgc caatatatcc tgtcaaacac tgatagttta aactgaaggc gggaaacgac   8100
aatctgatcc aagctcaagc taagcttgag ctctcccata tggtcgagat ctcctttgcc   8160
ccggagatca ccatggacga ctttctctat ctctacgatc taggaagaaa gttcgacgga   8220
gaaggtgacg ataccatgtt caccaccgat aatgagaaga ttagcctctt caatttcaga   8280
aagaatgctg acccacagat ggttagagag gcctacgcgg caggtctcat caagacgatc   8340
tacccgagta ataatctcca ggagatcaaa taccttccca agaaggttaa agatgcagtc   8400
aaaagattca ggactaactg catcaagaac acagagaaag atatatttct caagatcaga   8460
agtactattc cagtatggac gattcaaggc ttgcttcata aaccaaggca agtaatagag   8520
attggagtct ctaagaaagt agttcctact gaatcaaagg ccatggagtc aaaaattcag   8580
atcgaggatc taacagaact cgccgtgaag actggcgaac agttcataca gagtctttta   8640
cgactcaatg acaagaagaa aatcttcgtc aacatggtgg agcacgacac tctcgtctac   8700
tccaagaata tcaaagatac agtctcagaa gaccaaaggg ctattgagac ttttcaacaa   8760
agggtaatat cgggaaacct cctcggattc cattgcccag ctatctgtca cttcatcaaa   8820
aggacagtag aaaaggaagg tggcacctac aaatgccatc attgcgataa aggaaaggct   8880
atcgttcaag atgcccctgc cgacagtggt cccaaagatg gacccccacc cacgaggagc   8940
atcgtggaaa aagaagacgt tccaaccacg tcttcaaagc aagtggattg atgtgatatc   9000
tccactgacg taagggatga cgcacaatcc cactatcctt cgcaagaccc ttcctctata   9060
taaggaagtt catttcattt ggagaggact ccggtatttt tacaacaatt accacaacaa   9120
aacaaacaac aaacaacatt acaatttact attctagtcg acctgcaggc ggccgcacta   9180
gtgatatcac aagtttgtac aaaaaagcag gctgaattcc caccatggca aacaagcttt   9240
tcttggtgtg cgctaccttc gctctttgct tccttttgac taacgctcag gttcagctgc   9300
aggaatctgg tggtggactt gttcaagctg gtggatctct tagactctct tgcgctgctt   9360
ctggaaggac cttctctaga tatggaatgg gatggttcag gcagctccct ggaaaacaga   9420
gagagcttgt tacctctatc accaggggtg gaactaccac ctacgctgat tctgtgaagg   9480
gaaggttcac catctctagg gataacgcta agaacaccgt gtacctccag atgaactctc   9540
tcaagcctga ggataccgct gtgtactact gcaacgctag atctatttgg agggattact   9600
ggggacaggg aactcaggtc accgtttctt cagcggccgc acatcatcat caccatcatg   9660
gtgctgctaa ggatgagctt tgaggatcca cccagctttc ttgtacaaag tggtgatatc   9720
ccgcggccat gctagagtcc gcaaaaatca ccagtctctc tctacaaatc tatctctctc   9780
tatttttctc cagaataatg tgtgagtagt tcccagataa gggaattagg gttcttatag   9840
ggtttcgctc atgtgttgag catataagaa acccttagta tgtatttgta tttgtaaaat   9900
acttctatca ataaaatttc taattcctaa aaccaaaatc cagtgacctg caggcatgcg   9960
acgtcg                                                              9966
```

<210> SEQ ID NO 360

<211> LENGTH: 10641
<212> TYPE: DNA
<213> ORGANISM: Artificial Sequence
<220> FEATURE:
<223> OTHER INFORMATION: pK7WG2-35S:sec_41D01_hinge_Fc_His

<400> SEQUENCE: 360
ggccctctag aggatccccg ggtaccgcga attatcatac atgagaatta agggagtcac 60
gttatgaccc ccgccgatga cgcgggacaa gccgttttac gtttggaact gacagaaccg 120
caacgttgaa ggagccactc agccgcgggt ttctggagtt taatgagcta agcacatacg 180
tcagaaacca ttattgcgcg ttcaaaagtc gcctaaggtc actatcagct agcaaatatt 240
tcttgtcaaa aatgctccac tgacgttcca taaattcccc tcggtatcca attagagtct 300
catattcact ctcaactcga tcgaggcatg attgaacaag atggattgca cgcaggttct 360
ccggccgctt gggtggagag gctattcggc tatgactggg cacaacagac aatcggctgc 420
tctgatgccg ccgtgttccg gctgtcagcg caggggcgcc cggttctttt tgtcaagacc 480
gacctgtccg gtgccctgaa tgaactccaa gacgaggcag cgcggctatc gtggctggcc 540
acgacgggcg ttccttgcgc agctgtgctc gacgttgtca ctgaagcggg aagggactgg 600
ctgctattgg gcgaagtgcc ggggcaggat ctcctgtcat ctcaccttgc tcctgccgag 660
aaagtatcca tcatggctga tgcaatgcgg cggctgcata cgcttgatcc ggctacctgc 720
ccattcgacc accaagcgaa acatcgcatc gagcgaggac gtactcggat ggaagccggt 780
cttgtcgatc aggatgatct ggacgaagag catcaggggc tcgcgccagc cgaactgttc 840
gccaggctca aggcgcggat gcccgacggc gaggatctcg tcgtgaccca gggcgatgcc 900
tgcttgccga atatcatggt ggaaaatggc cgcttttctg gattcatcga ctgtggccgg 960
ctgggtgtgg cggaccgcta tcaggacata gcgttggcta cccgtgatat tgctgaagag 1020
cttggcggcg aatgggctga ccgcttcctc gtgctttacg gtatcgccgc tcccgattcg 1080
cagcgcatcg ccttctatcg ccttcttgac gagttcttct gagcgggact ctggggttcg 1140
gactctagct agagtcaagc agatcgttca aacatttggc aataaagttt cttaagattg 1200
aatcctgttg ccggtcttgc gatgattatc atataatttc tgttgaatta cgttaagcat 1260
gtaataatta acatgtaatg catgacgtta tttatgagat gggtttttg attagagtcc 1320 cgcaattata catttaatac gcgatagaaa acaaaatata gcgcgcaaac taggataaat 1380
tatcgcgcgc ggtgtcatct atgttactag atcgaccggc atgcaagctg ataattcaat 1440
tcggcgttaa ttcagtacat taaaaacgtc cgcaatgtgt tattaagttg tctaagcgtc 1500
aatttgttta caccacaata tatcctgcca ccagccagcc aacagctccc cgaccggcag 1560
ctcggcacaa aatcaccact cgatacaggc agcccatcag tccgggacgg cgtcagcggg 1620
agagccgttg taaggcggca gactttgctc atgttaccga tgctattcgg aagaacggca 1680
actaagctgc cgggtttgaa acacggatga tctcgcggag ggtagcatgt tgattgtaac 1740
gatgacagag cgttgctgcc tgtgatcaat tcgggcacga acccagtgga cataagcctc 1800
gttcggttcg taagctgtaa tgcaagtagc gtaactgccg tcacgcaact ggtccagaac 1860
cttgaccgaa cgcagcggtg gtaacggcgc agtggcggtt ttcatggctt cttgttatga 1920
catgtttttt tggggtacag tctatgcctc gggcatccaa gcagcaagcg cgttacgccg 1980
tgggtcgatg tttgatgtta tggagcagca acgatgttac gcagcagggc agtcgcccta 2040
aaacaaagtt aaacatcatg ggggaagcgg tgatcgccga agtatcgact caactatcag 2100
aggtagttgg cgtcatcgag cgccatctcg aaccgacgtt gctggccgta catttgtacg 2160

-continued

```
gctccgcagt ggatggcggc ctgaagccac acagtgatat tgatttgctg gttacggtga   2220
ccgtaaggct tgatgaaaca acgcggcgag ctttgatcaa cgaccttttg gaaacttcgg   2280
cttcccctgg agagagcgag attctccgcg ctgtagaagt caccattgtt gtgcacgacg   2340
acatcattcc gtggcgttat ccagctaagc gcgaactgca atttggagaa tggcagcgca   2400
atgacattct tgcaggtatc ttcgagccag ccacgatcga cattgatctg gctatcttgc   2460
tgacaaaagc aagagaacat agcgttgcct tggtaggtcc agcggcggag gaactctttg   2520
atccggttcc tgaacaggat ctatttgagg cgctaaatga aaccttaacg ctatggaact   2580
cgccgcccga ctgggctggc gatgagcgaa atgtagtgct tacgttgtcc cgcatttggt   2640
acagcgcagt aaccggcaaa atcgcgccga aggatgtcgc tgccgactgg gcaatggagc   2700
gcctgccggc ccagtatcag cccgtcatac ttgaagctag acaggcttat cttggacaag   2760
aagaagatcg cttggcctcg cgcgcagatc agttggaaga atttgtccac tacgtgaaag   2820
gcgagatcac caaggtagtc ggcaaataat gtctagctag aaattcgttc aagccgacgc   2880
cgcttcgccg gcgttaactc aagcgattag atgcactaag cacataattg ctcacagcca   2940
aactatcagg tcaagtctgc ttttattatt tttaagcgtg cataataagc cctacacaaa   3000
ttgggagata tatcatgcat gaccaaaatc ccttaacgtg agttttcgtt ccactgagcg   3060
tcagaccccg tagaaaagat caaaggatct tcttgagatc cttttttttct gcgcgtaatc   3120
tgctgcttgc aaacaaaaaa accaccgcta ccagcggtgg tttgtttgcc ggatcaagag   3180
ctaccaactc tttttccgaa ggtaactggc ttcagcagag cgcagatacc aaatactgtc   3240
cttctagtgt agccgtagtt aggccaccac ttcaagaact ctgtagcacc gcctacatac   3300
ctcgctctgc taatcctgtt accagtggct gctgccagtg gcgataagtc gtgtcttacc   3360
gggttggact caagacgata gttaccggat aaggcgcagc ggtcgggctg aacggggggt   3420
tcgtgcacac agcccagctt ggagcgaacg acctacaccg aactgagata cctacagcgt   3480
gagctatgag aaagcgccac gcttcccgaa gggagaaagg cggacaggta tccggtaagc   3540
ggcagggtcg gaacaggaga gcgcacgagg gagcttccag ggggaaacgc ctggtatctt   3600
tatagtcctg tcgggtttcg ccacctctga cttgagcgtc gatttttgtg atgctcgtca   3660
ggggggcgga gcctatggaa aaacgccagc aacgcggcct ttttacggtt cctggccttt   3720
tgctggcctt ttgctcacat gttctttcct gcgttatccc ctgattctgt ggataaccgt   3780
attaccgcct ttgagtgagc tgataccgct cgccgcagcc gaacgaccga gcgcagcgag   3840
tcagtgagcg aggaagcgga agagcgcctg atgcggtatt ttctccttac gcatctgtgc   3900
ggtatttcac accgcatatg gtgcactctc agtacaatct gctctgatgc cgcatagtta   3960
agccagtata cactccgcta tcgctacgtg actgggtcat ggctgcgccc cgacacccgc   4020
caacacccgc tgacgcgccc tgacgggctt gtctgctccc ggcatccgct tacagacaag   4080
ctgtgaccgt ctccgggagc tgcatgtgtc agaggttttc accgtcatca ccgaaacgcg   4140
cgaggcaggg tgccttgatg tgggcgccgg cggtcgagtg gcgacggcgc ggcttgtccg   4200
cgccctggta gattgcctgg ccgtaggcca gccatttttg agcggccagc ggccgcgata   4260
ggccgacgcg aagcggcggg gcgtagggag cgcagcgacc gaagggtagg cgctttttgc   4320
agctcttcgg ctgtgcgctg gccagacagt tatgcacagg ccaggcgggt tttaagagtt   4380
ttaataagtt ttaaagagtt ttaggcggaa aaatcgcctt ttttctcttt tatatcagtc   4440
acttacatgt gtgaccggtt cccaatgtac ggctttgggt tcccaatgta cgggttccgg   4500
```

-continued

```
ttcccaatgt acggctttgg gttcccaatg tacgtgctat ccacaggaaa gagacctttt   4560
cgaccttttt cccctgctag ggcaatttgc cctagcatct gctccgtaca ttaggaaccg   4620
gcggatgctt cgccctcgat caggttgcgg tagcgcatga ctaggatcgg gccagcctgc   4680
cccgcctcct ccttcaaatc gtactccggc aggtcatttg acccgatcag cttgcgcacg   4740
gtgaaacaga acttcttgaa ctctccggcg ctgccactgc gttcgtagat cgtcttgaac   4800
aaccatctgg cttctgcctt gcctgcggcg cggcgtgcca ggcggtagag aaaacggccg   4860
atgccgggat cgatcaaaaa gtaatcgggg tgaaccgtca gcacgtccgg gttcttgcct   4920
tctgtgatct cgcggtacat ccaatcagct agctcgatct cgatgtactc cggccgcccg   4980
gtttcgctct ttacgatctt gtagcggcta atcaaggctt caccctcgga taccgtcacc   5040
aggcggccgt tcttggcctt cttcgtacgc tgcatggcaa cgtgcgtggt gtttaaccga   5100
atgcaggttt ctaccaggtc gtctttctgc tttccgccat cggctcgccg gcagaacttg   5160
agtacgtccg caacgtgtgg acggaacacg cggccgggct tgtctccctt cccttcccgg   5220
tatcggttca tggattcggt tagatgggaa accgccatca gtaccaggtc gtaatcccac   5280
acactggcca tgccggccgg ccctgcggaa acctctacgt gcccgtctgg aagctcgtag   5340
cggatcacct cgccagctcg tcggtcacgc ttcgacagac ggaaaacggc cacgtccatg   5400
atgctgcgac tatcgcgggt gcccacgtca tagagcatcg gaacgaaaaa atctggttgc   5460
tcgtcgccct tgggcggctt cctaatcgac ggcgcaccgg ctgccggcgg ttgccgggat   5520
tctttgcgga ttcgatcagc ggccgcttgc cacgattcac cggggcgtgc ttctgcctcg   5580
atgcgttgcc gctgggcggc ctgcgcggcc ttcaacttct ccaccaggtc atcacccagc   5640
gccgcgccga tttgtaccgg gccggatggt ttgcgaccgt cacgccgatt cctcgggctt   5700
gggggttcca gtgccattgc agggccggca gacaacccag ccgcttacgc ctggccaacc   5760
gcccgttcct ccacacatgg ggcattccac ggcgtcggtg cctggttgtt cttgattttc   5820
catgccgcct cctttagccg ctaaaattca tctactcatt tattcatttg ctcatttact   5880
ctggtagctg cgcgatgtat tcagatagca gctcggtaat ggtcttgcct tggcgtaccg   5940
cgtacatctt cagcttggtg tgatcctccg ccggcaactg aaagttgacc cgcttcatgg   6000
ctggcgtgtc tgccaggctg gccaacgttg cagccttgct gctgcgtgcg ctcggacggc   6060
cggcacttag cgtgtttgtg cttttgctca ttttctcttt acctcattaa ctcaaatgag   6120
ttttgattta atttcagcgg ccagcgcctg gacctcgcgg gcagcgtcgc cctcgggttc   6180
tgattcaaga acggttgtgc cggcggcggc agtgcctggg tagctcacgc gctgcgtgat   6240
acgggactca agaatgggca gctcgtaccc ggccagcgcc tcggcaacct caccgccgat   6300
gcgcgtgcct ttgatcgccc gcgacacgac aaaggccgct tgtagccttc catccgtgac   6360
ctcaatgcgc tgcttaacca gctccaccag gtcggcggtg gcccatatgt cgtaagggct   6420
tggctgcacc ggaatcagca cgaagtcggc tgccttgatc gcggacacag ccaagtccgc   6480
cgcctggggc gctccgtcga tcactacgaa gtcgcgccgg ccgatggcct tcacgtcgcg   6540
gtcaatcgtc gggcggtcga tgccgacaac ggttagcggt tgatcttccc gcacggccgc   6600
ccaatcgcgg gcactgccct ggggatcgga atcgactaac agaacatcgg ccccggcgag   6660
ttgcagggcg cgggctagat gggttgcgat ggtcgtcttg cctgacccgc ctttctggtt   6720
aagtacagcg ataaccttca tgcgttcccc ttgcgtattt gtttatttac tcatcgcatc   6780
atatacgcag cgaccgcatg acgcaagctg ttttactcaa atacacatca ccttttttaga   6840
cggcggcgct cggtttcttc agcggccaag ctggccggcc aggccgccag cttggcatca   6900
```

-continued

```
gacaaaccgg ccaggatttc atgcagccgc acggttgaga cgtgcgcggg cggctcgaac   6960
acgtacccgg ccgcgatcat ctccgcctcg atctcttcgg taatgaaaaa cggttcgtcc   7020
tggccgtcct ggtgcggttt catgcttgtt cctcttggcg ttcattctcg gcggccgcca   7080
gggcgtcggc ctcggtcaat gcgtcctcac ggaaggcacc gcgccgcctg gcctcggtgg   7140
gcgtcacttc ctcgctgcgc tcaagtgcgc ggtacagggt cgagcgatgc acgccaagca   7200
gtgcagccgc ctctttcacg gtgcggcctt cctggtcgat cagctcgcgg gcgtgcgcga   7260
tctgtgccgg ggtgagggta gggcgggggc caaacttcac gcctcgggcc ttggcggcct   7320
cgcgcccgct ccgggtgcgg tcgatgatta gggaacgctc gaactcggca atgccggcga   7380
acacggtcaa caccatgcgg ccggccggcg tggtggtgtc ggcccacggc tctgccaggc   7440
tacgcaggcc cgcgccggcc tcctggatgc gctcggcaat gtccagtagg tcgcgggtgc   7500
tgcgggccag gcggtctagc ctggtcactg tcacaacgtc gccagggcgt aggtggtcaa   7560
gcatcctggc cagctccggg cggtcgcgcc tggtgccggt gatcttctcg gaaaacagct   7620
tggtgcagcc ggccgcgtgc agttcggccc gttggttggt caagtcctgg tcgtcggtgc   7680
tgacgcgggc atagcccagc aggccagcgg cggcgctctt gttcatggcg taatgtctcc   7740
ggttctagtc gcaagtattc tactttatgc gactaaaaca cgcgacaaga aaacgccagg   7800
aaaagggcag ggcggcagcc tgtcgcgtaa cttaggactt gtgcgacatg tcgttttcag   7860
aagacggctg cactgaacgt cagaagccga ctgcactata gcagcggagg ggttggatca   7920
aagtactttg atcccgaggg gaaccctgtg gttggcatgc acatacaaat ggacgaacgg   7980
ataaaccttt tcacgccctt ttaaatatcc gttattctaa taaacgctct tttctcttag   8040
gtttacccgc caatatatcc tgtcaaacac tgatagttta aactgaaggc gggaaacgac   8100
aatctgatcc aagctcaagc taagcttgag ctctcccata tggtcgagat ctcctttgcc   8160
ccggagatca ccatggacga ctttctctat ctctacgatc taggaagaaa gttcgacgga   8220
gaaggtgacg ataccatgtt caccaccgat aatgagaaga ttagcctctt caatttcaga   8280
aagaatgctg acccacagat ggttagagag gcctacgcgg caggtctcat caagacgatc   8340
tacccgagta ataatctcca ggagatcaaa taccttccca agaaggttaa agatgcagtc   8400
aaaagattca ggactaactg catcaagaac acagagaaag atatatttct caagatcaga   8460
agtactattc cagtatggac gattcaaggc ttgcttcata aaccaaggca agtaatagag   8520
attggagtct ctaagaaagt agttcctact gaatcaaagg ccatggagtc aaaaattcag   8580
atcgaggatc taacagaact cgccgtgaag actggcgaac agttcataca gagtctttta   8640
cgactcaatg acaagaagaa aatcttcgtc aacatggtgg agcacgacac tctcgtctac   8700
tccaagaata tcaaagatac agtctcagaa gaccaaaggg ctattgagac ttttcaacaa   8760
agggtaatat cgggaaacct cctcggattc cattgcccag ctatctgtca cttcatcaaa   8820
aggacagtag aaaaggaagg tggcacctac aaatgccatc attgcgataa aggaaaggct   8880
atcgttcaag atgcccctgc cgacagtggt cccaaagatg gacccccacc cacgaggagc   8940
atcgtggaaa aagaagacgt tccaaccacg tcttcaaagc aagtggattg atgtgatatc   9000
tccactgacg taagggatga cgcacaatcc cactatcctt cgcaagaccc ttcctctata   9060
taaggaagtt catttcattt ggagaggact ccggtatttt tacaacaatt accacaacaa   9120
aacaaacaac aaacaacatt acaatttact attctagtcg acctgcaggc ggccgcacta   9180
gtgatatcac aagtttgtac aaaaaagcag gctgaattcc caccatggca aacaagcttt   9240
```

-continued

```
tcttggtgtg cgctaccttc gctctttgct tccttttgac taacgctcag gttcagctgc   9300
aggaatctgg tggtggactt gttcaagctg gtggatctct tagactctct tgcgctgctt   9360
ctggaaggac cttctctaga tatggaatgg gatggttcag gcagctccct ggaaaacaga   9420
gagagcttgt tacctctatc accaggggtg gaactaccac ctacgctgat tctgtgaagg   9480
gaaggttcac catctctagg gataacgcta agaacaccgt gtacctccag atgaactctc   9540
tcaagcctga ggataccgct gtgtactact gcaacgctag atctatttgg agggattact   9600
ggggacaggg aactcaggtc accgtttctt cacctagaat ccctaagcct tctacccctc   9660
ctggatcttc ttgtcctcct ggaaatatcc tcggtggacc ttctgtgttc atcttcccac   9720
ctaagcctaa ggatgctctc atgatctcac tcacccctaa ggttacatgc gttgtggtgg   9780
atgtgtctga ggatgatcct gatgtgcacg tgtcatggtt cgtggataac aaagaggtgc   9840
acactgcttg gactcagcct agagaagctc agtacaactc taccttcagg gtggtgtctg   9900
ctctccctat ccaacaccaa gattggatga ggggtaaaga gttcaagtgc aaggtgaaca   9960
acaaggctct ccctgctcct atcgagagga ctatctctaa acctaaggga agggctcaga  10020
cccctcaagt gtatacaatt cctccaccta gggaacagat gtctaagaag aaggtttcac  10080
tcacttgcct cgtgaccaac ttcttcagtg aggctatctc tgttgagtgg gagaggaatg  10140
gtgagcttga gcaggattac aagaacaccc ctcctatcct cgattctgat ggaacctact  10200
tcctctactc taagctcacc gtggataccg attcttggtt gcagggtgag atcttcactt  10260
gctctgttgt gcatgaggct ctccacaacc atcacaccca gaagaacctc agtagatctc  10320
ctggtaaagc ggccgcacat catcatcacc atcattgagg atccacccag ctttcttgta  10380
caaagtggtg atatcccgcg gccatgctag agtccgcaaa aatcaccagt ctctctctac  10440
aaatctatct ctctctattt ttctccagaa taatgtgtga gtagttccca gataagggaa  10500
ttagggttct tatagggttt cgctcatgtg ttgagcatat aagaaaccct tagtatgtat  10560
ttgtatttgt aaaatacttc tatcaataaa atttctaatt cctaaaacca aaatccagtg  10620
acctgcaggc atgcgacgtc g                                            10641
```

```
<210> SEQ ID NO 361
<211> LENGTH: 10317
<212> TYPE: DNA
<213> ORGANISM: Artificial Sequence
<220> FEATURE:
<223> OTHER INFORMATION: pK7WG2-35S: sec_41D01-9GS-41D01_His

<400> SEQUENCE: 361
```

```
ggccctctag aggatccccg ggtaccgcga attatcatac atgagaatta agggagtcac     60
gttatgaccc ccgccgatga cgcgggacaa gccgttttac gtttggaact gacagaaccg    120
caacgttgaa ggagccactc agccgcgggt ttctggagtt taatgagcta agcacatacg    180
tcagaaacca ttattgcgcg ttcaaaagtc gcctaaggtc actatcagct agcaaatatt    240
tcttgtcaaa aatgctccac tgacgttcca taaattcccc tcggtatcca attagagtct    300
catattcact ctcaactcga tcgaggcatg attgaacaag atggattgca cgcaggttct    360
ccggccgctt gggtggagag gctattcggc tatgactggg cacaacagac aatcggctgc    420
tctgatgccg ccgtgttccg gctgtcagcg caggggcgcc cggttctttt tgtcaagacc    480
gacctgtccg gtgccctgaa tgaactccaa gacgaggcag cgcggctatc gtggctggcc    540
acgacgggcg ttccttgcgc agctgtgctc gacgttgtca ctgaagcggg aagggactgg    600
ctgctattgg gcgaagtgcc ggggcaggat ctcctgtcat ctcaccttgc tcctgccgag    660
```

-continued

```
aaagtatcca tcatggctga tgcaatgcgg cggctgcata cgcttgatcc ggctacctgc    720
ccattcgacc accaagcgaa acatcgcatc gagcgaggac gtactcggat ggaagccggt    780
cttgtcgatc aggatgatct ggacgaagag catcaggggc tcgcgccagc cgaactgttc    840
gccaggctca aggcgcggat gcccgacggc gaggatctcg tcgtgaccca gggcgatgcc    900
tgcttgccga atatcatggt ggaaaatggc cgcttttctg gattcatcga ctgtggccgg    960
ctgggtgtgg cggaccgcta tcaggacata gcgttggcta cccgtgatat tgctgaagag   1020
cttggcggcg aatgggctga ccgcttcctc gtgctttacg gtatcgccgc tcccgattcg   1080
cagcgcatcg ccttctatcg ccttcttgac gagttcttct gagcgggact ctggggttcg   1140
gactctagct agagtcaagc agatcgttca aacatttggc aataaagttt cttaagattg   1200
aatcctgttg ccggtcttgc gatgattatc atataatttc tgttgaatta cgttaagcat   1260
gtaataatta acatgtaatg catgacgtta tttatgagat gggtttttg attagagtcc    1320
cgcaattata catttaatac gcgatagaaa acaaaatata gcgcgcaaac taggataaat   1380
tatcgcgcgc ggtgtcatct atgttactag atcgaccggc atgcaagctg ataattcaat   1440
tcggcgttaa ttcagtacat taaaaacgtc cgcaatgtgt tattaagttg tctaagcgtc   1500
aatttgttta caccacaata tatcctgcca ccagccagcc aacagctccc cgaccggcag   1560
ctcggcacaa aatcaccact cgatacaggc agcccatcag tccgggacgg cgtcagcggg   1620
agagccgttg taaggcggca gactttgctc atgttaccga tgctattcgg aagaacggca   1680
actaagctgc cgggtttgaa acacggatga tctcgcggag ggtagcatgt tgattgtaac   1740
gatgacagag cgttgctgcc tgtgatcaat tcgggcacga acccagtgga cataagcctc   1800
gttcggttcg taagctgtaa tgcaagtagc gtaactgccg tcacgcaact ggtccagaac   1860
cttgaccgaa cgcagcggtg gtaacggcgc agtggcggtt ttcatggctt cttgttatga   1920
catgtttttt tggggtacag tctatgcctc gggcatccaa gcagcaagcg cgttacgccg   1980
tgggtcgatg tttgatgtta tggagcagca acgatgttac gcagcagggc agtcgcccta   2040
aaacaaagtt aaacatcatg ggggaagcgg tgatcgccga agtatcgact caactatcag   2100
aggtagttgg cgtcatcgag cgccatctcg aaccgacgtt gctggccgta catttgtacg   2160
gctccgcagt ggatggcggc ctgaagccac acagtgatat tgatttgctg gttacggtga   2220
ccgtaaggct tgatgaaaca acgcggcgag ctttgatcaa cgaccttttg gaaacttcgg   2280
cttcccctgg agagagcgag attctccgcg ctgtagaagt caccattgtt gtgcacgacg   2340
acatcattcc gtggcgttat ccagctaagc gcgaactgca atttggagaa tggcagcgca   2400
atgacattct tgcaggtatc ttcgagccag ccacgatcga cattgatctg gctatcttgc   2460
tgacaaaagc aagagaacat agcgttgcct tggtaggtcc agcggcggag gaactctttg   2520
atccggttcc tgaacaggat ctatttgagg cgctaaatga aaccttaacg ctatggaact   2580
cgccgcccga ctgggctggc gatgagcgaa atgtagtgct tacgttgtcc cgcatttggt   2640
acagcgcagt aaccggcaaa atcgcgccga aggatgtcgc tgccgactgg gcaatggagc   2700
gcctgccggc ccagtatcag cccgtcatac ttgaagctag acaggcttat cttggacaag   2760
aagaagatcg cttggcctcg cgcgcagatc agttggaaga atttgtccac tacgtgaaag   2820
gcgagatcac caaggtagtc ggcaaataat gtctagctag aaattcgttc aagccgacgc   2880
cgcttcgccg gcgttaactc aagcgattag atgcactaag cacataattg ctcacagcca   2940
aactatcagg tcaagtctgc ttttattatt tttaagcgtg cataataagc cctacacaaa   3000
```

ttgggagata tatcatgcat gaccaaaatc ccttaacgtg agttttcgtt ccactgagcg 3060
tcagaccccg tagaaaagat caaaggatct tcttgagatc cttttttttct gcgcgtaatc 3120 tgctgcttgc aaacaaaaaa accaccgcta ccagcggtgg tttgtttgcc ggatcaagag 3180
ctaccaactc tttttccgaa ggtaactggc ttcagcagag cgcagatacc aaatactgtc 3240
cttctagtgt agccgtagtt aggccaccac ttcaagaact ctgtagcacc gcctacatac 3300
ctcgctctgc taatcctgtt accagtggct gctgccagtg gcgataagtc gtgtcttacc 3360
gggttggact caagacgata gttaccggat aaggcgcagc ggtcgggctg aacggggggt 3420
tcgtgcacac agcccagctt ggagcgaacg acctacaccg aactgagata cctacagcgt 3480
gagctatgag aaagcgccac gcttcccgaa gggagaaagg cggacaggta tccggtaagc 3540
ggcagggtcg gaacaggaga gcgcacgagg gagcttccag ggggaaacgc ctggtatctt 3600
tatagtcctg tcgggtttcg ccacctctga cttgagcgtc gatttttgtg atgctcgtca 3660
ggggggcgga gcctatggaa aaacgccagc aacgcggcct ttttacggtt cctggccttt 3720
tgctggcctt ttgctcacat gttctttcct gcgttatccc ctgattctgt ggataaccgt 3780
attaccgcct ttgagtgagc tgataccgct cgccgcagcc gaacgaccga gcgcagcgag 3840
tcagtgagcg aggaagcgga agagcgcctg atgcggtatt ttctccttac gcatctgtgc 3900
ggtatttcac accgcatatg gtgcactctc agtacaatct gctctgatgc cgcatagtta 3960
agccagtata cactccgcta tcgctacgtg actgggtcat ggctgcgccc cgacacccgc 4020
caacacccgc tgacgcgccc tgacgggctt gtctgctccc ggcatccgct tacagacaag 4080
ctgtgaccgt ctccgggagc tgcatgtgtc agaggttttc accgtcatca ccgaaacgcg 4140
cgaggcaggg tgccttgatg tgggcgccgg cggtcgagtg gcgacggcgc ggcttgtccg 4200
cgccctggta gattgcctgg ccgtaggcca gccatttttg agcggccagc ggccgcgata 4260
ggccgacgcg aagcggcggg gcgtagggag cgcagcgacc gaagggtagg cgctttttgc 4320
agctcttcgg ctgtgcgctg gccagacagt tatgcacagg ccaggcgggt tttaagagtt 4380
ttaataagtt ttaaagagtt ttaggcggaa aaatcgcctt ttttctcttt tatatcagtc 4440
acttacatgt gtgaccggtt cccaatgtac ggctttgggt tcccaatgta cgggttccgg 4500
ttcccaatgt acggctttgg gttcccaatg tacgtgctat ccacaggaaa gagacctttt 4560
cgaccttttt cccctgctag ggcaatttgc cctagcatct gctccgtaca ttaggaaccg 4620
gcggatgctt cgccctcgat caggttgcgg tagcgcatga ctaggatcgg gccagcctgc 4680
cccgcctcct ccttcaaatc gtactccggc aggtcatttg acccgatcag cttgcgcacg 4740
gtgaaacaga acttcttgaa ctctccggcg ctgccactgc gttcgtagat cgtcttgaac 4800
aaccatctgg cttctgcctt gcctgcggcg cggcgtgcca ggcggtagag aaaacggccg 4860
atgccgggat cgatcaaaaa gtaatcgggg tgaaccgtca gcacgtccgg gttcttgcct 4920
tctgtgatct cgcggtacat ccaatcagct agctcgatct cgatgtactc cggccgcccg 4980
gtttcgctct ttacgatctt gtagcggcta atcaaggctt caccctcgga taccgtcacc 5040
aggcggccgt tcttggcctt cttcgtacgc tgcatggcaa cgtgcgtggt gtttaaccga 5100
atgcaggttt ctaccaggtc gtctttctgc tttccgccat cggctcgccg gcagaacttg 5160
agtacgtccg caacgtgtgg acggaacacg cggccgggct tgtctccctt cccttcccgg 5220
tatcggttca tggattcggt tagatgggaa accgccatca gtaccaggtc gtaatcccac 5280
acactggcca tgccggccgg ccctgcggaa acctctacgt gcccgtctgg aagctcgtag 5340
cggatcacct cgccagctcg tcggtcacgc ttcgacagac ggaaaacggc cacgtccatg 5400
atgctgcgac tatcgcgggt gcccacgtca tagagcatcg gaacgaaaaa atctggttgc 5460
tcgtcgccct tgggcggctt cctaatcgac ggcgcaccgg ctgccggcgg ttgccgggat 5520
tctttgcgga ttcgatcagc ggccgcttgc cacgattcac cggggcgtgc ttctgcctcg 5580
atgcgttgcc gctgggcggc ctgcgcggcc ttcaacttct ccaccaggtc atcacccagc 5640
gccgcgccga tttgtaccgg gccggatggt ttgcgaccgt cacgccgatt cctcgggctt 5700
gggggttcca gtgccattgc agggccggca gacaacccag ccgcttacgc ctggccaacc 5760
gcccgttcct ccacacatgg ggcattccac ggcgtcggtg cctggttgtt cttgattttc 5820
catgccgcct cctttagccg ctaaaattca tctactcatt tattcatttg ctcatttact 5880
ctggtagctg cgcgatgtat tcagatagca gctcggtaat ggtcttgcct tggcgtaccg 5940
cgtacatctt cagcttggtg tgatcctccg ccggcaactg aaagttgacc cgcttcatgg 6000
ctggcgtgtc tgccaggctg gccaacgttg cagccttgct gctgcgtgcg ctcggacggc 6060
cggcacttag cgtgtttgtg cttttgctca ttttctcttt acctcattaa ctcaaatgag 6120
ttttgattta atttcagcgg ccagcgcctg gacctcgcgg gcagcgtcgc cctcgggttc 6180
tgattcaaga acggttgtgc cggcggcggc agtgcctggg tagctcacgc gctgcgtgat 6240
acgggactca agaatgggca gctcgtaccc ggccagcgcc tcggcaacct caccgccgat 6300
gcgcgtgcct ttgatcgccc gcgacacgac aaaggccgct tgtagccttc catccgtgac 6360
ctcaatgcgc tgcttaacca gctccaccag gtcggcggtg gcccatatgt cgtaagggct 6420
tggctgcacc ggaatcagca cgaagtcggc tgccttgatc gcggacacag ccaagtccgc 6480
cgcctggggc gctccgtcga tcactacgaa gtcgcgccgg ccgatggcct tcacgtcgcg 6540
gtcaatcgtc gggcggtcga tgccgacaac ggttagcggt tgatcttccc gcacggccgc 6600
ccaatcgcgg gcactgccct ggggatcgga atcgactaac agaacatcgg ccccggcgag 6660
ttgcagggcg cgggctagat gggttgcgat ggtcgtcttg cctgacccgc ctttctggtt 6720
aagtacagcg ataaccttca tgcgttcccc ttgcgtattt gtttatttac tcatcgcatc 6780
atatacgcag cgaccgcatg acgcaagctg ttttactcaa atacacatca cctttttaga 6840
cggcggcgct cggtttcttc agcggccaag ctggccggcc aggccgccag cttggcatca 6900
gacaaaccgg ccaggatttc atgcagccgc acggttgaga cgtgcgcggg cggctcgaac 6960
acgtacccgg ccgcgatcat ctccgcctcg atctcttcgg taatgaaaaa cggttcgtcc 7020
tggccgtcct ggtgcggttt catgcttgtt cctcttggcg ttcattctcg gcggccgcca 7080
gggcgtcggc ctcggtcaat gcgtcctcac ggaaggcacc gcgccgcctg gcctcggtgg 7140
gcgtcacttc ctcgctgcgc tcaagtgcgc ggtacagggt cgagcgatgc acgccaagca 7200
gtgcagccgc ctctttcacg gtgcggcctt cctggtcgat cagctcgcgg gcgtgcgcga 7260
tctgtgccgg ggtgagggta gggcgggggc caaacttcac gcctcgggcc ttggcggcct 7320
cgcgcccgct ccgggtgcgg tcgatgatta gggaacgctc gaactcggca atgccggcga 7380
acacggtcaa caccatgcgg ccggccggcg tggtggtgtc ggcccacggc tctgccaggc 7440
tacgcaggcc cgcgccggcc tcctggatgc gctcggcaat gtccagtagg tcgcgggtgc 7500
tgcgggccag gcggtctagc ctggtcactg tcacaacgtc gccagggcgt aggtggtcaa 7560
gcatcctggc cagctccggg cggtcgcgcc tggtgccggt gatcttctcg gaaaacagct 7620
tggtgcagcc ggccgcgtgc agttcggccc gttggttggt caagtcctgg tcgtcggtgc 7680
tgacgcgggc atagcccagc aggccagcgg cggcgctctt gttcatggcg taatgtctcc 7740
ggttctagtc gcaagtattc tactttatgc gactaaaaca cgcgacaaga aaacgccagg 7800
aaaagggcag ggcggcagcc tgtcgcgtaa cttaggactt gtgcgacatg tcgttttcag 7860
aagacggctg cactgaacgt cagaagccga ctgcactata gcagcggagg ggttggatca 7920
aagtactttg atcccgaggg gaaccctgtg gttggcatgc acatacaaat ggacgaacgg 7980
ataaaccttt tcacgccctt ttaaatatcc gttattctaa taaacgctct tttctcttag 8040
gtttacccgc caatatatcc tgtcaaacac tgatagttta aactgaaggc gggaaacgac 8100
aatctgatcc aagctcaagc taagcttgag ctctcccata tggtcgagat ctcctttgcc 8160
ccggagatca ccatggacga ctttctctat ctctacgatc taggaagaaa gttcgacgga 8220
gaaggtgacg ataccatgtt caccaccgat aatgagaaga ttagcctctt caatttcaga 8280
aagaatgctg acccacagat ggttagagag gcctacgcgg caggtctcat caagacgatc 8340
tacccgagta ataatctcca ggagatcaaa taccttccca agaaggttaa agatgcagtc 8400
aaaagattca ggactaactg catcaagaac acagagaaag atatatttct caagatcaga 8460
agtactattc cagtatggac gattcaaggc ttgcttcata aaccaaggca agtaatagag 8520
attggagtct ctaagaaagt agttcctact gaatcaaagg ccatggagtc aaaaattcag 8580
atcgaggatc taacagaact cgccgtgaag actggcgaac agttcataca gagtctttta 8640
cgactcaatg acaagaagaa aatcttcgtc aacatggtgg agcacgacac tctcgtctac 8700
tccaagaata tcaaagatac agtctcagaa gaccaaaggg ctattgagac ttttcaacaa 8760
agggtaatat cgggaaacct cctcggattc cattgcccag ctatctgtca cttcatcaaa 8820
aggacagtag aaaaggaagg tggcacctac aaatgccatc attgcgataa aggaaaggct 8880
atcgttcaag atgcccctgc cgacagtggt cccaaagatg gacccccacc cacgaggagc 8940
atcgtggaaa aagaagacgt tccaaccacg tcttcaaagc aagtggattg atgtgatatc 9000
tccactgacg taagggatga cgcacaatcc cactatcctt cgcaagaccc ttcctctata 9060
taaggaagtt catttcattt ggagaggact ccggtatttt tacaacaatt accacaacaa 9120
aacaaacaac aaacaacatt acaatttact attctagtcg acctgcaggc ggccgcacta 9180
gtgatatcac aagtttgtac aaaaaagcag gctgaattcc caccatggca aacaagcttt 9240
tcttggtgtg cgctaccttc gctctttgct tccttttgac taacgctcag gttcaattgc 9300
aagagtctgg tggtggactt gttcaggctg gtggatctct tagactttct tgcgctgctt 9360
ctggaaggac cttctctaga tatggaatgg gatggttcag gcagctccct ggaaaacaga 9420
gagagcttgt tacctctatc accaggggtg gaactaccac ctacgctgat tctgtgaagg 9480
gaaggttcac catctctagg gataacgcta agaacaccgt gtacctccag atgaactctc 9540
tcaagcctga ggataccgct gtgtactact gcaacgctag atctatttgg agggattact 9600
ggggacaggg aactcaggtc accgtttctt caggtggtgg tggaagtggt ggtggttctc 9660
aagttcaact gcaggaatca ggtggtggat tggtgcaagc tggtggttct ttgaggttgt 9720
catgtgctgc tagtggtagg accttcagta ggtacggtat gggatggttt agacagttgc 9780
ctggtaagca gagggaactc gtgacttcaa tcactagagg tggaaccact acttacgcag 9840
atagtgttaa gggaagattc actatcagta gagataatgc aaagaacact gtttacttgc 9900
aaatgaactc attgaagcca gaggatacag cagtttatta ctgtaacgca agaagtattt 9960
ggagagatta ttggggtcaa ggtactcaag tgaccgttag ttcagcggcc gcacatcatc 10020
atcaccatca ttgaggatcc acccagcttt cttgtacaaa gtggtgatat cccgcggcca 10080
tgctagagtc cgcaaaaatc accagtctct ctctacaaat ctatctctct ctatttttct 10140

```
ccagaataat gtgtgagtag ttcccagata agggaattag ggttcttata gggtttcgct  10200

catgtgttga gcatataaga aacccttagt atgtatttgt atttgtaaaa tacttctatc  10260

aataaaattt ctaattccta aaaccaaaat ccagtgacct gcaggcatgc gacgtcg     10317


<210> SEQ ID NO 362
<211> LENGTH: 9945
<212> TYPE: DNA
<213> ORGANISM: Artificial Sequence
<220> FEATURE:
<223> OTHER INFORMATION: pK7WG2-35S: sec_41D01_His

<400> SEQUENCE: 362

ggccctctag aggatccccg ggtaccgcga attatcatac atgagaatta agggagtcac     60

gttatgaccc ccgccgatga cgcgggacaa gccgttttac gtttggaact gacagaaccg    120

caacgttgaa ggagccactc agccgcgggt ttctggagtt taatgagcta agcacatacg    180

tcagaaacca ttattgcgcg ttcaaaagtc gcctaaggtc actatcagct agcaaatatt    240

tcttgtcaaa aatgctccac tgacgttcca taaattcccc tcggtatcca attagagtct    300

catattcact ctcaactcga tcgaggcatg attgaacaag atggattgca cgcaggttct    360

ccggccgctt gggtggagag gctattcggc tatgactggg cacaacagac aatcggctgc    420

tctgatgccg ccgtgttccg gctgtcagcg caggggcgcc cggttctttt tgtcaagacc    480

gacctgtccg gtgccctgaa tgaactccaa gacgaggcag cgcggctatc gtggctggcc    540

acgacgggcg ttccttgcgc agctgtgctc gacgttgtca ctgaagcggg aagggactgg    600

ctgctattgg gcgaagtgcc ggggcaggat ctcctgtcat ctcaccttgc tcctgccgag    660

aaagtatcca tcatggctga tgcaatgcgg cggctgcata cgcttgatcc ggctacctgc    720

ccattcgacc accaagcgaa acatcgcatc gagcgaggac gtactcggat ggaagccggt    780

cttgtcgatc aggatgatct ggacgaagag catcaggggc tcgcgccagc cgaactgttc    840

gccaggctca aggcgcggat gcccgacggc gaggatctcg tcgtgaccca gggcgatgcc    900

tgcttgccga atatcatggt ggaaaatggc cgcttttctg gattcatcga ctgtggccgg    960

ctgggtgtgg cggaccgcta tcaggacata gcgttggcta cccgtgatat tgctgaagag   1020

cttggcggcg aatgggctga ccgcttcctc gtgctttacg gtatcgccgc tcccgattcg   1080

cagcgcatcg ccttctatcg ccttcttgac gagttcttct gagcgggact ctggggttcg   1140

gactctagct agagtcaagc agatcgttca aacatttggc aataaagttt cttaagattg   1200

aatcctgttg ccggtcttgc gatgattatc atataatttc tgttgaatta cgttaagcat   1260

gtaataatta acatgtaatg catgacgtta tttatgagat gggtttttg attagagtcc   1320

cgcaattata catttaatac gcgatagaaa acaaaatata gcgcgcaaac taggataaat   1380

tatcgcgcgc ggtgtcatct atgttactag atcgaccggc atgcaagctg ataattcaat   1440

tcggcgttaa ttcagtacat taaaaacgtc cgcaatgtgt tattaagttg tctaagcgtc   1500

aatttgttta caccacaata tatcctgcca ccagccagcc aacagctccc cgaccggcag   1560

ctcggcacaa aatcaccact cgatacaggc agcccatcag tccgggacgg cgtcagcggg   1620

agagccgttg taaggcggca gactttgctc atgttaccga tgctattcgg aagaacggca   1680

actaagctgc cgggtttgaa acacggatga tctcgcggag ggtagcatgt tgattgtaac   1740

gatgacagag cgttgctgcc tgtgatcaat tcgggcacga acccagtgga cataagcctc   1800

gttcggttcg taagctgtaa tgcaagtagc gtaactgccg tcacgcaact ggtccagaac   1860
```

-continued

```
cttgaccgaa cgcagcggtg gtaacggcgc agtggcggtt ttcatggctt cttgttatga   1920
catgtttttt tggggtacag tctatgcctc gggcatccaa gcagcaagcg cgttacgccg   1980
tgggtcgatg tttgatgtta tggagcagca acgatgttac gcagcagggc agtcgcccta   2040
aaacaaagtt aaacatcatg ggggaagcgg tgatcgccga agtatcgact caactatcag   2100
aggtagttgg cgtcatcgag cgccatctcg aaccgacgtt gctggccgta catttgtacg   2160
gctccgcagt ggatggcggc ctgaagccac acagtgatat tgatttgctg gttacggtga   2220
ccgtaaggct tgatgaaaca acgcggcgag ctttgatcaa cgaccttttg gaaacttcgg   2280
cttcccctgg agagagcgag attctccgcg ctgtagaagt caccattgtt gtgcacgacg   2340
acatcattcc gtggcgttat ccagctaagc gcgaactgca atttggagaa tggcagcgca   2400
atgacattct tgcaggtatc ttcgagccag ccacgatcga cattgatctg gctatcttgc   2460
tgacaaaagc aagagaacat agcgttgcct tggtaggtcc agcggcggag gaactctttg   2520
atccggttcc tgaacaggat ctatttgagg cgctaaatga aaccttaacg ctatggaact   2580
cgccgcccga ctgggctggc gatgagcgaa atgtagtgct tacgttgtcc cgcatttggt   2640
acagcgcagt aaccggcaaa atcgcgccga aggatgtcgc tgccgactgg gcaatggagc   2700
gcctgccggc ccagtatcag cccgtcatac ttgaagctag acaggcttat cttggacaag   2760
aagaagatcg cttggcctcg cgcgcagatc agttggaaga atttgtccac tacgtgaaag   2820
gcgagatcac caaggtagtc ggcaaataat gtctagctag aaattcgttc aagccgacgc   2880
cgcttcgccg gcgttaactc aagcgattag atgcactaag cacataattg ctcacagcca   2940
aactatcagg tcaagtctgc ttttattatt tttaagcgtg cataataagc cctacacaaa   3000
ttgggagata tatcatgcat gaccaaaatc ccttaacgtg agttttcgtt ccactgagcg   3060
tcagaccccg tagaaaagat caaaggatct tcttgagatc ctttttttct gcgcgtaatc   3120
tgctgcttgc aaacaaaaaa accaccgcta ccagcggtgg tttgtttgcc ggatcaagag   3180
ctaccaactc tttttccgaa ggtaactggc ttcagcagag cgcagatacc aaatactgtc   3240
cttctagtgt agccgtagtt aggccaccac ttcaagaact ctgtagcacc gcctacatac   3300
ctcgctctgc taatcctgtt accagtggct gctgccagtg gcgataagtc gtgtcttacc   3360
gggttggact caagacgata gttaccggat aaggcgcagc ggtcgggctg aacggggggt   3420
tcgtgcacac agcccagctt ggagcgaacg acctacaccg aactgagata cctacagcgt   3480
gagctatgag aaagcgccac gcttcccgaa gggagaaagg cggacaggta tccggtaagc   3540
ggcagggtcg gaacaggaga gcgcacgagg gagcttccag ggggaaacgc ctggtatctt   3600
tatagtcctg tcgggtttcg ccacctctga cttgagcgtc gatttttgtg atgctcgtca   3660
ggggggcgga gcctatggaa aaacgccagc aacgcggcct ttttacggtt cctggccttt   3720
tgctggcctt ttgctcacat gttctttcct gcgttatccc ctgattctgt ggataaccgt   3780
attaccgcct ttgagtgagc tgataccgct cgccgcagcc gaacgaccga gcgcagcgag   3840
tcagtgagcg aggaagcgga agagcgcctg atgcggtatt ttctccttac gcatctgtgc   3900
ggtatttcac accgcatatg gtgcactctc agtacaatct gctctgatgc cgcatagtta   3960
agccagtata cactccgcta tcgctacgtg actgggtcat ggctgcgccc cgacacccgc   4020
caacacccgc tgacgcgccc tgacgggctt gtctgctccc ggcatccgct tacagacaag   4080
ctgtgaccgt ctccgggagc tgcatgtgtc agaggttttc accgtcatca ccgaaacgcg   4140
cgaggcaggg tgccttgatg tgggcgccgg cggtcgagtg gcgacggcgc ggcttgtccg   4200
cgccctggta gattgcctgg ccgtaggcca gccatttttg agcggccagc ggccgcgata   4260
```

ggccgacgcg aagcggcggg gcgtagggag cgcagcgacc gaagggtagg cgctttttgc 4320
agctcttcgg ctgtgcgctg gccagacagt tatgcacagg ccaggcgggt tttaagagtt 4380
ttaataagtt ttaaagagtt ttaggcggaa aaatcgcctt ttttctcttt tatatcagtc 4440
acttacatgt gtgaccggtt cccaatgtac ggctttgggt tcccaatgta cgggttccgg 4500
ttcccaatgt acggctttgg gttcccaatg tacgtgctat ccacaggaaa gagacctttt 4560
cgaccttttt cccctgctag ggcaatttgc cctagcatct gctccgtaca ttaggaaccg 4620
gcggatgctt cgccctcgat caggttgcgg tagcgcatga ctaggatcgg gccagcctgc 4680
cccgcctcct ccttcaaatc gtactccggc aggtcatttg acccgatcag cttgcgcacg 4740
gtgaaacaga acttcttgaa ctctccggcg ctgccactgc gttcgtagat cgtcttgaac 4800
aaccatctgg cttctgcctt gcctgcggcg cggcgtgcca ggcggtagag aaaacggccg 4860
atgccgggat cgatcaaaaa gtaatcgggg tgaaccgtca gcacgtccgg gttcttgcct 4920
tctgtgatct cgcggtacat ccaatcagct agctcgatct cgatgtactc cggccgcccg 4980
gtttcgctct ttacgatctt gtagcggcta atcaaggctt caccctcgga taccgtcacc 5040
aggcggccgt tcttggcctt cttcgtacgc tgcatggcaa cgtgcgtggt gtttaaccga 5100
atgcaggttt ctaccaggtc gtctttctgc tttccgccat cggctcgccg gcagaacttg 5160
agtacgtccg caacgtgtgg acggaacacg cggccgggct tgtctccctt cccttcccgg 5220
tatcggttca tggattcggt tagatgggaa accgccatca gtaccaggtc gtaatcccac 5280
acactggcca tgccggccgg ccctgcggaa acctctacgt gcccgtctgg aagctcgtag 5340
cggatcacct cgccagctcg tcggtcacgc ttcgacagac ggaaaacggc cacgtccatg 5400
atgctgcgac tatcgcgggt gcccacgtca tagagcatcg gaacgaaaaa atctggttgc 5460
tcgtcgccct tgggcggctt cctaatcgac ggcgcaccgg ctgccggcgg ttgccgggat 5520
tctttgcgga ttcgatcagc ggccgcttgc cacgattcac cggggcgtgc ttctgcctcg 5580
atgcgttgcc gctgggcggc ctgcgcggcc ttcaacttct ccaccaggtc atcacccagc 5640
gccgcgccga tttgtaccgg gccggatggt ttgcgaccgt cacgccgatt cctcgggctt 5700
gggggttcca gtgccattgc agggccggca gacaacccag ccgcttacgc ctggccaacc 5760
gcccgttcct ccacacatgg ggcattccac ggcgtcggtg cctggttgtt cttgattttc 5820
catgccgcct cctttagccg ctaaaattca tctactcatt tattcatttg ctcatttact 5880
ctggtagctg cgcgatgtat tcagatagca gctcggtaat ggtcttgcct tggcgtaccg 5940
cgtacatctt cagcttggtg tgatcctccg ccggcaactg aaagttgacc cgcttcatgg 6000
ctggcgtgtc tgccaggctg gccaacgttg cagccttgct gctgcgtgcg ctcggacggc 6060
cggcacttag cgtgtttgtg cttttgctca ttttctcttt acctcattaa ctcaaatgag 6120
ttttgattta atttcagcgg ccagcgcctg gacctcgcgg gcagcgtcgc cctcgggttc 6180
tgattcaaga acggttgtgc cggcggcggc agtgcctggg tagctcacgc gctgcgtgat 6240
acgggactca agaatgggca gctcgtaccc ggccagcgcc tcggcaacct caccgccgat 6300
gcgcgtgcct ttgatcgccc gcgacacgac aaaggccgct tgtagccttc catccgtgac 6360
ctcaatgcgc tgcttaacca gctccaccag gtcggcggtg gcccatatgt cgtaagggct 6420
tggctgcacc ggaatcagca cgaagtcggc tgccttgatc gcggacacag ccaagtccgc 6480
cgcctggggc gctccgtcga tcactacgaa gtcgcgccgg ccgatggcct tcacgtcgcg 6540
gtcaatcgtc gggcggtcga tgccgacaac ggttagcggt tgatcttccc gcacggccgc 6600

-continued

```
ccaatcgcgg gcactgccct ggggatcgga atcgactaac agaacatcgg ccccggcgag   6660
ttgcagggcg cgggctagat gggttgcgat ggtcgtcttg cctgacccgc ctttctggtt   6720
aagtacagcg ataaccttca tgcgttcccc ttgcgtattt gtttatttac tcatcgcatc   6780
atatacgcag cgaccgcatg acgcaagctg ttttactcaa atacacatca cctttttaga   6840
cggcggcgct cggtttcttc agcggccaag ctggccggcc aggccgccag cttggcatca   6900
gacaaaccgg ccaggatttc atgcagccgc acggttgaga cgtgcgcggg cggctcgaac   6960
acgtacccgg ccgcgatcat ctccgcctcg atctcttcgg taatgaaaaa cggttcgtcc   7020
tggccgtcct ggtgcggttt catgcttgtt cctcttggcg ttcattctcg gcggccgcca   7080
gggcgtcggc ctcggtcaat gcgtcctcac ggaaggcacc gcgccgcctg gcctcggtgg   7140
gcgtcacttc ctcgctgcgc tcaagtgcgc ggtacagggt cgagcgatgc acgccaagca   7200
gtgcagccgc ctctttcacg gtgcggcctt cctggtcgat cagctcgcgg gcgtgcgcga   7260
tctgtgccgg ggtgagggta gggcgggggc caaacttcac gcctcgggcc ttggcggcct   7320
cgcgcccgct ccgggtgcgg tcgatgatta gggaacgctc gaactcggca atgccggcga   7380
acacggtcaa caccatgcgg ccggccggcg tggtggtgtc ggcccacggc tctgccaggc   7440
tacgcaggcc cgcgccggcc tcctggatgc gctcggcaat gtccagtagg tcgcgggtgc   7500
tgcgggccag gcggtctagc ctggtcactg tcacaacgtc gccagggcgt aggtggtcaa   7560
gcatcctggc cagctccggg cggtcgcgcc tggtgccggt gatcttctcg gaaaacagct   7620
tggtgcagcc ggccgcgtgc agttcggccc gttggttggt caagtcctgg tcgtcggtgc   7680
tgacgcgggc atagcccagc aggccagcgg cggcgctctt gttcatggcg taatgtctcc   7740
ggttctagtc gcaagtattc tactttatgc gactaaaaca cgcgacaaga aaacgccagg   7800
aaaagggcag ggcggcagcc tgtcgcgtaa cttaggactt gtgcgacatg tcgttttcag   7860
aagacggctg cactgaacgt cagaagccga ctgcactata gcagcggagg ggttggatca   7920
aagtactttg atcccgaggg gaaccctgtg gttggcatgc acatacaaat ggacgaacgg   7980
ataaaccttt tcacgccctt ttaaatatcc gttattctaa taaacgctct tttctcttag   8040
gtttacccgc caatatatcc tgtcaaacac tgatagttta aactgaaggc gggaaacgac   8100
aatctgatcc aagctcaagc taagcttgag ctctcccata tggtcgagat ctcctttgcc   8160
ccggagatca ccatggacga ctttctctat ctctacgatc taggaagaaa gttcgacgga   8220
gaaggtgacg ataccatgtt caccaccgat aatgagaaga ttagcctctt caatttcaga   8280
aagaatgctg acccacagat ggttagagag gcctacgcgg caggtctcat caagacgatc   8340
tacccgagta ataatctcca ggagatcaaa taccttccca agaaggttaa agatgcagtc   8400
aaaagattca ggactaactg catcaagaac acagagaaag atatatttct caagatcaga   8460
agtactattc cagtatggac gattcaaggc ttgcttcata aaccaaggca agtaatagag   8520
attggagtct ctaagaaagt agttcctact gaatcaaagg ccatggagtc aaaaattcag   8580
atcgaggatc taacagaact cgccgtgaag actggcgaac agttcataca gagtctttta   8640
cgactcaatg acaagaagaa aatcttcgtc aacatggtgg agcacgacac tctcgtctac   8700
tccaagaata tcaaagatac agtctcagaa gaccaaaggg ctattgagac ttttcaacaa   8760
agggtaatat cgggaaacct cctcggattc cattgcccag ctatctgtca cttcatcaaa   8820
aggacagtag aaaaggaagg tggcacctac aaatgccatc attgcgataa aggaaaggct   8880
atcgttcaag atgcccctgc cgacagtggt cccaaagatg gacccccacc cacgaggagc   8940
atcgtggaaa aagaagacgt tccaaccacg tcttcaaagc aagtggattg atgtgatatc   9000
```

```
tccactgacg taagggatga cgcacaatcc cactatcctt cgcaagaccc ttcctctata   9060

taaggaagtt catttcattt ggagaggact ccggtatttt tacaacaatt accacaacaa   9120

aacaaacaac aaacaacatt acaatttact attctagtcg acctgcaggc ggccgcacta   9180

gtgatatcac aagtttgtac aaaaaagcag gctgaattcc caccatggca aacaagcttt   9240

tcttggtgtg cgctaccttc gctctttgct tcctttttgac taacgctcag gttcagctgc   9300

aggaatctgg tggtggactt gttcaagctg gtggatctct tagactctct tgcgctgctt   9360

ctggaaggac cttctctaga tatggaatgg gatggttcag gcagctccct ggaaaacaga   9420

gagagcttgt tacctctatc accaggggtg gaactaccac ctacgctgat tctgtgaagg   9480

gaaggttcac catctctagg gataacgcta agaacaccgt gtacctccag atgaactctc   9540

tcaagcctga ggataccgct gtgtactact gcaacgctag atctatttgg agggattact   9600

ggggacaggg aactcaggtc accgtttctt cagcggccgc acatcatcat caccatcatt   9660

gaggatccac ccagctttct tgtacaaagt ggtgatatcc cgcggccatg ctagagtccg   9720

caaaaatcac cagtctctct ctacaaatct atctctctct atttttctcc agaataatgt   9780

gtgagtagtt cccagataag ggaattaggg ttcttatagg gtttcgctca tgtgttgagc   9840

atataagaaa cccttagtat gtatttgtat ttgtaaaata cttctatcaa taaaatttct   9900

aattcctaaa accaaaatcc agtgacctgc aggcatgcga cgtcg                  9945
```

<210> SEQ ID NO 363
<211> LENGTH: 9885
<212> TYPE: DNA
<213> ORGANISM: Artificial Sequence
<220> FEATURE:
<223> OTHER INFORMATION: pK7WG2-35S: cyto_41D01_His

<400> SEQUENCE: 363

```
ggccctctag aggatccccg ggtaccgcga attatcatac atgagaatta agggagtcac     60

gttatgaccc ccgccgatga cgcgggacaa gccgttttac gtttggaact gacagaaccg    120

caacgttgaa ggagccactc agccgcgggt ttctggagtt taatgagcta agcacatacg    180

tcagaaacca ttattgcgcg ttcaaaagtc gcctaaggtc actatcagct agcaaatatt    240

tcttgtcaaa aatgctccac tgacgttcca taaattcccc tcggtatcca attagagtct    300

catattcact ctcaactcga tcgaggcatg attgaacaag atggattgca cgcaggttct    360

ccggccgctt gggtggagag gctattcggc tatgactggg cacaacagac aatcggctgc    420

tctgatgccg ccgtgttccg gctgtcagcg caggggcgcc cggttctttt tgtcaagacc    480

gacctgtccg gtgccctgaa tgaactccaa gacgaggcag cgcggctatc gtggctggcc    540

acgacgggcg ttccttgcgc agctgtgctc gacgttgtca ctgaagcggg aagggactgg    600

ctgctattgg gcgaagtgcc ggggcaggat ctcctgtcat ctcaccttgc tcctgccgag    660

aaagtatcca tcatggctga tgcaatgcgg cggctgcata cgcttgatcc ggctacctgc    720

ccattcgacc accaagcgaa acatcgcatc gagcgaggac gtactcggat ggaagccggt    780

cttgtcgatc aggatgatct ggacgaagag catcaggggc tcgcgccagc cgaactgttc    840

gccaggctca aggcgcggat gcccgacggc gaggatctcg tcgtgaccca gggcgatgcc    900

tgcttgccga atatcatggt ggaaaatggc cgcttttctg gattcatcga ctgtggccgg    960

ctgggtgtgg cggaccgcta tcaggacata gcgttggcta cccgtgatat tgctgaagag   1020

cttggcggcg aatgggctga ccgcttcctc gtgctttacg gtatcgccgc tcccgattcg   1080
```

-continued

```
cagcgcatcg ccttctatcg ccttcttgac gagttcttct gagcgggact ctggggttcg   1140
gactctagct agagtcaagc agatcgttca aacatttggc aataaagttt cttaagattg   1200
aatcctgttg ccggtcttgc gatgattatc atataatttc tgttgaatta cgttaagcat   1260
gtaataatta acatgtaatg catgacgtta tttatgagat gggtttttttg attagagtcc   1320
cgcaattata catttaatac gcgatagaaa acaaaatata gcgcgcaaac taggataaat   1380
tatcgcgcgc ggtgtcatct atgttactag atcgaccggc atgcaagctg ataattcaat   1440
tcggcgttaa ttcagtacat taaaaacgtc cgcaatgtgt tattaagttg tctaagcgtc   1500
aatttgttta caccacaata tatcctgcca ccagccagcc aacagctccc cgaccggcag   1560
ctcggcacaa aatcaccact cgatacaggc agcccatcag tccgggacgg cgtcagcggg   1620
agagccgttg taaggcggca gactttgctc atgttaccga tgctattcgg aagaacggca   1680
actaagctgc cgggtttgaa acacggatga tctcgcggag ggtagcatgt tgattgtaac   1740
gatgacagag cgttgctgcc tgtgatcaat tcgggcacga acccagtgga cataagcctc   1800
gttcggttcg taagctgtaa tgcaagtagc gtaactgccg tcacgcaact ggtccagaac   1860
cttgaccgaa cgcagcggtg gtaacggcgc agtggcggtt ttcatggctt cttgttatga   1920
catgtttttt tggggtacag tctatgcctc gggcatccaa gcagcaagcg cgttacgccg   1980
tgggtcgatg tttgatgtta tggagcagca acgatgttac gcagcagggc agtcgcccta   2040
aaacaaagtt aaacatcatg ggggaagcgg tgatcgccga agtatcgact caactatcag   2100
aggtagttgg cgtcatcgag cgccatctcg aaccgacgtt gctggccgta catttgtacg   2160
gctccgcagt ggatggcggc ctgaagccac acagtgatat tgatttgctg gttacggtga   2220
ccgtaaggct tgatgaaaca acgcggcgag ctttgatcaa cgaccttttg gaaacttcgg   2280
cttcccctgg agagagcgag attctccgcg ctgtagaagt caccattgtt gtgcacgacg   2340
acatcattcc gtggcgttat ccagctaagc gcgaactgca atttggagaa tggcagcgca   2400
atgacattct tgcaggtatc ttcgagccag ccacgatcga cattgatctg gctatcttgc   2460
tgacaaaagc aagagaacat agcgttgcct tggtaggtcc agcggcggag gaactctttg   2520
atccggttcc tgaacaggat ctatttgagg cgctaaatga aaccttaacg ctatggaact   2580
cgccgcccga ctgggctggc gatgagcgaa atgtagtgct tacgttgtcc cgcatttggt   2640
acagcgcagt aaccggcaaa atcgcgccga aggatgtcgc tgccgactgg gcaatggagc   2700
gcctgccggc ccagtatcag cccgtcatac ttgaagctag acaggcttat cttggacaag   2760
aagaagatcg cttggcctcg cgcgcagatc agttggaaga atttgtccac tacgtgaaag   2820
gcgagatcac caaggtagtc ggcaaataat gtctagctag aaattcgttc aagccgacgc   2880
cgcttcgccg gcgttaactc aagcgattag atgcactaag cacataattg ctcacagcca   2940
aactatcagg tcaagtctgc ttttattatt tttaagcgtg cataataagc cctacacaaa   3000
ttgggagata tatcatgcat gaccaaaatc ccttaacgtg agttttcgtt ccactgagcg   3060
tcagaccccg tagaaaagat caaaggatct tcttgagatc cttttttctt gcgcgtaatc   3120
tgctgcttgc aaacaaaaaa accaccgcta ccagcggtgg tttgtttgcc ggatcaagag   3180
ctaccaactc tttttccgaa ggtaactggc ttcagcagag cgcagatacc aaatactgtc   3240
cttctagtgt agccgtagtt aggccaccac ttcaagaact ctgtagcacc gcctacatac   3300
ctcgctctgc taatcctgtt accagtggct gctgccagtg gcgataagtc gtgtcttacc   3360
gggttggact caagacgata gttaccggat aaggcgcagc ggtcgggctg aacggggggt   3420
tcgtgcacac agcccagctt ggagcgaacg acctacaccg aactgagata cctacagcgt   3480
```

```
gagctatgag aaagcgccac gcttcccgaa gggagaaagg cggacaggta tccggtaagc   3540
ggcagggtcg gaacaggaga gcgcacgagg gagcttccag ggggaaacgc ctggtatctt   3600
tatagtcctg tcgggtttcg ccacctctga cttgagcgtc gatttttgtg atgctcgtca   3660
gggggggcgga gcctatggaa aaacgccagc aacgcggcct ttttacggtt cctggccttt   3720
tgctggcctt ttgctcacat gttctttcct gcgttatccc ctgattctgt ggataaccgt   3780
attaccgcct ttgagtgagc tgataccgct cgccgcagcc gaacgaccga gcgcagcgag   3840
tcagtgagcg aggaagcgga agagcgcctg atgcggtatt ttctccttac gcatctgtgc   3900
ggtatttcac accgcatatg gtgcactctc agtacaatct gctctgatgc cgcatagtta   3960
agccagtata cactccgcta tcgctacgtg actgggtcat ggctgcgccc cgacacccgc   4020
caacacccgc tgacgcgccc tgacgggctt gtctgctccc ggcatccgct tacagacaag   4080
ctgtgaccgt ctccgggagc tgcatgtgtc agaggttttc accgtcatca ccgaaacgcg   4140
cgaggcaggg tgccttgatg tgggcgccgg cggtcgagtg gcgacggcgc ggcttgtccg   4200
cgccctggta gattgcctgg ccgtaggcca gccatttttg agcggccagc ggccgcgata   4260
ggccgacgcg aagcggcggg gcgtagggag cgcagcgacc gaagggtagg cgctttttgc   4320
agctcttcgg ctgtgcgctg gccagacagt tatgcacagg ccaggcgggt tttaagagtt   4380
ttaataagtt ttaaagagtt ttaggcggaa aaatcgcctt ttttctcttt tatatcagtc   4440
acttacatgt gtgaccggtt cccaatgtac ggctttgggt tcccaatgta cgggttccgg   4500
ttcccaatgt acggctttgg gttcccaatg tacgtgctat ccacaggaaa gagacctttt   4560
cgaccttttt cccctgctag ggcaatttgc cctagcatct gctccgtaca ttaggaaccg   4620
gcggatgctt cgccctcgat caggttgcgg tagcgcatga ctaggatcgg gccagcctgc   4680
cccgcctcct ccttcaaatc gtactccggc aggtcatttg acccgatcag cttgcgcacg   4740
gtgaaacaga acttcttgaa ctctccggcg ctgccactgc gttcgtagat cgtcttgaac   4800
aaccatctgg cttctgcctt gcctgcggcg cggcgtgcca ggcggtagag aaaacggccg   4860
atgccgggat cgatcaaaaa gtaatcgggg tgaaccgtca gcacgtccgg gttcttgcct   4920
tctgtgatct cgcggtacat ccaatcagct agctcgatct cgatgtactc cggccgcccg   4980
gtttcgctct ttacgatctt gtagcggcta atcaaggctt caccctcgga taccgtcacc   5040
aggcggccgt tcttggcctt cttcgtacgc tgcatggcaa cgtgcgtggt gtttaaccga   5100
atgcaggttt ctaccaggtc gtctttctgc tttccgccat cggctcgccg gcagaacttg   5160
agtacgtccg caacgtgtgg acggaacacg cggccgggct tgtctccctt cccttcccgg   5220
tatcggttca tggattcggt tagatgggaa accgccatca gtaccaggtc gtaatcccac   5280
acactggcca tgccggccgg ccctgcggaa acctctacgt gcccgtctgg aagctcgtag   5340
cggatcacct cgccagctcg tcggtcacgc ttcgacagac ggaaaacggc cacgtccatg   5400
atgctgcgac tatcgcgggt gcccacgtca tagagcatcg gaacgaaaaa atctggttgc   5460
tcgtcgccct tgggcggctt cctaatcgac ggcgcaccgg ctgccggcgg ttgccgggat   5520
tctttgcgga ttcgatcagc ggccgcttgc cacgattcac cggggcgtgc ttctgcctcg   5580
atgcgttgcc gctgggcggc ctgcgcggcc ttcaacttct ccaccaggtc atcacccagc   5640
gccgcgccga tttgtaccgg gccggatggt ttgcgaccgt cacgccgatt cctcgggctt   5700
gggggttcca gtgccattgc agggccggca gacaacccag ccgcttacgc ctggccaacc   5760
gcccgttcct ccacacatgg ggcattccac ggcgtcggtg cctggttgtt cttgatttc   5820
```

```
catgccgcct cctttagccg ctaaaattca tctactcatt tattcatttg ctcatttact   5880
ctggtagctg cgcgatgtat tcagatagca gctcggtaat ggtcttgcct tggcgtaccg   5940
cgtacatctt cagcttggtg tgatcctccg ccggcaactg aaagttgacc cgcttcatgg   6000
ctggcgtgtc tgccaggctg gccaacgttg cagccttgct gctgcgtgcg ctcggacggc   6060
cggcacttag cgtgtttgtg cttttgctca ttttctcttt acctcattaa ctcaaatgag   6120
ttttgattta atttcagcgg ccagcgcctg gacctcgcgg gcagcgtcgc cctcgggttc   6180
tgattcaaga acggttgtgc cggcggcggc agtgcctggg tagctcacgc gctgcgtgat   6240
acgggactca agaatgggca gctcgtaccc ggccagcgcc tcggcaacct caccgccgat   6300
gcgcgtgcct ttgatcgccc gcgacacgac aaaggccgct tgtagccttc catccgtgac   6360
ctcaatgcgc tgcttaacca gctccaccag gtcggcggtg gcccatatgt cgtaagggct   6420
tggctgcacc ggaatcagca cgaagtcggc tgccttgatc gcggacacag ccaagtccgc   6480
cgcctggggc gctccgtcga tcactacgaa gtcgcgccgg ccgatggcct tcacgtcgcg   6540
gtcaatcgtc gggcggtcga tgccgacaac ggttagcggt tgatcttccc gcacggccgc   6600
ccaatcgcgg gcactgccct ggggatcgga atcgactaac agaacatcgg ccccggcgag   6660
ttgcagggcg cgggctagat gggttgcgat ggtcgtcttg cctgacccgc ctttctggtt   6720
aagtacagcg ataaccttca tgcgttcccc ttgcgtattt gtttatttac tcatcgcatc   6780
atatacgcag cgaccgcatg acgcaagctg ttttactcaa atacacatca ccttttttaga   6840
cggcggcgct cggtttcttc agcggccaag ctggccggcc aggccgccag cttggcatca   6900
gacaaaccgg ccaggatttc atgcagccgc acggttgaga cgtgcgcggg cggctcgaac   6960
acgtacccgg ccgcgatcat ctccgcctcg atctcttcgg taatgaaaaa cggttcgtcc   7020
tggccgtcct ggtgcggttt catgcttgtt cctcttggcg ttcattctcg gcggccgcca   7080
gggcgtcggc ctcggtcaat gcgtcctcac ggaaggcacc gcgccgcctg gcctcggtgg   7140
gcgtcacttc ctcgctgcgc tcaagtgcgc ggtacagggt cgagcgatgc acgccaagca   7200
gtgcagccgc ctctttcacg gtgcggcctt cctggtcgat cagctcgcgg gcgtgcgcga   7260
tctgtgccgg ggtgagggta gggcgggggc caaacttcac gcctcgggcc ttggcggcct   7320
cgcgcccgct ccgggtgcgg tcgatgatta gggaacgctc gaactcggca atgccggcga   7380
acacggtcaa caccatgcgg ccggccggcg tggtggtgtc ggcccacggc tctgccaggc   7440
tacgcaggcc cgcgccggcc tcctggatgc gctcggcaat gtccagtagg tcgcgggtgc   7500
tgcgggccag gcggtctagc ctggtcactg tcacaacgtc gccagggcgt aggtggtcaa   7560
gcatcctggc cagctccggg cggtcgcgcc tggtgccggt gatcttctcg gaaaacagct   7620
tggtgcagcc ggccgcgtgc agttcggccc gttggttggt caagtcctgg tcgtcggtgc   7680
tgacgcgggc atagcccagc aggccagcgg cggcgctctt gttcatggcg taatgtctcc   7740
ggttctagtc gcaagtattc tactttatgc gactaaaaca cgcgacaaga aaacgccagg   7800
aaaagggcag ggcggcagcc tgtcgcgtaa cttaggactt gtgcgacatg tcgttttcag   7860
aagacggctg cactgaacgt cagaagccga ctgcactata gcagcggagg ggttggatca   7920
aagtactttg atcccgaggg gaaccctgtg gttggcatgc acatacaaat ggacgaacgg   7980
ataaaccttt tcacgccctt ttaaatatcc gttattctaa taaacgctct tttctcttag   8040
gtttacccgc caatatatcc tgtcaaacac tgatagttta aactgaaggc gggaaacgac   8100
aatctgatcc aagctcaagc taagcttgag ctctcccata tggtcgagat ctcctttgcc   8160
ccggagatca ccatggacga ctttctctat ctctacgatc taggaagaaa gttcgacgga   8220
```

gaaggtgacg ataccatgtt caccaccgat aatgagaaga ttagcctctt caatttcaga 8280
aagaatgctg acccacagat ggttagagag gcctacgcgg caggtctcat caagacgatc 8340
tacccgagta ataatctcca ggagatcaaa taccttccca agaaggttaa agatgcagtc 8400
aaaagattca ggactaactg catcaagaac acagagaaag atatatttct caagatcaga 8460
agtactattc cagtatggac gattcaaggc ttgcttcata aaccaaggca agtaatagag 8520
attggagtct ctaagaaagt agttcctact gaatcaaagg ccatggagtc aaaaattcag 8580
atcgaggatc taacagaact cgccgtgaag actggcgaac agttcataca gagtctttta 8640
cgactcaatg acaagaagaa aatcttcgtc aacatggtgg agcacgacac tctcgtctac 8700
tccaagaata tcaaagatac agtctcagaa gaccaaaggg ctattgagac ttttcaacaa 8760
agggtaatat cgggaaacct cctcggattc cattgcccag ctatctgtca cttcatcaaa 8820
aggacagtag aaaaggaagg tggcacctac aaatgccatc attgcgataa aggaaaggct 8880
atcgttcaag atgcccctgc cgacagtggt cccaaagatg gacccccacc cacgaggagc 8940
atcgtggaaa aagaagacgt tccaaccacg tcttcaaagc aagtggattg atgtgatatc 9000
tccactgacg taagggatga cgcacaatcc cactatcctt cgcaagaccc ttcctctata 9060
taaggaagtt catttcattt ggagaggact ccggtatttt tacaacaatt accacaacaa 9120
aacaaacaac aaacaacatt acaatttact attctagtcg acctgcaggc ggccgcacta 9180
gtgatatcac aagtttgtac aaaaaagcag gctgaattcc caccatgcag gttcagctgc 9240
aggaatctgg tggtggactt gttcaagctg gtggatctct tagactctct tgcgctgctt 9300
ctggaaggac cttctctaga tatggaatgg gatggttcag gcagctccct ggaaaacaga 9360
gagagcttgt tacctctatc accaggggtg gaactaccac ctacgctgat tctgtgaagg 9420
gaaggttcac catctctagg gataacgcta agaacaccgt gtacctccag atgaactctc 9480
tcaagcctga ggataccgct gtgtactact gcaacgctag atctatttgg agggattact 9540
ggggacaggg aactcaggtc accgtttctt cagcggccgc acatcatcat caccatcatt 9600
gaggatccac ccagctttct tgtacaaagt ggtgatatcc cgcggccatg ctagagtccg 9660
caaaaatcac cagtctctct ctacaaatct atctctctct atttttctcc agaataatgt 9720
gtgagtagtt cccagataag ggaattaggg ttcttatagg gtttcgctca tgtgttgagc 9780
atataagaaa cccttagtat gtatttgtat ttgtaaaata cttctatcaa taaaatttct 9840
aattcctaaa accaaaatcc agtgacctgc aggcatgcga cgtcg 9885

<210> SEQ ID NO 364
<211> LENGTH: 9984
<212> TYPE: DNA
<213> ORGANISM: Artificial Sequence
<220> FEATURE:
<223> OTHER INFORMATION: pK7WG2-35S: 56F11_His_KDEL

<400> SEQUENCE: 364
ggccctctag aggatccccg ggtaccgcga attatcatac atgagaatta agggagtcac 60
gttatgaccc ccgccgatga cgcgggacaa gccgttttac gtttggaact gacagaaccg 120
caacgttgaa ggagccactc agccgcgggt ttctggagtt taatgagcta agcacatacg 180
tcagaaacca ttattgcgcg ttcaaaagtc gcctaaggtc actatcagct agcaaatatt 240
tcttgtcaaa aatgctccac tgacgttcca taaattcccc tcggtatcca attagagtct 300
catattcact ctcaactcga tcgaggcatg attgaacaag atggattgca cgcaggttct 360

-continued

```
ccggccgctt gggtggagag gctattcggc tatgactggg cacaacagac aatcggctgc    420
tctgatgccg ccgtgttccg gctgtcagcg caggggcgcc cggttctttt tgtcaagacc    480
gacctgtccg gtgccctgaa tgaactccaa gacgaggcag cgcggctatc gtggctggcc    540
acgacgggcg ttccttgcgc agctgtgctc gacgttgtca ctgaagcggg aagggactgg    600
ctgctattgg gcgaagtgcc ggggcaggat ctcctgtcat ctcaccttgc tcctgccgag    660
aaagtatcca tcatggctga tgcaatgcgg cggctgcata cgcttgatcc ggctacctgc    720
ccattcgacc accaagcgaa acatcgcatc gagcgaggac gtactcggat ggaagccggt    780
cttgtcgatc aggatgatct ggacgaagag catcaggggc tcgcgccagc cgaactgttc    840
gccaggctca aggcgcggat gcccgacggc gaggatctcg tcgtgaccca gggcgatgcc    900
tgcttgccga atatcatggt ggaaaatggc cgcttttctg gattcatcga ctgtggccgg    960
ctgggtgtgg cggaccgcta tcaggacata gcgttggcta cccgtgatat tgctgaagag   1020
cttggcggcg aatgggctga ccgcttcctc gtgctttacg gtatcgccgc tcccgattcg   1080
cagcgcatcg ccttctatcg ccttcttgac gagttcttct gagcgggact ctggggttcg   1140
gactctagct agagtcaagc agatcgttca aacatttggc aataaagttt cttaagattg   1200
aatcctgttg ccggtcttgc gatgattatc atataatttc tgttgaatta cgttaagcat   1260
gtaataatta acatgtaatg catgacgtta tttatgagat gggtttttg attagagtcc    1320
cgcaattata catttaatac gcgatagaaa acaaaatata gcgcgcaaac taggataaat   1380
tatcgcgcgc ggtgtcatct atgttactag atcgaccggc atgcaagctg ataattcaat   1440
tcggcgttaa ttcagtacat taaaaacgtc cgcaatgtgt tattaagttg tctaagcgtc   1500
aatttgttta caccacaata tatcctgcca ccagccagcc aacagctccc cgaccggcag   1560
ctcggcacaa aatcaccact cgatacaggc agcccatcag tccgggacgg cgtcagcggg   1620
agagccgttg taaggcggca gactttgctc atgttaccga tgctattcgg aagaacggca   1680
actaagctgc cgggtttgaa acacggatga tctcgcggag ggtagcatgt tgattgtaac   1740
gatgacagag cgttgctgcc tgtgatcaat tcgggcacga acccagtgga cataagcctc   1800
gttcggttcg taagctgtaa tgcaagtagc gtaactgccg tcacgcaact ggtccagaac   1860
cttgaccgaa cgcagcggtg gtaacggcgc agtggcggtt ttcatggctt cttgttatga   1920
catgtttttt tggggtacag tctatgcctc gggcatccaa gcagcaagcg cgttacgccg   1980
tgggtcgatg tttgatgtta tggagcagca acgatgttac gcagcagggc agtcgcccta   2040
aaacaaagtt aaacatcatg ggggaagcgg tgatcgccga agtatcgact caactatcag   2100
aggtagttgg cgtcatcgag cgccatctcg aaccgacgtt gctggccgta catttgtacg   2160
gctccgcagt ggatggcggc ctgaagccac acagtgatat tgatttgctg gttacggtga   2220
ccgtaaggct tgatgaaaca acgcggcgag ctttgatcaa cgaccttttg gaaacttcgg   2280
cttcccctgg agagagcgag attctccgcg ctgtagaagt caccattgtt gtgcacgacg   2340
acatcattcc gtggcgttat ccagctaagc gcgaactgca atttggagaa tggcagcgca   2400
atgacattct tgcaggtatc ttcgagccag ccacgatcga cattgatctg gctatcttgc   2460
tgacaaaagc aagagaacat agcgttgcct tggtaggtcc agcggcggag gaactctttg   2520
atccggttcc tgaacaggat ctatttgagg cgctaaatga aaccttaacg ctatggaact   2580
cgccgcccga ctgggctggc gatgagcgaa atgtagtgct tacgttgtcc cgcatttggt   2640
acagcgcagt aaccggcaaa atcgcgccga aggatgtcgc tgccgactgg gcaatggagc   2700
gcctgccggc ccagtatcag cccgtcatac ttgaagctag acaggcttat cttggacaag   2760
```

aagaagatcg cttggcctcg cgcgcagatc agttggaaga atttgtccac tacgtgaaag 2820
gcgagatcac caaggtagtc ggcaaataat gtctagctag aaattcgttc aagccgacgc 2880
cgcttcgccg gcgttaactc aagcgattag atgcactaag cacataattg ctcacagcca 2940
aactatcagg tcaagtctgc ttttattatt tttaagcgtg cataataagc cctacacaaa 3000
ttgggagata tatcatgcat gaccaaaatc ccttaacgtg agttttcgtt ccactgagcg 3060
tcagaccccg tagaaaagat caaaggatct tcttgagatc cttttttct gcgcgtaatc 3120 tgctgcttgc aaacaaaaaa accaccgcta ccagcggtgg tttgtttgcc ggatcaagag 3180
ctaccaactc tttttccgaa ggtaactggc ttcagcagag cgcagatacc aaatactgtc 3240
cttctagtgt agccgtagtt aggccaccac ttcaagaact ctgtagcacc gcctacatac 3300
ctcgctctgc taatcctgtt accagtggct gctgccagtg gcgataagtc gtgtcttacc 3360
gggttggact caagacgata gttaccggat aaggcgcagc ggtcgggctg aacggggggt 3420
tcgtgcacac agcccagctt ggagcgaacg acctacaccg aactgagata cctacagcgt 3480
gagctatgag aaagcgccac gcttcccgaa gggagaaagg cggacaggta tccggtaagc 3540
ggcagggtcg gaacaggaga gcgcacgagg gagcttccag ggggaaacgc ctggtatctt 3600
tatagtcctg tcgggtttcg ccacctctga cttgagcgtc gatttttgtg atgctcgtca 3660 gggggcgga gcctatggaa aaacgccagc aacgcggcct ttttacggtt cctggccttt 3720
tgctggcctt ttgctcacat gttctttcct gcgttatccc ctgattctgt ggataaccgt 3780
attaccgcct ttgagtgagc tgataccgct cgccgcagcc gaacgaccga gcgcagcgag 3840
tcagtgagcg aggaagcgga agagcgcctg atgcggtatt ttctccttac gcatctgtgc 3900
ggtatttcac accgcatatg gtgcactctc agtacaatct gctctgatgc cgcatagtta 3960
agccagtata cactccgcta tcgctacgtg actgggtcat ggctgcgccc cgacacccgc 4020
caacacccgc tgacgcgccc tgacgggctt gtctgctccc ggcatccgct tacagacaag 4080
ctgtgaccgt ctccgggagc tgcatgtgtc agaggttttc accgtcatca ccgaaacgcg 4140
cgaggcaggg tgccttgatg tgggcgccgg cggtcgagtg gcgacggcgc ggcttgtccg 4200
cgccctggta gattgcctgg ccgtaggcca gccatttttg agcggccagc ggccgcgata 4260
ggccgacgcg aagcggcggg gcgtagggag cgcagcgacc gaagggtagg cgctttttgc 4320
agctcttcgg ctgtgcgctg gccagacagt tatgcacagg ccaggcgggt tttaagagtt 4380
ttaataagtt ttaaagagtt ttaggcggaa aaatcgcctt ttttctcttt tatatcagtc 4440
acttacatgt gtgaccggtt cccaatgtac ggctttgggt tcccaatgta cgggttccgg 4500
ttcccaatgt acggctttgg gttcccaatg tacgtgctat ccacaggaaa gagacctttt 4560
cgaccttttt cccctgctag ggcaatttgc cctagcatct gctccgtaca ttaggaaccg 4620
gcggatgctt cgccctcgat caggttgcgg tagcgcatga ctaggatcgg gccagcctgc 4680
cccgcctcct ccttcaaatc gtactccggc aggtcatttg acccgatcag cttgcgcacg 4740
gtgaaacaga acttcttgaa ctctccggcg ctgccactgc gttcgtagat cgtcttgaac 4800
aaccatctgg cttctgcctt gcctgcggcg cggcgtgcca ggcggtagag aaaacggccg 4860
atgccgggat cgatcaaaaa gtaatcgggg tgaaccgtca gcacgtccgg gttcttgcct 4920
tctgtgatct cgcggtacat ccaatcagct agctcgatct cgatgtactc cggccgcccg 4980
gtttcgctct ttacgatctt gtagcggcta atcaaggctt caccctcgga taccgtcacc 5040
aggcggccgt tcttggcctt cttcgtacgc tgcatggcaa cgtgcgtggt gtttaaccga 5100

```
atgcaggttt ctaccaggtc gtctttctgc tttccgccat cggctcgccg gcagaacttg   5160
agtacgtccg caacgtgtgg acggaacacg cggccgggct tgtctccctt cccttcccgg   5220
tatcggttca tggattcggt tagatgggaa accgccatca gtaccaggtc gtaatcccac   5280
acactggcca tgccggccgg ccctgcggaa acctctacgt gcccgtctgg aagctcgtag   5340
cggatcacct cgccagctcg tcggtcacgc ttcgacagac ggaaaacggc cacgtccatg   5400
atgctgcgac tatcgcgggt gcccacgtca tagagcatcg gaacgaaaaa atctggttgc   5460
tcgtcgccct tgggcggctt cctaatcgac ggcgcaccgg ctgccggcgg ttgccgggat   5520
tctttgcgga ttcgatcagc ggccgcttgc cacgattcac cggggcgtgc ttctgcctcg   5580
atgcgttgcc gctgggcggc ctgcgcggcc ttcaacttct ccaccaggtc atcacccagc   5640
gccgcgccga tttgtaccgg gccggatggt ttgcgaccgt cacgccgatt cctcgggctt   5700
gggggttcca gtgccattgc agggccggca gacaacccag ccgcttacgc ctggccaacc   5760
gcccgttcct ccacacatgg ggcattccac ggcgtcggtg cctggttgtt cttgattttc   5820
catgccgcct cctttagccg ctaaaattca tctactcatt tattcatttg ctcatttact   5880
ctggtagctg cgcgatgtat tcagatagca gctcggtaat ggtcttgcct tggcgtaccg   5940
cgtacatctt cagcttggtg tgatcctccg ccggcaactg aaagttgacc cgcttcatgg   6000
ctggcgtgtc tgccaggctg gccaacgttg cagccttgct gctgcgtgcg ctcggacggc   6060
cggcacttag cgtgtttgtg cttttgctca ttttctcttt acctcattaa ctcaaatgag   6120
ttttgattta atttcagcgg ccagcgcctg gacctcgcgg gcagcgtcgc cctcgggttc   6180
tgattcaaga acggttgtgc cggcggcggc agtgcctggg tagctcacgc gctgcgtgat   6240
acgggactca agaatgggca gctcgtaccc ggccagcgcc tcggcaacct caccgccgat   6300
gcgcgtgcct ttgatcgccc gcgacacgac aaaggccgct tgtagccttc catccgtgac   6360
ctcaatgcgc tgcttaacca gctccaccag gtcggcggtg gcccatatgt cgtaagggct   6420
tggctgcacc ggaatcagca cgaagtcggc tgccttgatc gcggacacag ccaagtccgc   6480
cgcctggggc gctccgtcga tcactacgaa gtcgcgccgg ccgatggcct tcacgtcgcg   6540
gtcaatcgtc gggcggtcga tgccgacaac ggttagcggt tgatcttccc gcacggccgc   6600
ccaatcgcgg gcactgccct ggggatcgga atcgactaac agaacatcgg ccccggcgag   6660
ttgcagggcg cgggctagat gggttgcgat ggtcgtcttg cctgacccgc ctttctggtt   6720
aagtacagcg ataaccttca tgcgttcccc ttgcgtattt gtttatttac tcatcgcatc   6780
atatacgcag cgaccgcatg acgcaagctg ttttactcaa atacacatca ccttttttaga   6840
cggcggcgct cggtttcttc agcggccaag ctggccggcc aggccgccag cttggcatca   6900
gacaaaccgg ccaggatttc atgcagccgc acggttgaga cgtgcgcggg cggctcgaac   6960
acgtacccgg ccgcgatcat ctccgcctcg atctcttcgg taatgaaaaa cggttcgtcc   7020
tggccgtcct ggtgcggttt catgcttgtt cctcttggcg ttcattctcg gcggccgcca   7080
gggcgtcggc ctcggtcaat gcgtcctcac ggaaggcacc gcgccgcctg gcctcggtgg   7140
gcgtcacttc ctcgctgcgc tcaagtgcgc ggtacagggt cgagcgatgc acgccaagca   7200
gtgcagccgc ctctttcacg gtgcggcctt cctggtcgat cagctcgcgg gcgtgcgcga   7260
tctgtgccgg ggtgagggta gggcgggggc caaacttcac gcctcgggcc ttggcggcct   7320
cgcgcccgct ccgggtgcgg tcgatgatta gggaacgctc gaactcggca atgccggcga   7380
acacggtcaa caccatgcgg ccggccggcg tggtggtgtc ggcccacggc tctgccaggc   7440
tacgcaggcc cgcgccggcc tcctggatgc gctcggcaat gtccagtagg tcgcgggtgc   7500
```

-continued

```
tgcgggccag gcggtctagc ctggtcactg tcacaacgtc gccagggcgt aggtggtcaa   7560
gcatcctggc cagctccggg cggtcgcgcc tggtgccggt gatcttctcg gaaaacagct   7620
tggtgcagcc ggccgcgtgc agttcggccc gttggttggt caagtcctgg tcgtcggtgc   7680
tgacgcgggc atagcccagc aggccagcgg cggcgctctt gttcatggcg taatgtctcc   7740
ggttctagtc gcaagtattc tactttatgc gactaaaaca cgcgacaaga aaacgccagg   7800
aaaagggcag ggcggcagcc tgtcgcgtaa cttaggactt gtgcgacatg tcgttttcag   7860
aagacggctg cactgaacgt cagaagccga ctgcactata gcagcggagg ggttggatca   7920
aagtactttg atcccgaggg gaaccctgtg gttggcatgc acatacaaat ggacgaacgg   7980
ataaaccttt tcacgccctt ttaaatatcc gttattctaa taaacgctct tttctcttag   8040
gtttacccgc caatatatcc tgtcaaacac tgatagttta aactgaaggc gggaaacgac   8100
aatctgatcc aagctcaagc taagcttgag ctctcccata tggtcgagat ctcctttgcc   8160
ccggagatca ccatggacga ctttctctat ctctacgatc taggaagaaa gttcgacgga   8220
gaaggtgacg ataccatgtt caccaccgat aatgagaaga ttagcctctt caatttcaga   8280
aagaatgctg acccacagat ggttagagag gcctacgcgg caggtctcat caagacgatc   8340
tacccgagta ataatctcca ggagatcaaa taccttccca agaaggttaa agatgcagtc   8400
aaaagattca ggactaactg catcaagaac acagagaaag atatatttct caagatcaga   8460
agtactattc cagtatggac gattcaaggc ttgcttcata aaccaaggca agtaatagag   8520
attggagtct ctaagaaagt agttcctact gaatcaaagg ccatggagtc aaaaattcag   8580
atcgaggatc taacagaact cgccgtgaag actggcgaac agttcataca gagtctttta   8640
cgactcaatg acaagaagaa aatcttcgtc aacatggtgg agcacgacac tctcgtctac   8700
tccaagaata tcaaagatac agtctcagaa gaccaaaggg ctattgagac ttttcaacaa   8760
agggtaatat cgggaaacct cctcggattc cattgcccag ctatctgtca cttcatcaaa   8820
aggacagtag aaaaggaagg tggcacctac aaatgccatc attgcgataa aggaaaggct   8880
atcgttcaag atgcccctgc cgacagtggt cccaaagatg gacccccacc cacgaggagc   8940
atcgtggaaa aagaagacgt tccaaccacg tcttcaaagc aagtggattg atgtgatatc   9000
tccactgacg taagggatga cgcacaatcc cactatcctt cgcaagaccc ttcctctata   9060
taaggaagtt catttcattt ggagaggact ccggtatttt tacaacaatt accacaacaa   9120
aacaaacaac aaacaacatt acaatttact attctagtcg acctgcaggc ggccgcacta   9180
gtgatatcac aagtttgtac aaaaaagcag gctgaattcc caccatggca aacaagcttt   9240
tcttggtgtg cgctaccttc gctctttgct tccttttgac taacgctcag gttcagctgc   9300
aggaatctgg tggtggactt gttcagtctg gtggatctct cagactctct tgcgtgcact   9360
ctaagaccac cttcaccaga aatgctatgg gatggtacag acaggctctc ggaaaagaga   9420
gagagcttgt tgctaccatc acctctggtg gaactaccaa ctacgctgat tctgtgaagg   9480
gaaggttcac catctctatg gattctgcta agaacaccgt gtacctccag atgaactctc   9540
tcaagcctga ggataccgct gtgtactact gcaacgtgaa caccagaagg atcttcggag   9600
gaaccgttag agaatactgg ggacaaggta ctcaggtcac cgtttcttca gcggccgcac   9660
atcatcatca ccatcatggt gctgctaagg atgagctttg aggatccacc cagctttctt   9720
gtacaaagtg gtgatatccc gcggccatgc tagagtccgc aaaaatcacc agtctctctc   9780
tacaaatcta tctctctcta tttttctcca gaataatgtg tgagtagttc ccagataagg   9840
```

gaattagggt tcttataggg tttcgctcat gtgttgagca tataagaaac ccttagtatg 9900
tatttgtatt tgtaaaatac ttctatcaat aaaatttcta attcctaaaa ccaaaatcca 9960
gtgacctgca ggcatgcgac gtcg 9984

<210> SEQ ID NO 365
<211> LENGTH: 10659
<212> TYPE: DNA
<213> ORGANISM: Artificial Sequence
<220> FEATURE:
<223> OTHER INFORMATION: pK7WG2-35S: sec_56F11_hinge_Fc_His

<400> SEQUENCE: 365
ggccctctag aggatccccg ggtaccgcga attatcatac atgagaatta agggagtcac 60
gttatgaccc ccgccgatga cgcgggacaa gccgttttac gtttggaact gacagaaccg 120
caacgttgaa ggagccactc agccgcgggt ttctggagtt taatgagcta agcacatacg 180
tcagaaacca ttattgcgcg ttcaaaagtc gcctaaggtc actatcagct agcaaatatt 240
tcttgtcaaa aatgctccac tgacgttcca taaattcccc tcggtatcca attagagtct 300
catattcact ctcaactcga tcgaggcatg attgaacaag atggattgca cgcaggttct 360
ccggccgctt gggtggagag gctattcggc tatgactggg cacaacagac aatcggctgc 420
tctgatgccg ccgtgttccg gctgtcagcg caggggcgcc cggttctttt tgtcaagacc 480
gacctgtccg gtgccctgaa tgaactccaa gacgaggcag cgcggctatc gtggctggcc 540
acgacgggcg ttccttgcgc agctgtgctc gacgttgtca ctgaagcggg aagggactgg 600
ctgctattgg gcgaagtgcc ggggcaggat ctcctgtcat ctcaccttgc tcctgccgag 660
aaagtatcca tcatggctga tgcaatgcgg cggctgcata cgcttgatcc ggctacctgc 720
ccattcgacc accaagcgaa acatcgcatc gagcgagcac gtactcggat ggaagccggt 780
cttgtcgatc aggatgatct ggacgaagag catcaggggc tcgcgccagc cgaactgttc 840
gccaggctca aggcgcggat gcccgacggc gaggatctcg tcgtgaccca gggcgatgcc 900
tgcttgccga atatcatggt ggaaaatggc cgcttttctg gattcatcga ctgtggccgg 960
ctgggtgtgg cggaccgcta tcaggacata gcgttggcta cccgtgatat tgctgaagag 1020
cttggcggcg aatgggctga ccgcttcctc gtgctttacg gtatcgccgc tcccgattcg 1080
cagcgcatcg ccttctatcg ccttcttgac gagttcttct gagcgggact ctggggttcg 1140
gactctagct agagtcaagc agatcgttca aacatttggc aataaagttt cttaagattg 1200
aatcctgttg ccggtcttgc gatgattatc atataatttc tgttgaatta cgttaagcat 1260
gtaataatta acatgtaatg catgacgtta tttatgagat gggtttttg attagagtcc 1320 cgcaattata catttaatac gcgatagaaa acaaaatata gcgcgcaaac taggataaat 1380
tatcgcgcgc ggtgtcatct atgttactag atcgaccggc atgcaagctg ataattcaat 1440
tcggcgttaa ttcagtacat taaaaacgtc cgcaatgtgt tattaagttg tctaagcgtc 1500
aatttgttta caccacaata tatcctgcca ccagccagcc aacagctccc cgaccggcag 1560
ctcggcacaa aatcaccact cgatacaggc agcccatcag tccgggacgg cgtcagcggg 1620
agagccgttg taaggcggca gactttgctc atgttaccga tgctattcgg aagaacggca 1680
actaagctgc cgggtttgaa acacggatga tctcgcggag ggtagcatgt tgattgtaac 1740
gatgacagag cgttgctgcc tgtgatcaat tcgggcacga acccagtgga cataagcctc 1800
gttcggttcg taagctgtaa tgcaagtagc gtaactgccg tcacgcaact ggtccagaac 1860
cttgaccgaa cgcagcggtg gtaacggcgc agtggcggtt ttcatggctt cttgttatga 1920

```
catgtttttt tggggtacag tctatgcctc gggcatccaa gcagcaagcg cgttacgccg   1980
tgggtcgatg tttgatgtta tggagcagca acgatgttac gcagcagggc agtcgcccta   2040
aaacaaagtt aaacatcatg ggggaagcgg tgatcgccga agtatcgact caactatcag   2100
aggtagttgg cgtcatcgag cgccatctcg aaccgacgtt gctggccgta catttgtacg   2160
gctccgcagt ggatggcggc ctgaagccac acagtgatat tgatttgctg gttacggtga   2220
ccgtaaggct tgatgaaaca acgcggcgag ctttgatcaa cgaccttttg gaaacttcgg   2280
cttcccctgg agagagcgag attctccgcg ctgtagaagt caccattgtt gtgcacgacg   2340
acatcattcc gtggcgttat ccagctaagc gcgaactgca atttggagaa tggcagcgca   2400
atgacattct tgcaggtatc ttcgagccag ccacgatcga cattgatctg gctatcttgc   2460
tgacaaaagc aagagaacat agcgttgcct tggtaggtcc agcggcggag gaactctttg   2520
atccggttcc tgaacaggat ctatttgagg cgctaaatga aaccttaacg ctatggaact   2580
cgccgcccga ctgggctggc gatgagcgaa atgtagtgct tacgttgtcc cgcatttggt   2640
acagcgcagt aaccggcaaa atcgcgccga aggatgtcgc tgccgactgg gcaatggagc   2700
gcctgccggc ccagtatcag cccgtcatac ttgaagctag acaggcttat cttggacaag   2760
aagaagatcg cttggcctcg cgcgcagatc agttggaaga atttgtccac tacgtgaaag   2820
gcgagatcac caaggtagtc ggcaaataat gtctagctag aaattcgttc aagccgacgc   2880
cgcttcgccg gcgttaactc aagcgattag atgcactaag cacataattg ctcacagcca   2940
aactatcagg tcaagtctgc ttttattatt tttaagcgtg cataataagc cctacacaaa   3000
ttgggagata tatcatgcat gaccaaaatc ccttaacgtg agttttcgtt ccactgagcg   3060
tcagaccccg tagaaaagat caaaggatct tcttgagatc cttttttttct gcgcgtaatc   3120
tgctgcttgc aaacaaaaaa accaccgcta ccagcggtgg tttgtttgcc ggatcaagag   3180
ctaccaactc tttttccgaa ggtaactggc ttcagcagag cgcagatacc aaatactgtc   3240
cttctagtgt agccgtagtt aggccaccac ttcaagaact ctgtagcacc gcctacatac   3300
ctcgctctgc taatcctgtt accagtggct gctgccagtg gcgataagtc gtgtcttacc   3360
gggttggact caagacgata gttaccggat aaggcgcagc ggtcgggctg aacggggggt   3420
tcgtgcacac agcccagctt ggagcgaacg acctacaccg aactgagata cctacagcgt   3480
gagctatgag aaagcgccac gcttcccgaa gggagaaagg cggacaggta tccggtaagc   3540
ggcagggtcg gaacaggaga gcgcacgagg gagcttccag ggggaaacgc ctggtatctt   3600
tatagtcctg tcgggtttcg ccacctctga cttgagcgtc gatttttgtg atgctcgtca   3660
gggggcgga gcctatggaa aaacgccagc aacgcggcct ttttacggtt cctggccttt   3720
tgctggcctt ttgctcacat gttctttcct gcgttatccc ctgattctgt ggataaccgt   3780
attaccgcct ttgagtgagc tgataccgct cgccgcagcc gaacgaccga gcgcagcgag   3840
tcagtgagcg aggaagcgga agagcgcctg atgcggtatt ttctccttac gcatctgtgc   3900
ggtatttcac accgcatatg gtgcactctc agtacaatct gctctgatgc cgcatagtta   3960
agccagtata cactccgcta tcgctacgtg actgggtcat ggctgcgccc cgacacccgc   4020
caacacccgc tgacgcgccc tgacgggctt gtctgctccc ggcatccgct tacagacaag   4080
ctgtgaccgt ctccgggagc tgcatgtgtc agaggttttc accgtcatca ccgaaacgcg   4140
cgaggcaggg tgccttgatg tgggcgccgg cggtcgagtg gcgacggcgc ggcttgtccg   4200
cgccctggta gattgcctgg ccgtaggcca gccatttttg agcggccagc ggccgcgata   4260
```

ggccgacgcg aagcggcggg gcgtagggag cgcagcgacc gaagggtagg cgctttttgc 4320
agctcttcgg ctgtgcgctg gccagacagt tatgcacagg ccaggcgggt tttaagagtt 4380
ttaataagtt ttaaagagtt ttaggcggaa aaatcgcctt ttttctcttt tatatcagtc 4440
acttacatgt gtgaccggtt cccaatgtac ggctttgggt tcccaatgta cgggttccgg 4500
ttcccaatgt acggctttgg gttcccaatg tacgtgctat ccacaggaaa gagacctttt 4560
cgaccttttt cccctgctag ggcaatttgc cctagcatct gctccgtaca ttaggaaccg 4620
gcggatgctt cgccctcgat caggttgcgg tagcgcatga ctaggatcgg gccagcctgc 4680
cccgcctcct ccttcaaatc gtactccggc aggtcatttg acccgatcag cttgcgcacg 4740
gtgaaacaga acttcttgaa ctctccggcg ctgccactgc gttcgtagat cgtcttgaac 4800
aaccatctgg cttctgcctt gcctgcggcg cggcgtgcca ggcggtagag aaaacggccg 4860
atgccgggat cgatcaaaaa gtaatcgggg tgaaccgtca gcacgtccgg gttcttgcct 4920
tctgtgatct cgcggtacat ccaatcagct agctcgatct cgatgtactc cggccgcccg 4980
gtttcgctct ttacgatctt gtagcggcta atcaaggctt caccctcgga taccgtcacc 5040
aggcggccgt tcttggcctt cttcgtacgc tgcatggcaa cgtgcgtggt gtttaaccga 5100
atgcaggttt ctaccaggtc gtctttctgc tttccgccat cggctcgccg gcagaacttg 5160
agtacgtccg caacgtgtgg acggaacacg cggccgggct tgtctccctt cccttcccgg 5220
tatcggttca tggattcggt tagatgggaa accgccatca gtaccaggtc gtaatcccac 5280
acactggcca tgccggccgg ccctgcggaa acctctacgt gcccgtctgg aagctcgtag 5340
cggatcacct cgccagctcg tcggtcacgc ttcgacagac ggaaaacggc cacgtccatg 5400
atgctgcgac tatcgcgggt gcccacgtca tagagcatcg gaacgaaaaa atctggttgc 5460
tcgtcgccct tgggcggctt cctaatcgac ggcgcaccgg ctgccggcgg ttgccgggat 5520
tctttgcgga ttcgatcagc ggccgcttgc cacgattcac cggggcgtgc ttctgcctcg 5580
atgcgttgcc gctgggcggc ctgcgcggcc ttcaacttct ccaccaggtc atcacccagc 5640
gccgcgccga tttgtaccgg gccggatggt ttgcgaccgt cacgccgatt cctcgggctt 5700
gggggttcca gtgccattgc agggccggca gacaacccag ccgcttacgc ctggccaacc 5760
gcccgttcct ccacacatgg ggcattccac ggcgtcggtg cctggttgtt cttgattttc 5820
catgccgcct cctttagccg ctaaaattca tctactcatt tattcatttg ctcatttact 5880
ctggtagctg cgcgatgtat tcagatagca gctcggtaat ggtcttgcct tggcgtaccg 5940
cgtacatctt cagcttggtg tgatcctccg ccggcaactg aaagttgacc cgcttcatgg 6000
ctggcgtgtc tgccaggctg gccaacgttg cagccttgct gctgcgtgcg ctcggacggc 6060
cggcacttag cgtgtttgtg cttttgctca ttttctcttt acctcattaa ctcaaatgag 6120
ttttgattta atttcagcgg ccagcgcctg gacctcgcgg gcagcgtcgc cctcgggttc 6180
tgattcaaga acggttgtgc cggcggcggc agtgcctggg tagctcacgc gctgcgtgat 6240
acgggactca agaatgggca gctcgtaccc ggccagcgcc tcggcaacct caccgccgat 6300
gcgcgtgcct ttgatcgccc gcgacacgac aaaggccgct tgtagccttc catccgtgac 6360
ctcaatgcgc tgcttaacca gctccaccag gtcggcggtg gcccatatgt cgtaagggct 6420
tggctgcacc ggaatcagca cgaagtcggc tgccttgatc gcggacacag ccaagtccgc 6480
cgcctggggc gctccgtcga tcactacgaa gtcgcgccgg ccgatggcct tcacgtcgcg 6540
gtcaatcgtc gggcggtcga tgccgacaac ggttagcggt tgatcttccc gcacggccgc 6600
ccaatcgcgg gcactgccct ggggatcgga atcgactaac agaacatcgg ccccggcgag 6660

-continued

```
ttgcagggcg cgggctagat gggttgcgat ggtcgtcttg cctgacccgc ctttctggtt   6720
aagtacagcg ataaccttca tgcgttcccc ttgcgtattt gtttatttac tcatcgcatc   6780
atatacgcag cgaccgcatg acgcaagctg ttttactcaa atacacatca cctttttaga   6840
cggcggcgct cggtttcttc agcggccaag ctggccggcc aggccgccag cttggcatca   6900
gacaaaccgg ccaggatttc atgcagccgc acggttgaga cgtgcgcggg cggctcgaac   6960
acgtacccgg ccgcgatcat ctccgcctcg atctcttcgg taatgaaaaa cggttcgtcc   7020
tggccgtcct ggtgcggttt catgcttgtt cctcttggcg ttcattctcg gcggccgcca   7080
gggcgtcggc ctcggtcaat gcgtcctcac ggaaggcacc gcgccgcctg gcctcggtgg   7140
gcgtcacttc ctcgctgcgc tcaagtgcgc ggtacagggt cgagcgatgc acgccaagca   7200
gtgcagccgc ctctttcacg gtgcggcctt cctggtcgat cagctcgcgg gcgtgcgcga   7260
tctgtgccgg ggtgagggta gggcgggggc caaacttcac gcctcgggcc ttggcggcct   7320
cgcgcccgct ccgggtgcgg tcgatgatta gggaacgctc gaactcggca atgccggcga   7380
acacggtcaa caccatgcgg ccggccggcg tggtggtgtc ggcccacggc tctgccaggc   7440
tacgcaggcc cgcgccggcc tcctggatgc gctcggcaat gtccagtagg tcgcgggtgc   7500
tgcgggccag gcggtctagc ctggtcactg tcacaacgtc gccagggcgt aggtggtcaa   7560
gcatcctggc cagctccggg cggtcgcgcc tggtgccggt gatcttctcg gaaaacagct   7620
tggtgcagcc ggccgcgtgc agttcggccc gttggttggt caagtcctgg tcgtcggtgc   7680
tgacgcgggc atagcccagc aggccagcgg cggcgctctt gttcatggcg taatgtctcc   7740
ggttctagtc gcaagtattc tactttatgc gactaaaaca cgcgacaaga aaacgccagg   7800
aaaagggcag ggcggcagcc tgtcgcgtaa cttaggactt gtgcgacatg tcgttttcag   7860
aagacggctg cactgaacgt cagaagccga ctgcactata gcagcggagg ggttggatca   7920
aagtactttg atcccgaggg gaaccctgtg gttggcatgc acatacaaat ggacgaacgg   7980
ataaaccttt tcacgccctt ttaaatatcc gttattctaa taaacgctct tttctcttag   8040
gtttacccgc caatatatcc tgtcaaacac tgatagttta aactgaaggc gggaaacgac   8100
aatctgatcc aagctcaagc taagcttgag ctctcccata tggtcgagat ctcctttgcc   8160
ccggagatca ccatggacga ctttctctat ctctacgatc taggaagaaa gttcgacgga   8220
gaaggtgacg ataccatgtt caccaccgat aatgagaaga ttagcctctt caatttcaga   8280
aagaatgctg acccacagat ggttagagag gcctacgcgg caggtctcat caagacgatc   8340
tacccgagta ataatctcca ggagatcaaa taccttccca agaaggttaa agatgcagtc   8400
aaaagattca ggactaactg catcaagaac acagagaaag atatatttct caagatcaga   8460
agtactattc cagtatggac gattcaaggc ttgcttcata aaccaaggca agtaatagag   8520
attggagtct ctaagaaagt agttcctact gaatcaaagg ccatggagtc aaaaattcag   8580
atcgaggatc taacagaact cgccgtgaag actggcgaac agttcataca gagtctttta   8640
cgactcaatg acaagaagaa aatcttcgtc aacatggtgg agcacgacac tctcgtctac   8700
tccaagaata tcaaagatac agtctcagaa gaccaaaggg ctattgagac ttttcaacaa   8760
agggtaatat cgggaaacct cctcggattc cattgcccag ctatctgtca cttcatcaaa   8820
aggacagtag aaaaggaagg tggcacctac aaatgccatc attgcgataa aggaaaggct   8880
atcgttcaag atgcccctgc cgacagtggt cccaaagatg gacccccacc cacgaggagc   8940
atcgtggaaa aagaagacgt tccaaccacg tcttcaaagc aagtggattg atgtgatatc   9000
```

```
tccactgacg taagggatga cgcacaatcc cactatcctt cgcaagaccc ttcctctata   9060
taaggaagtt catttcattt ggagaggact ccggtatttt tacaacaatt accacaacaa   9120
aacaaacaac aaacaacatt acaatttact attctagtcg acctgcaggc ggccgcacta   9180
gtgatatcac aagtttgtac aaaaaagcag gctgaattcc caccatggca aacaagcttt   9240
tcttggtgtg cgctaccttc gctctttgct tccttttgac taacgctcag gttcagctgc   9300
aggaatctgg tggtggactt gttcagtctg gtggatctct cagactctct tgcgtgcact   9360
ctaagaccac cttcaccaga aatgctatgg gatggtacag acaggctctc ggaaaagaga   9420
gagagcttgt tgctaccatc acctctggtg gaactaccaa ctacgctgat tctgtgaagg   9480
gaaggttcac catctctatg gattctgcta agaacaccgt gtacctccag atgaactctc   9540
tcaagcctga ggataccgct gtgtactact gcaacgtgaa caccagaagg atcttcggag   9600
gaaccgttag agaatactgg ggacaaggta ctcaggtcac cgtttcttca cctagaatcc   9660
ctaagccttc taccccctcct ggatcttctt gtcctcctgg aaatatcctc ggaggacctt   9720
cagtgttcat cttcccacct aagcctaagg atgctctcat gatctcactc accccctaagg   9780
ttacatgcgt tgtggtggat gtgtctgagg atgatcctga tgtgcacgtg tcatggttcg   9840
tggataacaa agaggtgcac actgcttgga ctcagcctag agaagctcag tacaactcta   9900
ccttcagggt ggtgtctgct ctccctatcc aacaccaaga ttggatgagg ggtaaagagt   9960
tcaagtgcaa ggtgaacaac aaggctctcc ctgctcctat cgagaggact atctctaaac  10020
ctaagggaag ggctcagacc cctcaagtgt atacaattcc tccacctagg gaacagatgt  10080
ctaagaagaa ggtttcactc acttgcctcg tgaccaactt cttcagtgag gctatctctg  10140
ttgagtggga gaggaatggt gagcttgagc aggattacaa gaacacccct cctatcctcg  10200
attctgatgg aacctacttc ctctactcta agctcaccgt ggataccgat tcttggttgc  10260
agggtgagat cttcacttgc tctgttgtgc atgaggctct ccacaaccat cacacccaga  10320
agaacctcag tagatctcct ggtaaagcgg ccgcacatca tcatcaccat cattgaggat  10380
ccacccagct ttcttgtaca aagtggtgat atcccgcggc catgctagag tccgcaaaaa  10440
tcaccagtct ctctctacaa atctatctct ctctattttt ctccagaata atgtgtgagt  10500
agttcccaga taagggaatt agggttctta tagggtttcg ctcatgtgtt gagcatataa  10560
gaaaccctta gtatgtattt gtatttgtaa aatacttcta tcaataaaat ttctaattcc  10620
taaaaccaaa atccagtgac ctgcaggcat gcgacgtcg                         10659
```

<210> SEQ ID NO 366
<211> LENGTH: 10353
<212> TYPE: DNA
<213> ORGANISM: Artificial Sequence
<220> FEATURE:
<223> OTHER INFORMATION: pK7WG2-35S: sec_56F11-9GS-56F11_His

<400> SEQUENCE: 366

```
ggccctctag aggatccccg ggtaccgcga attatcatac atgagaatta agggagtcac     60
gttatgaccc ccgccgatga cgcgggacaa gccgttttac gtttggaact gacagaaccg    120
caacgttgaa ggagccactc agccgcgggt ttctggagtt taatgagcta agcacatacg    180
tcagaaacca ttattgcgcg ttcaaaagtc gcctaaggtc actatcagct agcaaatatt    240
tcttgtcaaa aatgctccac tgacgttcca taaattcccc tcggtatcca attagagtct    300
catattcact ctcaactcga tcgaggcatg attgaacaag atggattgca cgcaggttct    360
ccggccgctt gggtggagag gctattcggc tatgactggg cacaacagac aatcggctgc    420
```

-continued

```
tctgatgccg ccgtgttccg gctgtcagcg caggggcgcc cggttctttt tgtcaagacc    480
gacctgtccg gtgccctgaa tgaactccaa gacgaggcag cgcggctatc gtggctggcc    540
acgacgggcg ttccttgcgc agctgtgctc gacgttgtca ctgaagcggg aagggactgg    600
ctgctattgg gcgaagtgcc ggggcaggat ctcctgtcat ctcaccttgc tcctgccgag    660
aaagtatcca tcatggctga tgcaatgcgg cggctgcata cgcttgatcc ggctacctgc    720
ccattcgacc accaagcgaa acatcgcatc gagcgaggac gtactcggat ggaagccggt    780
cttgtcgatc aggatgatct ggacgaagag catcaggggc tcgcgccagc cgaactgttc    840
gccaggctca aggcgcggat gcccgacggc gaggatctcg tcgtgaccca gggcgatgcc    900
tgcttgccga atatcatggt ggaaaatggc cgcttttctg gattcatcga ctgtggccgg    960
ctgggtgtgg cggaccgcta tcaggacata gcgttggcta cccgtgatat tgctgaagag   1020
cttggcggcg aatgggctga ccgcttcctc gtgctttacg gtatcgccgc tcccgattcg   1080
cagcgcatcg ccttctatcg ccttcttgac gagttcttct gagcgggact ctggggttcg   1140
gactctagct agagtcaagc agatcgttca aacatttggc aataaagttt cttaagattg   1200
aatcctgttg ccggtcttgc gatgattatc atataatttc tgttgaatta cgttaagcat   1260
gtaataatta acatgtaatg catgacgtta tttatgagat gggtttttg attagagtcc   1320
cgcaattata catttaatac gcgatagaaa acaaaatata gcgcgcaaac taggataaat   1380
tatcgcgcgc ggtgtcatct atgttactag atcgaccggc atgcaagctg ataattcaat   1440
tcggcgttaa ttcagtacat taaaaacgtc cgcaatgtgt tattaagttg tctaagcgtc   1500
aatttgttta caccacaata tatcctgcca ccagccagcc aacagctccc cgaccggcag   1560
ctcggcacaa aatcaccact cgatacaggc agcccatcag tccgggacgg cgtcagcggg   1620
agagccgttg taaggcggca gactttgctc atgttaccga tgctattcgg aagaacggca   1680
actaagctgc cgggtttgaa acacggatga tctcgcggag ggtagcatgt tgattgtaac   1740
gatgacagag cgttgctgcc tgtgatcaat tcgggcacga acccagtgga cataagcctc   1800
gttcggttcg taagctgtaa tgcaagtagc gtaactgccg tcacgcaact ggtccagaac   1860
cttgaccgaa cgcagcggtg gtaacggcgc agtggcggtt ttcatggctt cttgttatga   1920
catgtttttt tggggtacag tctatgcctc gggcatccaa gcagcaagcg cgttacgccg   1980
tgggtcgatg tttgatgtta tggagcagca acgatgttac gcagcagggc agtcgcccta   2040
aaacaaagtt aaacatcatg ggggaagcgg tgatcgccga agtatcgact caactatcag   2100
aggtagttgg cgtcatcgag cgccatctcg aaccgacgtt gctggccgta catttgtacg   2160
gctccgcagt ggatggcggc ctgaagccac acagtgatat tgatttgctg gttacggtga   2220
ccgtaaggct tgatgaaaca acgcggcgag ctttgatcaa cgaccttttg gaaacttcgg   2280
cttcccctgg agagagcgag attctccgcg ctgtagaagt caccattgtt gtgcacgacg   2340
acatcattcc gtggcgttat ccagctaagc gcgaactgca atttggagaa tggcagcgca   2400
atgacattct tgcaggtatc ttcgagccag ccacgatcga cattgatctg gctatcttgc   2460
tgacaaaagc aagagaacat agcgttgcct tggtaggtcc agcggcggag gaactctttg   2520
atccggttcc tgaacaggat ctatttgagg cgctaaatga aaccttaacg ctatggaact   2580
cgccgcccga ctgggctggc gatgagcgaa atgtagtgct tacgttgtcc cgcatttggt   2640
acagcgcagt aaccggcaaa atcgcgccga aggatgtcgc tgccgactgg gcaatggagc   2700
gcctgccggc ccagtatcag cccgtcatac ttgaagctag acaggcttat cttggacaag   2760
```

-continued

```
aagaagatcg cttggcctcg cgcgcagatc agttggaaga atttgtccac tacgtgaaag   2820

gcgagatcac caaggtagtc ggcaaataat gtctagctag aaattcgttc aagccgacgc   2880

cgcttcgccg gcgttaactc aagcgattag atgcactaag cacataattg ctcacagcca   2940

aactatcagg tcaagtctgc ttttattatt tttaagcgtg cataataagc cctacacaaa   3000

ttgggagata tatcatgcat gaccaaaatc ccttaacgtg agttttcgtt ccactgagcg   3060

tcagaccccg tagaaaagat caaaggatct tcttgagatc cttttttct gcgcgtaatc   3120

tgctgcttgc aaacaaaaaa accaccgcta ccagcggtgg tttgtttgcc ggatcaagag   3180

ctaccaactc tttttccgaa ggtaactggc ttcagcagag cgcagatacc aaatactgtc   3240

cttctagtgt agccgtagtt aggccaccac ttcaagaact ctgtagcacc gcctacatac   3300

ctcgctctgc taatcctgtt accagtggct gctgccagtg gcgataagtc gtgtcttacc   3360

gggttggact caagacgata gttaccggat aaggcgcagc ggtcgggctg aacggggggt   3420

tcgtgcacac agcccagctt ggagcgaacg acctacaccg aactgagata cctacagcgt   3480

gagctatgag aaagcgccac gcttcccgaa gggagaaagg cggacaggta tccggtaagc   3540

ggcagggtcg gaacaggaga gcgcacgagg gagcttccag ggggaaacgc ctggtatctt   3600

tatagtcctg tcgggtttcg ccacctctga cttgagcgtc gatttttgtg atgctcgtca   3660

gggggcgga gcctatggaa aaacgccagc aacgcggcct ttttacggtt cctggccttt   3720

tgctggcctt ttgctcacat gttctttcct gcgttatccc ctgattctgt ggataaccgt   3780

attaccgcct ttgagtgagc tgataccgct cgccgcagcc gaacgaccga gcgcagcgag   3840

tcagtgagcg aggaagcgga agagcgcctg atgcggtatt ttctccttac gcatctgtgc   3900

ggtatttcac accgcatatg gtgcactctc agtacaatct gctctgatgc cgcatagtta   3960

agccagtata cactccgcta tcgctacgtg actgggtcat ggctgcgccc cgacacccgc   4020

caacacccgc tgacgcgccc tgacgggctt gtctgctccc ggcatccgct tacagacaag   4080

ctgtgaccgt ctccgggagc tgcatgtgtc agaggttttc accgtcatca ccgaaacgcg   4140

cgaggcaggg tgccttgatg tgggcgccgg cggtcgagtg gcgacggcgc ggcttgtccg   4200

cgccctggta gattgcctgg ccgtaggcca gccatttttg agcggccagc ggccgcgata   4260

ggccgacgcg aagcggcggg gcgtagggag cgcagcgacc gaagggtagg cgctttttgc   4320

agctcttcgg ctgtgcgctg gccagacagt tatgcacagg ccaggcgggt tttaagagtt   4380

ttaataagtt ttaaagagtt ttaggcggaa aaatcgcctt ttttctcttt tatatcagtc   4440

acttacatgt gtgaccggtt cccaatgtac ggctttgggt tcccaatgta cgggttccgg   4500

ttcccaatgt acggctttgg gttcccaatg tacgtgctat ccacaggaaa gagacctttt   4560

cgaccttttt cccctgctag ggcaatttgc cctagcatct gctccgtaca ttaggaaccg   4620

gcggatgctt cgccctcgat caggttgcgg tagcgcatga ctaggatcgg gccagcctgc   4680

cccgcctcct ccttcaaatc gtactccggc aggtcatttg acccgatcag cttgcgcacg   4740

gtgaaacaga acttcttgaa ctctccggcg ctgccactgc gttcgtagat cgtcttgaac   4800

aaccatctgg cttctgcctt gcctgcggcg cggcgtgcca ggcggtagag aaaacggccg   4860

atgccgggat cgatcaaaaa gtaatcgggg tgaaccgtca gcacgtccgg gttcttgcct   4920

tctgtgatct cgcggtacat ccaatcagct agctcgatct cgatgtactc cggccgcccg   4980

gtttcgctct ttacgatctt gtagcggcta atcaaggctt caccctcgga taccgtcacc   5040

aggcggccgt tcttggcctt cttcgtacgc tgcatggcaa cgtgcgtggt gtttaaccga   5100

atgcaggttt ctaccaggtc gtctttctgc tttccgccat cggctcgccg gcagaacttg   5160
```

-continued agtacgtccg caacgtgtgg acggaacacg cggccgggct tgtctccctt cccttcccgg 5220
tatcggttca tggattcggt tagatgggaa accgccatca gtaccaggtc gtaatcccac 5280
acactggcca tgccggccgg ccctgcggaa acctctacgt gcccgtctgg aagctcgtag 5340
cggatcacct cgccagctcg tcggtcacgc ttcgacagac ggaaaacggc cacgtccatg 5400
atgctgcgac tatcgcgggt gcccacgtca tagagcatcg gaacgaaaaa atctggttgc 5460
tcgtcgccct tgggcggctt cctaatcgac ggcgcaccgg ctgccggcgg ttgccgggat 5520
tctttgcgga ttcgatcagc ggccgcttgc cacgattcac cggggcgtgc ttctgcctcg 5580
atgcgttgcc gctgggcggc ctgcgcggcc ttcaacttct ccaccaggtc atcacccagc 5640
gccgcgccga tttgtaccgg gccggatggt ttgcgaccgt cacgccgatt cctcgggctt 5700
gggggttcca gtgccattgc agggccggca gacaacccag ccgcttacgc ctggccaacc 5760
gcccgttcct ccacacatgg ggcattccac ggcgtcggtg cctggttgtt cttgattttc 5820
catgccgcct cctttagccg ctaaaattca tctactcatt tattcatttg ctcatttact 5880
ctggtagctg cgcgatgtat tcagatagca gctcggtaat ggtcttgcct tggcgtaccg 5940
cgtacatctt cagcttggtg tgatcctccg ccggcaactg aaagttgacc cgcttcatgg 6000
ctggcgtgtc tgccaggctg gccaacgttg cagccttgct gctgcgtgcg ctcggacggc 6060
cggcacttag cgtgtttgtg cttttgctca ttttctcttt acctcattaa ctcaaatgag 6120
ttttgattta atttcagcgg ccagcgcctg gacctcgcgg gcagcgtcgc cctcgggttc 6180
tgattcaaga acggttgtgc cggcggcggc agtgcctggg tagctcacgc gctgcgtgat 6240
acgggactca agaatgggca gctcgtaccc ggccagcgcc tcggcaacct caccgccgat 6300
gcgcgtgcct ttgatcgccc gcgacacgac aaaggccgct tgtagccttc catccgtgac 6360
ctcaatgcgc tgcttaacca gctccaccag gtcggcggtg gcccatatgt cgtaagggct 6420
tggctgcacc ggaatcagca cgaagtcggc tgccttgatc gcggacacag ccaagtccgc 6480
cgcctggggc gctccgtcga tcactacgaa gtcgcgccgg ccgatggcct tcacgtcgcg 6540
gtcaatcgtc gggcggtcga tgccgacaac ggttagcggt tgatcttccc gcacggccgc 6600
ccaatcgcgg gcactgccct ggggatcgga atcgactaac agaacatcgg ccccggcgag 6660
ttgcagggcg cgggctagat gggttgcgat ggtcgtcttg cctgacccgc ctttctggtt 6720
aagtacagcg ataaccttca tgcgttcccc ttgcgtattt gtttatttac tcatcgcatc 6780
atatacgcag cgaccgcatg acgcaagctg ttttactcaa atacacatca cctttttaga 6840
cggcggcgct cggtttcttc agcggccaag ctggccggcc aggccgccag cttggcatca 6900
gacaaaccgg ccaggatttc atgcagccgc acggttgaga cgtgcgcggg cggctcgaac 6960
acgtacccgg ccgcgatcat ctccgcctcg atctcttcgg taatgaaaaa cggttcgtcc 7020
tggccgtcct ggtgcggttt catgcttgtt cctcttggcg ttcattctcg gcggccgcca 7080
gggcgtcggc ctcggtcaat gcgtcctcac ggaaggcacc gcgccgcctg gcctcggtgg 7140
gcgtcacttc ctcgctgcgc tcaagtgcgc ggtacagggt cgagcgatgc acgccaagca 7200
gtgcagccgc ctctttcacg gtgcggcctt cctggtcgat cagctcgcgg gcgtgcgcga 7260
tctgtgccgg ggtgagggta gggcgggggc caaacttcac gcctcgggcc ttggcggcct 7320
cgcgcccgct ccgggtgcgg tcgatgatta gggaacgctc gaactcggca atgccggcga 7380
acacggtcaa caccatgcgg ccggccggcg tggtggtgtc ggcccacggc tctgccaggc 7440
tacgcaggcc cgcgccggcc tcctggatgc gctcggcaat gtccagtagg tcgcgggtgc 7500

```
tgcgggccag gcggtctagc ctggtcactg tcacaacgtc gccagggcgt aggtggtcaa   7560
gcatcctggc cagctccggg cggtcgcgcc tggtgccggt gatcttctcg gaaaacagct   7620
tggtgcagcc ggccgcgtgc agttcggccc gttggttggt caagtcctgg tcgtcggtgc   7680
tgacgcgggc atagcccagc aggccagcgg cggcgctctt gttcatggcg taatgtctcc   7740
ggttctagtc gcaagtattc tactttatgc gactaaaaca cgcgacaaga aaacgccagg   7800
aaaagggcag ggcggcagcc tgtcgcgtaa cttaggactt gtgcgacatg tcgttttcag   7860
aagacggctg cactgaacgt cagaagccga ctgcactata gcagcggagg ggttggatca   7920
aagtactttg atcccgaggg gaaccctgtg gttggcatgc acatacaaat ggacgaacgg   7980
ataaaccttt tcacgccctt ttaaatatcc gttattctaa taaacgctct tttctcttag   8040
gtttacccgc caatatatcc tgtcaaacac tgatagttta aactgaaggc gggaaacgac   8100
aatctgatcc aagctcaagc taagcttgag ctctcccata tggtcgagat ctcctttgcc   8160
ccggagatca ccatggacga ctttctctat ctctacgatc taggaagaaa gttcgacgga   8220
gaaggtgacg ataccatgtt caccaccgat aatgagaaga ttagcctctt caatttcaga   8280
aagaatgctg acccacagat ggttagagag gcctacgcgg caggtctcat caagacgatc   8340
tacccgagta ataatctcca ggagatcaaa taccttccca agaaggttaa agatgcagtc   8400
aaaagattca ggactaactg catcaagaac acagagaaag atatatttct caagatcaga   8460
agtactattc cagtatggac gattcaaggc ttgcttcata aaccaaggca agtaatagag   8520
attggagtct ctaagaaagt agttcctact gaatcaaagg ccatggagtc aaaaattcag   8580
atcgaggatc taacagaact cgccgtgaag actggcgaac agttcataca gagtctttta   8640
cgactcaatg acaagaagaa aatcttcgtc aacatggtgg agcacgacac tctcgtctac   8700
tccaagaata tcaaagatac agtctcagaa gaccaaaggg ctattgagac ttttcaacaa   8760
agggtaatat cgggaaacct cctcggattc cattgcccag ctatctgtca cttcatcaaa   8820
aggacagtag aaaaggaagg tggcacctac aaatgccatc attgcgataa aggaaaggct   8880
atcgttcaag atgcccctgc cgacagtggt cccaaagatg gacccccacc cacgaggagc   8940
atcgtggaaa aagaagacgt tccaaccacg tcttcaaagc aagtggattg atgtgatatc   9000
tccactgacg taagggatga cgcacaatcc cactatcctt cgcaagaccc ttcctctata   9060
taaggaagtt catttcattt ggagaggact ccggtatttt tacaacaatt accacaacaa   9120
aacaaacaac aaacaacatt acaatttact attctagtcg acctgcaggc ggccgcacta   9180
gtgatatcac aagtttgtac aaaaaagcag gctgaattcc caccatggca aacaagcttt   9240
tcttggtgtg cgctaccttc gctctttgct tccttttgac taacgctcag gttcaattgc   9300
aagagtctgg tggtggactc gtgcaatctg gtggatctct tagactctct tgcgtgcact   9360
ctaagaccac cttcaccaga aatgctatgg gatggtacag acaggctctc ggaaaagaga   9420
gagagcttgt tgctaccatc acctctggtg gaactaccaa ctacgctgat tctgtgaagg   9480
gaaggttcac catctctatg gattctgcta agaacaccgt gtacctccag atgaactctc   9540
tcaagcctga ggataccgct gtgtactact gcaacgtgaa caccagaagg atcttcggag   9600
gaaccgttag agaatactgg ggacaaggta ctcaggtcac cgtttcttca ggtggtggtg   9660
gaagtggtgg tggttctcaa gttcaactgc aggaatcagg tggtggattg gttcagtctg   9720
gtggttctct caggttgtca tgcgttcaca gtaagactac tttcactagg aacgcaatgg   9780
gatggtatag gcaagcactt ggtaaagaga gggaactcgt tgcaactatc acaagtggtg   9840
gaaccactaa ttacgcagat agtgttaagg gaagattcac tattagtatg gatagtgcaa   9900
```

-continued

```
agaacactgt ttacttgcaa atgaactcat tgaagccaga ggatacagca gtttattact    9960

gtaatgttaa cactagaaga attttcggtg gtactgtgag agagtattgg ggacagggaa   10020

cccaggttac agttagttca gcggccgcac atcatcacca tcaccattga ggatccaccc   10080

agctttcttg tacaaagtgg tgatatcccg cggccatgct agagtccgca aaaatcacca   10140

gtctctctct acaaatctat ctctctctat ttttctccag aataatgtgt gagtagttcc   10200

cagataaggg aattagggtt cttatagggt ttcgctcatg tgttgagcat ataagaaacc   10260

cttagtatgt atttgtattt gtaaaatact tctatcaata aaatttctaa ttcctaaaac   10320

caaaatccag tgacctgcag gcatgcgacg tcg                                10353
```

<210> SEQ ID NO 367
<211> LENGTH: 9963
<212> TYPE: DNA
<213> ORGANISM: Artificial Sequence
<220> FEATURE:
<223> OTHER INFORMATION: pK7WG2-35S: sec_56F11_His

<400> SEQUENCE: 367

```
ggccctctag aggatccccg ggtaccgcga attatcatac atgagaatta agggagtcac      60

gttatgaccc ccgccgatga cgcgggacaa gccgttttac gtttggaact gacagaaccg     120

caacgttgaa ggagccactc agccgcgggt ttctggagtt taatgagcta agcacatacg     180

tcagaaacca ttattgcgcg ttcaaaagtc gcctaaggtc actatcagct agcaaatatt     240

tcttgtcaaa aatgctccac tgacgttcca taaattcccc tcggtatcca attagagtct     300

catattcact ctcaactcga tcgaggcatg attgaacaag atggattgca cgcaggttct     360

ccggccgctt gggtggagag gctattcggc tatgactggg cacaacagac aatcggctgc     420

tctgatgccg ccgtgttccg gctgtcagcg caggggcgcc cggttctttt tgtcaagacc     480

gacctgtccg gtgccctgaa tgaactccaa gacgaggcag cgcggctatc gtggctggcc     540

acgacgggcg ttccttgcgc agctgtgctc gacgttgtca ctgaagcggg aagggactgg     600

ctgctattgg gcgaagtgcc ggggcaggat ctcctgtcat ctcaccttgc tcctgccgag     660

aaagtatcca tcatggctga tgcaatgcgg cggctgcata cgcttgatcc ggctacctgc     720

ccattcgacc accaagcgaa acatcgcatc gagcgaggac gtactcggat ggaagccggt     780

cttgtcgatc aggatgatct ggacgaagag catcaggggc tcgcgccagc cgaactgttc     840

gccaggctca aggcgcggat gcccgacggc gaggatctcg tcgtgaccca gggcgatgcc     900

tgcttgccga atatcatggt ggaaaatggc cgcttttctg gattcatcga ctgtggccgg     960

ctgggtgtgg cggaccgcta tcaggacata gcgttggcta cccgtgatat tgctgaagag    1020

cttggcggcg aatgggctga ccgcttcctc gtgctttacg gtatcgccgc tcccgattcg    1080

cagcgcatcg ccttctatcg ccttcttgac gagttcttct gagcgggact ctggggttcg    1140

gactctagct agagtcaagc agatcgttca aacatttggc aataaagttt cttaagattg    1200

aatcctgttg ccggtcttgc gatgattatc atataatttc tgttgaatta cgttaagcat    1260

gtaataatta acatgtaatg catgacgtta tttatgagat gggtttttg attagagtcc     1320

cgcaattata catttaatac gcgatagaaa acaaaatata gcgcgcaaac taggataaat    1380

tatcgcgcgc ggtgtcatct atgttactag atcgaccggc atgcaagctg ataattcaat    1440

tcggcgttaa ttcagtacat taaaaacgtc cgcaatgtgt tattaagttg tctaagcgtc    1500

aatttgttta caccacaata tatcctgcca ccagccagcc aacagctccc cgaccggcag    1560
```

-continued

```
ctcggcacaa aatcaccact cgatacaggc agcccatcag tccgggacgg cgtcagcggg   1620
agagccgttg taaggcggca gactttgctc atgttaccga tgctattcgg aagaacggca   1680
actaagctgc cgggtttgaa acacggatga tctcgcggag ggtagcatgt tgattgtaac   1740
gatgacagag cgttgctgcc tgtgatcaat tcgggcacga acccagtgga cataagcctc   1800
gttcggttcg taagctgtaa tgcaagtagc gtaactgccg tcacgcaact ggtccagaac   1860
cttgaccgaa cgcagcggtg gtaacggcgc agtggcggtt ttcatggctt cttgttatga   1920
catgtttttt tggggtacag tctatgcctc gggcatccaa gcagcaagcg cgttacgccg   1980
tgggtcgatg tttgatgtta tggagcagca acgatgttac gcagcagggc agtcgcccta   2040
aaacaaagtt aaacatcatg ggggaagcgg tgatcgccga agtatcgact caactatcag   2100
aggtagttgg cgtcatcgag cgccatctcg aaccgacgtt gctggccgta catttgtacg   2160
gctccgcagt ggatggcggc ctgaagccac acagtgatat tgatttgctg gttacggtga   2220
ccgtaaggct tgatgaaaca acgcggcgag ctttgatcaa cgaccttttg gaaacttcgg   2280
cttcccctgg agagagcgag attctccgcg ctgtagaagt caccattgtt gtgcacgacg   2340
acatcattcc gtggcgttat ccagctaagc gcgaactgca atttggagaa tggcagcgca   2400
atgacattct tgcaggtatc ttcgagccag ccacgatcga cattgatctg gctatcttgc   2460
tgacaaaagc aagagaacat agcgttgcct tggtaggtcc agcggcggag gaactctttg   2520
atccggttcc tgaacaggat ctatttgagg cgctaaatga aaccttaacg ctatggaact   2580
cgccgcccga ctgggctggc gatgagcgaa atgtagtgct tacgttgtcc cgcatttggt   2640
acagcgcagt aaccggcaaa atcgcgccga aggatgtcgc tgccgactgg gcaatggagc   2700
gcctgccggc ccagtatcag cccgtcatac ttgaagctag acaggcttat cttggacaag   2760
aagaagatcg cttggcctcg cgcgcagatc agttggaaga atttgtccac tacgtgaaag   2820
gcgagatcac caaggtagtc ggcaaataat gtctagctag aaattcgttc aagccgacgc   2880
cgcttcgccg gcgttaactc aagcgattag atgcactaag cacataattg ctcacagcca   2940
aactatcagg tcaagtctgc ttttattatt tttaagcgtg cataataagc cctacacaaa   3000
ttgggagata tatcatgcat gaccaaaatc ccttaacgtg agttttcgtt ccactgagcg   3060
tcagaccccg tagaaaagat caaaggatct tcttgagatc cttttttct gcgcgtaatc   3120
tgctgcttgc aaacaaaaaa accaccgcta ccagcggtgg tttgtttgcc ggatcaagag   3180
ctaccaactc tttttccgaa ggtaactggc ttcagcagag cgcagatacc aaatactgtc   3240
cttctagtgt agccgtagtt aggccaccac ttcaagaact ctgtagcacc gcctacatac   3300
ctcgctctgc taatcctgtt accagtggct gctgccagtg gcgataagtc gtgtcttacc   3360
gggttggact caagacgata gttaccggat aaggcgcagc ggtcgggctg aacggggggt   3420
tcgtgcacac agcccagctt ggagcgaacg acctacaccg aactgagata cctacagcgt   3480
gagctatgag aaagcgccac gcttcccgaa gggagaaagg cggacaggta tccggtaagc   3540
ggcagggtcg gaacaggaga gcgcacgagg gagcttccag ggggaaacgc ctggtatctt   3600
tatagtcctg tcgggtttcg ccacctctga cttgagcgtc gatttttgtg atgctcgtca   3660
ggggggcgga gcctatggaa aaacgccagc aacgcggcct ttttacggtt cctggccttt   3720
tgctggcctt ttgctcacat gttctttcct gcgttatccc ctgattctgt ggataaccgt   3780
attaccgcct ttgagtgagc tgataccgct cgccgcagcc gaacgaccga gcgcagcgag   3840
tcagtgagcg aggaagcgga agagcgcctg atgcggtatt ttctccttac gcatctgtgc   3900
ggtatttcac accgcatatg gtgcactctc agtacaatct gctctgatgc cgcatagtta   3960
```

agccagtata cactccgcta tcgctacgtg actgggtcat ggctgcgccc cgacacccgc 4020
caacacccgc tgacgcgccc tgacgggctt gtctgctccc ggcatccgct tacagacaag 4080
ctgtgaccgt ctccgggagc tgcatgtgtc agaggttttc accgtcatca ccgaaacgcg 4140
cgaggcaggg tgccttgatg tgggcgccgg cggtcgagtg gcgacggcgc ggcttgtccg 4200
cgccctggta gattgcctgg ccgtaggcca gccatttttg agcggccagc ggccgcgata 4260
ggccgacgcg aagcggcggg gcgtagggag cgcagcgacc gaagggtagg cgctttttgc 4320
agctcttcgg ctgtgcgctg gccagacagt tatgcacagg ccaggcgggt tttaagagtt 4380
ttaataagtt ttaaagagtt ttaggcggaa aaatcgcctt ttttctcttt tatatcagtc 4440
acttacatgt gtgaccggtt cccaatgtac ggctttgggt tcccaatgta cgggttccgg 4500
ttcccaatgt acggctttgg gttcccaatg tacgtgctat ccacaggaaa gagacctttt 4560
cgaccttttt cccctgctag ggcaatttgc cctagcatct gctccgtaca ttaggaaccg 4620
gcggatgctt cgccctcgat caggttgcgg tagcgcatga ctaggatcgg gccagcctgc 4680
cccgcctcct ccttcaaatc gtactccggc aggtcatttg acccgatcag cttgcgcacg 4740
gtgaaacaga acttcttgaa ctctccggcg ctgccactgc gttcgtagat cgtcttgaac 4800
aaccatctgg cttctgcctt gcctgcggcg cggcgtgcca ggcggtagag aaaacggccg 4860
atgccgggat cgatcaaaaa gtaatcgggg tgaaccgtca gcacgtccgg gttcttgcct 4920
tctgtgatct cgcggtacat ccaatcagct agctcgatct cgatgtactc cggccgcccg 4980
gtttcgctct ttacgatctt gtagcggcta atcaaggctt caccctcgga taccgtcacc 5040
aggcggccgt tcttggcctt cttcgtacgc tgcatggcaa cgtgcgtggt gtttaaccga 5100
atgcaggttt ctaccaggtc gtctttctgc tttccgccat cggctcgccg gcagaacttg 5160
agtacgtccg caacgtgtgg acggaacacg cggccgggct tgtctccctt cccttcccgg 5220
tatcggttca tggattcggt tagatgggaa accgccatca gtaccaggtc gtaatcccac 5280
acactggcca tgccggccgg ccctgcggaa acctctacgt gcccgtctgg aagctcgtag 5340
cggatcacct cgccagctcg tcggtcacgc ttcgacagac ggaaaacggc cacgtccatg 5400
atgctgcgac tatcgcgggt gcccacgtca tagagcatcg gaacgaaaaa atctggttgc 5460
tcgtcgccct tgggcggctt cctaatcgac ggcgcaccgg ctgccggcgg ttgccgggat 5520
tctttgcgga ttcgatcagc ggccgcttgc cacgattcac cggggcgtgc ttctgcctcg 5580
atgcgttgcc gctgggcggc ctgcgcggcc ttcaacttct ccaccaggtc atcacccagc 5640
gccgcgccga tttgtaccgg gccggatggt ttgcgaccgt cacgccgatt cctcgggctt 5700
gggggttcca gtgccattgc agggccggca gacaacccag ccgcttacgc ctggccaacc 5760
gcccgttcct ccacacatgg ggcattccac ggcgtcggtg cctggttgtt cttgattttc 5820
catgccgcct cctttagccg ctaaaattca tctactcatt tattcatttg ctcatttact 5880
ctggtagctg cgcgatgtat tcagatagca gctcggtaat ggtcttgcct tggcgtaccg 5940
cgtacatctt cagcttggtg tgatcctccg ccggcaactg aaagttgacc cgcttcatgg 6000
ctggcgtgtc tgccaggctg gccaacgttg cagccttgct gctgcgtgcg ctcggacggc 6060
cggcacttag cgtgtttgtg cttttgctca ttttctcttt acctcattaa ctcaaatgag 6120
ttttgattta atttcagcgg ccagcgcctg gacctcgcgg gcagcgtcgc cctcgggttc 6180
tgattcaaga acggttgtgc cggcggcggc agtgcctggg tagctcacgc gctgcgtgat 6240
acgggactca agaatgggca gctcgtaccc ggccagcgcc tcggcaacct caccgccgat 6300

-continued

```
gcgcgtgcct ttgatcgccc gcgacacgac aaaggccgct tgtagccttc catccgtgac   6360
ctcaatgcgc tgcttaacca gctccaccag gtcggcggtg gcccatatgt cgtaagggct   6420
tggctgcacc ggaatcagca cgaagtcggc tgccttgatc gcggacacag ccaagtccgc   6480
cgcctggggc gctccgtcga tcactacgaa gtcgcgccgg ccgatggcct tcacgtcgcg   6540
gtcaatcgtc gggcggtcga tgccgacaac ggttagcggt tgatcttccc gcacggccgc   6600
ccaatcgcgg gcactgccct ggggatcgga atcgactaac agaacatcgg ccccggcgag   6660
ttgcagggcg cgggctagat gggttgcgat ggtcgtcttg cctgacccgc ctttctggtt   6720
aagtacagcg ataaccttca tgcgttcccc ttgcgtattt gtttatttac tcatcgcatc   6780
atatacgcag cgaccgcatg acgcaagctg ttttactcaa atacacatca cctttttaga   6840
cggcggcgct cggtttcttc agcggccaag ctggccggcc aggccgccag cttggcatca   6900
gacaaaccgg ccaggatttc atgcagccgc acggttgaga cgtgcgcggg cggctcgaac   6960
acgtacccgg ccgcgatcat ctccgcctcg atctcttcgg taatgaaaaa cggttcgtcc   7020
tggccgtcct ggtgcggttt catgcttgtt cctcttggcg ttcattctcg gcggccgcca   7080
gggcgtcggc ctcggtcaat gcgtcctcac ggaaggcacc gcgccgcctg gcctcggtgg   7140
gcgtcacttc ctcgctgcgc tcaagtgcgc ggtacagggt cgagcgatgc acgccaagca   7200
gtgcagccgc ctctttcacg gtgcggcctt cctggtcgat cagctcgcgg gcgtgcgcga   7260
tctgtgccgg ggtgagggta gggcgggggc caaacttcac gcctcgggcc ttggcggcct   7320
cgcgcccgct ccgggtgcgg tcgatgatta gggaacgctc gaactcggca atgccggcga   7380
acacggtcaa caccatgcgg ccggccggcg tggtggtgtc ggcccacggc tctgccaggc   7440
tacgcaggcc cgcgccggcc tcctggatgc gctcggcaat gtccagtagg tcgcgggtgc   7500
tgcgggccag gcggtctagc ctggtcactg tcacaacgtc gccagggcgt aggtggtcaa   7560
gcatcctggc cagctccggg cggtcgcgcc tggtgccggt gatcttctcg gaaaacagct   7620
tggtgcagcc ggccgcgtgc agttcggccc gttggttggt caagtcctgg tcgtcggtgc   7680
tgacgcgggc atagcccagc aggccagcgg cggcgctctt gttcatggcg taatgtctcc   7740
ggttctagtc gcaagtattc tactttatgc gactaaaaca cgcgacaaga aaacgccagg   7800
aaaagggcag ggcggcagcc tgtcgcgtaa cttaggactt gtgcgacatg tcgttttcag   7860
aagacggctg cactgaacgt cagaagccga ctgcactata gcagcggagg ggttggatca   7920
aagtactttg atcccgaggg gaaccctgtg gttggcatgc acatacaaat ggacgaacgg   7980
ataaaccttt tcacgccctt ttaaatatcc gttattctaa taaacgctct tttctcttag   8040
gtttacccgc caatatatcc tgtcaaacac tgatagttta aactgaaggc gggaaacgac   8100
aatctgatcc aagctcaagc taagcttgag ctctcccata tggtcgagat ctcctttgcc   8160
ccggagatca ccatggacga ctttctctat ctctacgatc taggaagaaa gttcgacgga   8220
gaaggtgacg ataccatgtt caccaccgat aatgagaaga ttagcctctt caatttcaga   8280
aagaatgctg acccacagat ggttagagag gcctacgcgg caggtctcat caagacgatc   8340
tacccgagta ataatctcca ggagatcaaa taccttccca agaaggttaa agatgcagtc   8400
aaaagattca ggactaactg catcaagaac acagagaaag atatatttct caagatcaga   8460
agtactattc cagtatggac gattcaaggc ttgcttcata aaccaaggca agtaatagag   8520
attggagtct ctaagaaagt agttcctact gaatcaaagg ccatggagtc aaaaattcag   8580
atcgaggatc taacagaact cgccgtgaag actggcgaac agttcataca gagtctttta   8640
cgactcaatg acaagaagaa aatcttcgtc aacatggtgg agcacgacac tctcgtctac   8700
```

tccaagaata tcaaagatac agtctcagaa gaccaaaggg ctattgagac ttttcaacaa 8760
agggtaatat cgggaaacct cctcggattc cattgcccag ctatctgtca cttcatcaaa 8820
aggacagtag aaaaggaagg tggcacctac aaatgccatc attgcgataa aggaaaggct 8880
atcgttcaag atgcccctgc cgacagtggt cccaaagatg gacccccacc cacgaggagc 8940
atcgtggaaa aagaagacgt tccaaccacg tcttcaaagc aagtggattg atgtgatatc 9000
tccactgacg taagggatga cgcacaatcc cactatcctt cgcaagaccc ttcctctata 9060
taaggaagtt catttcattt ggagaggact ccggtatttt tacaacaatt accacaacaa 9120
aacaaacaac aaacaacatt acaatttact attctagtcg acctgcaggc ggccgcacta 9180
gtgatatcac aagtttgtac aaaaaagcag gctgaattcc caccatggca aacaagcttt 9240
tcttggtgtg cgctaccttc gctctttgct tccttttgac taacgctcag gttcagctgc 9300
aggaatctgg tggtggactt gttcagtctg gtggatctct cagactctct tgcgtgcact 9360
ctaagaccac cttcaccaga aatgctatgg gatggtacag acaggctctc ggaaaagaga 9420
gagagcttgt tgctaccatc acctctggtg gaactaccaa ctacgctgat tctgtgaagg 9480
gaaggttcac catctctatg gattctgcta agaacaccgt gtacctccag atgaactctc 9540
tcaagcctga ggataccgct gtgtactact gcaacgtgaa caccagaagg atcttcggag 9600
gaaccgttag agaatactgg ggacaaggta ctcaggtcac cgtttcttca gcggccgcac 9660
atcatcatca ccatcattga ggatccaccc agctttcttg tacaaagtgg tgatatcccg 9720
cggccatgct agagtccgca aaaatcacca gtctctctct acaaatctat ctctctctat 9780
ttttctccag aataatgtgt gagtagttcc cagataaggg aattagggtt cttatagggt 9840
ttcgctcatg tgttgagcat ataagaaacc cttagtatgt atttgtattt gtaaaatact 9900
tctatcaata aaatttctaa ttcctaaaac caaaatccag tgacctgcag gcatgcgacg 9960
tcg 9963

<210> SEQ ID NO 368
<211> LENGTH: 9903
<212> TYPE: DNA
<213> ORGANISM: Artificial Sequence
<220> FEATURE:
<223> OTHER INFORMATION: pK7WG2-35S: cyto_56F11_His

<400> SEQUENCE: 368
ggccctctag aggatccccg ggtaccgcga attatcatac atgagaatta agggagtcac 60
gttatgaccc ccgccgatga cgcgggacaa gccgttttac gtttggaact gacagaaccg 120
caacgttgaa ggagccactc agccgcgggt ttctggagtt taatgagcta agcacatacg 180
tcagaaacca ttattgcgcg ttcaaaagtc gcctaaggtc actatcagct agcaaatatt 240
tcttgtcaaa aatgctccac tgacgttcca taaattcccc tcggtatcca attagagtct 300
catattcact ctcaactcga tcgaggcatg attgaacaag atggattgca cgcaggttct 360
ccggccgctt gggtggagag gctattcggc tatgactggg cacaacagac aatcggctgc 420
tctgatgccg ccgtgttccg gctgtcagcg caggggcgcc cggttctttt tgtcaagacc 480
gacctgtccg gtgccctgaa tgaactccaa gacgaggcag cgcggctatc gtggctggcc 540
acgacgggcg ttccttgcgc agctgtgctc gacgttgtca ctgaagcggg aagggactgg 600
ctgctattgg gcgaagtgcc ggggcaggat ctcctgtcat ctcaccttgc tcctgccgag 660
aaagtatcca tcatggctga tgcaatgcgg cggctgcata cgcttgatcc ggctacctgc 720

```
ccattcgacc accaagcgaa acatcgcatc gagcgaggac gtactcggat ggaagccggt    780
cttgtcgatc aggatgatct ggacgaagag catcaggggc tcgcgccagc cgaactgttc    840
gccaggctca aggcgcggat gcccgacggc gaggatctcg tcgtgaccca gggcgatgcc    900
tgcttgccga atatcatggt ggaaaatggc cgcttttctg gattcatcga ctgtggccgg    960
ctgggtgtgg cggaccgcta tcaggacata gcgttggcta cccgtgatat tgctgaagag   1020
cttggcggcg aatgggctga ccgcttcctc gtgctttacg gtatcgccgc tcccgattcg   1080
cagcgcatcg ccttctatcg ccttcttgac gagttcttct gagcgggact ctggggttcg   1140
gactctagct agagtcaagc agatcgttca aacatttggc aataaagttt cttaagattg   1200
aatcctgttg ccggtcttgc gatgattatc atataatttc tgttgaatta cgttaagcat   1260
gtaataatta acatgtaatg catgacgtta tttatgagat gggtttttg attagagtcc    1320
cgcaattata catttaatac gcgatagaaa acaaaatata gcgcgcaaac taggataaat   1380
tatcgcgcgc ggtgtcatct atgttactag atcgaccggc atgcaagctg ataattcaat   1440
tcggcgttaa ttcagtacat taaaaacgtc cgcaatgtgt tattaagttg tctaagcgtc   1500
aatttgttta caccacaata tatcctgcca ccagccagcc aacagctccc cgaccggcag   1560
ctcggcacaa aatcaccact cgatacaggc agcccatcag tccgggacgg cgtcagcggg   1620
agagccgttg taaggcggca gactttgctc atgttaccga tgctattcgg aagaacggca   1680
actaagctgc cgggtttgaa acacggatga tctcgcggag ggtagcatgt tgattgtaac   1740
gatgacagag cgttgctgcc tgtgatcaat tcgggcacga acccagtgga cataagcctc   1800
gttcggttcg taagctgtaa tgcaagtagc gtaactgccg tcacgcaact ggtccagaac   1860
cttgaccgaa cgcagcggtg gtaacggcgc agtggcggtt ttcatggctt cttgttatga   1920
catgtttttt tggggtacag tctatgcctc gggcatccaa gcagcaagcg cgttacgccg   1980
tgggtcgatg tttgatgtta tggagcagca acgatgttac gcagcagggc agtcgcccta   2040
aaacaaagtt aaacatcatg ggggaagcgg tgatcgccga agtatcgact caactatcag   2100
aggtagttgg cgtcatcgag cgccatctcg aaccgacgtt gctggccgta catttgtacg   2160
gctccgcagt ggatggcggc ctgaagccac acagtgatat tgatttgctg gttacggtga   2220
ccgtaaggct tgatgaaaca acgcggcgag ctttgatcaa cgaccttttg gaaacttcgg   2280
cttcccctgg agagagcgag attctccgcg ctgtagaagt caccattgtt gtgcacgacg   2340
acatcattcc gtggcgttat ccagctaagc gcgaactgca atttggagaa tggcagcgca   2400
atgacattct tgcaggtatc ttcgagccag ccacgatcga cattgatctg gctatcttgc   2460
tgacaaaagc aagagaacat agcgttgcct tggtaggtcc agcggcggag gaactctttg   2520
atccggttcc tgaacaggat ctatttgagg cgctaaatga aaccttaacg ctatggaact   2580
cgccgcccga ctgggctggc gatgagcgaa atgtagtgct tacgttgtcc cgcatttggt   2640
acagcgcagt aaccggcaaa atcgcgccga aggatgtcgc tgccgactgg gcaatggagc   2700
gcctgccggc ccagtatcag cccgtcatac ttgaagctag acaggcttat cttggacaag   2760
aagaagatcg cttggcctcg cgcgcagatc agttggaaga atttgtccac tacgtgaaag   2820
gcgagatcac caaggtagtc ggcaaataat gtctagctag aaattcgttc aagccgacgc   2880
cgcttcgccg gcgttaactc aagcgattag atgcactaag cacataattg ctcacagcca   2940
aactatcagg tcaagtctgc ttttattatt tttaagcgtg cataataagc cctacacaaa   3000
ttgggagata tatcatgcat gaccaaaatc ccttaacgtg agttttcgtt ccactgagcg   3060
tcagaccccg tagaaaagat caaaggatct tcttgagatc cttttttct gcgcgtaatc    3120
```

tgctgcttgc aaacaaaaaa accaccgcta ccagcggtgg tttgtttgcc ggatcaagag 3180
ctaccaactc tttttccgaa ggtaactggc ttcagcagag cgcagatacc aaatactgtc 3240
cttctagtgt agccgtagtt aggccaccac ttcaagaact ctgtagcacc gcctacatac 3300
ctcgctctgc taatcctgtt accagtggct gctgccagtg gcgataagtc gtgtcttacc 3360
gggttggact caagacgata gttaccggat aaggcgcagc ggtcgggctg aacggggggt 3420
tcgtgcacac agcccagctt ggagcgaacg acctacaccg aactgagata cctacagcgt 3480
gagctatgag aaagcgccac gcttcccgaa gggagaaagg cggacaggta tccggtaagc 3540
ggcagggtcg gaacaggaga gcgcacgagg gagcttccag ggggaaacgc ctggtatctt 3600
tatagtcctg tcgggtttcg ccacctctga cttgagcgtc gatttttgtg atgctcgtca 3660
gggggcgga gcctatggaa aaacgccagc aacgcggcct ttttacggtt cctggccttt 3720
tgctggcctt ttgctcacat gttctttcct gcgttatccc ctgattctgt ggataaccgt 3780
attaccgcct ttgagtgagc tgataccgct cgccgcagcc gaacgaccga gcgcagcgag 3840
tcagtgagcg aggaagcgga agagcgcctg atgcggtatt ttctccttac gcatctgtgc 3900
ggtatttcac accgcatatg gtgcactctc agtacaatct gctctgatgc cgcatagtta 3960
agccagtata cactccgcta tcgctacgtg actgggtcat ggctgcgccc cgacacccgc 4020
caacacccgc tgacgcgccc tgacgggctt gtctgctccc ggcatccgct tacagacaag 4080
ctgtgaccgt ctccgggagc tgcatgtgtc agaggttttc accgtcatca ccgaaacgcg 4140
cgaggcaggg tgccttgatg tgggcgccgg cggtcgagtg gcgacggcgc ggcttgtccg 4200
cgccctggta gattgcctgg ccgtaggcca gccatttttg agcggccagc ggccgcgata 4260
ggccgacgcg aagcggcggg gcgtagggag cgcagcgacc gaagggtagg cgctttttgc 4320
agctcttcgg ctgtgcgctg gccagacagt tatgcacagg ccaggcgggt tttaagagtt 4380
ttaataagtt ttaaagagtt ttaggcggaa aaatcgcctt ttttctcttt tatatcagtc 4440
acttacatgt gtgaccggtt cccaatgtac ggctttgggt tcccaatgta cgggttccgg 4500
ttcccaatgt acggctttgg gttcccaatg tacgtgctat ccacaggaaa gagacctttt 4560
cgaccttttt cccctgctag ggcaatttgc cctagcatct gctccgtaca ttaggaaccg 4620
gcggatgctt cgccctcgat caggttgcgg tagcgcatga ctaggatcgg gccagcctgc 4680
cccgcctcct ccttcaaatc gtactccggc aggtcatttg acccgatcag cttgcgcacg 4740
gtgaaacaga acttcttgaa ctctccggcg ctgccactgc gttcgtagat cgtcttgaac 4800
aaccatctgg cttctgcctt gcctgcggcg cggcgtgcca ggcggtagag aaaacggccg 4860
atgccgggat cgatcaaaaa gtaatcgggg tgaaccgtca gcacgtccgg gttcttgcct 4920
tctgtgatct cgcggtacat ccaatcagct agctcgatct cgatgtactc cggccgcccg 4980
gtttcgctct ttacgatctt gtagcggcta atcaaggctt caccctcgga taccgtcacc 5040
aggcggccgt tcttggcctt cttcgtacgc tgcatggcaa cgtgcgtggt gtttaaccga 5100
atgcaggttt ctaccaggtc gtctttctgc tttccgccat cggctcgccg gcagaacttg 5160
agtacgtccg caacgtgtgg acggaacacg cggccgggct tgtctccctt cccttcccgg 5220
tatcggttca tggattcggt tagatgggaa accgccatca gtaccaggtc gtaatcccac 5280
acactggcca tgccggccgg ccctgcggaa acctctacgt gcccgtctgg aagctcgtag 5340
cggatcacct cgccagctcg tcggtcacgc ttcgacagac ggaaaacggc cacgtccatg 5400
atgctgcgac tatcgcgggt gcccacgtca tagagcatcg gaacgaaaaa atctggttgc 5460

-continued

```
tcgtcgccct tgggcggctt cctaatcgac ggcgcaccgg ctgccggcgg ttgccgggat   5520
tctttgcgga ttcgatcagc ggccgcttgc cacgattcac cggggcgtgc ttctgcctcg   5580
atgcgttgcc gctgggcggc ctgcgcggcc ttcaacttct ccaccaggtc atcacccagc   5640
gccgcgccga tttgtaccgg gccggatggt ttgcgaccgt cacgccgatt cctcgggctt   5700
gggggttcca gtgccattgc agggccggca gacaacccag ccgcttacgc ctggccaacc   5760
gcccgttcct ccacacatgg ggcattccac ggcgtcggtg cctggttgtt cttgattttc   5820
catgccgcct cctttagccg ctaaaattca tctactcatt tattcatttg ctcatttact   5880
ctggtagctg cgcgatgtat tcagatagca gctcggtaat ggtcttgcct tggcgtaccg   5940
cgtacatctt cagcttggtg tgatcctccg ccggcaactg aaagttgacc cgcttcatgg   6000
ctggcgtgtc tgccaggctg gccaacgttg cagccttgct gctgcgtgcg ctcggacggc   6060
cggcacttag cgtgtttgtg cttttgctca ttttctcttt acctcattaa ctcaaatgag   6120
ttttgattta atttcagcgg ccagcgcctg gacctcgcgg gcagcgtcgc cctcgggttc   6180
tgattcaaga acggttgtgc cggcggcggc agtgcctggg tagctcacgc gctgcgtgat   6240
acgggactca agaatgggca gctcgtaccc ggccagcgcc tcggcaacct caccgccgat   6300
gcgcgtgcct ttgatcgccc gcgacacgac aaaggccgct tgtagccttc catccgtgac   6360
ctcaatgcgc tgcttaacca gctccaccag gtcggcggtg gcccatatgt cgtaagggct   6420
tggctgcacc ggaatcagca cgaagtcggc tgccttgatc gcggacacag ccaagtccgc   6480
cgcctggggc gctccgtcga tcactacgaa gtcgcgccgg ccgatggcct tcacgtcgcg   6540
gtcaatcgtc gggcggtcga tgccgacaac ggttagcggt tgatcttccc gcacggccgc   6600
ccaatcgcgg gcactgccct ggggatcgga atcgactaac agaacatcgg ccccggcgag   6660
ttgcagggcg cgggctagat gggttgcgat ggtcgtcttg cctgacccgc ctttctggtt   6720
aagtacagcg ataaccttca tgcgttcccc ttgcgtattt gtttatttac tcatcgcatc   6780
atatacgcag cgaccgcatg acgcaagctg ttttactcaa atacacatca cctttttaga   6840
cggcggcgct cggtttcttc agcggccaag ctggccggcc aggccgccag cttggcatca   6900
gacaaaccgg ccaggatttc atgcagccgc acggttgaga cgtgcgcggg cggctcgaac   6960
acgtacccgg ccgcgatcat ctccgcctcg atctcttcgg taatgaaaaa cggttcgtcc   7020
tggccgtcct ggtgcggttt catgcttgtt cctcttggcg ttcattctcg gcggccgcca   7080
gggcgtcggc ctcggtcaat gcgtcctcac ggaaggcacc gcgccgcctg gcctcggtgg   7140
gcgtcacttc ctcgctgcgc tcaagtgcgc ggtacagggt cgagcgatgc acgccaagca   7200
gtgcagccgc ctctttcacg gtgcggcctt cctggtcgat cagctcgcgg gcgtgcgcga   7260
tctgtgccgg ggtgagggta gggcgggggc caaacttcac gcctcgggcc ttggcggcct   7320
cgcgcccgct ccgggtgcgg tcgatgatta gggaacgctc gaactcggca atgccggcga   7380
acacggtcaa caccatgcgg ccggccggcg tggtggtgtc ggcccacggc tctgccaggc   7440
tacgcaggcc cgcgccggcc tcctggatgc gctcggcaat gtccagtagg tcgcgggtgc   7500
tgcgggccag gcggtctagc ctggtcactg tcacaacgtc gccagggcgt aggtggtcaa   7560
gcatcctggc cagctccggg cggtcgcgcc tggtgccggt gatcttctcg gaaaacagct   7620
tggtgcagcc ggccgcgtgc agttcggccc gttggttggt caagtcctgg tcgtcggtgc   7680
tgacgcgggc atagcccagc aggccagcgg cggcgctctt gttcatggcg taatgtctcc   7740
ggttctagtc gcaagtattc tactttatgc gactaaaaca cgcgacaaga aaacgccagg   7800
aaaagggcag ggcggcagcc tgtcgcgtaa cttaggactt gtgcgacatg tcgttttcag   7860
```

-continued

```
aagacggctg cactgaacgt cagaagccga ctgcactata gcagcggagg ggttggatca   7920
aagtactttg atcccgaggg gaaccctgtg gttggcatgc acatacaaat ggacgaacgg   7980
ataaaccttt tcacgccctt ttaaatatcc gttattctaa taaacgctct tttctcttag   8040
gtttacccgc caatatatcc tgtcaaacac tgatagttta aactgaaggc gggaaacgac   8100
aatctgatcc aagctcaagc taagcttgag ctctcccata tggtcgagat ctcctttgcc   8160
ccggagatca ccatggacga ctttctctat ctctacgatc taggaagaaa gttcgacgga   8220
gaaggtgacg ataccatgtt caccaccgat aatgagaaga ttagcctctt caatttcaga   8280
aagaatgctg acccacagat ggttagagag gcctacgcgg caggtctcat caagacgatc   8340
tacccgagta ataatctcca ggagatcaaa taccttccca agaaggttaa agatgcagtc   8400
aaaagattca ggactaactg catcaagaac acagagaaag atatatttct caagatcaga   8460
agtactattc cagtatggac gattcaaggc ttgcttcata aaccaaggca agtaatagag   8520
attggagtct ctaagaaagt agttcctact gaatcaaagg ccatggagtc aaaaattcag   8580
atcgaggatc taacagaact cgccgtgaag actggcgaac agttcataca gagtctttta   8640
cgactcaatg acaagaagaa aatcttcgtc aacatggtgg agcacgacac tctcgtctac   8700
tccaagaata tcaaagatac agtctcagaa gaccaaaggg ctattgagac ttttcaacaa   8760
agggtaatat cgggaaacct cctcggattc cattgcccag ctatctgtca cttcatcaaa   8820
aggacagtag aaaaggaagg tggcacctac aaatgccatc attgcgataa aggaaaggct   8880
atcgttcaag atgcccctgc cgacagtggt cccaaagatg gacccccacc cacgaggagc   8940
atcgtggaaa aagaagacgt tccaaccacg tcttcaaagc aagtggattg atgtgatatc   9000
tccactgacg taagggatga cgcacaatcc cactatcctt cgcaagaccc ttcctctata   9060
taaggaagtt catttcattt ggagaggact ccggtatttt tacaacaatt accacaacaa   9120
aacaaacaac aaacaacatt acaatttact attctagtcg acctgcaggc ggccgcacta   9180
gtgatatcac aagtttgtac aaaaaagcag gctgaattcc caccatgcag gttcagctgc   9240
aggaatctgg tggtggactt gttcagtctg gtggatctct cagactctct tgcgtgcact   9300
ctaagaccac cttcaccaga aatgctatgg gatggtacag acaggctctc ggaaaagaga   9360
gagagcttgt tgctaccatc acctctggtg gaactaccaa ctacgctgat tctgtgaagg   9420
gaaggttcac catctctatg gattctgcta agaacaccgt gtacctccag atgaactctc   9480
tcaagcctga ggataccgct gtgtactact gcaacgtgaa caccagaagg atcttcggag   9540
gaaccgttag agaatactgg ggacaaggta ctcaggtcac cgtttcttca gcggccgcac   9600
atcatcatca ccatcattga ggatccaccc agctttcttg tacaaagtgg tgatatcccg   9660
cggccatgct agagtccgca aaaatcacca gtctctctct acaaatctat ctctctctat   9720
ttttctccag aataatgtgt gagtagttcc cagataaggg aattagggtt cttatagggt   9780
ttcgctcatg tgttgagcat ataagaaacc cttagtatgt atttgtattt gtaaaatact   9840
tctatcaata aaatttctaa ttcctaaaac caaaatccag tgacctgcag gcatgcgacg   9900
tcg                                                                  9903
```